(12) United States Patent
Kraus et al.

(10) Patent No.: US 9,532,927 B2
(45) Date of Patent: Jan. 3, 2017

(54) SAFETY DRUG HANDLING DEVICE

(71) Applicant: TEVA MEDICAL LTD., Ashdod (IL)

(72) Inventors: Menachem Kraus, Rehovot (IL); Eli Shemesh, Ashdod (IL)

(73) Assignee: TEVA MEDICAL LTD., Ashdod (IL)

( * ) Notice: Subject to any disclaimer, the term of this patent is extended or adjusted under 35 U.S.C. 154(b) by 298 days.

(21) Appl. No.: 13/955,375

(22) Filed: Jul. 31, 2013

(65) Prior Publication Data
US 2014/0020792 A1  Jan. 23, 2014

Related U.S. Application Data

(62) Division of application No. 13/357,004, filed on Jan. 24, 2012, now Pat. No. 8,511,352, which is a division
(Continued)

(51) Int. Cl.
*A61J 1/20* (2006.01)
*A61M 5/162* (2006.01)
(Continued)

(52) U.S. Cl.
CPC .............. *A61J 1/2096* (2013.01); *A61J 1/2089* (2013.01); *A61M 5/162* (2013.01); *A61J 1/10* (2013.01);
(Continued)

(58) Field of Classification Search
CPC .......... A61J 1/10; A61J 1/1475; A61J 1/2089; A61J 1/2096; A61J 2001/201; A61J 2001/2013; A61J 2001/2017; A61J 2001/2034; A61J 2001/2055; A61J 2001/2058; A61J 2001/2062; A61J 2001/2075; A61J 2001/2082; A61M 2005/1623; A61M 2205/75; A61M 39/02; A61M 39/223; A61M 5/162
(Continued)

(56) References Cited

U.S. PATENT DOCUMENTS 2,842,276 A   7/1958 Butler
3,359,977 A   12/1967 Burke
(Continued)

FOREIGN PATENT DOCUMENTS

CN   2126081    12/1992
CN   1237892    12/1999
(Continued)

OTHER PUBLICATIONS

An Office Action dated Oct. 1, 2012, which issued during the prosecution of U.S. Appl. No. 13/357,004.
(Continued)

*Primary Examiner* — Timothy L Maust
(74) *Attorney, Agent, or Firm* — Ladas & Parry LLP

(57) ABSTRACT

A drug mixing system including at least one receptacle port adaptor adapted to be inserted into a port of a fluid receptacle, at least one syringe adaptor adapted to be attached to a syringe and to the at least one receptacle port adaptor and at least one vial adaptor adapted for connection to a vial containing a drug and adapted for connection to the at least one syringe adaptor, the system being characterized in that at least one of the receptacle port adaptor, the at least one syringe adaptor and the at least one vial adaptor being vented to the atmosphere in a manner which prevents release to the atmosphere of possibly harmful contents of the vial in a liquid, solid or gaseous form.

19 Claims, 108 Drawing Sheets

Related U.S. Application Data of application No. 10/577,618, filed as application No. PCT/IL2004/000993 on Oct. 29, 2004, now Pat. No. 8,122,923.

(60) Provisional application No. 60/516,613, filed on Oct. 30, 2003.

(51) Int. Cl.

| | | |
|---|---|---|
| A61J 1/10 | (2006.01) | |
| A61J 1/14 | (2006.01) | |
| A61M 39/02 | (2006.01) | |
| A61M 39/22 | (2006.01) | |

(52) U.S. Cl.
CPC .............. *A61J 1/1475* (2013.01); *A61J 1/201* (2015.05); *A61J 1/2013* (2015.05); *A61J 1/2017* (2015.05); *A61J 1/2034* (2015.05); *A61J 1/2055* (2015.05); *A61J 1/2058* (2015.05); *A61J 1/2062* (2015.05); *A61J 1/2075* (2015.05); *A61J 1/2082* (2015.05); *A61M 39/02* (2013.01); *A61M 39/223* (2013.01); *A61M 2005/1623* (2013.01); *A61M 2205/75* (2013.01)

(58) Field of Classification Search
USPC ...... 141/319, 329; 604/87–89, 406, 411–415
See application file for complete search history.

(56) References Cited

U.S. PATENT DOCUMENTS

| | | | |
|---|---|---|---|
| 3,872,867 A * | 3/1975 | Killinger ..................... 604/413 |
| 4,128,098 A | 12/1978 | Bloom et al. |
| 4,576,211 A | 3/1986 | Valentini et al. |
| 4,588,403 A | 5/1986 | Weiss et al. |
| 4,600,040 A | 7/1986 | Naslund |
| 4,619,651 A * | 10/1986 | Kopfer et al. ................ 604/415 |
| 4,673,404 A | 6/1987 | Gustavsson |
| 4,759,756 A | 7/1988 | Forman et al. |
| 4,775,376 A | 10/1988 | Strung |
| 4,834,149 A | 5/1989 | Fournier et al. |
| 4,834,152 A | 5/1989 | Howson et al. |
| 4,919,658 A | 4/1990 | Badia |
| 5,100,010 A | 3/1992 | Watser |
| 5,100,394 A | 3/1992 | Dudar et al. |
| 5,137,524 A * | 8/1992 | Lynn ..................... A61M 39/04 604/414 |
| 5,184,652 A | 2/1993 | Fan |
| 5,238,031 A | 8/1993 | Baeumer |
| 5,340,359 A | 8/1994 | Badia |
| 5,354,287 A * | 10/1994 | Wacks ........................ 604/232 |
| 5,647,409 A | 7/1997 | Christ et al. |
| 5,647,845 A | 7/1997 | Haber |
| 5,738,663 A | 4/1998 | Lopez |
| 5,810,792 A * | 9/1998 | Fangrow, Jr. ....... A61M 39/045 285/319 |
| 5,827,262 A | 10/1998 | Neftel |
| 6,070,623 A | 6/2000 | Aneas |
| 6,221,041 B1 | 4/2001 | Russo |
| 6,258,078 B1 | 7/2001 | Thilly |
| 6,378,576 B2 | 4/2002 | Thibault et al. |
| 6,409,708 B1 | 6/2002 | Wessman |
| 6,478,788 B1 | 11/2002 | Aneas |
| 6,571,837 B2 * | 6/2003 | Jansen et al. ................ 141/329 |
| 6,715,520 B2 | 4/2004 | Andreasson et al. |
| 6,948,522 B2 | 9/2005 | Newbrough et al. |
| 7,086,431 B2 | 8/2006 | D'Antonio |
| 7,470,258 B2 | 12/2008 | Barker et al. |
| 7,867,215 B2 * | 1/2011 | Åkerlund et al. ........... 604/413 |
| 8,122,923 B2 | 2/2012 | Kraus |
| 8,177,772 B2 * | 5/2012 | Christensen ....... A61M 25/0075 604/246 |
| 8,196,614 B2 | 6/2012 | Kriheli |
| 8,267,127 B2 | 9/2012 | Kriheli |
| 8,317,743 B2 | 11/2012 | Denenburg |
| 8,377,039 B2 | 2/2013 | Utterberg et al. |
| 8,511,352 B2 | 8/2013 | Kraus |
| 8,752,598 B2 | 6/2014 | Denenburg et al. |
| 2002/0087118 A1 | 7/2002 | Reynolds et al. |
| 2002/0189712 A1 | 12/2002 | Safabash |
| 2002/0193777 A1 | 12/2002 | Aneas |
| 2003/0153895 A1 | 8/2003 | Leinsing |
| 2003/0181863 A1 | 9/2003 | Ackley et al. |
| 2007/0079894 A1 | 4/2007 | Kraus |
| 2012/0123381 A1 | 5/2012 | Kraus |
| 2013/0231630 A1 | 9/2013 | Kraus |

FOREIGN PATENT DOCUMENTS

| | | |
|---|---|---|
| CN | 2452515 | 10/2001 |
| EP | 0 126 718 | 11/1984 |
| EP | 1181921 | 2/2002 |
| EP | 1323403 | 7/2003 |
| EP | 1228776 | 11/2003 |
| EP | 1 145 702 | 5/2010 |
| EP | 2463201 | 6/2012 |
| FR | 2560049 | 8/1985 |
| FR | 2815328 | 4/2002 |
| GB | 1257419 | 12/1971 |
| JP | S60/222059 | 11/1985 |
| JP | 4832585 | 12/2011 |
| WO | 84/04673 | 12/1984 |
| WO | 85/04801 | 11/1985 |
| WO | 97/46203 | 12/1997 |
| WO | 98/19724 | 5/1998 |
| WO | 99/27886 | 6/1999 |
| WO | 99/43282 | 9/1999 |
| WO | 00/35517 | 6/2000 |
| WO | 02/11794 | 2/2002 |
| WO | 02/053087 | 9/2002 |
| WO | 02/072173 | 9/2002 |
| WO | 03/051761 | 6/2003 |
| WO | 03/086529 | 10/2003 |
| WO | 03/086530 | 10/2003 |
| WO | 2004/004806 | 1/2004 |
| WO | 2005/041846 | 5/2005 |
| WO | 2007/124926 | 11/2007 |

OTHER PUBLICATIONS

A Notice of Allowance dated Apr. 15, 2013, which issued during the prosecution of U.S. Appl. No. 13/357,004.
A Restriction Requirement dated Feb. 8, 2011, which issued during the prosecution of U.S. Appl. No. 10/577,618.
A Notice of Allowance dated Oct. 28, 2011, which issued during the prosecution of U.S. Appl. No. 10/577,618.
A Communication dated Jul. 4, 2011, which issued during the prosecution of Japanese Patent Application No. 2010-200146.
A Communication dated Aug. 11, 2011, which issued during the prosecution of European Patent Application No. 04791853.7.
An English Translation of the Notification of Reason for Refusal dated Apr. 12, 2011, which issued during the prosecution of Japanese Patent Application No. JP2010-188726.
Supplementary European search report dated Jun. 30, 2014, which issued during the prosecution of Applicant's European App No. 13 179 757.3.
U.S. Appl. No. 60/516,613, filed Oct. 30, 2003.
3$^{rd}$ party observations dated May 28, 2009, which issued during the prosecution of Applicant's European Patent Application No. 04791853.7.
An office action dated Nov. 15, 2010, which issued during the prosecution of Applicant's Japanese Patent Application No. JP 2010-188726, including an English translation.
Microfilm of Utility Model application No. S61-176496 (Publication of Unexamined Utility Model Application No. S63-84239) draft on Apr. 23, 2010.
An office action together with English comments dated Apr. 23, 2010, which issued during the prosecution of Applicant's Japanese Patent Application No. JP 2006-537556.

(56) References Cited

OTHER PUBLICATIONS

An International Search Report dated Oct. 10, 2008, which issued during the prosecution of Applicant's PCT/IL2008/000077.
An English Translation of an Office Action dated Dec. 31, 2008, which issued during the prosecution of Applicant's Chinese Patent Application No. 200480035389.8.
A Supplementary European Search Report dated Jan. 20, 2009, which issued during the prosecution of Applicant's European Patent Application No. 04791853.7.
An office action dated Mar. 24, 2011, which issued during the prosecution of U.S. Appl. No. 10/577,618.
An office action dated Jul. 11, 2011, which issued during the prosecution of Canadian Patent Application No. 2,541,615.
An International Search Report and a Written Opinion both dated Jun. 6, 2005, which issued during the prosecution of Applicant's PCT/IL2004/000993.
An International Preliminary Report on Patentability dated Feb. 15, 2006, which issued during the prosecution of Applicant's PCT/IL2004/000993.
Extended European Search Report dated May 15, 2012, which issued during the prosecution of European Application No. 12154647.7.
An Office Action dated Nov. 16, 2015, which issued during the prosecution of U.S. Appl. No. 13/854,348.
Notice of Allowance dated Jan. 26, 2016, which issued during the prosecution of U.S. Appl. No. 13/854,348.
An Office Action dated Jan. 4, 2016, which issued during the prosecution of Canadian Patent Application No. 2,792,014.

* cited by examiner

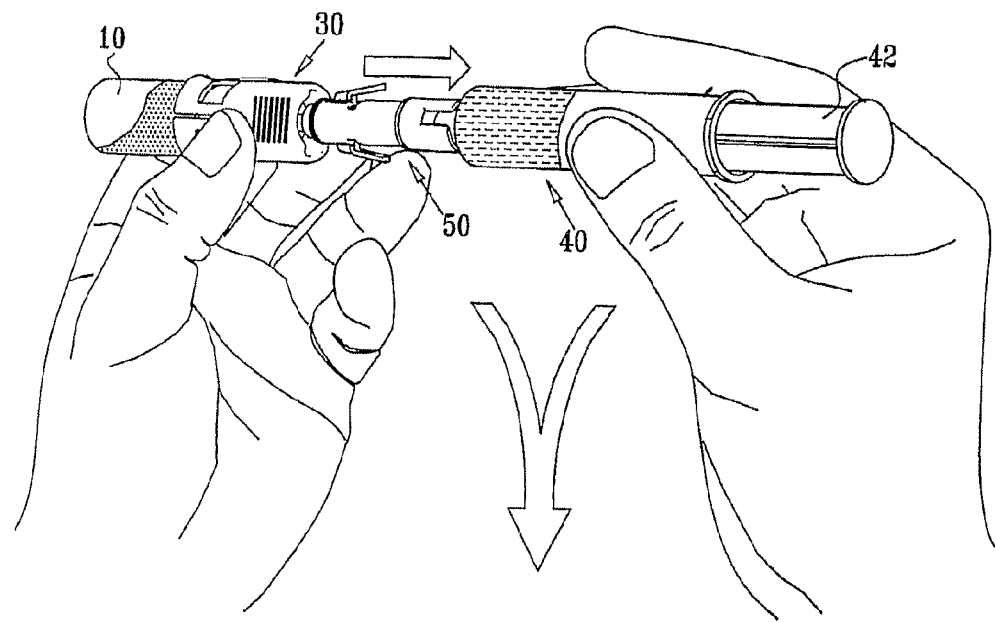
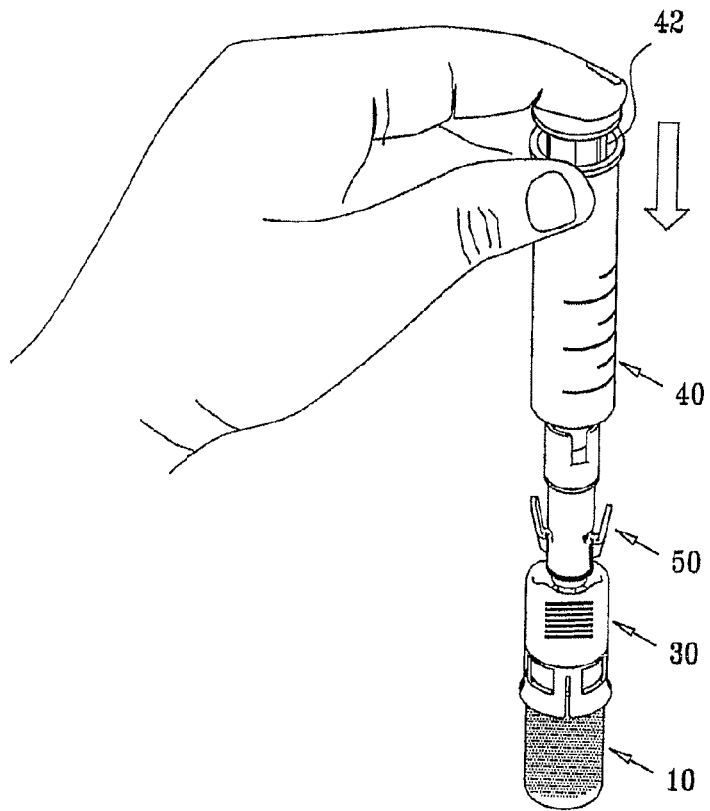
FIG. 1G

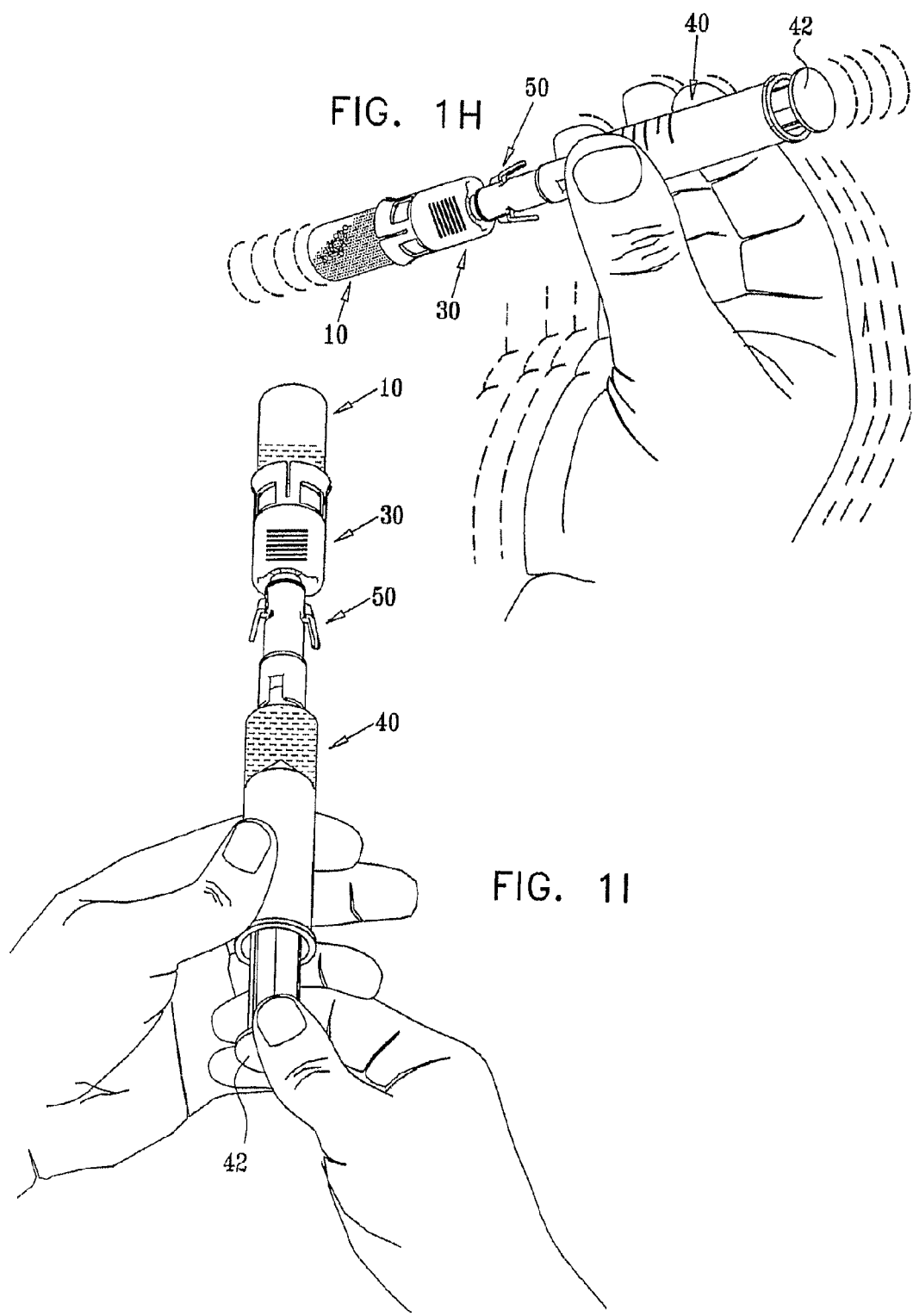

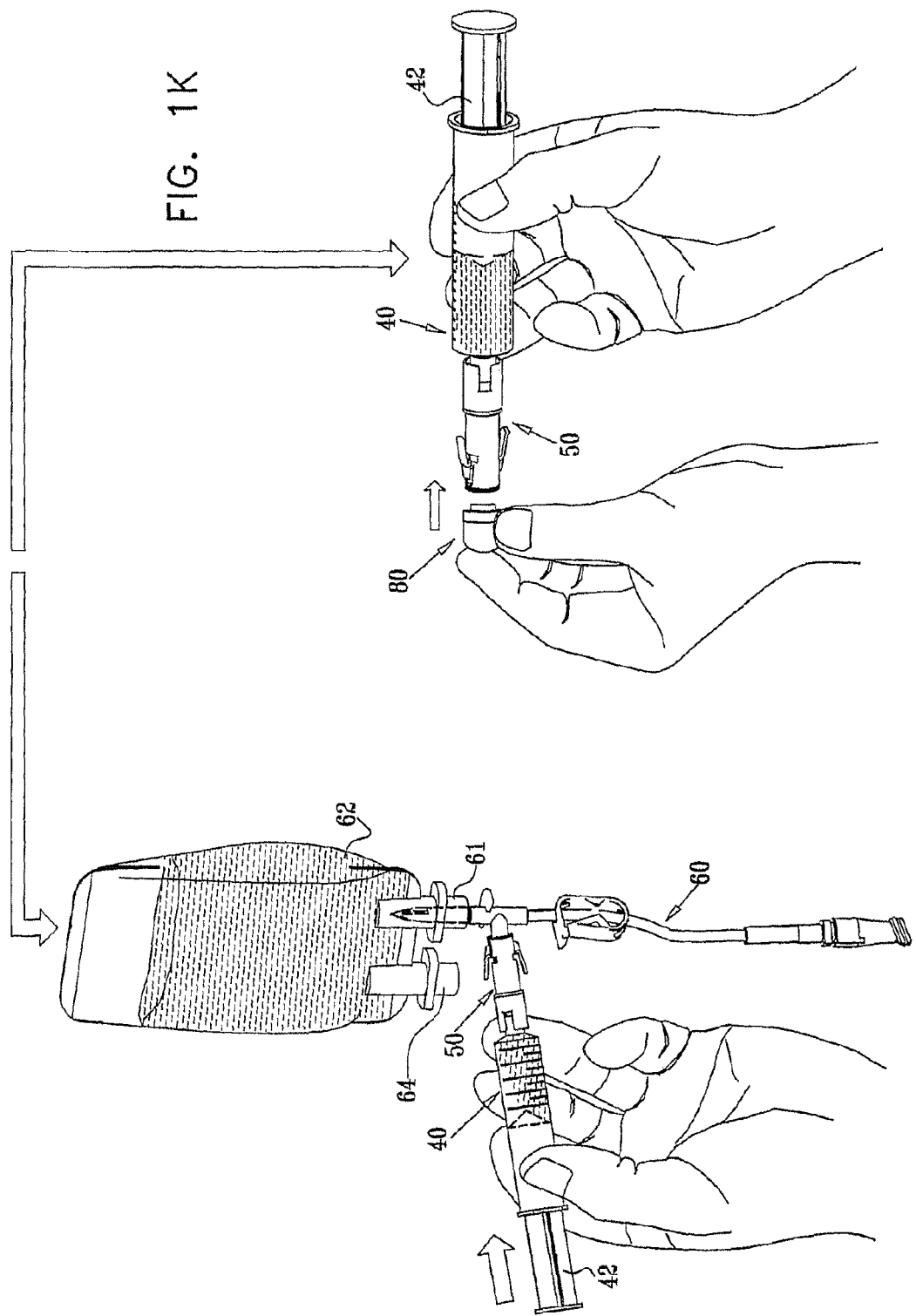

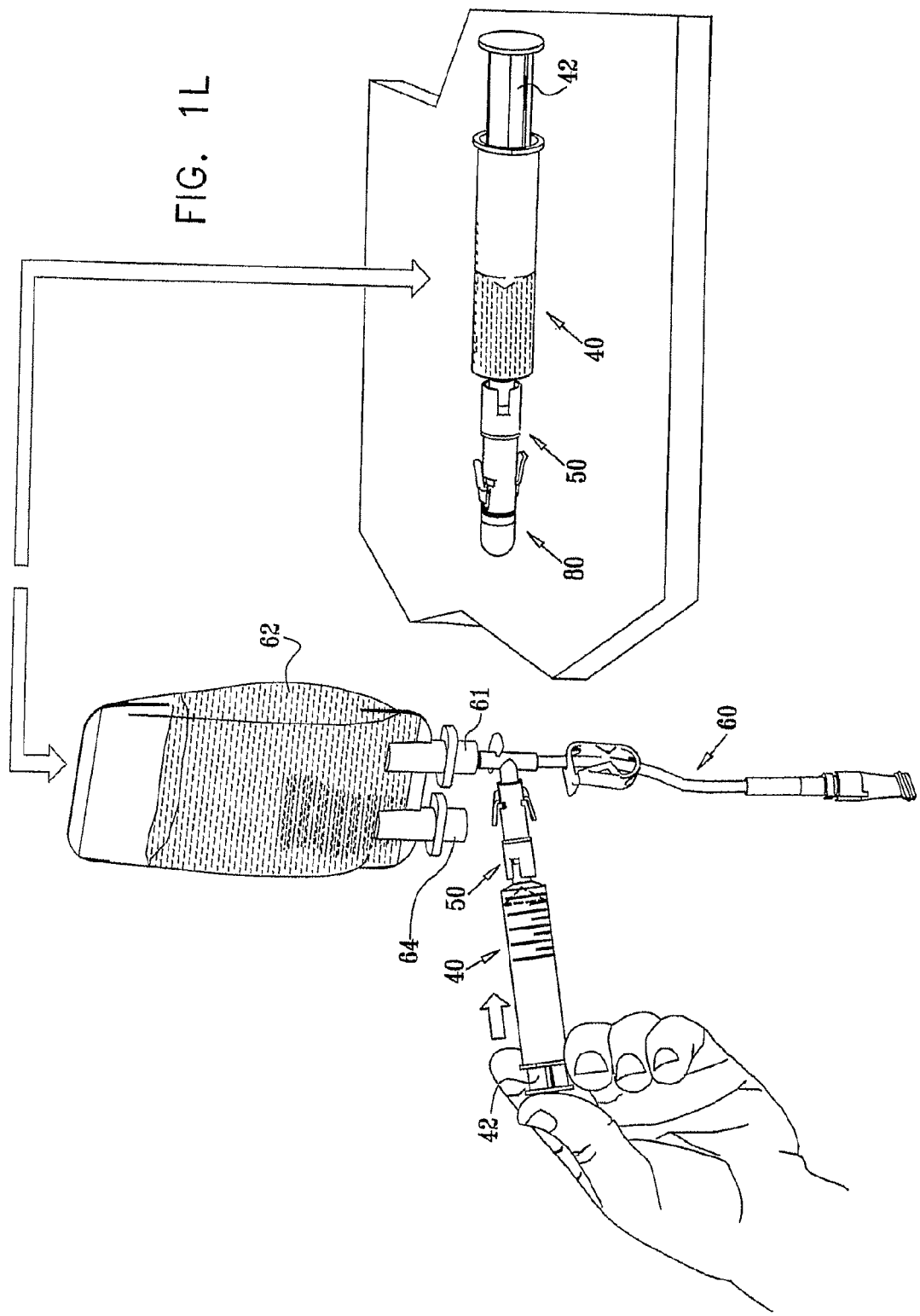

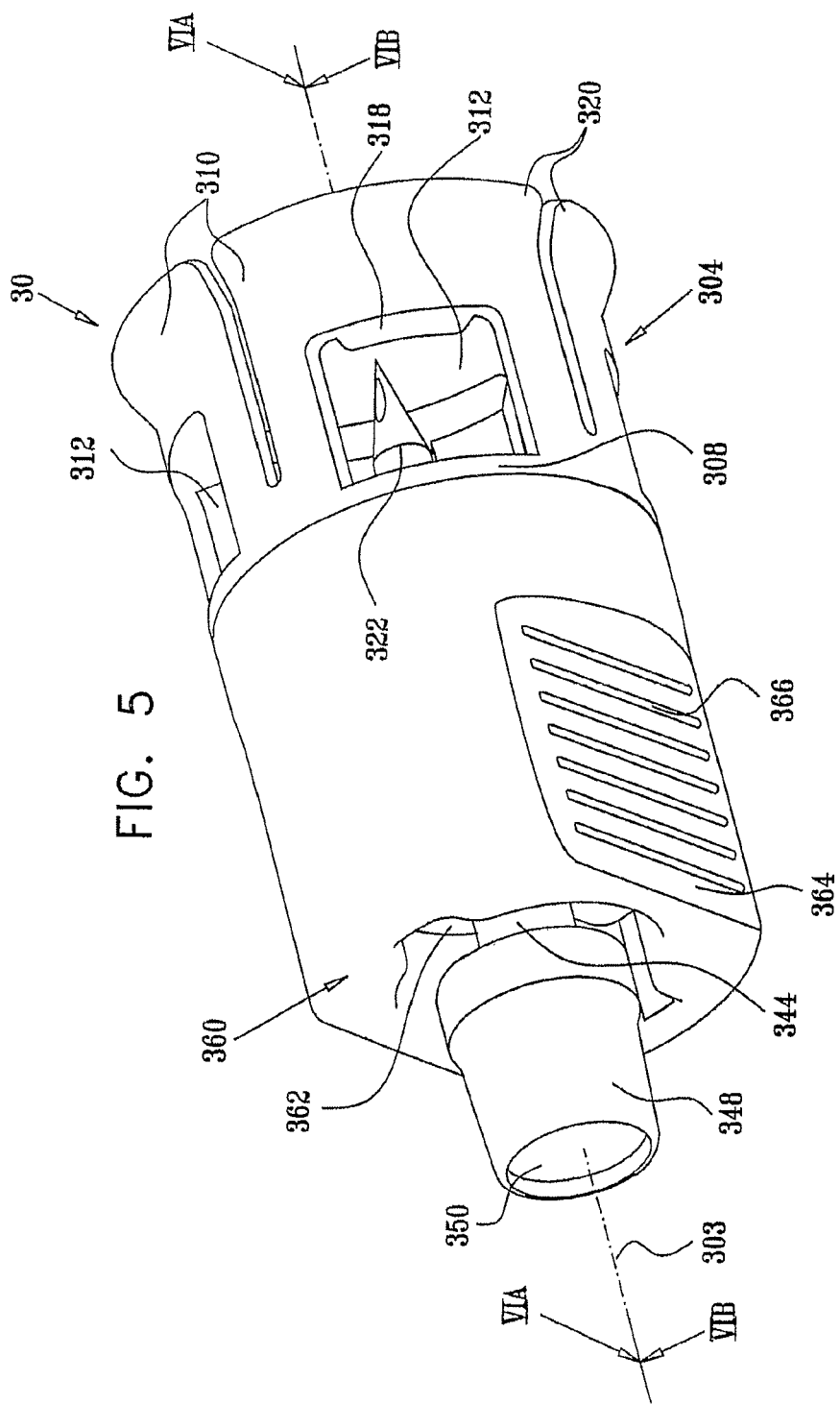

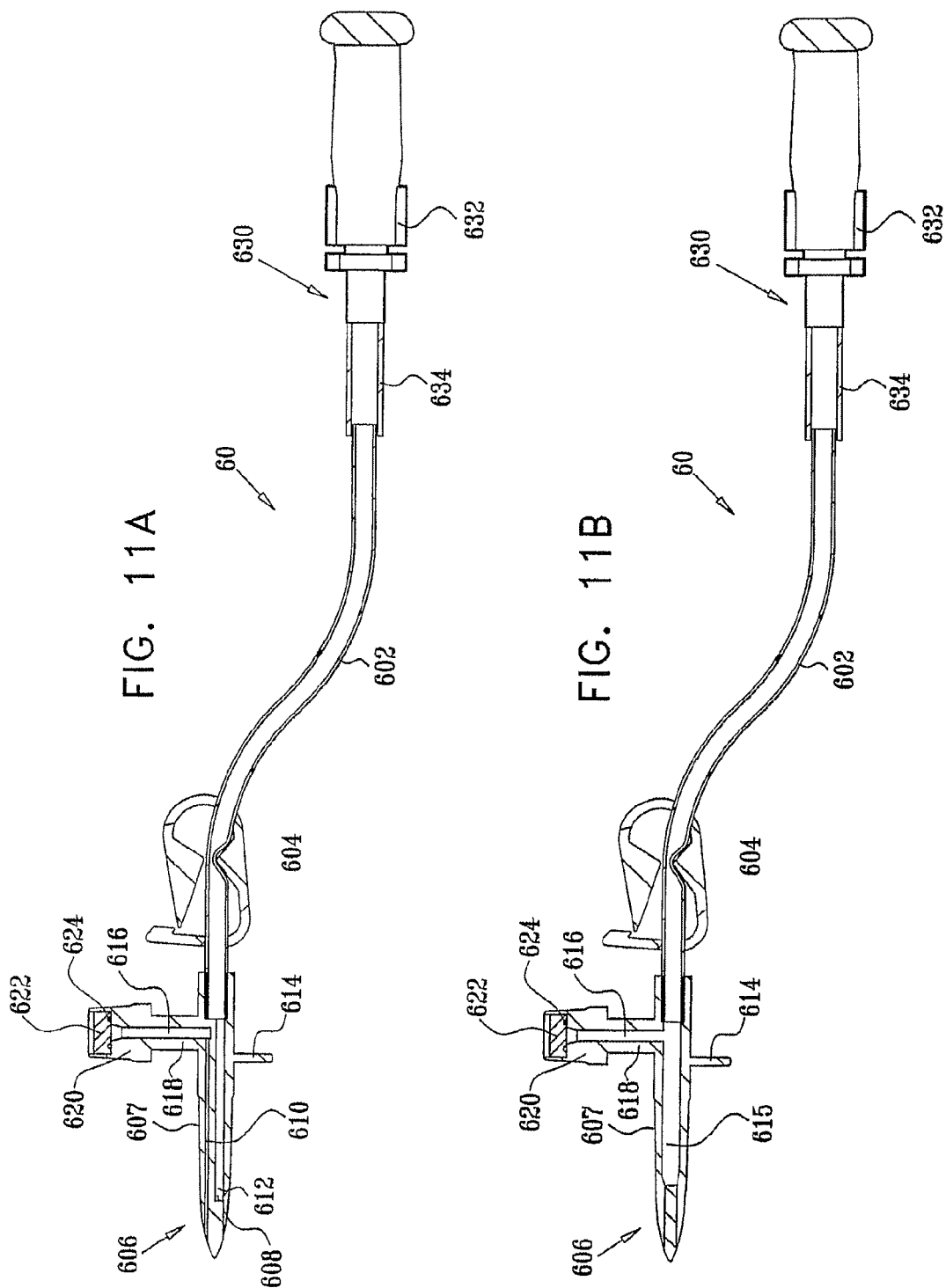

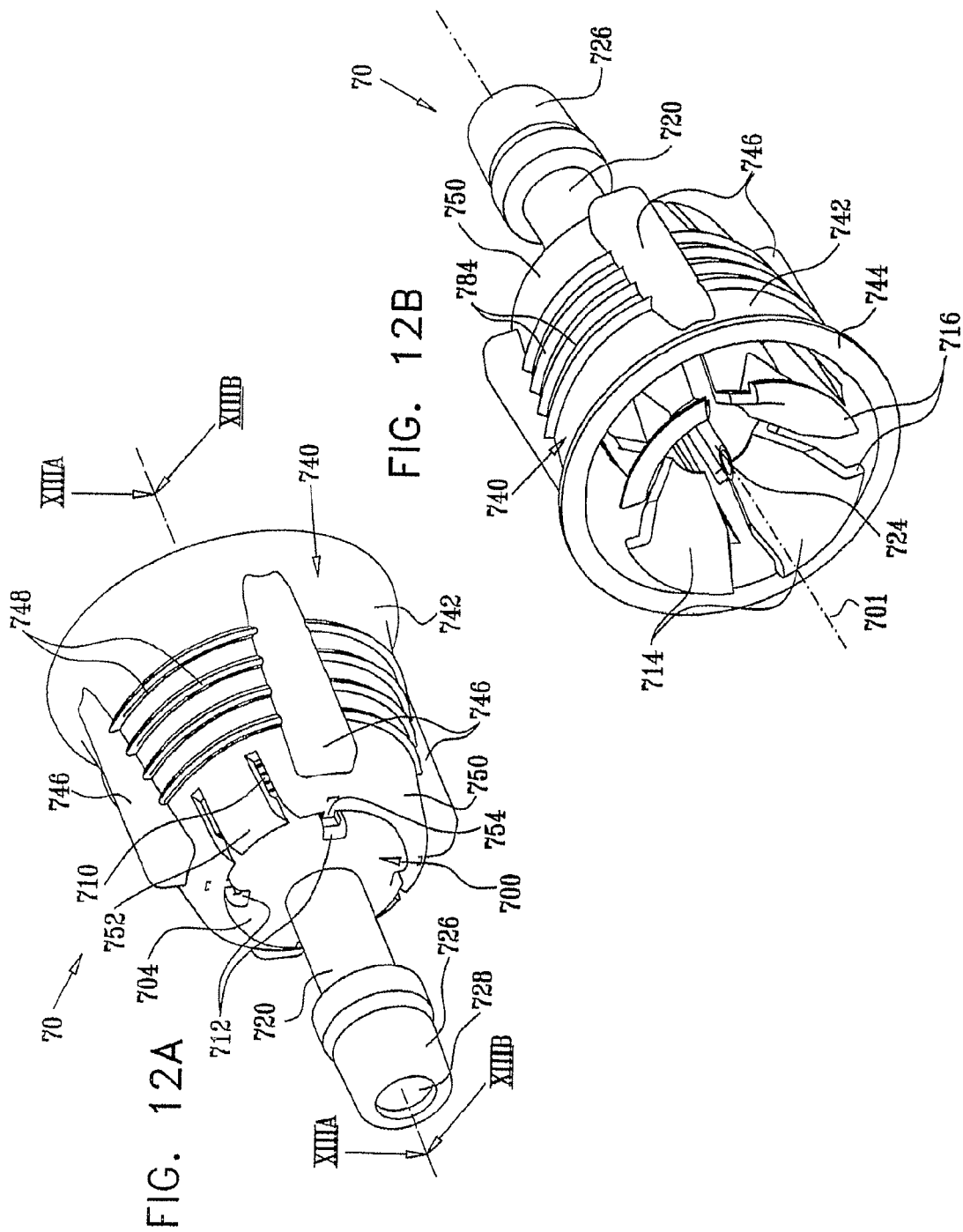

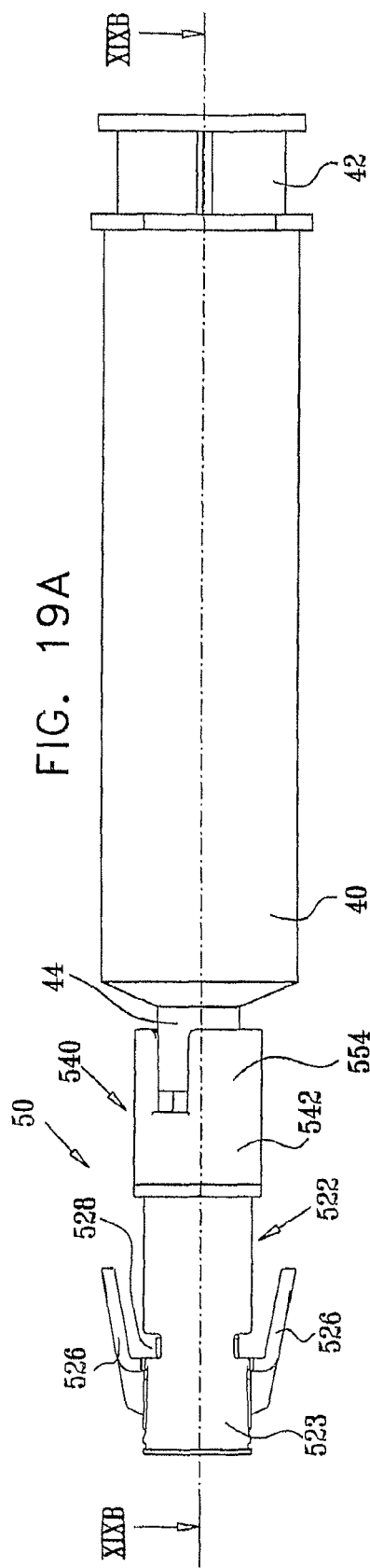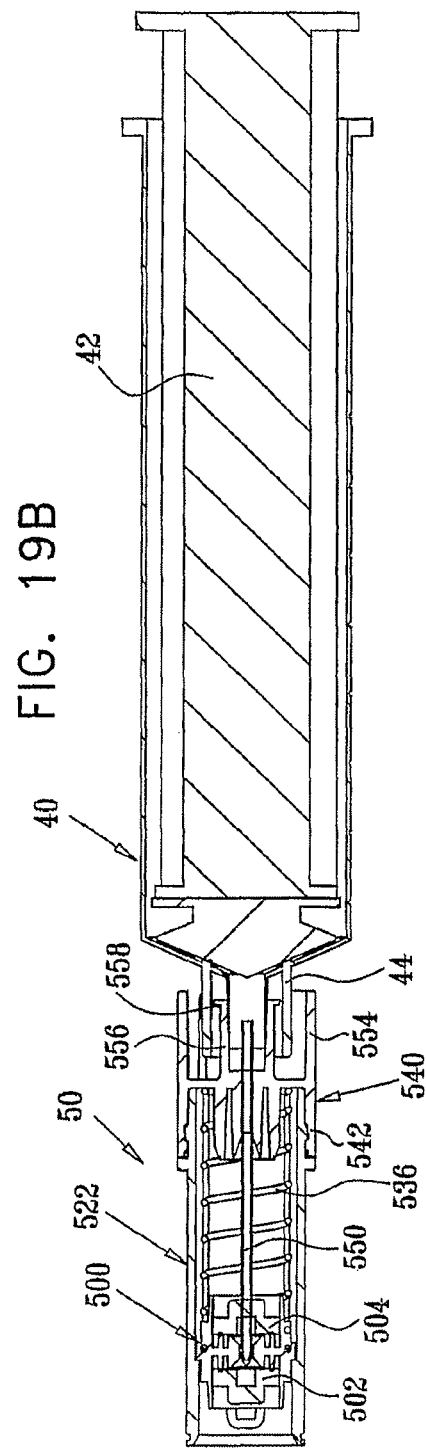

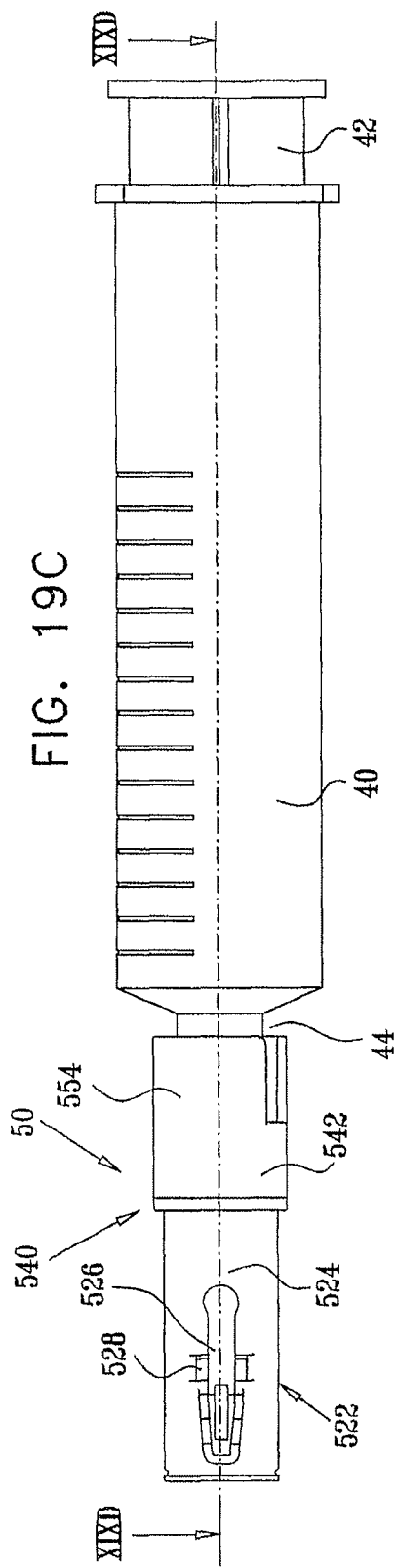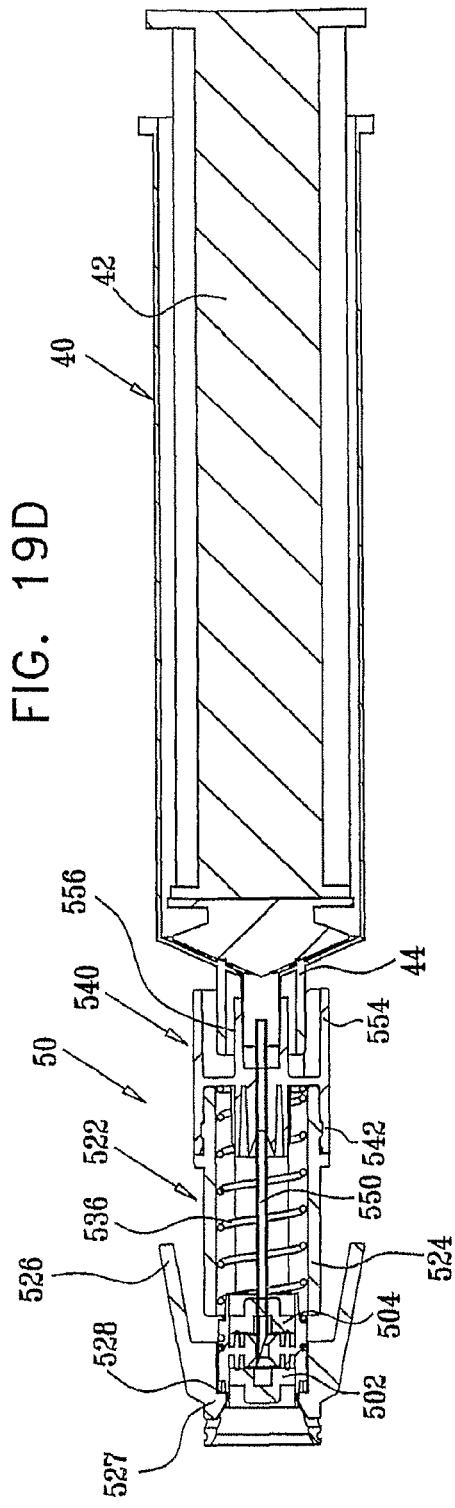

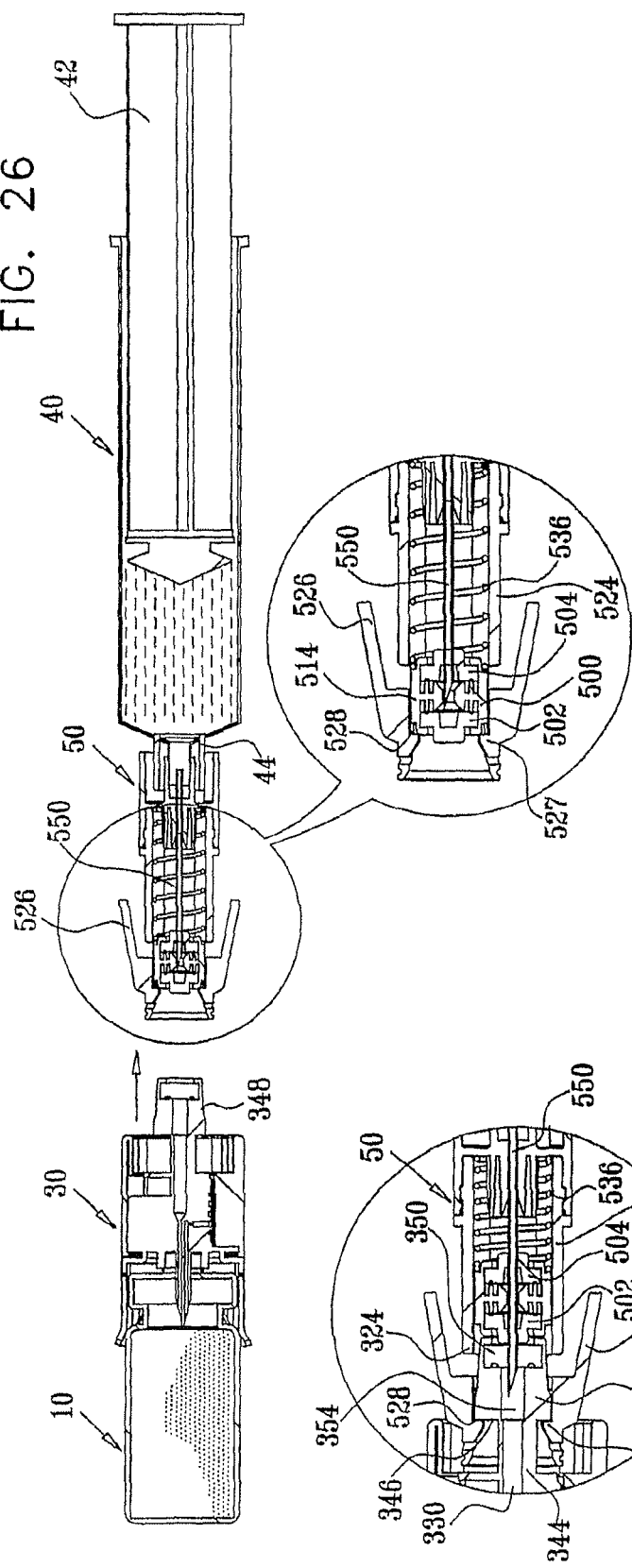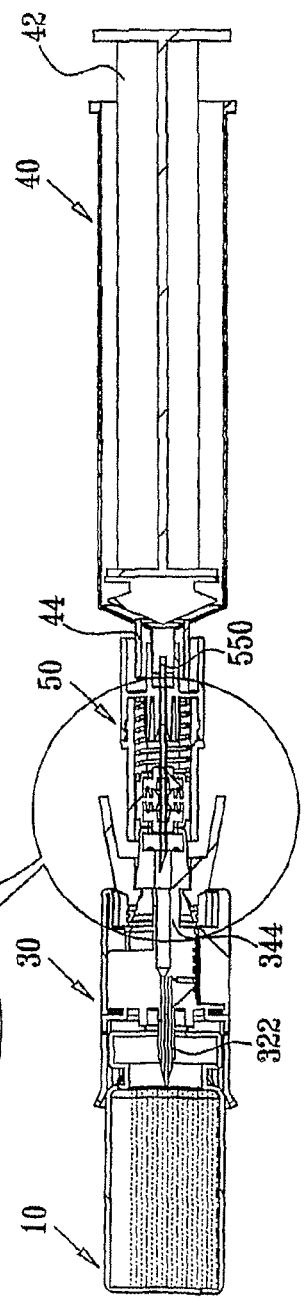

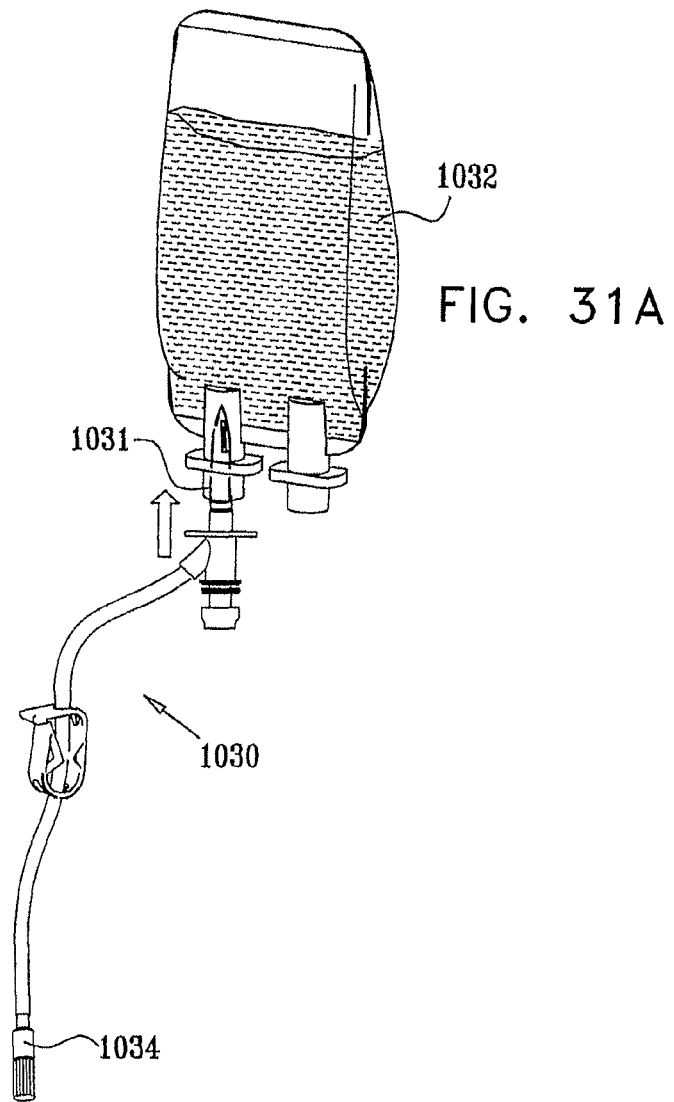

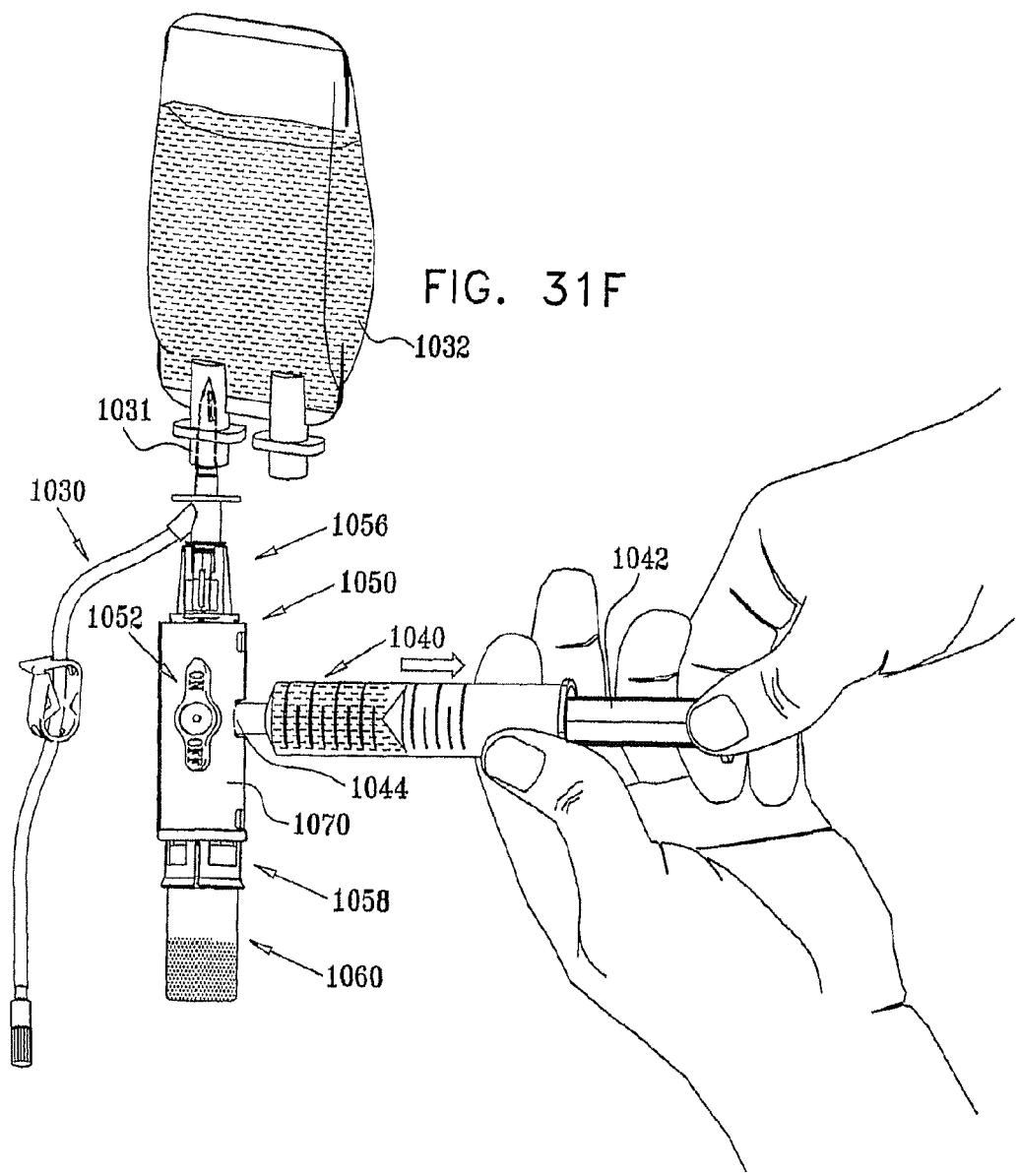

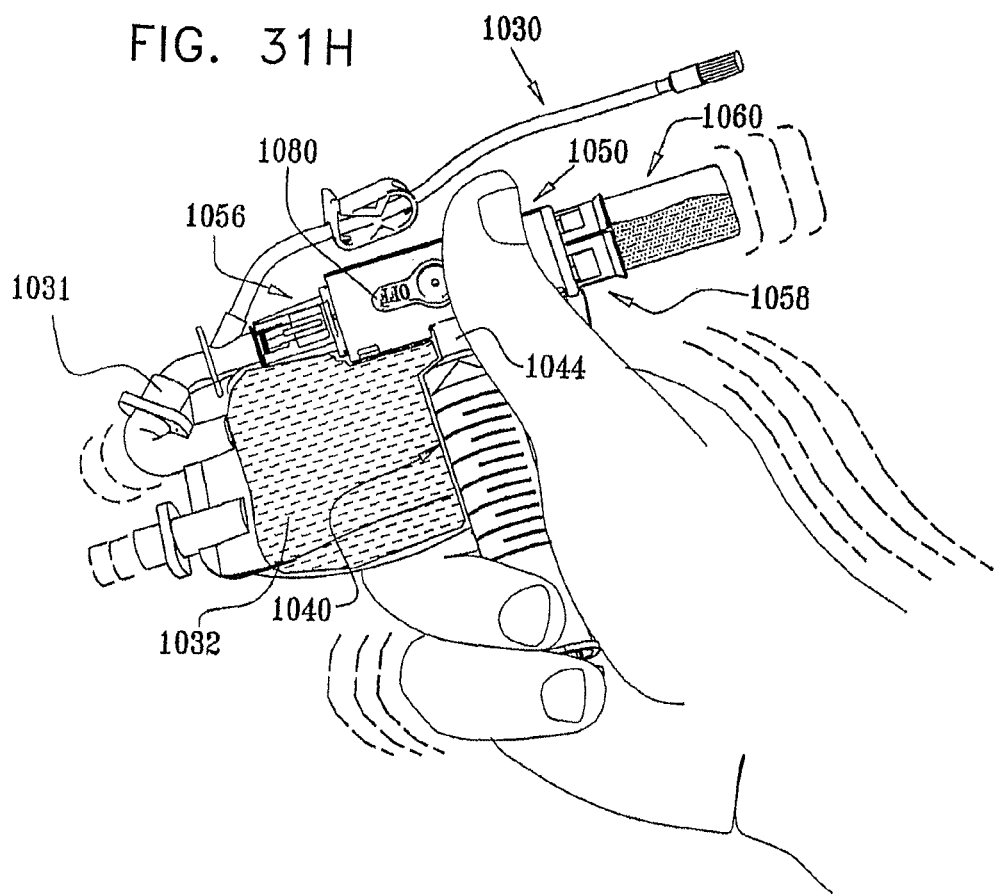

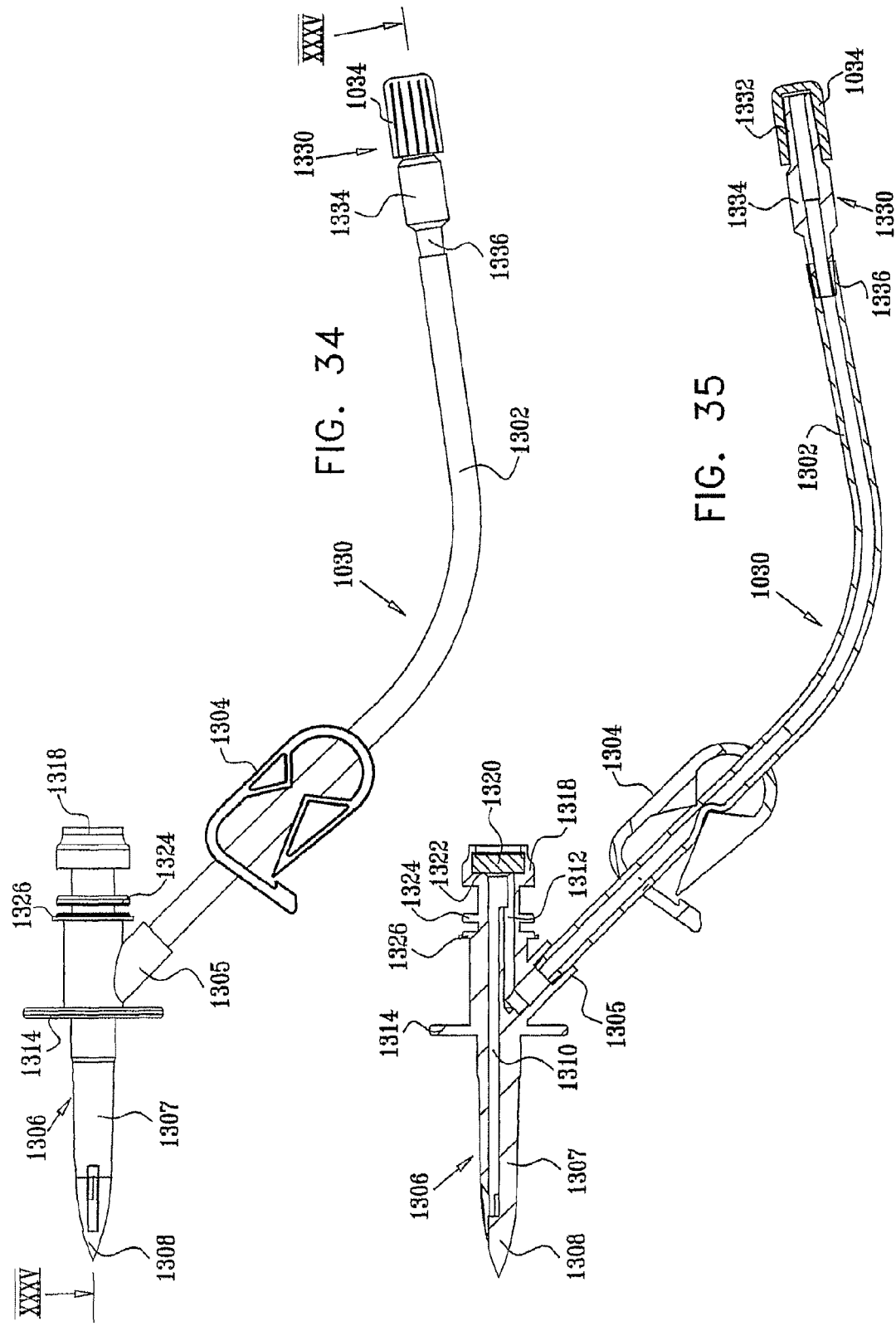

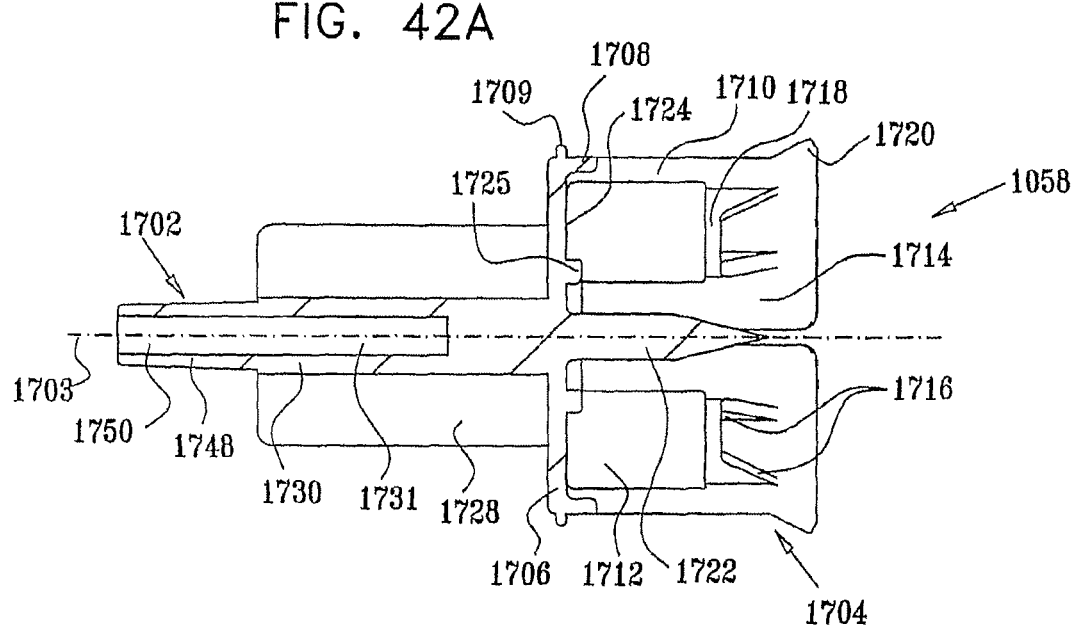
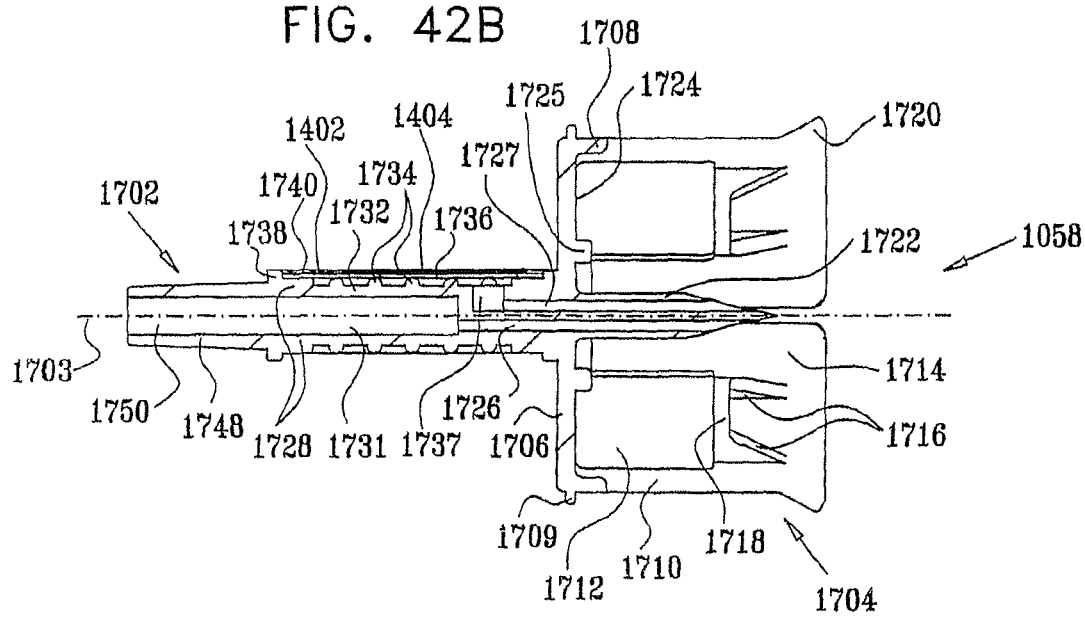

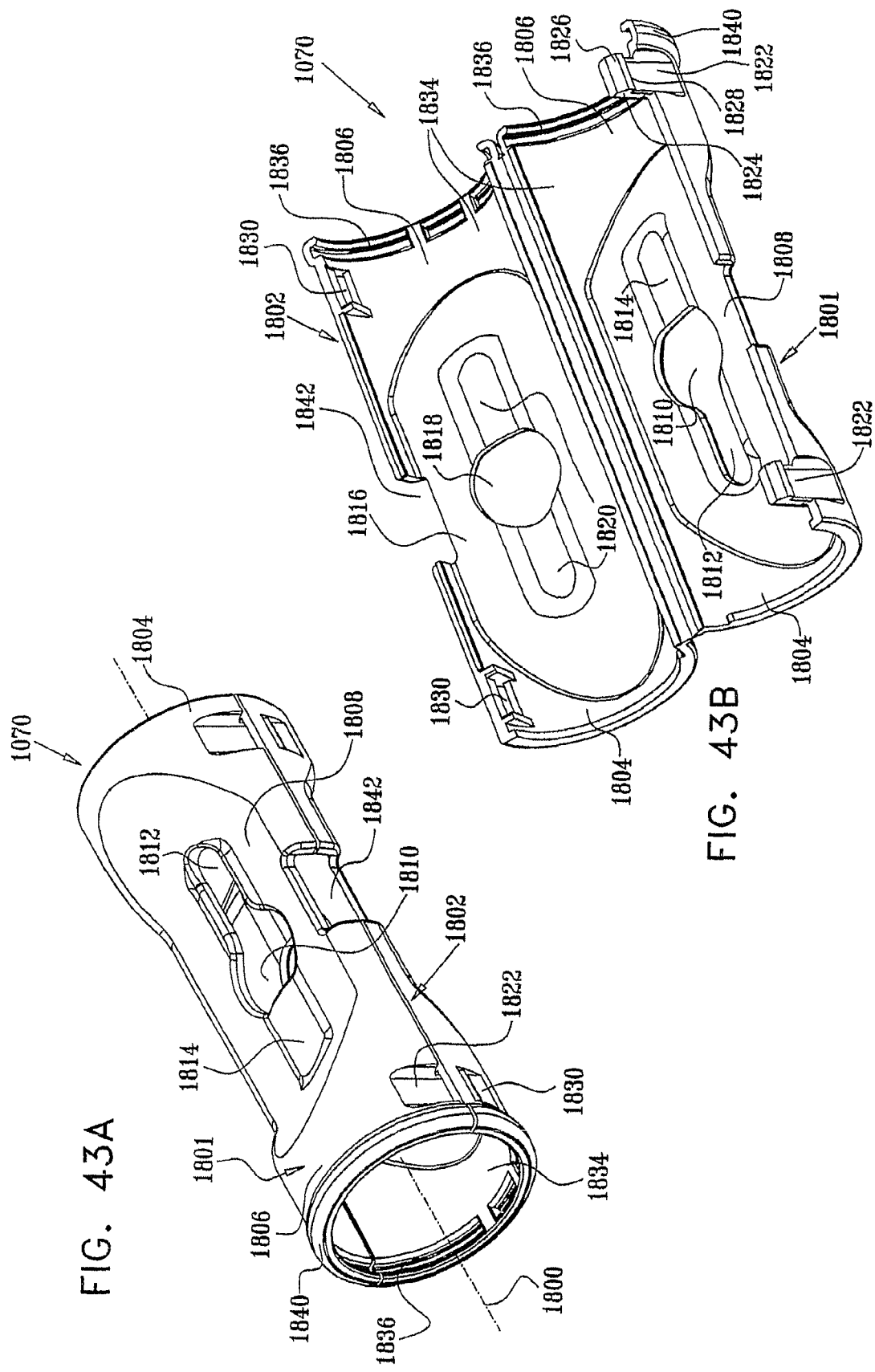

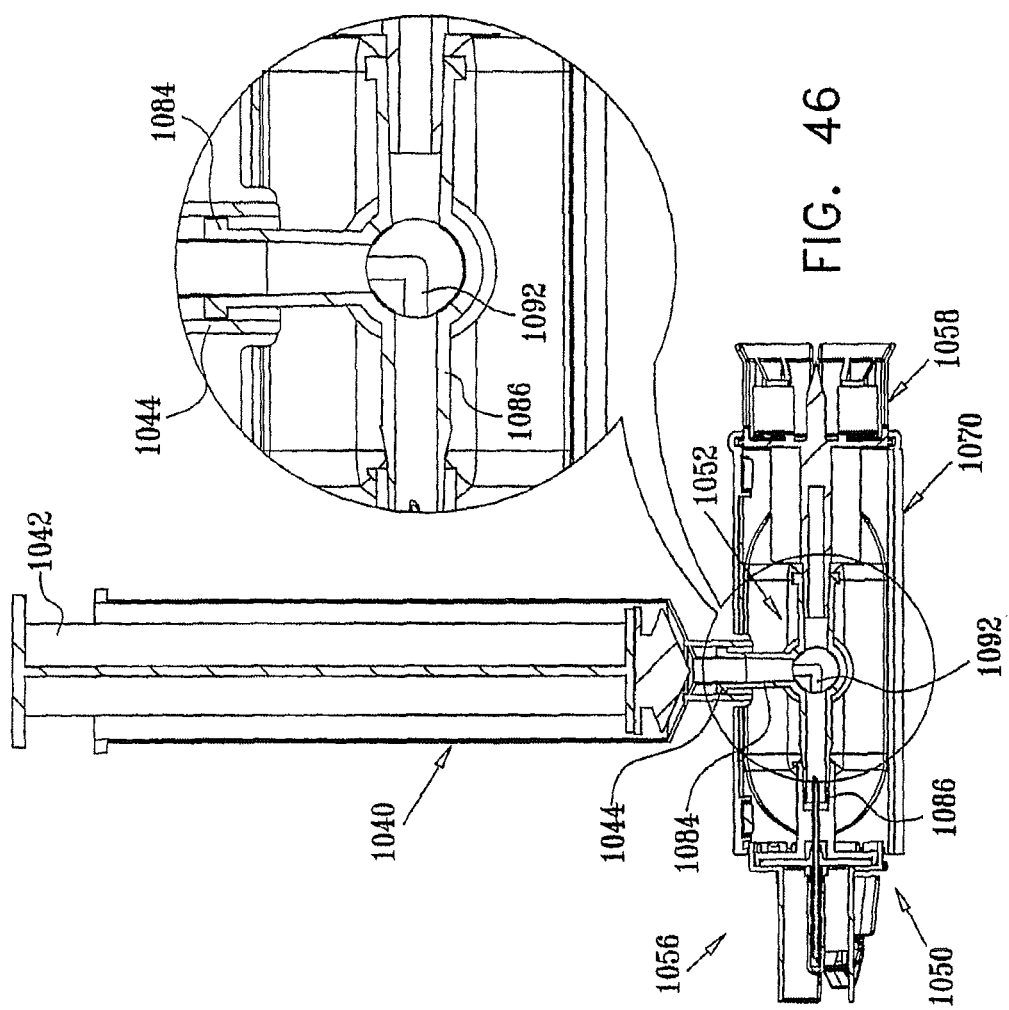

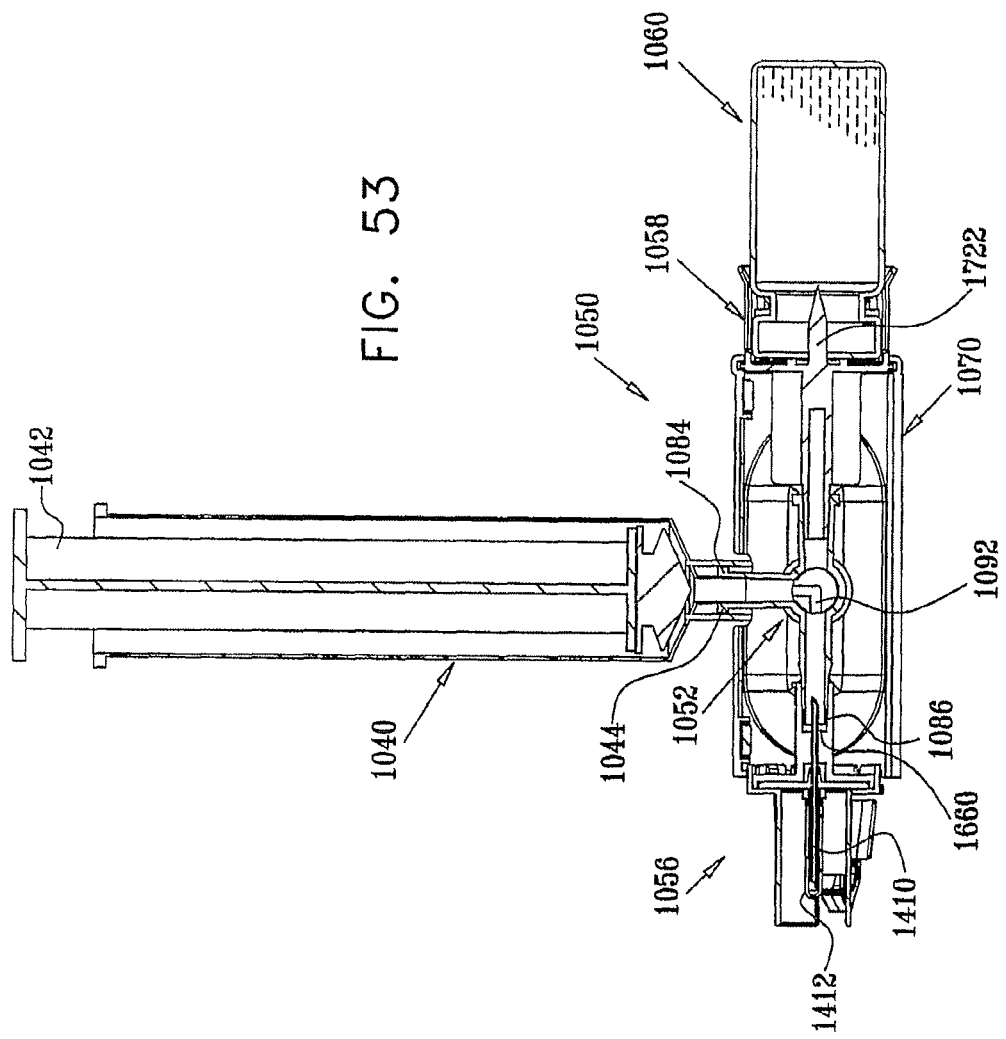

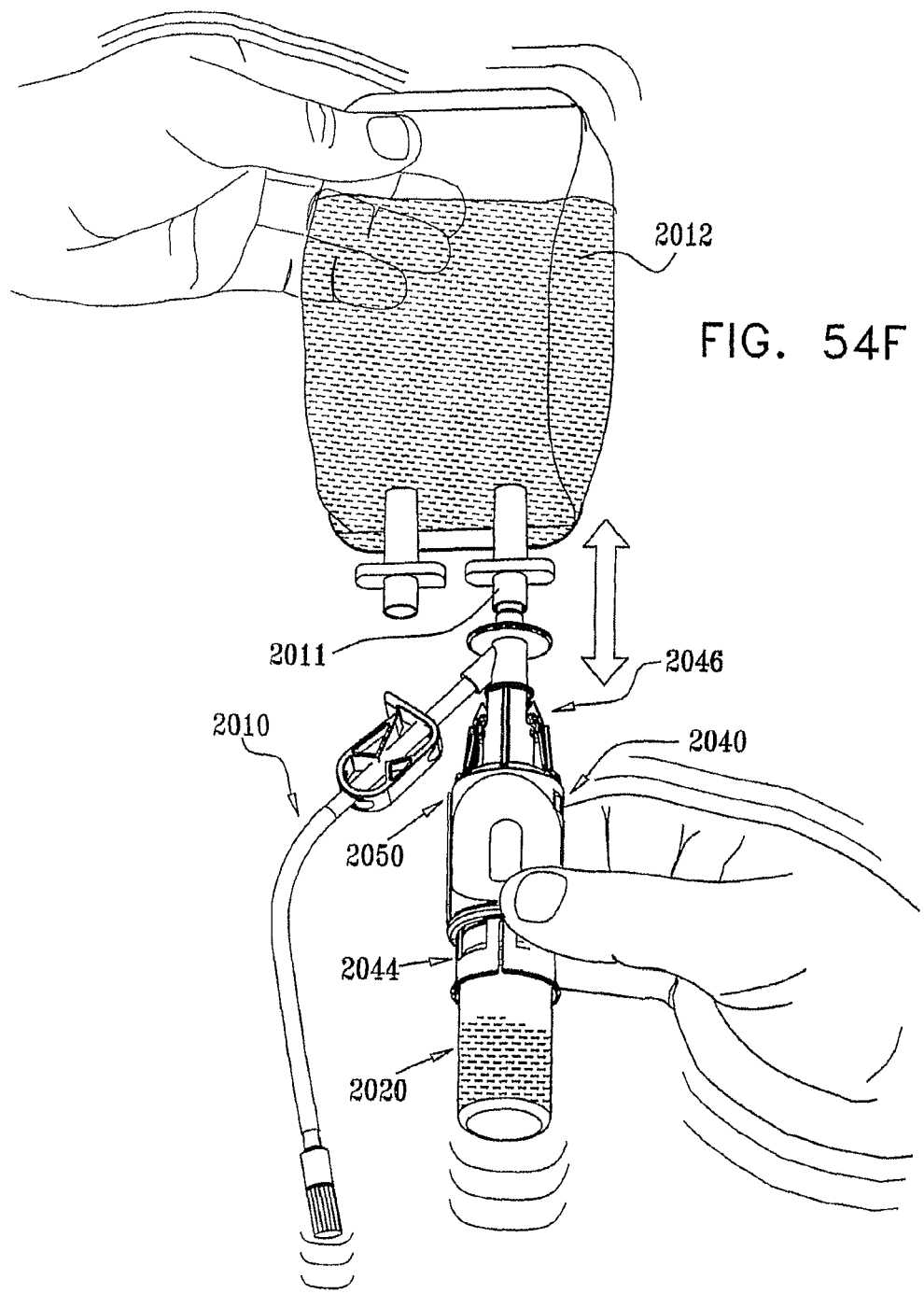

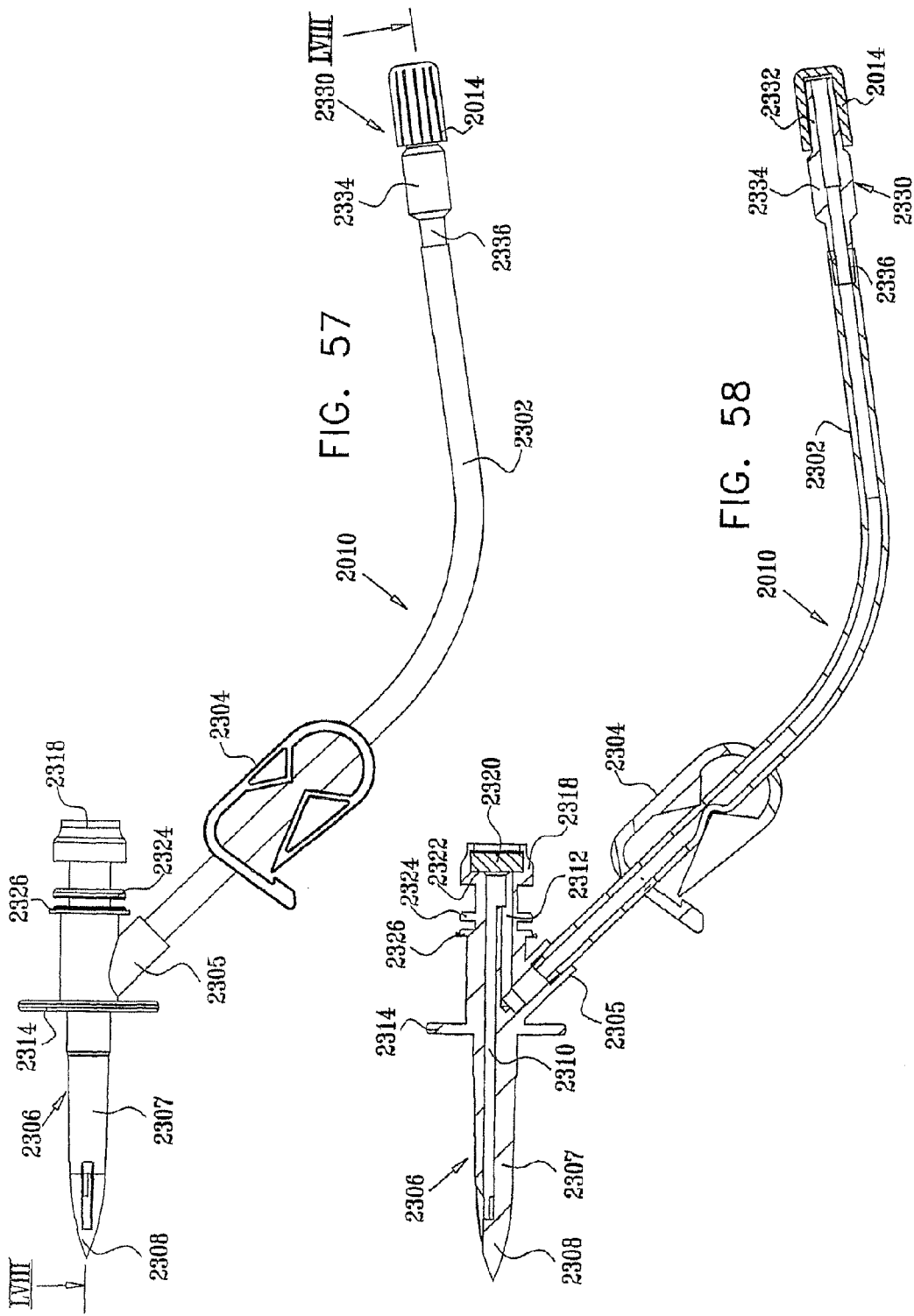

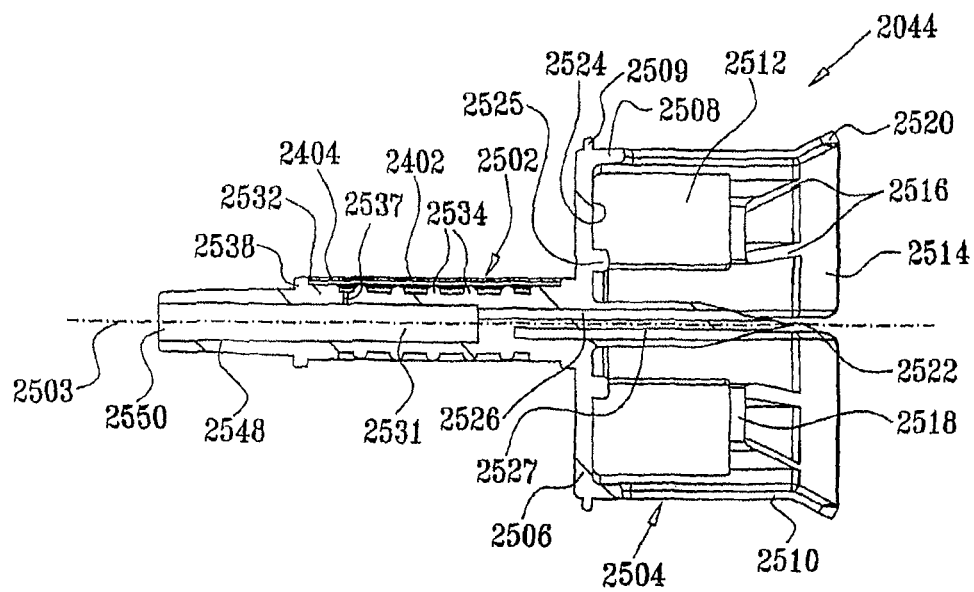
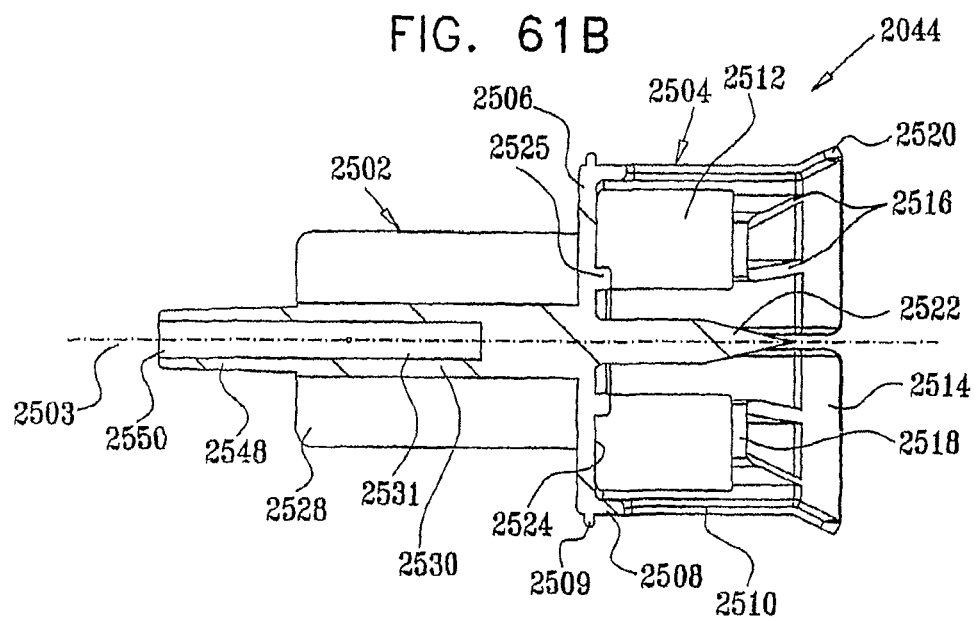

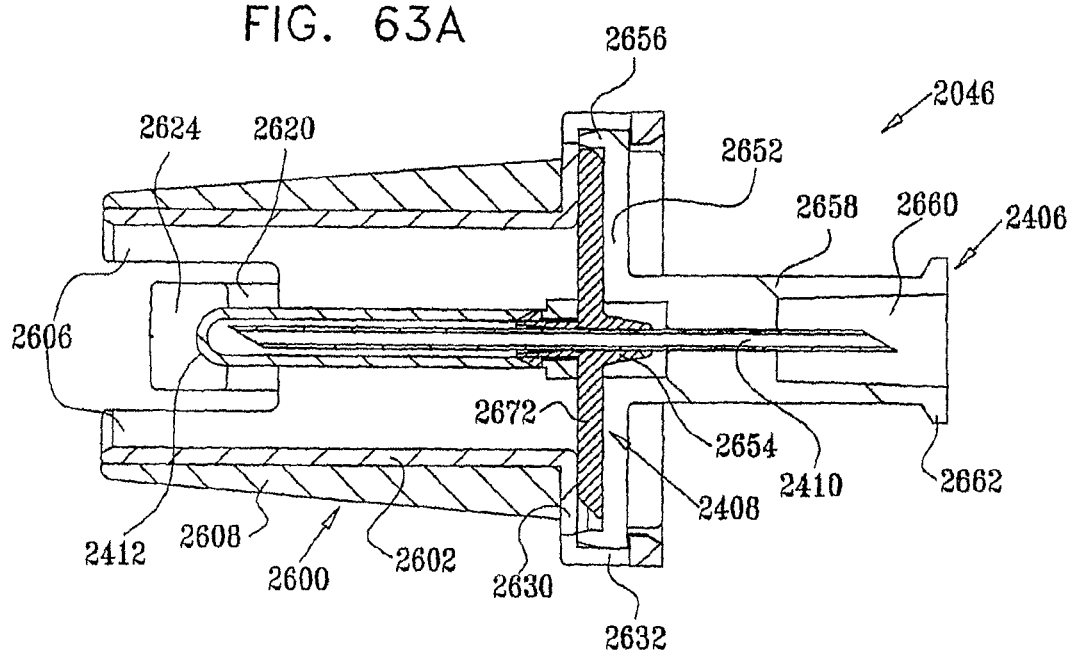
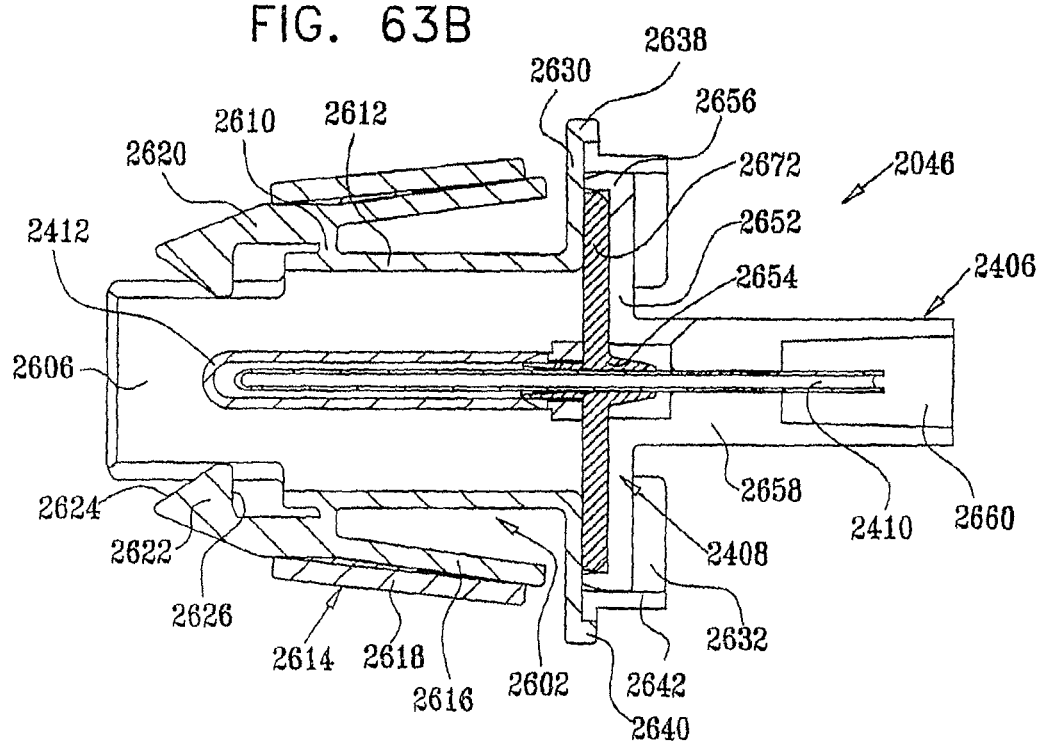

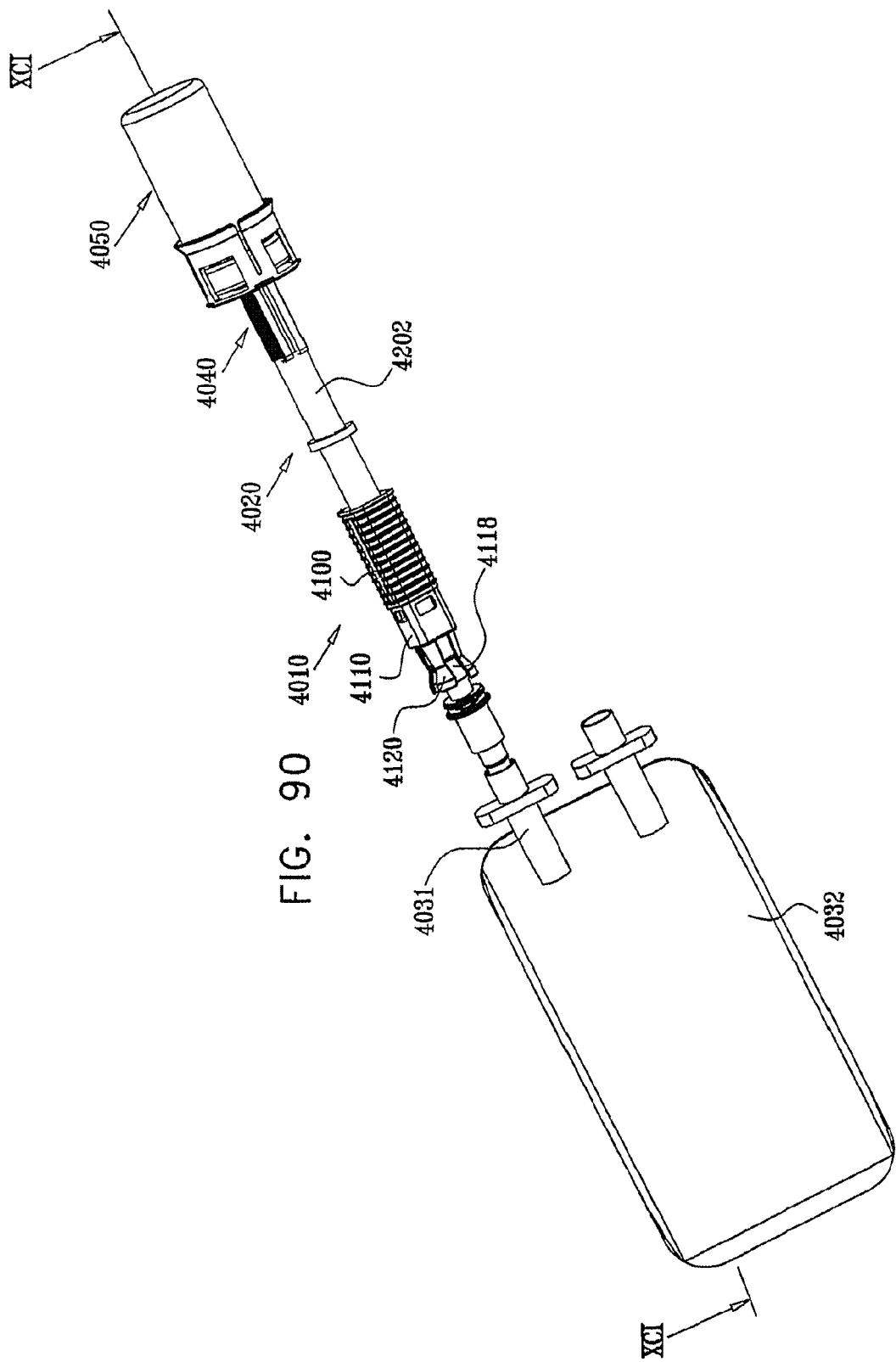

SAFETY DRUG HANDLING DEVICE

REFERENCE TO RELATED APPLICATIONS

This application is a continuation of copending application Ser. No. 13/357,004 filed Jan. 24, 2012, which is a divisional of application Ser. No. 10/577,618 filed on Dec. 29, 2006 (now U.S. Pat. No. 8,122,923) which is a 371 of International Application PCT/IL2004/000993 filed on 29 Oct. 2004, and entitled "SAFETY DRUG HANDLING DEVICE", which was published in the English language on 5 Dec. 2005, with International Publication Number WO/2005/041846 which claims priority from U.S. Provisional Patent Application 60/516,613, filed 30 Oct. 30 2003, the content of which are incorporated herein by reference.

The present application is related to and claims priority from the following patent applications, the disclosure of which is hereby incorporated by reference:

U.S. Provisional Patent Application No. 60/516,613.

FIELD OF THE INVENTION

The present invention relates to drug mixing systems generally.

BACKGROUND OF THE INVENTION

The following U.S. Patents and non-U.S. patent publications are believed to represent the current state of the art:

U.S. Pat. Nos. 6,221,041; 6,715,520; 6,409,708; PCT US02/40596; WO 2004004806; WO 03086529; WO 9819724; WO 03/086530; WO 0035517 and WO 0211794.

SUMMARY OF THE INVENTION

The present invention seeks to provide an improved drug mixing system, operative for use with a luer fitted hypodermic syringe, which is particularly useful in handling toxic drugs such as antineoplastic drugs.

There is thus provided in accordance with a preferred embodiment of the present invention a drug mixing system including at least one receptacle port adaptor adapted to be inserted into a port of a fluid receptacle, at least one vial adaptor adapted for connection to a vial containing a drug and at least one syringe adaptor adapted to be attached to a syringe and to at least one of the at least one receptacle port adaptor and the at least one vial adaptor, the system being characterized in that at least one of the at least one receptacle port adaptor, the at least one syringe adaptor and the at least one vial adaptor being vented to the atmosphere in a manner which prevents release to the atmosphere of possibly harmful contents of the vial in a liquid, solid or gaseous form.

There is also provided in accordance with another preferred embodiment of the present invention a drug mixing system including at least one receptacle port adaptor adapted to be inserted into a port of a fluid receptacle, at least one vial adaptor adapted for connection to a vial containing a drug and at least one syringe adaptor adapted to be attached to a syringe and to at least one of the at least one receptacle port adaptor and the at least one vial adaptor, the system being characterized in that the at least one vial adaptor being vented to the atmosphere in a manner which prevents release to the atmosphere of possibly harmful contents of the vial.

Preferably, the drug mixing system also includes a membrane vent operative to vent at least one of the at least one receptacle port adaptor, the at least one syringe adaptor and the at least one vial adaptor to the atmosphere. Additionally, the membrane vent includes a filter. Additionally or alternatively, the membrane vent includes a hydrophobic membrane.

There is also provided in accordance with another preferred embodiment of the present invention a drug mixing system including at least one receptacle port adaptor adapted to be inserted into a port of a fluid receptacle, at least one vial adaptor adapted for connection to a vial containing a drug and at least one syringe adaptor adapted to be attached to a syringe and to at least one of the at least one receptacle port adaptor and the at least one vial adaptor, the system being characterized in that the at least one syringe adaptor is adapted to be brought into fluid communication and mechanically locked to at least one of the at least one receptacle port adaptor and the at least one vial adaptor in a single step.

Preferably, at least one of the at least one vial adaptor, the at least one receptacle port adaptor and the at least one syringe adaptor are vented to the atmosphere without permitting potentially harmful contents of the vial to reach the atmosphere.

Preferably, the drug mixing system also includes a stopcock connected to the at least one vial adaptor and to the at least one receptacle port adaptor.

There is further provided in accordance with yet another preferred embodiment of the present invention a drug mixing system including at least one receptacle port adaptor adapted to be inserted into a port of a fluid receptacle and at least one vial adaptor adapted for connection to a vial containing a drug and connected to the at least one receptacle port adaptor, the system being characterized in that at least one of the at least one receptacle port adaptor and the at least one vial adaptor is vented to the atmosphere in a manner which prevents release to the atmosphere of possibly harmful contents of the vial.

There is even further provided in accordance with still another preferred embodiment of the present invention a drug mixing system including at least one receptacle port adaptor adapted to be inserted into a port of a fluid receptacle and at least one vial adaptor adapted for connection to a vial containing a drug and connected to the at least one receptacle port adaptor, the at least one vial adaptor including a venting and sealing element, operative to allow air into the drug mixing system and adapted to prevent air from escaping from the drug mixing system.

Preferably, the venting and sealing element includes a hydrophobic membrane and a narrow bore.

Preferably, the narrow bore is irreversibly filled with liquid upon flow of liquid from the fluid receptacle to the vial, thus preventing air from escaping.

Alternatively or additionally, the receptacle port adaptor includes an elastomer covered needle and the receptacle port adaptor and the vial adaptor are integrally formed. Alternatively, the receptacle port adaptor includes an elastomer covered needle and the receptacle port adaptor, the syringe adaptor and the vial adaptor are integrally formed.

Preferably, the at least one vial adaptor also includes a protective vial housing operative to prevent release to the atmosphere of possibly harmful contents of the vial in a liquid, solid or gaseous form in the event of breakage of the vial.

In another preferred embodiment, the fluid receptacle includes a spike port and the at least one receptacle port adaptor includes a spike port adaptor. Additionally or alternatively, the fluid receptacle includes a needle port and the at least one receptacle port adaptor includes a needle port adaptor. Additionally, the needle port adaptor includes a needle, the needle being protected by a needle protector. Preferably, the needle protector includes a latex needle cover.

Preferably, the drug mixing system also includes a vial head adaptor adapted for connection between the vial adaptor and the vial.

In another preferred embodiment, the at least one receptacle port adaptor and the fluid receptacle are adapted to be connected to an intravenous cannula on a patient via an intravenous infusion set.

Preferably, the at least one syringe adaptor and the syringe are adapted to be connected to an intravenous cannula on a patient via an intravenous infusion set using an infusion set adaptor. Additionally or alternatively, the syringe adaptor is covered by a syringe cover element.

There is yet further provided in accordance with another preferred embodiment of the present invention a drug mixing system including at least one drug mixing element including atmospheric venting functionality, characterized in that it prevents potentially harmful drug material from being released to the atmosphere via the venting functionality, the potentially harmful drug material including at least one of solid, liquid, gas and aerosol.

There is even further provided in accordance with yet another preferred embodiment of the present invention a drug mixing method including attaching a luer fitted hypodermic syringe having a plunger to a syringe adaptor, inserting a receptacle port adaptor into a port in a receptacle containing a fluid, attaching the syringe adaptor, having the syringe attached thereto, to the receptacle port adaptor, retracting the plunger, thereby at least partially filling the syringe with fluid drawn from the receptacle in a manner which ensures that the fluid remains sterile and that a user is not exposed to the fluid, connecting the syringe adaptor having the syringe attached thereto, to a vial adaptor assembly, having a drug containing vial attached thereto, pushing the plunger, thus injecting the fluid contained in the syringe into the drug containing vial, thereby producing a drug solution in the vial and retracting the plunger, thus drawing at least part of the contents of the vial into the syringe, wherein at least one of the receptacle port adaptor, the syringe adaptor and the vial adaptor being vented to the atmosphere in a manner which prevents release to the atmosphere of possibly harmful contents of the vial in a liquid, solid or gaseous form.

There is still further provided in accordance with yet another preferred embodiment of the present invention a drug mixing method including attaching a luer fitted hypodermic syringe having a plunger to a syringe adaptor, inserting a receptacle port adaptor into a port in a receptacle containing a fluid, attaching the syringe adaptor, having the syringe attached thereto, to the receptacle port adaptor, retracting the plunger, thereby at least partially filling the syringe with fluid drawn from the receptacle in a manner which ensures that the fluid remains sterile and that a user is not exposed to the fluid, connecting the syringe adaptor having the syringe attached thereto, to a vial adaptor assembly, having a drug containing vial attached thereto, pushing the plunger, thus injecting the fluid contained in the syringe into the drug containing vial, thereby producing a drug solution in the vial and retracting the plunger, thus drawing at least part of the contents of the vial into the syringe, wherein the syringe adaptor is adapted to be brought into fluid communication and mechanically locked to at least one of the receptacle port adaptor and the vial adaptor in a single step.

There is yet further provided in accordance with another preferred embodiment of the present invention a drug mixing method including attaching a luer fitted hypodermic syringe having a plunger to a syringe adaptor, inserting a receptacle port adaptor into a port in a receptacle containing a fluid, connecting the syringe adaptor having the syringe attached thereto, to a vial adaptor assembly, having a drug containing vial attached thereto, retracting the plunger, thus drawing at least part of the contents of the vial into the syringe, connecting the syringe adaptor having the syringe attached thereto, to the receptacle port adaptor and pushing the plunger, thus injecting the at least part of the contents of the vial into the receptacle, wherein at least one of the receptacle port adaptor, the syringe adaptor and the vial adaptor is vented to the atmosphere in a manner which prevents release to the atmosphere of possibly harmful contents of the vial in a liquid, solid or gaseous form.

There is still further provided in accordance with yet another preferred embodiment of the present invention a drug mixing method including attaching a luer fitted hypodermic syringe having a plunger to a syringe adaptor, inserting a receptacle port adaptor into a port in a receptacle containing a fluid, connecting the syringe adaptor having the syringe attached thereto, to a vial adaptor assembly, having a drug containing vial attached thereto, retracting the plunger, thus drawing at least part of the contents of the vial into the syringe, connecting the syringe adaptor having the syringe attached thereto, to the receptacle port adaptor and pushing the plunger, thus injecting the at least part of the contents of the vial into the receptacle, wherein the syringe adaptor is adapted to be brought into fluid communication and mechanically locked to at least one of the receptacle port adaptor and the vial adaptor in a single step.

There is even further provided in accordance with another preferred embodiment of the present invention a drug mixing method including attaching a luer fitted hypodermic syringe having a plunger to a syringe adaptor, connecting the syringe adaptor having the syringe attached thereto, to a vial adaptor assembly, having a drug containing vial attached thereto, retracting the plunger, thus drawing at least part of the contents of the vial into the syringe and pushing the plunger, thus injecting the at least part of the contents of the vial into an infusion line, wherein at least one of the receptacle port adaptor, the syringe adaptor and the vial adaptor is vented to the atmosphere in a manner which prevents release to the atmosphere of possibly harmful contents of the vial in a liquid, solid or gaseous form.

There is still further provided in accordance with yet another preferred embodiment of the present invention a drug mixing method including attaching a luer fitted hypodermic syringe having a plunger to a syringe adaptor, connecting the syringe adaptor having the syringe attached thereto, to a vial adaptor assembly, having a drug containing vial attached thereto, retracting the plunger, thus drawing at least part of the contents of the vial into the syringe and pushing the plunger, thus injecting the at least part of the contents of the vial into an infusion line, wherein the syringe adaptor is adapted to be brought into fluid communication and mechanically locked to at least one of the receptacle port adaptor and the vial adaptor in a single step.

Preferably, the connecting the syringe adaptor also includes disconnecting the syringe adaptor from the receptacle adaptor prior to the connecting.

Preferably, the connecting the syringe adaptor having the syringe attached thereto to the receptacle port adaptor also includes disconnecting the syringe adaptor from the vial adaptor prior to the connecting.

Additionally or alternatively, the connecting the syringe adaptor includes connecting the drug containing vial to a vial head adaptor and connecting the drug containing vial having the vial head adaptor attached thereto to the vial adaptor assembly, prior to the connecting the syringe to the vial adaptor assembly. Alternatively or additionally, the drug mixing method also includes attaching the syringe adaptor, having the syringe containing at least part of the drug solution attached thereto, to the receptacle port adaptor and injecting contents of the syringe into the receptacle.

There is still further provided in accordance with still another preferred embodiment of the present invention a drug mixing method including inserting a receptacle port adaptor into a port in a receptacle containing a fluid, connecting a drug containing vial to the receptacle port adaptor, transferring at least a portion of the fluid from the receptacle to the drug containing vial, thereby producing a drug solution in the vial and subsequently transferring the drug solution from the vial to the receptacle.

Preferably, the connecting the drug containing vial includes connecting the drug containing vial to a vial head adaptor prior to the connecting the drug containing vial. Additionally or alternatively, the receptacle port adaptor includes at least one of a spike port adaptor and a needle port adaptor.

There is yet further provided in accordance with another preferred embodiment of the present invention a vial adaptor adapted for connection to a vial containing a drug and adapted for connection to other elements of a drug mixing system, the vial adaptor including a spike adapted for penetrating the vial, a mechanical lock for locking the vial adaptor to the vial once the spike penetrates the vial and an element operative to vent the interior of the vial to the atmosphere without permitting potentially harmful contents of the vial to reach the atmosphere.

Preferably, the vial adaptor also includes a membrane vent operative to vent the vial adaptor to the atmosphere. Additionally, the membrane vent includes a filter. Alternatively or additionally, the membrane vent includes a hydrophobic membrane.

Preferably, the vial adaptor also includes a septum equipped syringe port. Additionally or alternatively, the vial adaptor includes at least one locking element, operative to irreversibly lock the vial adaptor to the vial. Preferably, the at least one locking element includes at least one radially extending portion and at least one transversely extending portion.

There is further provided in accordance with yet another preferred embodiment of the present invention a vial adaptor adapted for connection to a vial containing a drug and being adapted for connection to other elements of a drug mixing system, the vial adaptor including at least one locking element, operative to irreversibly lock the vial adaptor to the vial.

Preferably, the at least one locking element includes at least one radially extending portion and at least one transversely extending portion.

There is still further provided in accordance with another preferred embodiment of the present invention a vial adaptor adapted for connection to a vial containing a drug and being adapted for connection to a fluid transfer device, the vial adaptor being vented to the atmosphere in a manner which prevents release to the atmosphere of possibly harmful contents of the vial in a liquid, solid or gaseous form.

Preferably, the vial adaptor also includes a membrane vent operative to vent the vial adaptor to the atmosphere. Additionally, the membrane vent includes a filter. Alternatively or additionally, the membrane vent includes a hydrophobic membrane.

There is yet further provided in accordance with still another preferred embodiment of the present invention a syringe adaptor adapted for connection to a syringe and adapted for connection to at least one other element of a drug mixing system, the syringe adaptor including a septa housing, at least two septa enclosed in the septa housing defining a space therebetween and a needle, including a tip located in the space when the syringe adaptor is not connected to the at least one other element.

Preferably, the septa housing is movable relative to the needle, thereby to expose the tip. Additionally or alternatively, at least a portion of the needle is protected by a needle protector. Additionally, the needle protector includes an elastomeric tubing element.

There is still further provided in accordance with yet a further preferred embodiment of the present invention a vial head adaptor for use in connecting a vial with a first head circumference to a vial adaptor adapted for use with a vial with a second head circumference, the second head circumference being greater than the first head circumference, the vial head adaptor including at least one locking element.

Preferably, the at least one locking element includes four locking elements arranged generally at right angles to each other. Additionally, the at least one locking element includes a locking tooth.

There is even further provided in accordance with still another preferred embodiment of the present invention a receptacle port adaptor for use in a drug mixing system including a housing, a needle located within the housing and adapted to be inserted into a port of a fluid receptacle, a septum located in the housing and a locking mechanism to fix the receptacle port adaptor to the port.

Preferably, the needle is protected by a needle protector. Additionally, the needle protector includes a latex needle cover. Alternatively or additionally, the needle moves between a protected position and a piercing position.

There is also provided in accordance with yet another preferred embodiment of the present invention a protective vial housing for use with a drug mixing system including a fluid flow passageway adapted to connect a vial containing a drug to the drug mixing system, the protective vial housing being operative to prevent release to the atmosphere of possibly harmful contents of the vial in a liquid, solid or gaseous form in the event of breakage of the vial.

BRIEF DESCRIPTION OF THE DRAWINGS

The present invention will be understood and appreciated more fully from the following detailed description, taken in conjunction with the drawings in which:

FIGS. 1A, 1B, 1C, 1D, 1E, 1F, 1G, 1H, 1I, 1J, 1K, 1L and 1M are simplified pictorial illustrations of various stages of assembly and typical use of a drug mixing system constructed and operative in accordance with a preferred embodiment of the present invention;

FIG. 5 is a simplified assembled pictorial illustration of the vial adaptor assembly of FIG. 4;

FIGS. 11A and 11B are sectional illustrations taken along section lines XI-XI in FIG. 10, of two different inner structures of the spike port adaptor element;

FIGS. 12A and 12B are simplified pictorial illustrations of a needle port adaptor element which forms part of the drug mixing system of FIGS. 1A-1M;

FIGS. 19A and 19B are, respectively, a top view simplified planar illustration and a simplified sectional illustration of the drug mixing system of FIG. 1C during attachment of the syringe adaptor, the sectional illustration being taken along lines XIXB-XIXB in FIG. 19A;

FIGS. 19C and 19D are respectively, a side view simplified planar illustration and a simplified sectional illustration of the drug mixing system of FIG. 1C during attachment of the syringe adaptor, the sectional illustration being taken along lines XIXD-XIXD in FIG. 19C;

FIG. 26 is a sectional illustration of the drug mixing system of FIG. 1G prior to drug dilution;

FIG. 27 is a sectional illustration of the drug mixing system of FIG. 1H following drug dilution;

FIGS. 31A, 31B, 31C, 31D, 31E, 31F, 31G, 31H, 31I, 31J, 31K and 31L are simplified pictorial illustrations of various stages of assembly and typical use of a drug mixing system constructed and operative in accordance with another preferred embodiment of the present invention;

FIG. 34 is a simplified pictorial illustration of a spike port adaptor element which forms part of the drug mixing system of FIGS. 31A-31L;

FIG. 35 is a sectional illustration taken along section lines XXXV-XXXV in FIG. 34;

FIGS. 42A and 42B are sectional illustrations taken along respective section lines XLIIA-XLIIA and XLIIB-XLIIB in FIG. 41;

FIGS. 43A and 43B are simplified pictorial illustrations of a housing element which forms part of the adaptor assembly of FIG. 36 in closed and open orientations, respectively;

FIG. 46 is a sectional illustration of the drug mixing system of FIG. 31C during attachment of a syringe to the adaptor assembly of FIGS. 44-45B;

FIG. 53 is a sectional illustration of the drug mixing system of FIG. 31L when ready for storage;

FIGS. 54A, 54B, 54C, 54D, 54E, 54F, 54G and 54H are simplified pictorial illustrations of various stages of assembly and typical use of a drug mixing system constructed and operative in accordance with yet another preferred embodiment of the present invention;

FIG. 57 is a simplified pictorial illustration of a spike port adaptor element which forms part of the drug mixing system of FIGS. 54A-54H;

FIG. 58 is a sectional illustration taken along section lines LVIII-LVIII in FIG. 57;

FIGS. 61A and 61B are sectional illustrations taken along respective section lines LXIA-LXIA and LXIB-LXIB in FIG. 60;

FIGS. 63A and 63B are sectional illustrations taken along respective section lines LXIIIA-LXIIIA and LXIIIB-LXIIIB in FIG. 62;

FIG. 90 is a pictorial illustration of the receptacle adaptor subassembly of FIG. 88 when assembled to a vial adaptor subassembly in accordance with a preferred embodiment of the present invention, prior to connection of a needle to a receptacle port element;

DETAILED DESCRIPTION OF PREFERRED EMBODIMENTS

Reference is now made to FIGS. 1A, 1B, 1C, 1D, 1E, 1F, 1G, 1H, 1I, 1J, 1K, 1L and 1M which are simplified pictorial illustrations of various stages of assembly and typical use of a drug mixing system constructed and operative in accordance with a preferred embodiment of the present invention.

Figure 1A:
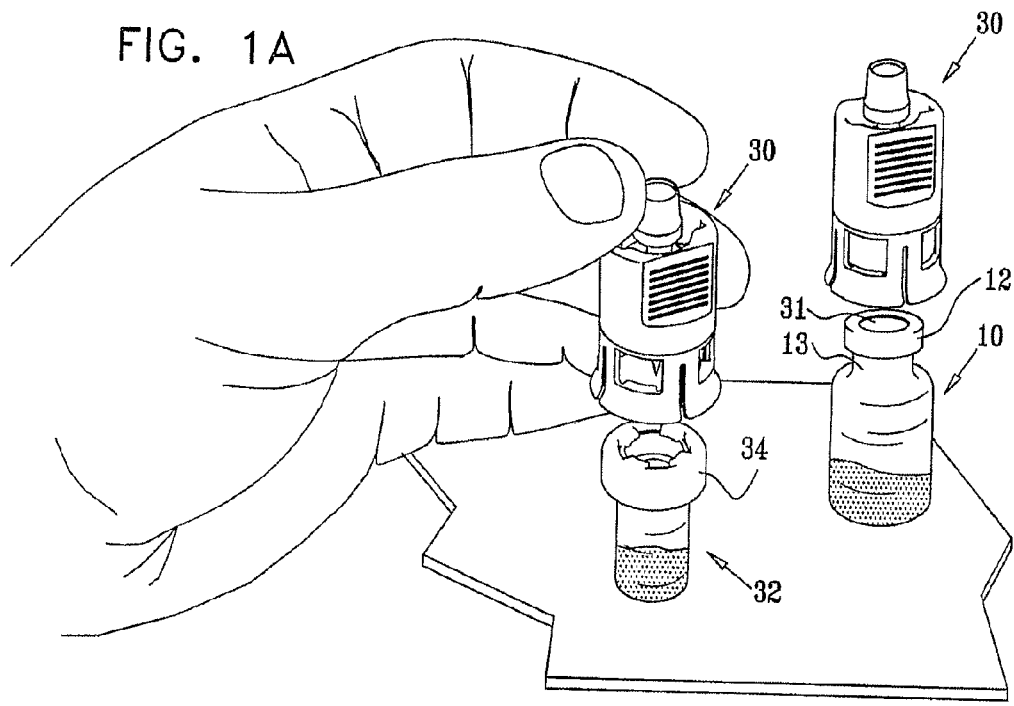
Figure 1B:
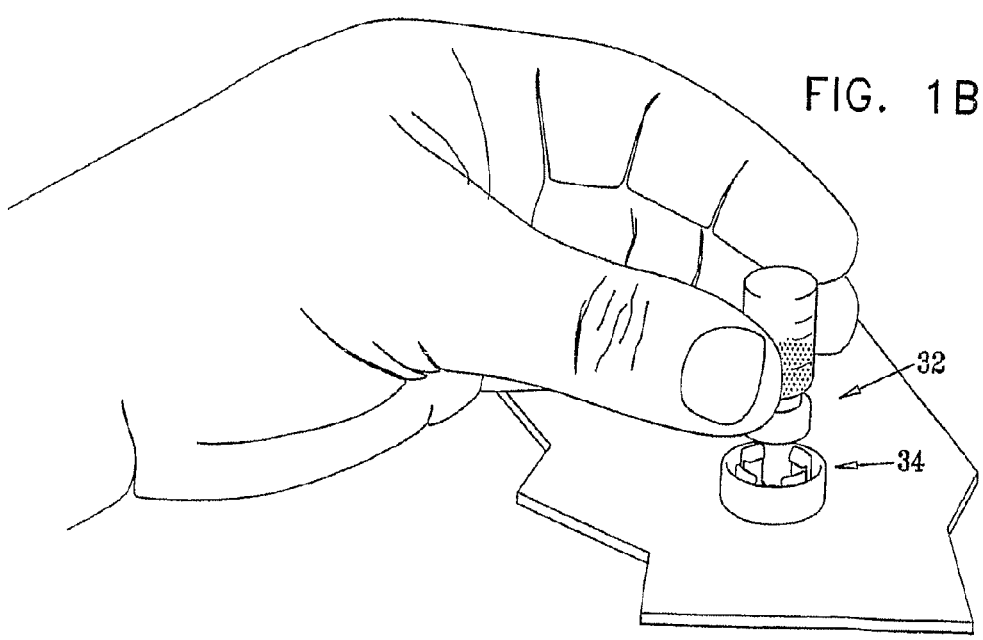
Figure 18A:
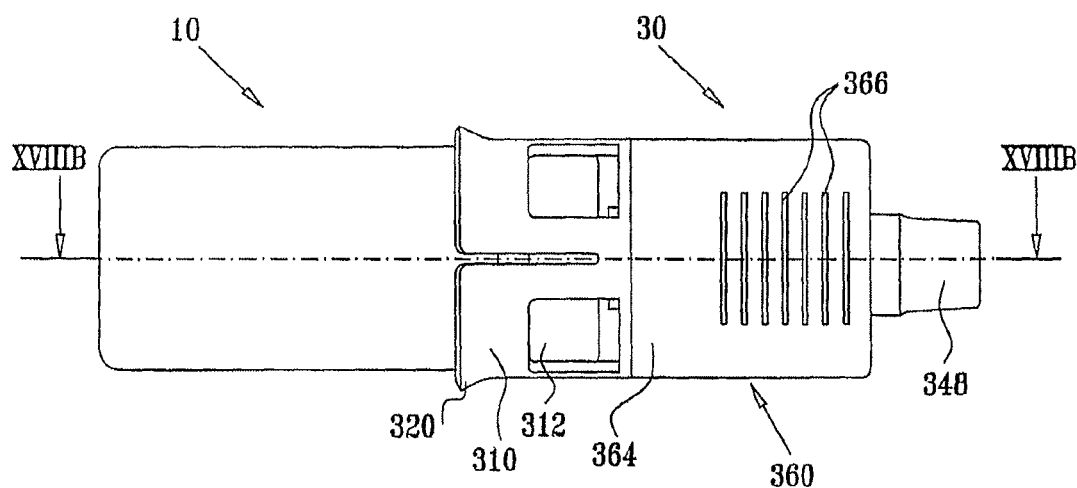
FIGS. 18A and 18B are, respectively, a simplified planar illustration and a simplified sectional illustration of the drug mixing system of FIG. 1A during attachment of the vial adaptor, the sectional illustration being taken along lines XVIIIB-XVIIIB in FIG. 18A.
Figure 18B:
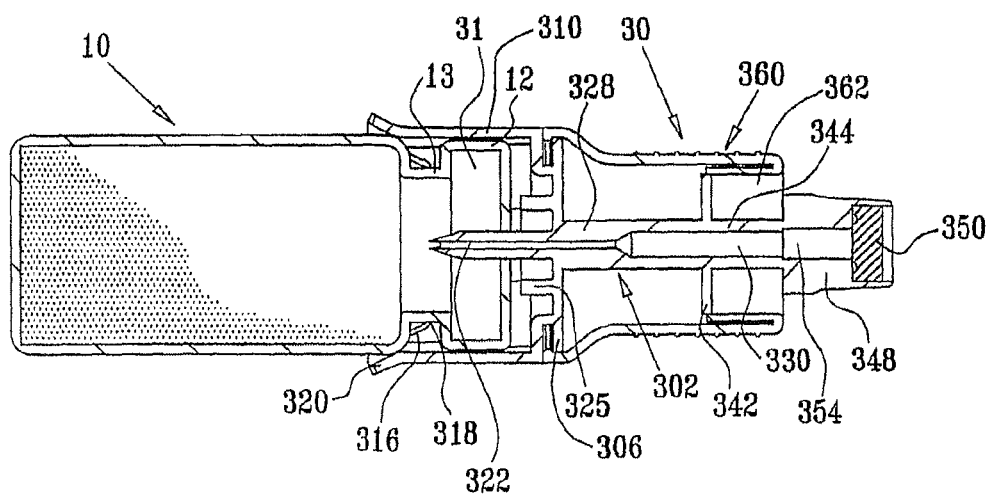

As seen in FIG. 1A, a conventional vial 10, including a top portion 12 and a neck portion 13, is pushed into engagement with a vial adaptor assembly 30 which is described hereinbelow with reference to FIGS. 4-6B. Top portion 12 of vial 10 preferably has a septum 31 sealingly seated therein. FIGS. 18A-18B show a sectional view of the drug mixing system at this stage:

Alternatively, if a small vial 32 is used, small vial 32 is pushed into engagement with a vial head adaptor element 34 which is described hereinbelow with reference to FIGS. 2-3 as shown in FIG. 1B, and is then pushed into engagement with vial adaptor assembly 30. The vials 10 and 32 typically contain a drug in a soluble powder form, in a solution or in other suitable form.

Figure 1C:
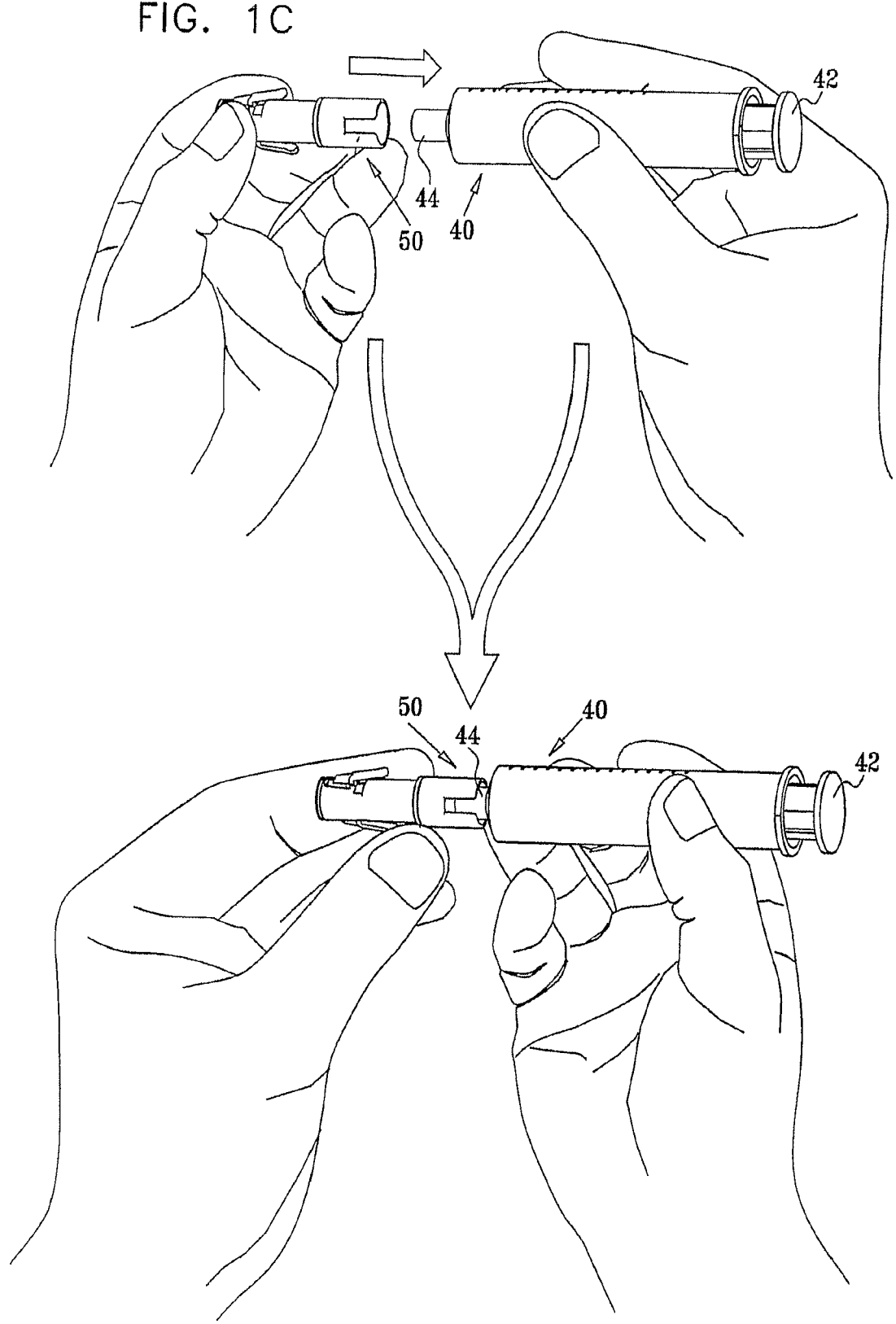

As shown in FIG. 1C, a luer fitted hypodermic syringe 40 having a plunger 42 and a luer tip 44 is attached to a syringe adaptor element 50 which is described hereinbelow with reference to FIGS. 7-9B. FIGS. 19A-19D show planar and sectional views of the drug mixing system at this stage.

Figure 1D:
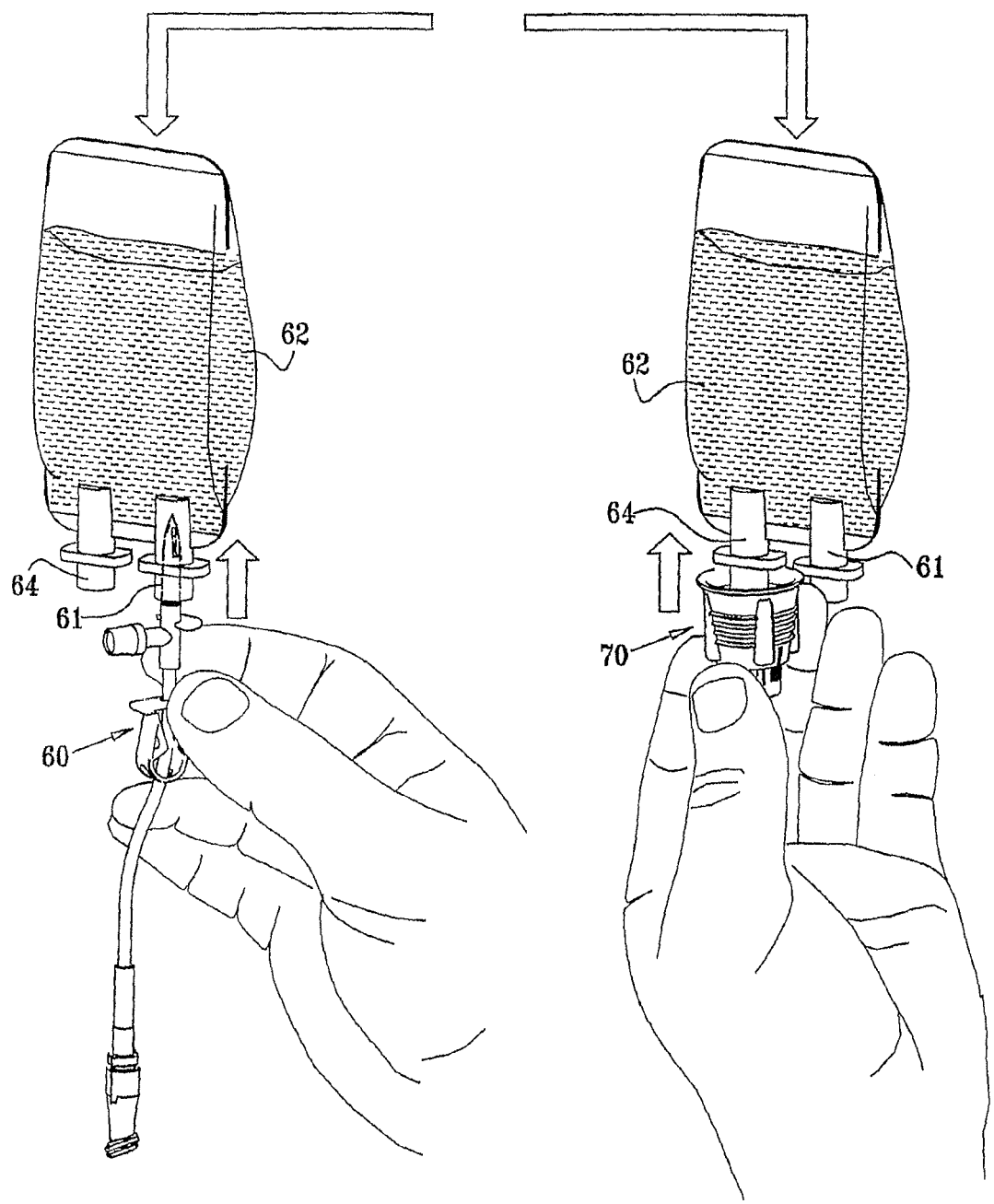
Figure 20:
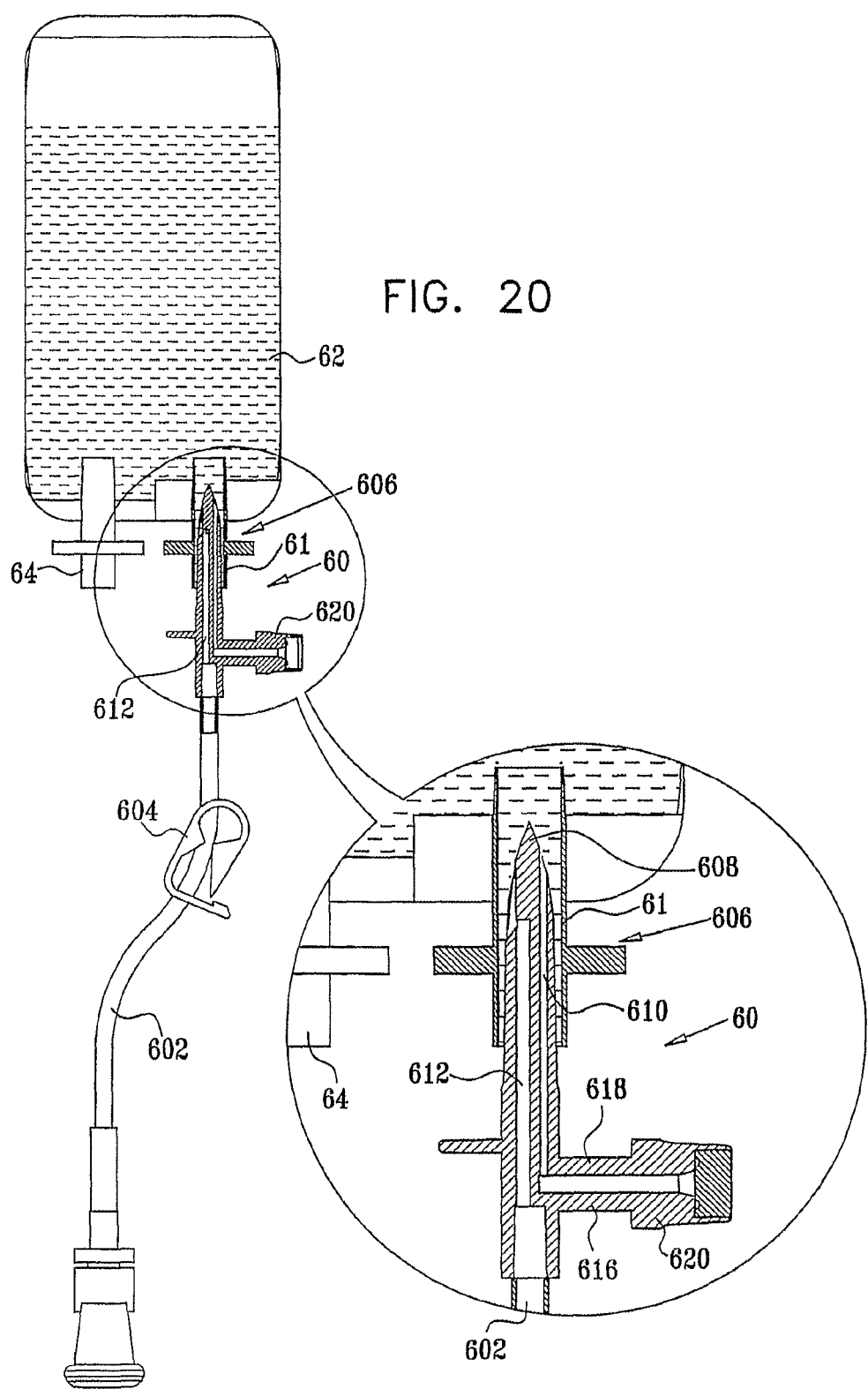
FIG. 20 is a partially pictorial partially sectional illustration of the drug mixing system of FIG. 1D during attachment of the spike port adaptor element.

FIG. 1D shows a spike port adaptor element 60, as described hereinbelow with reference to FIGS. 10-11, being inserted into a spike port 61 in a receptacle 62 containing a fluid. FIG. 20 shows a partially pictorial partially sectional view of the drug mixing system at this stage. Typically, receptacle 62 comprises a bag, and the fluid contained therein is sterile saline solution, water, or any other suitable sterile solution or pure fluid.

Figure 21:
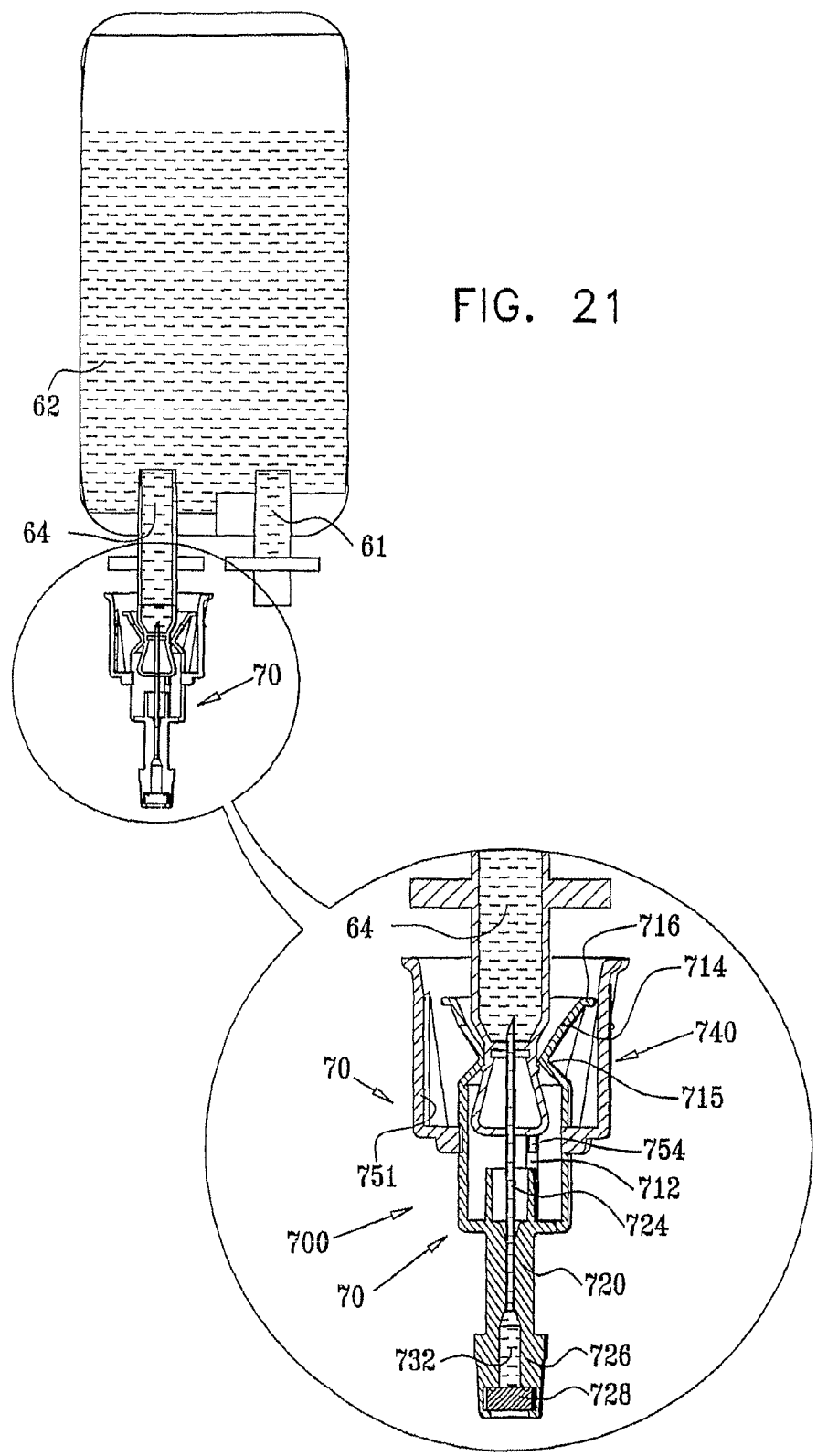
FIG. 21 is a partially pictorial partially sectional illustration of the drug mixing system of FIG. 1D during attachment of the needle port adaptor element.

Alternatively, a needle port adaptor element 70, as described hereinbelow with reference to FIGS. 12A-13B, is inserted into a needle port 64 in receptacle 62. FIG. 21 shows a sectional view of the drug mixing system at this stage.

It will be appreciated by persons skilled in the art that the assembly steps shown in FIGS. 1B-1D may be performed in any suitable sequence.

Figure 1E:
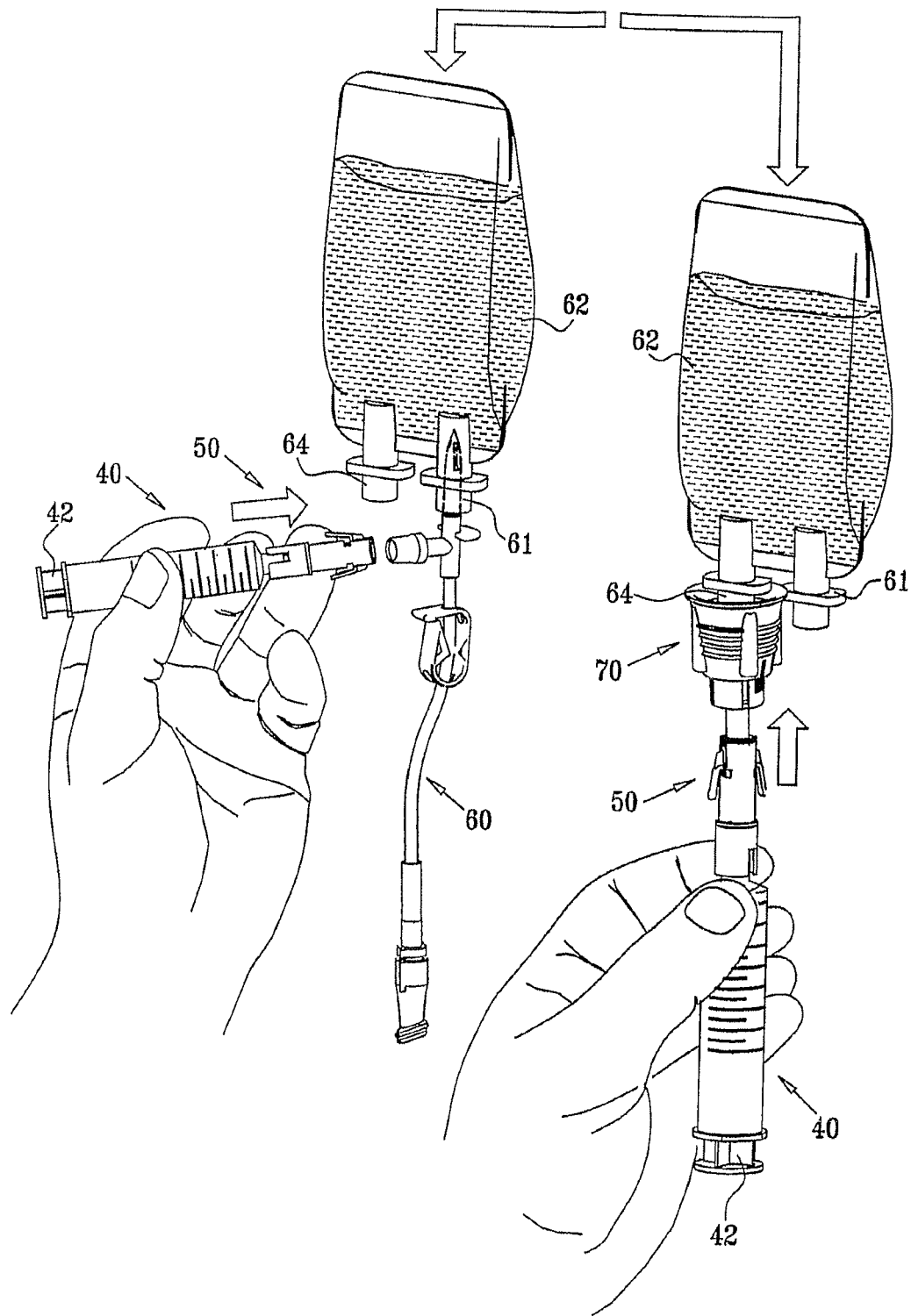

As seen in FIG. 1E, syringe adaptor element 50, having syringe 40 attached thereto (FIG. 1C), is connected to a connection port in either of spike port adaptor element 60 or needle port adaptor element 70 of FIG. 1D. FIGS. 22-23 and 24-25, respectively, show partially pictorial partially sectional views of the two alternate orientations of the drug mixing system at this stage.

Typically, plunger 42 of syringe 40 is fully pushed inward into syringe 40 before syringe adaptor element 50 is connected to either of spike port adaptor element 60 and needle port adaptor element 70.

Figure 1F:
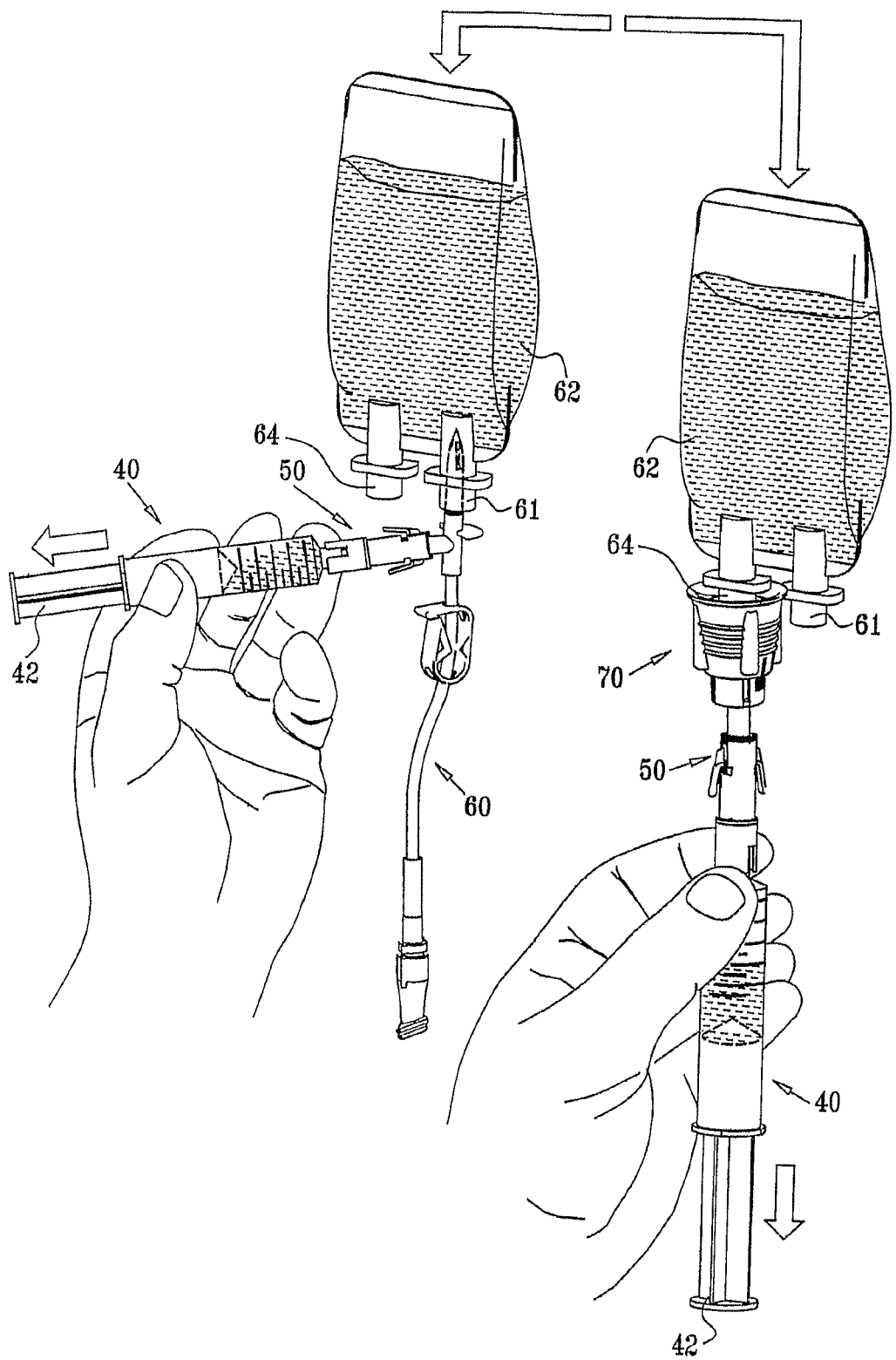

As seen in FIG. 1F, a user retracts plunger 42 in either of the operative orientations of FIG. 1E, thus at least partially filling syringe 40 with fluid drawn from receptacle 62. The fluid flows through the spike port adaptor element 60 or through the needle port adaptor element 70 directly into syringe 40. This flow of fluid ensures that the fluid remains sterile, and that the user is not exposed to the fluid. Subsequently, the syringe 40 and syringe adaptor element 50 are disconnected from the spike port adaptor element 60 or the needle port adaptor element 70. The drug mixing system of the present invention also ensures that the user is not exposed to the fluid during disconnection thereof, as explained further hereinbelow.

The user then connects syringe adaptor element 50, which is attached to syringe 40, to the vial adaptor assembly 30 having the vial 10 attached thereto, as shown in FIG. 1G. FIG. 26 shows a sectional view of the drug mixing system at this stage.

When the syringe 40 and vial 10 are connected and fluid can flow therebetween, the user pushes plunger 42 inward, with the vial positioned upright, thus injecting the fluid contained in syringe 40 into vial 10 and dissolving the drug contained therein. FIG. 27 shows a sectional view of the drug mixing system at this stage.

As seen in FIG. 1H, the user then shakes the drug mixing system of FIG. 1G to ensure that the drug in vial 10 is fully dissolved and that the resulting solution is homogenous.

It is appreciated that when vial 10 contains a drug in a pre-dissolved form, the steps described hereinabove with reference to FIGS. 1E-1H may be obviated.

Figure 1J:
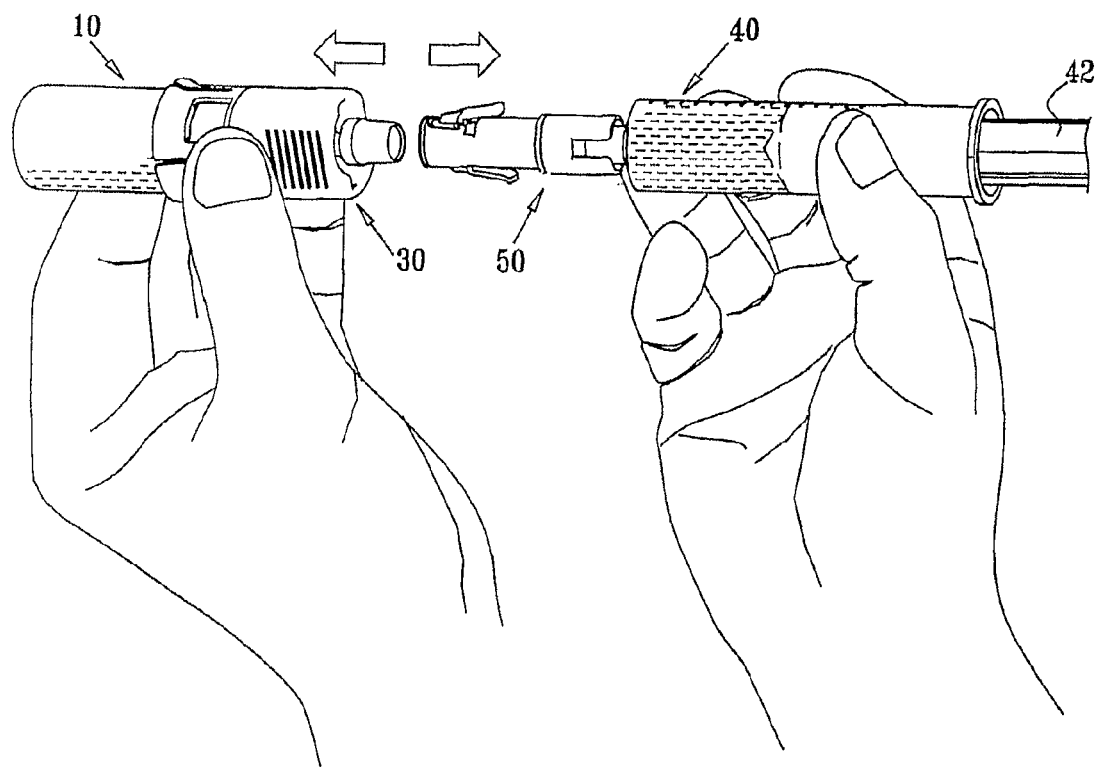

As seen in FIG. 1I, the user turns the drug mixing system upside down and retracts plunger 42, thus drawing at least part of the solution from the vial 10 into syringe 40. Subsequently, syringe 40 and syringe adaptor element 50 are disconnected from vial 10 and vial adaptor assembly 30, as shown in FIG. 1J. At this stage, if some of the drug solution is left in vial 10, vial 10 and vial adaptor assembly 30, joined thereto, may be stored in a suitable facility for further use.

At a next stage, the drug solution contained in syringe 40 is prepared for delivery to a hospital ward for infusion into a patient. As shown in FIG. 1K, syringe 40 containing the drug solution is connected to spike port adaptor element 60 for transferring the drug into receptacle 62. Alternatively, syringe 40 may be connected to needle port adaptor element 70.

As a further alternative, the user may place a syringe protection cover 80, which is described hereinbelow with reference to FIGS. 14-15, onto the syringe adaptor element 50 which is attached to syringe 40, prior to delivering it to a hospital ward.

Figure 28:
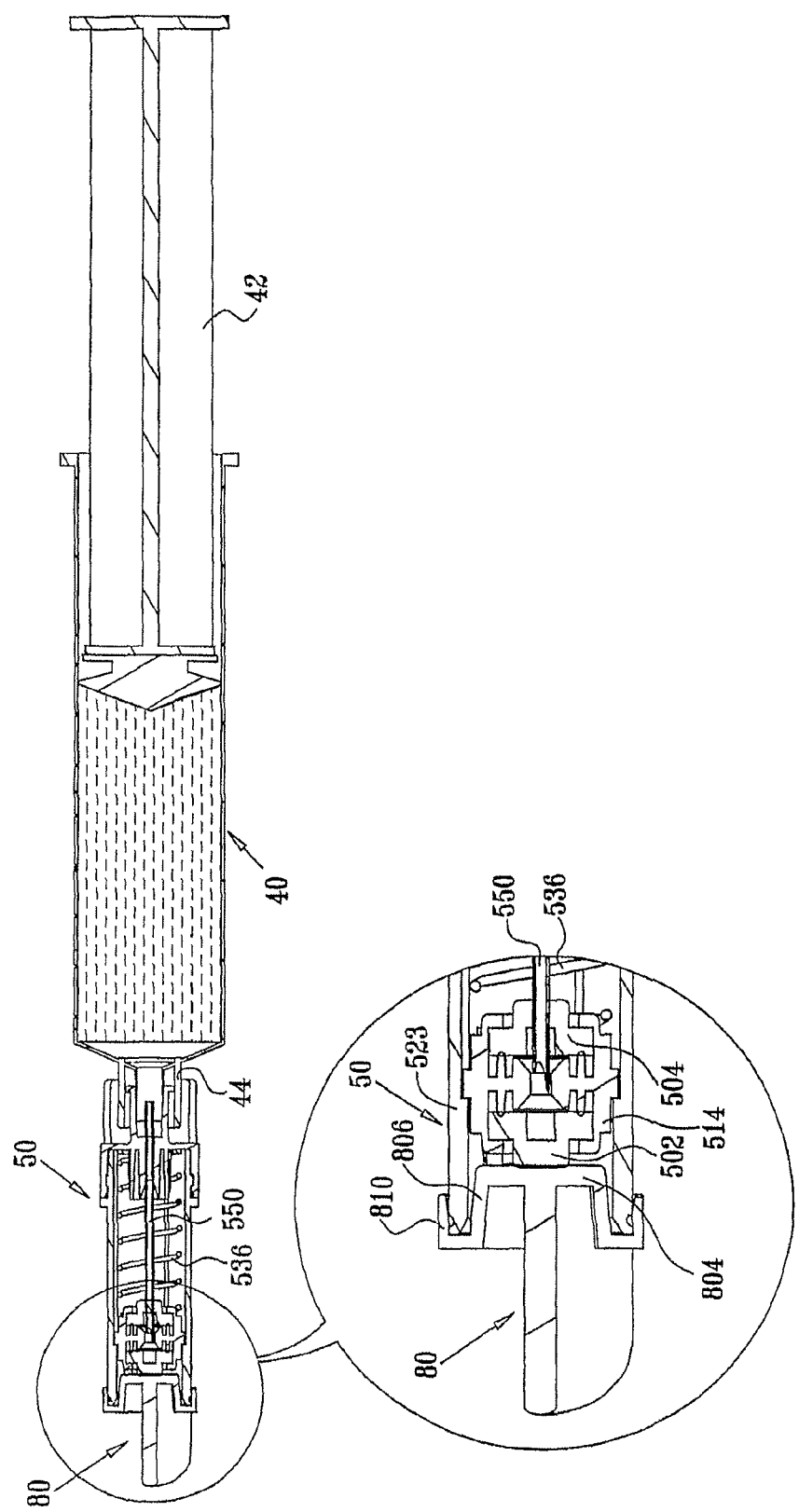
FIG. 28 is a sectional illustration of the drug mixing system of FIGS. 1K and 1L in a protected, ready for delivery state.

As seen in FIG. 1L, the user pushes plunger 42 of syringe 40 inward, thus injecting the drug solution into receptacle 62 and further diluting it prior to infusion into a patient. Alternatively, syringe 40 may be covered by the syringe protection cover 80 and is ready for delivery to the appropriate hospital ward. FIG. 28 is a sectional view of the drug mixing system at this stage.

Figure 1M:
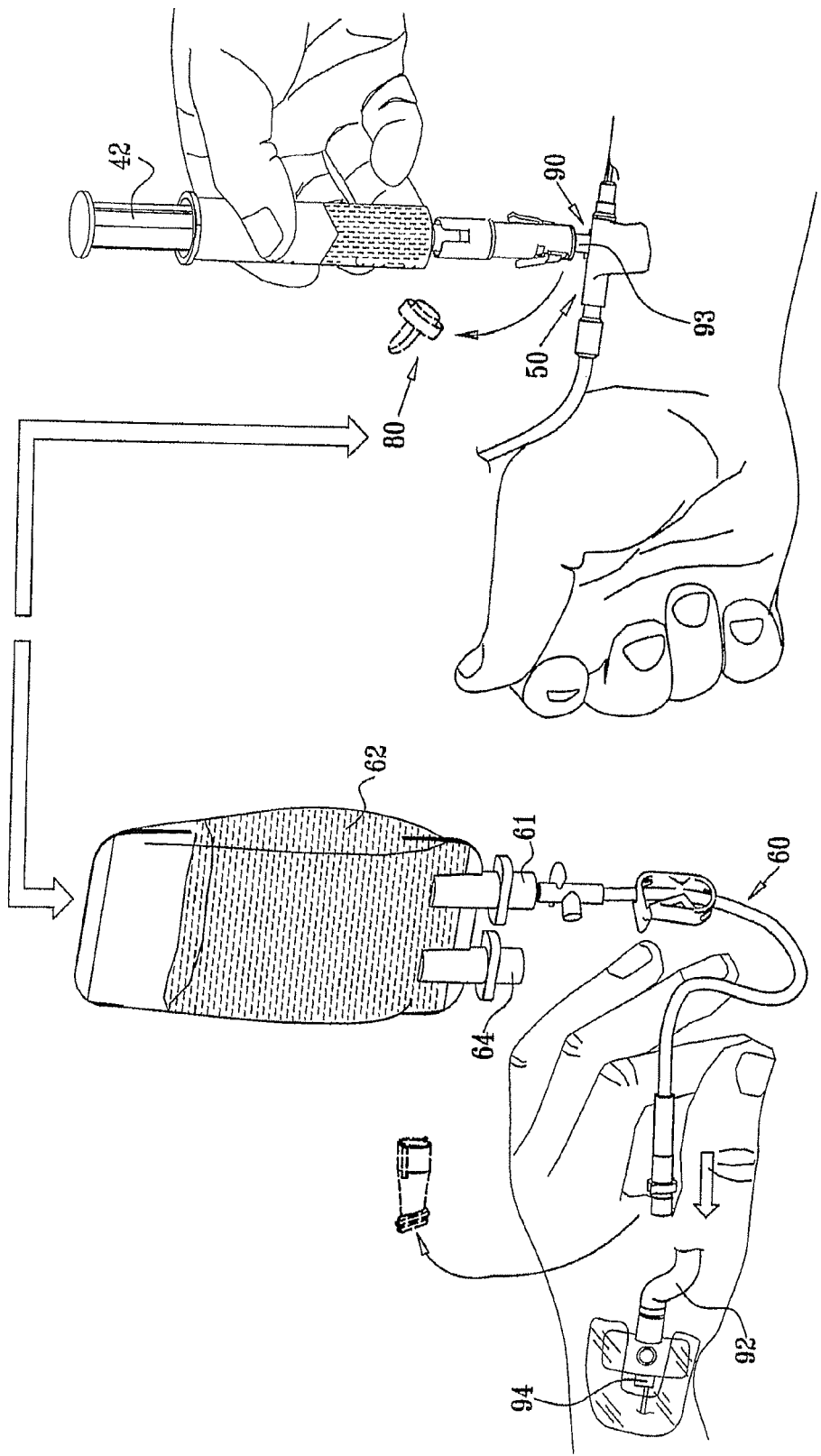
Figure 30:
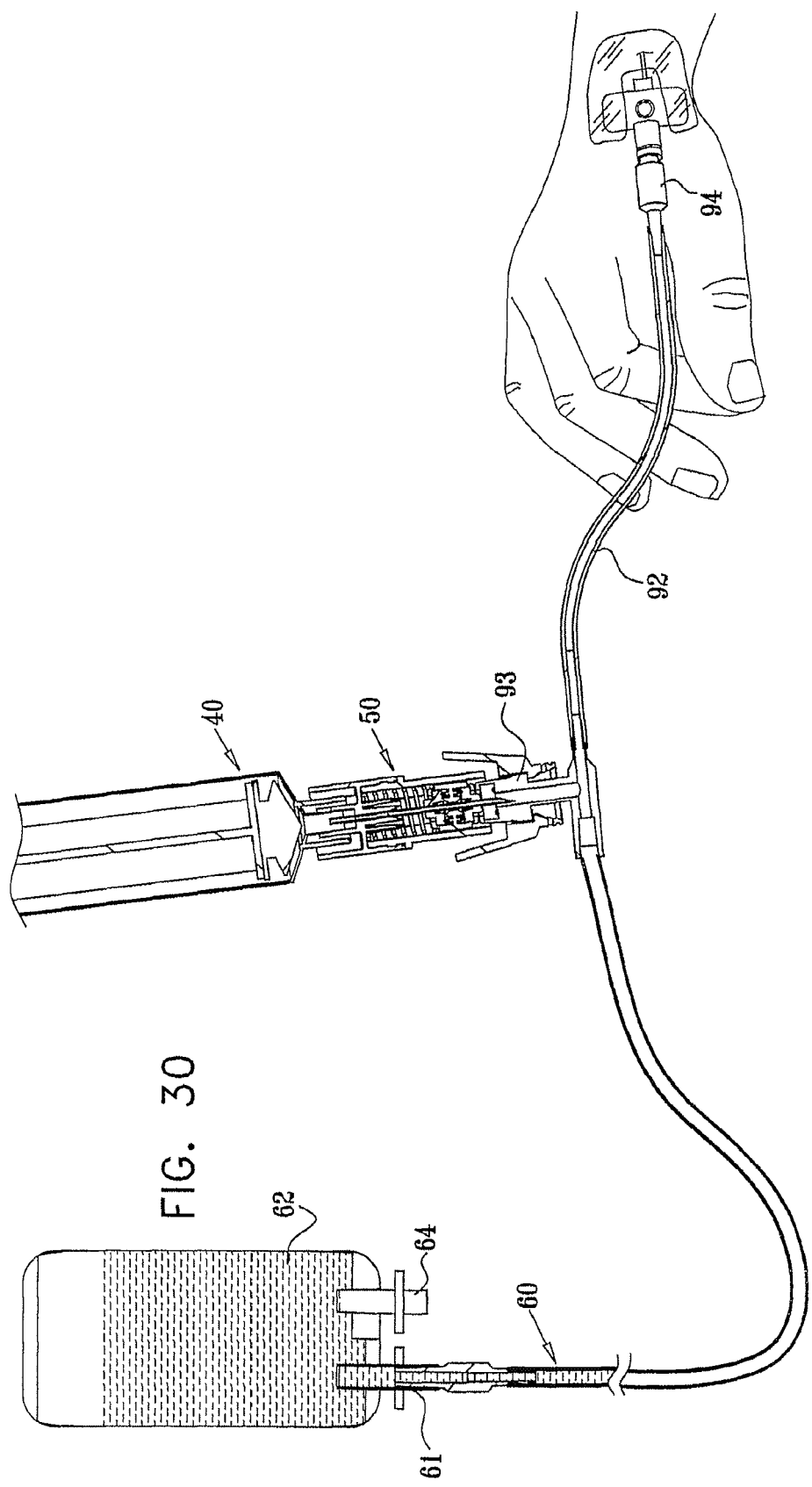
FIG. 30 is a partially pictorial partially sectional illustration of the drug mixing system of FIGS. 1M and 20 when ready for injection.

As seen in FIG. 1M, the receptacle 62 and spike port adaptor element 60 are connected via a standard infusion set 92 such as model IAS which is commercially available from Teva Medical Ltd. of Ashdod, Israel, to a patient's intravenous cannula. The connection to the spike port adaptor element 60 is performed after the removal of a connection element which is placed at the end of the spike port adaptor element 60. FIG. 30 is a sectional view of the drug mixing system at this stage.

Figure 29:
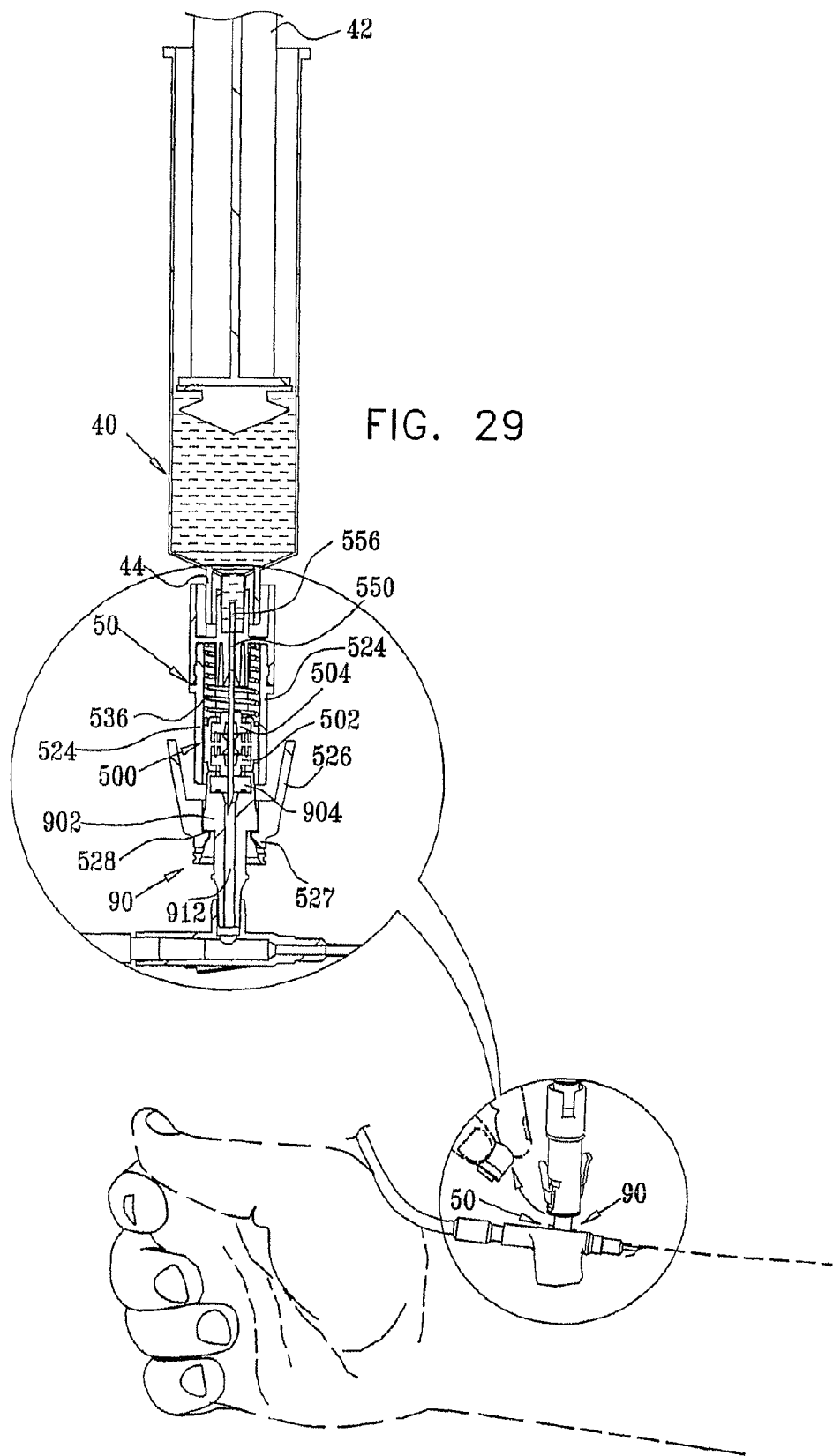
FIG. 29 is a partially pictorial partially sectional illustration of the drug mixing system of FIGS. 1M and 28 when ready for injection.

Alternatively, the syringe 40 and syringe adaptor element 50 may be connected via an infusion set adaptor element 90, which is described hereinbelow with reference to FIGS. 16-17, to an infusion set 92 including a port 93 and an intravenous cannula 94 which is placed at the injection site. Before syringe adaptor element 50 is attached to the infusion set adaptor element 90, the syringe protection cover 80 is removed from the end of the syringe adaptor element 50. FIG. 29 shows a partially pictorial partially sectional view of the drug mixing system at this stage.

The structure of elements of the drug mixing system of FIGS. 1A-1M is described hereinbelow with reference to FIGS. 2-17.

Figure 2:
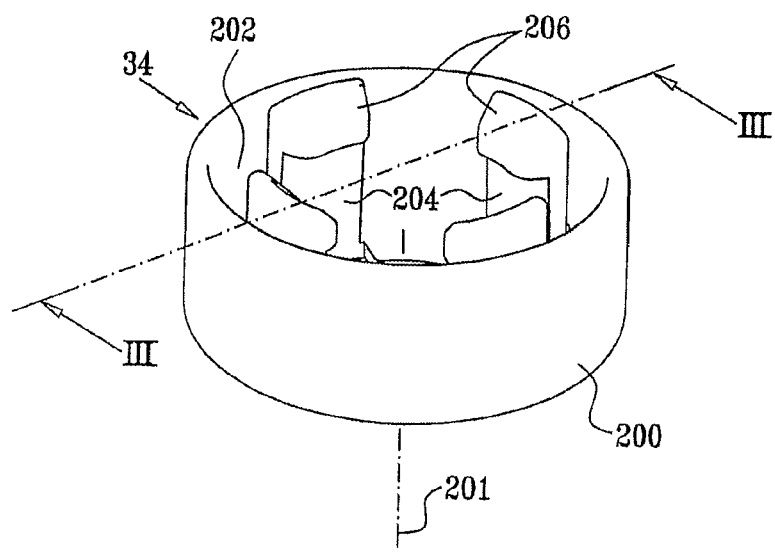
FIG. 2 is a simplified pictorial illustration of a vial head adaptor element which forms part of the drug mixing system of FIGS. 1A-1M.
Figure 3:
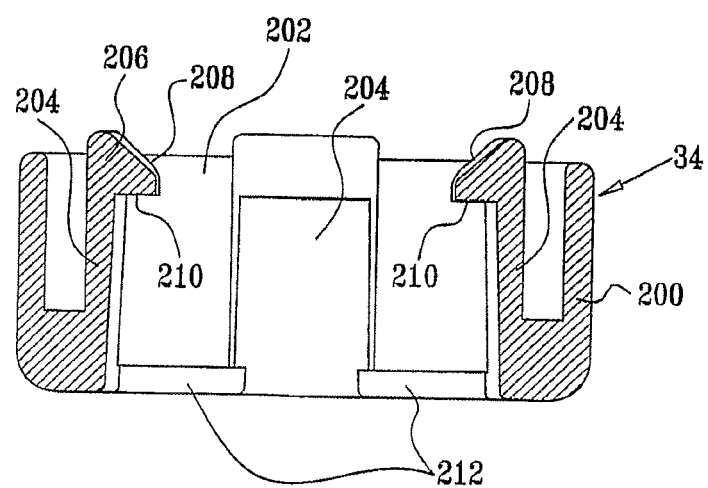
FIG. 3 is a sectional illustration taken along section lines III-III in FIG. 2.

Reference is now made to FIG. 2, which is a simplified pictorial illustration of a vial head adaptor element 34 which forms part of the drug mixing system of FIGS. 1A-1M, and to FIG. 3, which is a sectional illustration taken along section lines III-III in FIG. 2.

As seen in FIG. 2, vial head adaptor element 34 is preferably a side-to-side symmetric integrally formed element, which is preferably injection molded of plastic.

Vial head adaptor element 20 preferably includes a generally cylindrical main body portion 200 and has a central axis 201. An inner cylindrical surface 202 of main body portion 200 preferably has four arms 204 extending therefrom, each arm 204 being arranged at generally right angles with respect to its neighboring arms.

Each of arms 204 terminates at an upper end thereof, in the sense of FIG. 1B, in an inwardly facing generally triangular tooth 206 having a forwardly facing inclined surface 208 and a bottom-facing engagement surface 210 extending generally perpendicular to arm 204.

At bottom surface of vial head adaptor element 34, there are formed four inwardly protruding surfaces 212, extending generally perpendicular to inner surface 202 of main body portion 200. Each of neighboring surfaces 212 is preferably arranged at a generally right angle with respect to its neighboring surfaces 212. Surfaces 212 and arms 204 are rotationally offset from one another about axis 201.

Figure 4:
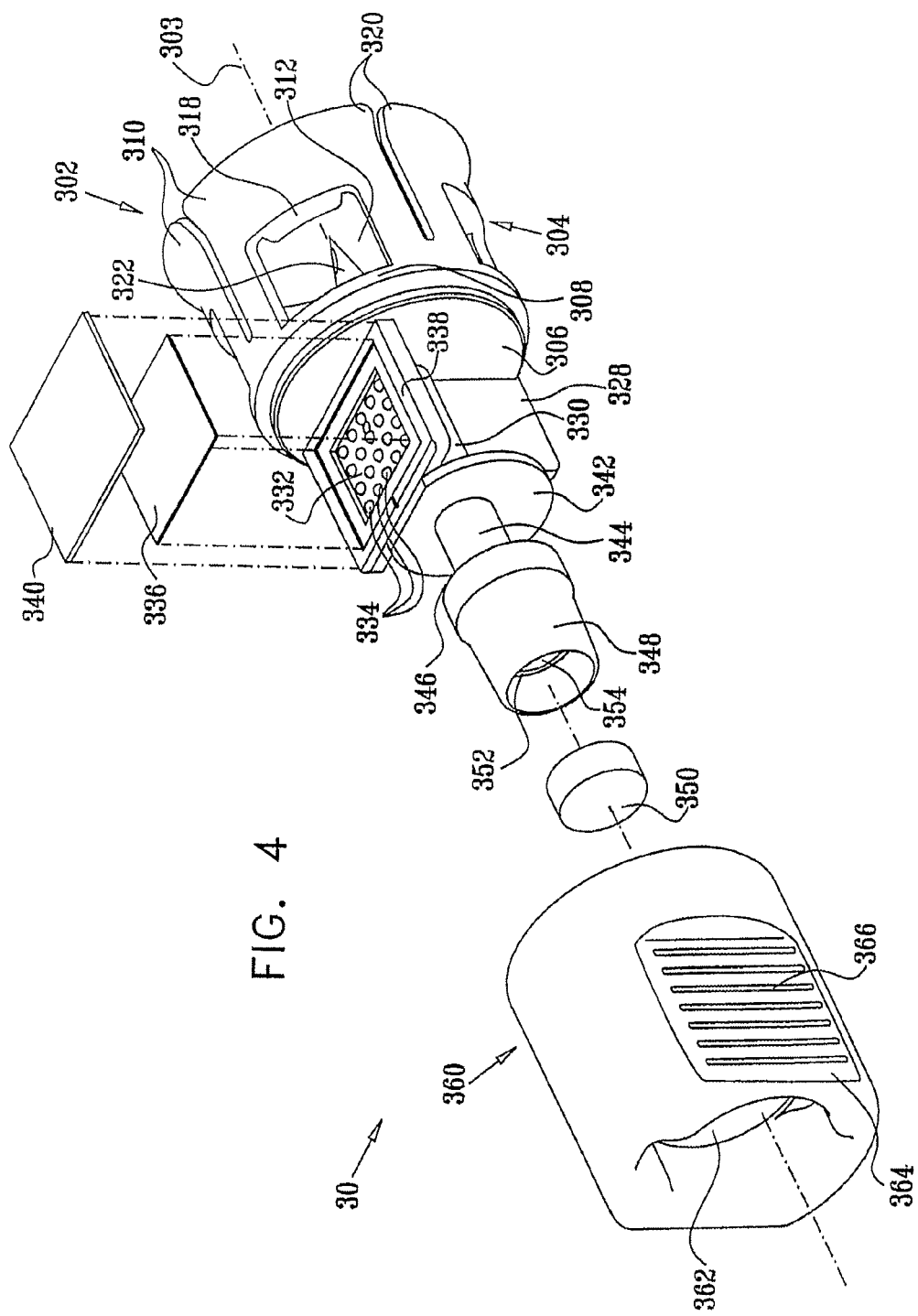
FIG. 4 is a simplified exploded view illustration of a vial adaptor assembly which forms part of the drug mixing system of FIGS. 1A-1M.
Figure 6A:
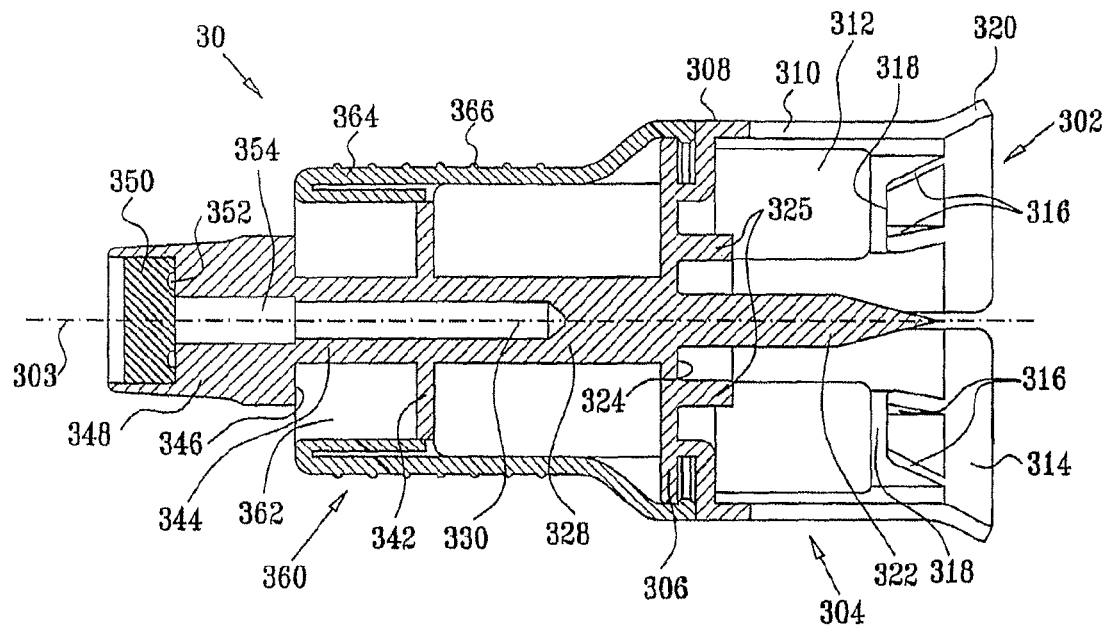
FIGS. 6A and 6B are sectional illustrations taken along respective section lines VIA-VIA and VIB-VIB in FIG. 5.
Figure 6B:
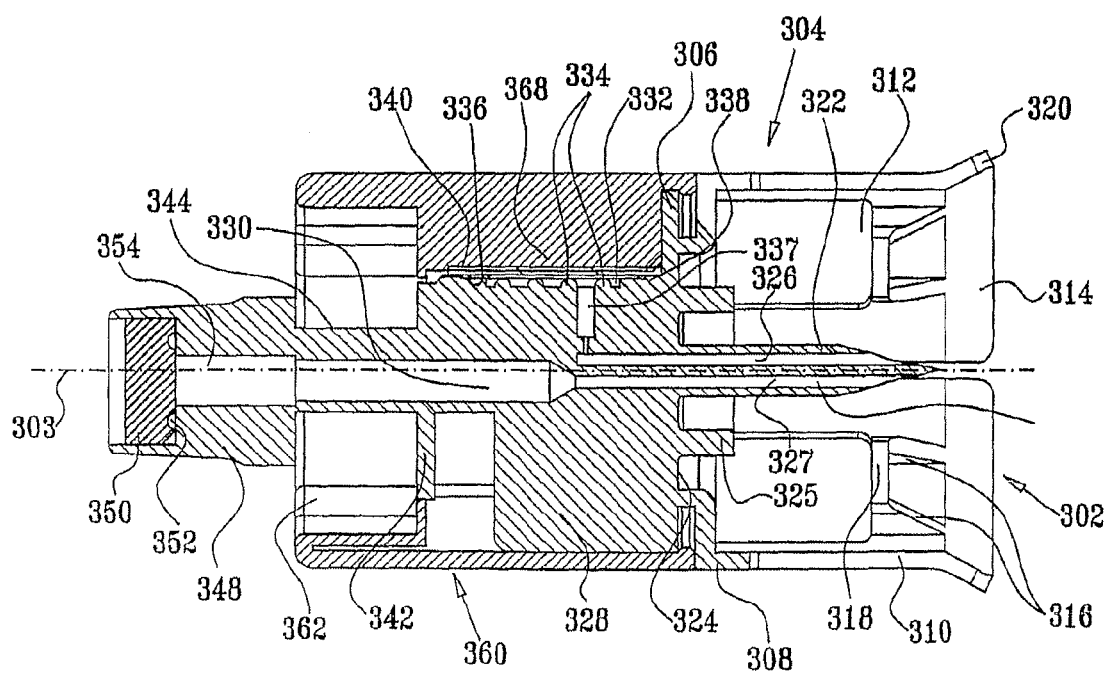

Reference is now made to FIG. 4, which is a simplified exploded view illustration of a preferred vial adaptor assembly 30 which forms part of the drug mixing system of FIGS. 1A-1M, to FIG. 5, which is a simplified assembled pictorial illustration of the vial adaptor assembly 30, and to FIGS. 6A and 6B, which are sectional illustrations taken along respective section lines VIA-VIA and VIB-VIB in FIG. 5.

As seen in FIGS. 4-6B, vial adaptor assembly 30 comprises a main body element 302 arranged generally about an axis 303. Main body element 302 is preferably integrally formed and preferably injection molded of plastic.

Main body element 302 is preferably side-to-side symmetric about axis 303, and preferably includes a rear portion 304, which is generally cylindrical and terminates in a forward wall 306. Rear portion 304 comprises a forward base section 308, rearward of which are preferably foisted four tabs 310 each having a rectangular window 312. Rearward of rectangular windows 312 and on an inner surface 314 of each of tabs 310 there are preferably formed two radially extending inwardly facing protrusions 316 each having an inclined surface. Protrusions 316 preferably terminate at a forward end thereof in an inwardly facing transversely extending protrusion 318. Rearward of protrusions 316, each of tabs 310 preferably includes an outwardly tapered portion 320.

A hollow vial puncturing spike 322 extends rearwardly from a rearward surface 324 of forward wall 306, and is surrounded by base section 308 and by tabs 310. Rearward surface 324 additionally includes a circular cylindrical protrusion 325, surrounding puncturing spike 322. Two radially extending bores 326 and 327 extend through vial puncturing spike 322.

Forward of forward wall 306 of rear portion 304 there is formed an intermediate portion 328 which is generally rectangular, and includes axial hollow tubular portion 330 which is in fluid flow engagement with bore 327 of vial puncturing spike 322.

At a top surface of intermediate portion 328 and slightly recessed with respect thereto there is formed a plastic membrane support surface 332, having formed thereon a plurality of generally evenly distributed spherical protrusions 334, which are adapted to support a hydrophobic membrane 336 and prevent it from excessive inflation and from cracking. Membrane 336 is adapted to allow free passage of air into the main body element 302, but to prevent passage therethrough of liquid and air-borne particles, microorganisms and aerosol. A preferred membrane 336 is Model Versapor R 0.2 Micron which is commercially available from Pall Corporation of New York, U.S.A. Membrane 336 is in fluid flow engagement with vial puncturing spike 322 via bore 326 and via a recess 337 formed in intermediate portion 328.

A rim 338 surrounding support surface 332 is adapted to support an optional carbon cloth filter 340 and maintain it in a raised position above and spaced from membrane 336. Carbon cloth filter 340 is adapted to prevent toxic vapors from escaping from main body element 302, thus protecting users. A preferred carbon cloth filter 340 is Model No. Zorflex EMI, which is commercially available from Charcoal Cloth International Ltd. of Houghton-le-Spring, England.

Intermediate portion 328 terminates at a forward end thereof in a generally circular wall 342. Forward of circular wall 342 there is formed a hollow neck portion 344, which is in fluid flow engagement with hollow tubular portion 330 and with hollow vial puncturing spike 322. Hollow neck portion 344 terminates at a forward end thereof in a generally circular wall surface 346.

Forward of neck portion 344 there is formed a forward facing portion 348, which is adapted to sealingly accommodate a generally circular septum 350 on a seat 352 which is located at a forward end of portion 348. Forward facing portion 348 defines a central bore 354 which communicates between tubular portion 330 and septum 350.

Vial adaptor assembly 30 preferably additionally includes a covering element 360 which supports and covers membrane 336 and carbon filter 340. Covering element 360 is a generally cylindrical, generally side-to-side symmetric, element and is preferably formed with a central opening 362 at a forward end thereof through which forward portion 348 extends.

A pair of outer side surfaces 364 of covering element 360 are each formed with ribbed grip regions 366. An inner top surface 368 of covering element 360 is preferably flat, and is adapted to support the top surfaces of membrane 336 and carbon filter 340 and to prevent excessive inflation and cracking thereof.

It is appreciated that the functionalities of membrane 336 and carbon cloth filter 340, to allow free passage of air into the drug mixing system while preventing passage thereinto of liquid and air-borne particles, microorganisms and aerosol and preventing toxic vapors from escaping from the drug mixing system, may be incorporated, using similar elements, into any of syringe adaptor element 50, spike port adaptor element 60 and needle port adaptor element 70.

Figure 7:
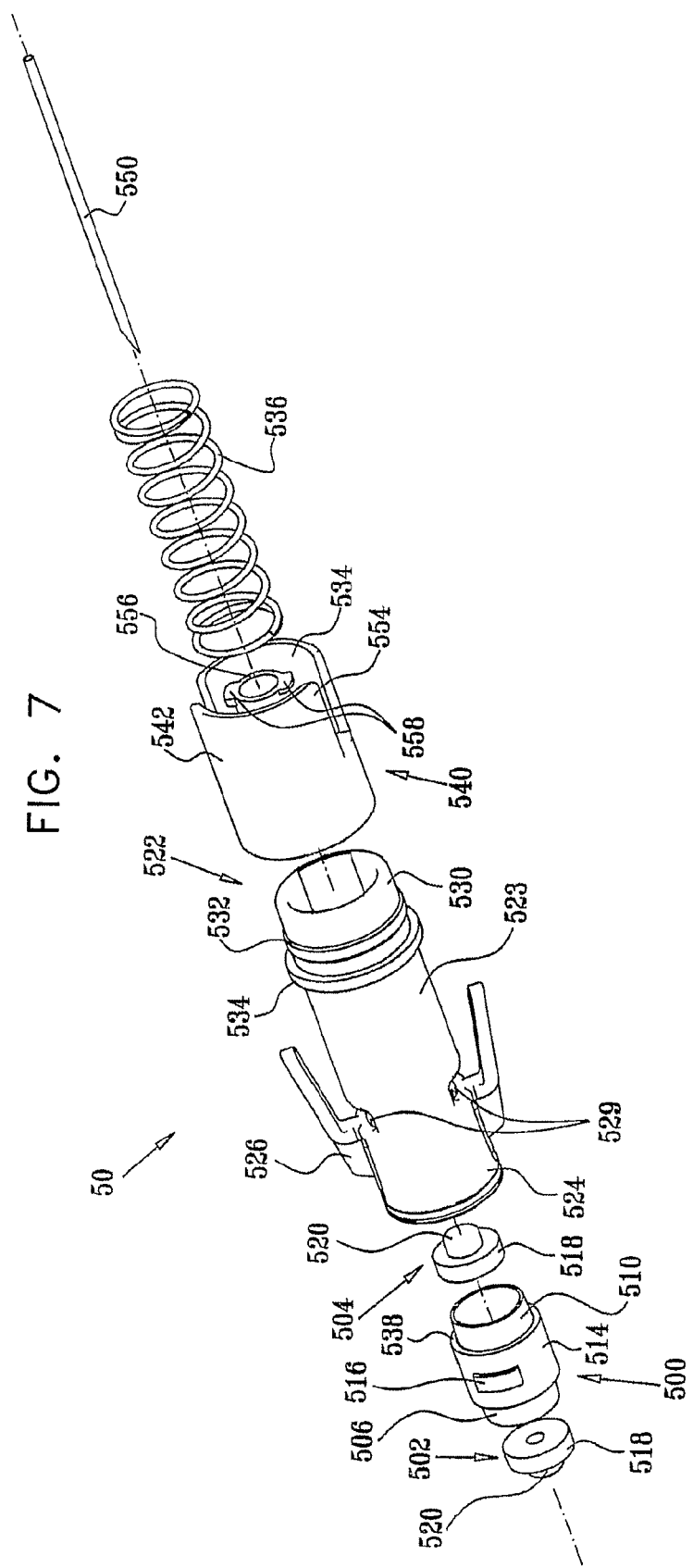
FIG. 7 is a simplified exploded view illustration of a syringe adaptor element which forms part of the drug mixing system of FIGS. 1A-1M.
Figure 8:
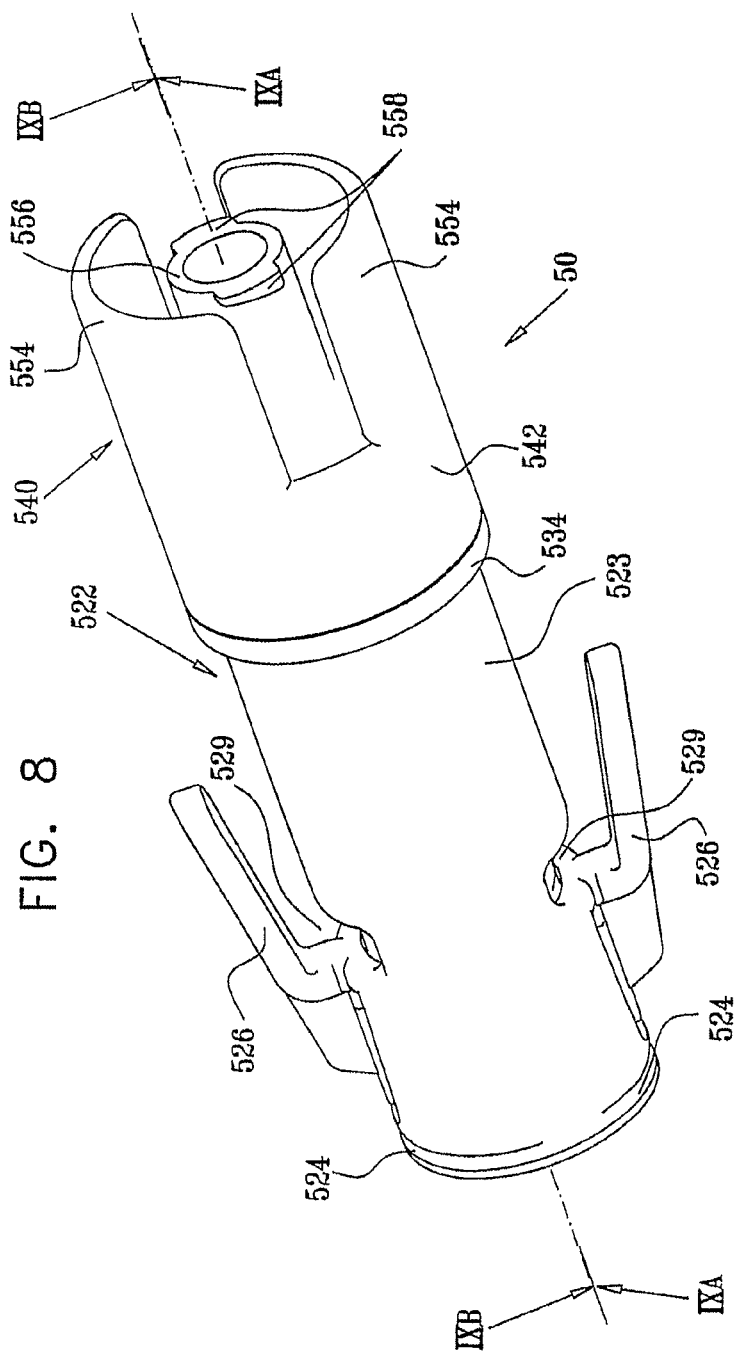
FIG. 8 is a simplified assembled pictorial illustration of the syringe adaptor element of FIG. 7.
Figure 9A:
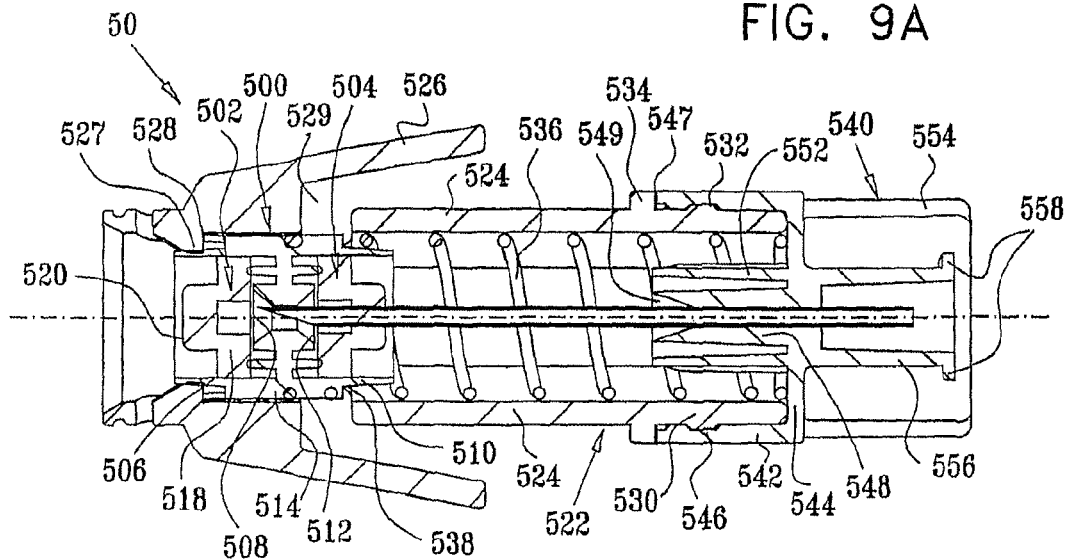
FIGS. 9A and 9B are sectional illustrations taken along respective section lines IXA-IXA and IXB-IXB in FIG. 8.
Figure 9B:
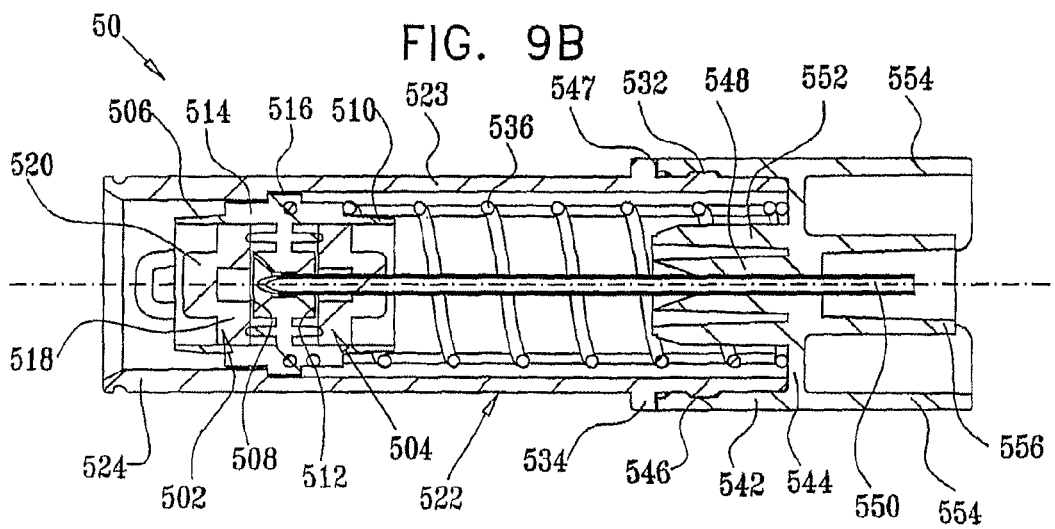
Figure 9C:
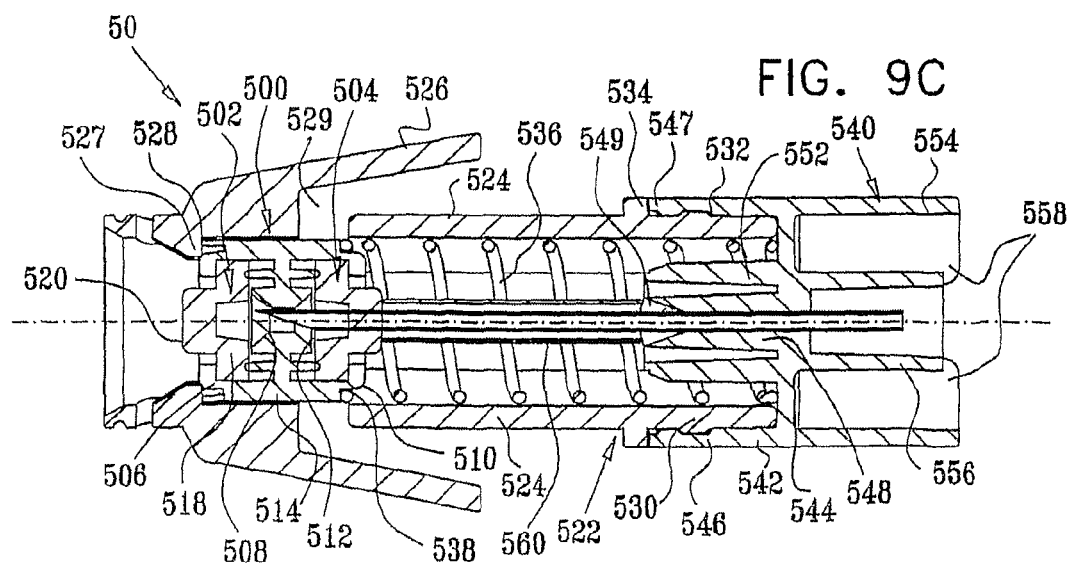
FIG. 9C is a sectional illustration of an alternative embodiment of the syringe adaptor element of FIG. 8, taken along section lines IXA-IXA in FIG. 8.

Reference is now made to FIG. 7, which is a simplified exploded view illustration of syringe adaptor element 50 which forms part of the drug mixing system of FIGS. 1A-1M, to FIG. 8, which is a simplified assembled pictorial illustration of syringe adaptor element 50 and to FIGS. 9A, 9B and 9C, which are sectional illustrations taken along respective section lines IXA-IXA and IXB-IXB in FIG. 8.

As seen with particular clarity in FIG. 7, syringe adaptor element 50 comprises a housing element 500, which has seated therein a forward septum 502 and a rearward septum 504.

Housing element 500 is preferably an integrally formed cylindrical hollow element made of plastic and is preferably side-to-side, top-to-bottom and forward-rearward symmetrical.

Preferably, a forward portion 506 of housing element 500 includes a seat 508 for forward septum 502, and a rear portion 510 of the housing element includes a seat 512 for rearward septum 504. An intermediate portion 514 of housing element 500 preferably includes on a top and a bottom surface thereof generally rectangular outwardly facing protrusions 516.

Septa 502 and 504 are preferably formed to have a generally circular portion 518 with a partially spherical protrusion 520 at one side thereof.

Surrounding housing element 500 there is formed a body 522, which defines a main body portion 523, which is generally cylindrical, preferably side-to-side and top-to-bottom symmetrical, and preferably formed of plastic, and side surfaces 524. Extending from a forward portion of each of side surfaces 524 is an outwardly protruding arm 526, defining at an inner facing forward end thereof a generally triangular tooth 527 having a transversely extending rearward facing surface 528 which is adapted to engage a forward facing surface of intermediate portion 514 of housing element 500.

Rearward of each of arms 526 there is formed a generally rectangular aperture 529. Adjacent a rearward portion 530 of housing element 500 there is formed a circumferential protrusion 532, forward of which is formed an additional circumferential protrusion 534, having a slightly larger outer circumference than that of protrusion 532.

A compression spring 536 is seated within housing element 500, on a shoulder 538 located between intermediate portion 514 and rear portion 510 of housing element 500.

A generally cylindrical rear sealing element 540 is located rearward of housing element 500. Rear sealing element 540 is preferably side to side symmetric, and is typically formed of plastic.

Rear sealing element 540 preferably defines a forward cowl 542 terminating at a rearward end thereof in a generally circular wall portion 544. Forward cowl 542 preferably includes a circumferential recess 546, which is adapted to engage circumferential protrusion 532 of housing element 500. A forward facing surface 547 of sealing element 540 is adapted to engage a rearward facing surface of additional circumferential protrusion 534 when the syringe adaptor element 500 is assembled. Wall portion 544 preferably defines a rear spring seat for compression spring 536.

A tapered inner portion 548 of rear sealing element 540, which has a smaller circumference than that of housing element 500, is preferably therewithin at a rear portion thereof. Inner portion 548 is formed forward of and immediately adjacent to wall portion 544 and lies within compression spring 536. A radially extending bore 549 is preferably formed in inner portion 548 and a hollow needle 550 is sealingly mounted therein. Inner portion 548 is preferably surrounded by a cylindrical portion 552, which terminates at a rearward end thereof in wall portion 544 and which also has a circumference which is smaller than that of housing element 500.

Needle 550 preferably extends axially within compression spring 536 and through the center of housing element 500 and rearward septum 504. A sharpened tip of needle 550 is preferably placed between forward septum 502 and rearward septum 504, thus maintaining the needle inaccessible to a user and to the atmosphere.

Two generally concave symmetric surfaces 554 forming a nearly complete cylinder, may extend rearwardly of wall portion 544 and preferably surround an inner rearward cylindrical portion 556, which is adapted to engage the luer tip 44 of luer fitted syringe 40, defining generally symmetric side-facing tabs 558 at rearward ends thereof. The rear portion of needle 550 preferably extends axially within inner cylindrical portion 556.

Referring specifically to FIG. 9C, which illustrates an alternative embodiment of the syringe adaptor element of FIG. 8, it is seen that a needle protector 560, preferably made of latex, at least partially covers needle 550, thus protecting it from the surrounding atmosphere.

Figure 10:
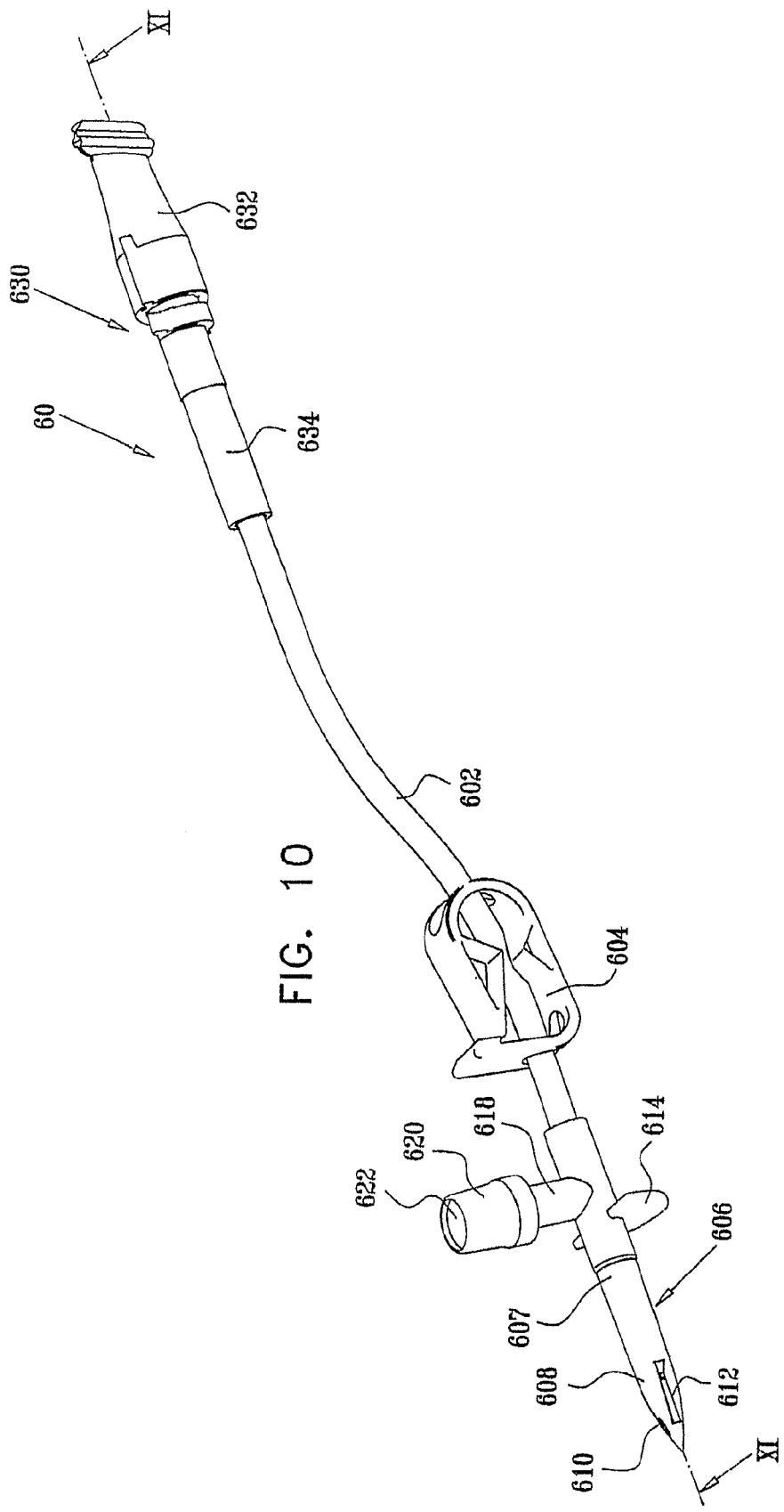
FIG. 10 is a simplified pictorial illustration of a spike port adaptor element which forms part of the drug mixing system of FIGS. 1A-1M.

Reference is now made to FIG. 10, which is a simplified pictorial illustration of spike port adaptor element 60 which forms part of the drug mixing system of FIGS. 1A-1M and to FIGS. 11A and 11B which are sectional illustrations taken along section lines XI-XI in FIG. 10.

Spike port adaptor element 60 preferably comprises a hollow flexible plastic tube 602 having associated therewith a standard clamp 604, which is commercially available from various manufacturers, such as Qosina of Italy.

At a forward end thereof, tube 602 is fitted with a hollow spike element 606 which is preferably side-to-side symmetric and formed of plastic. Spike element 606 is preferably formed of a main body portion 607 which preferably defines at a forward end thereof a spike 608, having formed therein apertures communicating with two axially extending bores 610 and 612. Rearward of spike 608, main body portion 607 defines a generally semi-circular planar protrusion 614 adapted to define the location at which a user grips the spike.

Alternatively, as seen with particular clarity in FIG. 11B, main body portion 607 may have formed therein a single aperture, which communicates with a single axially extending bore 615.

The interior of tube 602 is in fluid flow communication with bore 612. A bore 616 formed in a neck portion 618 which preferably extends transversely from main body portion 607 and communicates with bore 610. Hollow neck portion 618 preferably terminates in a forward facing cylindrical portion 620, which sealingly accommodates a generally circular septum 622 located on a seat 624 which communicates with bore 616.

A sealing assembly 630 is preferably attached to a rear end of tube 602. Sealing assembly 630 preferably includes at a rearwardmost end thereof a selectably removable tapered sealing section 632, forward of which there is formed a connecting tube portion 634 which is adapted to connect sealing section 632 to tube 602. Sealing assembly 630 is adapted to seal tube 602 during use of the drug mixing device, and may be removed from tube 602 when receptacle 62 is connected directly to an infusion set spike for infusion of the fluid contained therein to a patient.

It is appreciated that the spike connector of connection assembly 630 of spike port adaptor element 60 may optionally be replaced by a luer connector.

Figure 13A:
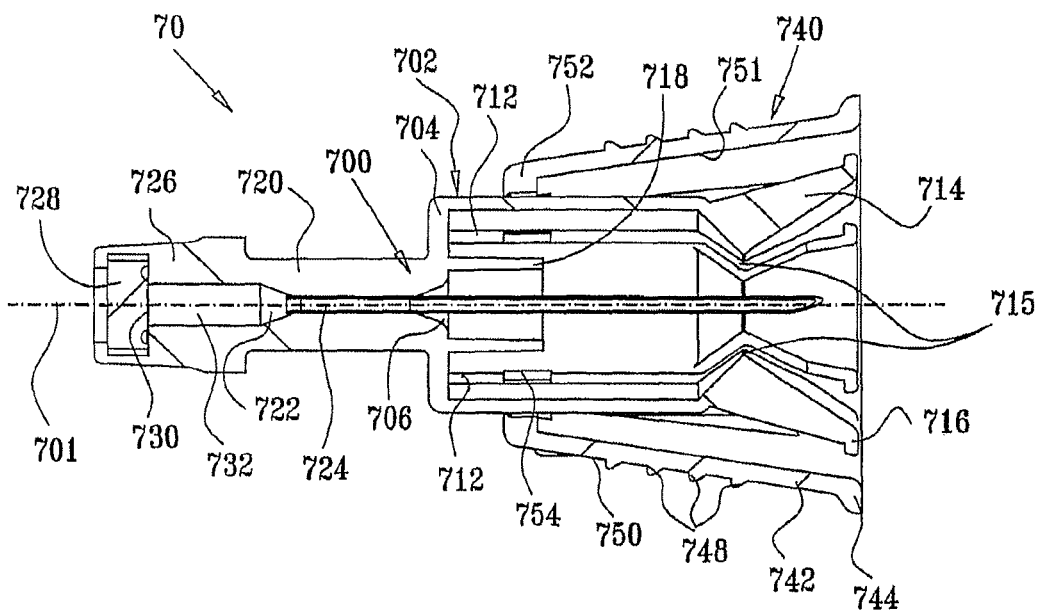
FIGS. 13A and 13B are sectional illustrations taken along respective section lines XIIIA-XIIIA and XIIIB-XIIIB in FIG. 12A.
Figure 13B:
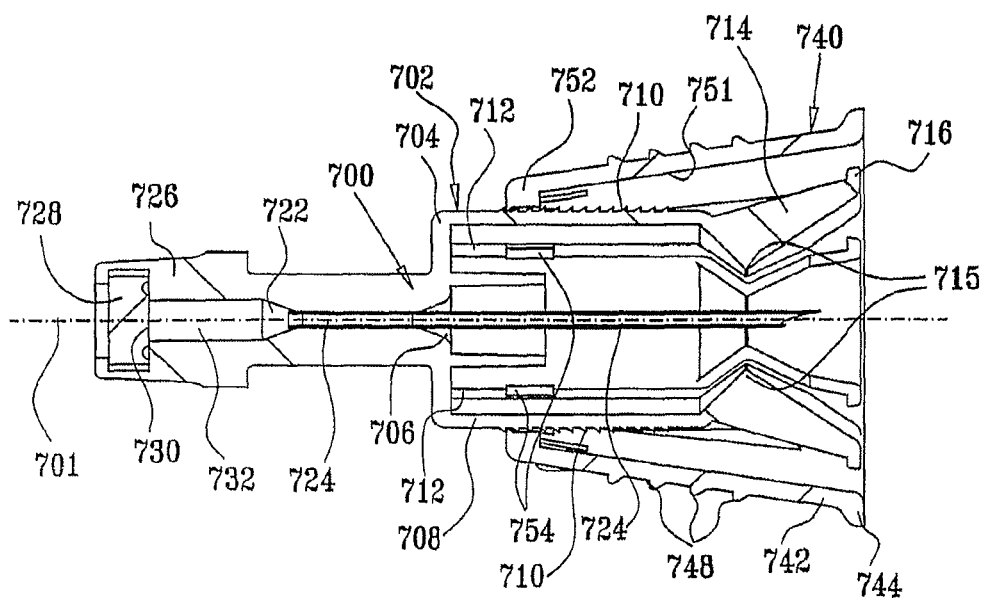

Reference is now made to FIGS. 12A and 12B, which are simplified pictorial illustrations of needle port adaptor element 70 which forms part of the drug mixing system of FIGS. 1A-1M and to FIGS. 13A and 13B, which are sectional illustrations taken along respective section lines XIIIA-XIIIA and XIIIB-XIIIB in FIG. 12A.

Needle port adaptor element 70 preferably comprises a main body element 700 arranged generally about an axis 701. Main body element 700 is preferably integrally formed and preferably injection molded of plastic.

Main body element 700 is preferably side-to-side symmetric about axis 701, and preferably includes a rear portion 702 which is generally cylindrical, terminating in a forward wall portion 704 having a bore 706 extending therethrough. Each of side surfaces 708 of rear portion 702 preferably includes a ribbed engagement surface portion 710.

Four axially extending slots 712 extend along rear portion 702, each slot 712 being arranged at generally right angles with respect to its neighboring slots. Defined between slots 712 at a rearward facing end of rear portion 702 are four outwardly tapering tabs 714. Each tab 714 includes an inwardly facing generally triangular tooth 715 and terminates in a transversely extending section 716. Rear portion 702 preferably surrounds a generally cylindrical portion 718, which extends rearwardly from forward wall portion 704.

Forward of wall portion 704 there is formed a neck portion 720, defining a radially extending bore 722. A hollow needle 724 is adhesively mounted in bore 722 and extends rearwardly thereof along axis 701.

Forward of neck portion 720 there is formed a forward facing cylindrical portion 726, which sealingly supports a generally circular septum 728 on a seat 730 which is located at a forward end of cylindrical portion 726. A bore 732 preferably extends radially through forward facing cylindrical portion 726. Bore 732 is preferably in fluid flow engagement with the interior of hollow needle 724.

A generally conical cover element 740 which is generally side-to-side and top-to-bottom symmetric about axis 701 preferably is axially slidable with respect to main body element 700 for selectably surrounding rear portion 702 of main body element 700.

A rear portion 742 of cover element 740 is preferably outwardly tapered, and terminates in a transversely extending edge surface 744. Four outwardly facing radially extending protrusions 746 lie along an outer surface of cover element 740, each protrusion 746 being arranged at generally right angles with respect to its neighboring protrusions.

Four outwardly facing generally circumferential protrusions 748 are preferably formed on an outer surface 750 of cover element 740 between protrusions 746 thus defining a grip region.

At a forward end thereof, an inner surface 751 of cover element 740 includes an inwardly tapered section 752, which is adapted to slidably engage ribbed engagement surface portion 710 of rear portion 702 of main body element 700. Four generally rectangular inwardly facing protrusions 754 extend from section 752, each protrusion 754 being arranged at generally right angles with respect to its neighboring protrusions. Protrusions 754 are adapted to slidably engage slots 712 of rear portion 702 of main body element 700.

Figure 14:
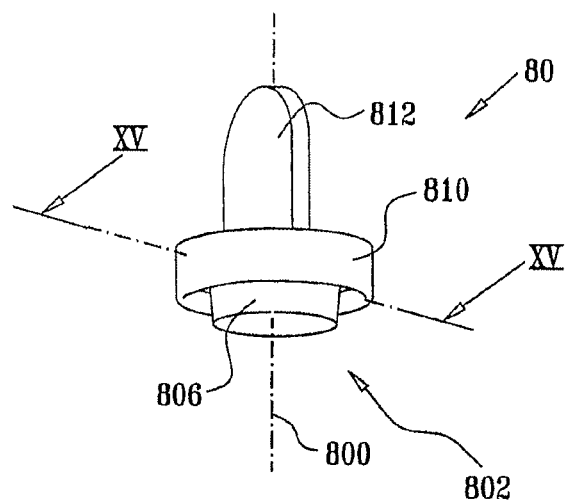
FIG. 14 is a simplified pictorial illustration of a syringe protection cover which fours part of the drug mixing system of FIGS. 1A-1M.
Figure 15:
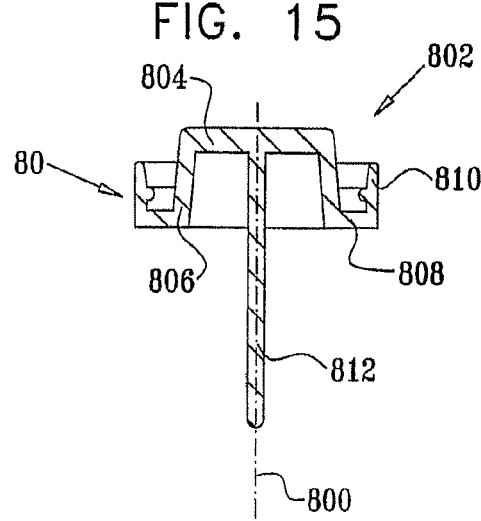
FIG. 15 is a sectional illustration taken along section lines XV-XV in FIG. 14.

Reference is now made to FIG. 14, which is a simplified pictorial illustration of syringe protection cover 80 which forms part of the drug mixing system of FIGS. 1A-1M and to FIG. 15, which is a sectional illustration taken along section lines XV-XV in FIG. 14.

Syringe protection cover 80 is preferably integrally formed, and is generally side to side symmetric about an axis 800. A generally circular locking element 802 is preferably formed at a bottom end of syringe protection cover 80.

Locking element 802 preferably includes a flat generally circular base surface 804, preferably extending along a plane which is perpendicular to axis 800. Surface 804 is integrally formed with a generally cylindrical portion 806. Cylindrical portion 806 terminates in a generally circular radially outwardly extending wall portion 808, which lies in a plane parallel to that defined by surface 804. Wall portion 808 terminates in a generally cylindrical portion 810, which generally surrounds cylindrical portion 806. An elongate tab 812 extends from surface 804 along axis 800.

Figure 16:
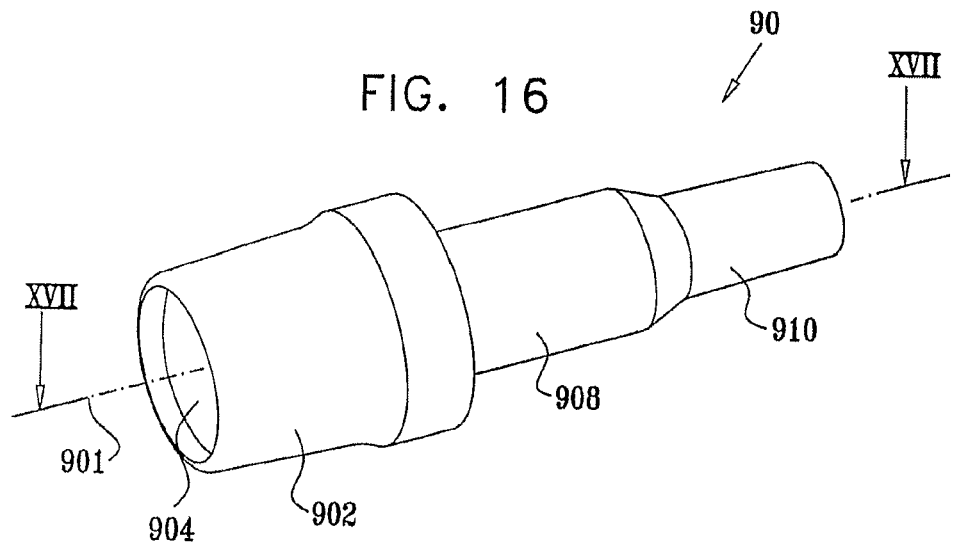
FIG. 16 is a simplified pictorial illustration of an injection set adaptor element which forms part of the drug mixing system of FIGS. 1A-1M.
Figure 17:
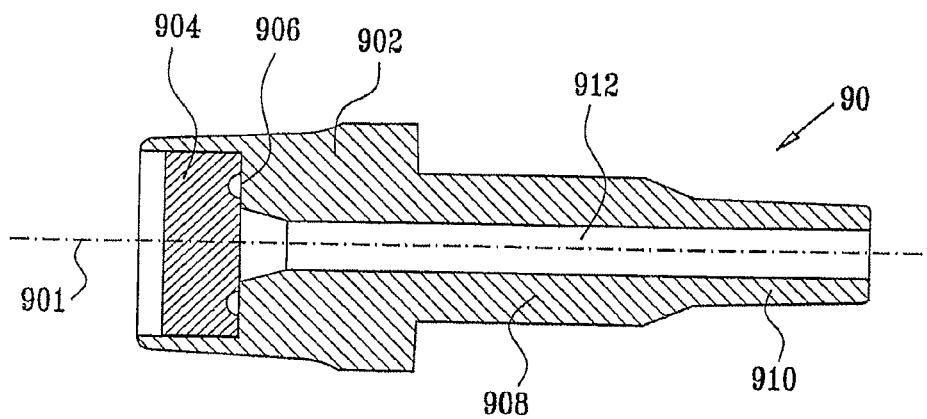
FIG. 17 is a sectional illustration taken along section lines XVII-XVII in FIG. 16.

Reference is now made to FIG. 16, which is a simplified pictorial illustration of infusion set adaptor element 90 which forms part of the drug mixing system of FIGS. 1A-1M and to FIG. 17, which is a sectional illustration taken along section lines XVII-XVII in FIG. 16.

As seen in FIGS. 16 and 17, infusion set adaptor element 90 is preferably integrally formed, and preferably is side-to-side symmetric along an axis 901.

Infusion set adaptor element 90 preferably includes a forward facing cylindrical portion 902, which is adapted to surround a generally circular septum 904 which is sealingly mounted onto a seat 906 which is located at a forward end of cylindrical portion 902.

A generally cylindrical intermediate portion 908 is formed rearward of cylindrical portion 902, having an outer circumference which is slightly smaller than that of cylindrical portion 902. At a rear end thereof, intermediate portion 908 tapers toward a cylindrical neck portion 910, which has an outer circumference which is smaller than that of intermediate portion 908.

An axially extending bore 912 extends through neck portion 910, intermediate portion 908 and cylindrical portion 902, thus allowing fluid flow through infusion set adaptor element 90 when the septum 904 is suitably pierced.

The assembled structure of the drug mixing system at various stages of use thereof is described hereinbelow with reference to FIGS. 18A-30.

Reference is now made to FIGS. 18A and 18B which are, respectively, a simplified planar illustration and a simplified sectional illustration of the drug mixing system of FIG. 1B during attachment of vial adaptor 30, the sectional illustration being taken along lines XVIIIB-XVIIIB in FIG. 18A.

As seen with particular clarity in FIG. 18B, vial puncturing spike 322 of vial adaptor assembly 30 punctures septum 31 located inside top portion 12 of vial 10, thus enabling fluid flow between the main body of vial 10 and forward facing portion 348 of main body element 302 of vial adaptor assembly 30. Preferably, puncturing of septum 31 releases any vacuum in vial 10 by entrance of air into vial 10 through carbon filter 340 (FIGS. 4 and 6B) and membrane 336 (FIGS. 4 and 6B).

Engagement between vial adaptor assembly 30 and vial 10 is preferably maintained by snap engagement of protrusions 316 and 318 of rear portion 304 of main body element 302 with a neck portion 13 of vial 10. The engagement of protrusions 316 and 318 with neck portion 13 ensures that vial adaptor assembly 30 is latched onto vial 10 and cannot be removed therefrom. Tabs 310 and outwardly tapered portions 320 generally surround top portion 12 and neck portion 13 of vial 10.

Reference is now made to FIGS. 19A and 19B and to FIGS. 19C and 19D which are, respectively, a top and a side view simplified planar illustration and a simplified sectional illustration of the drug mixing system of FIG. 1C during attachment of the syringe adaptor element 50 to syringe 40, the sectional illustrations being taken along lines XIXB-XIXB in FIG. 19A and XIXD-XIXD in FIG. 19C.

As seen in FIGS. 19A-19D, luer 44 of luer fitted hypodermic syringe 40 preferably engages inner rearward cylindrical portion 556 of sealing element 540 of syringe adaptor element 50 and tabs 558 formed thereon, such that needle 550 is in fluid flow engagement with the hollow body of syringe 40.

At this stage, the sharpened tip of needle 550 is preferably placed between septa 502 and 504, and compression spring 536 is relaxed. Preferably, when syringe 40 is connected to syringe adaptor assembly 50, plunger 42 of syringe 40 is pushed fully inward with respect to the syringe.

Reference is now made to FIG. 20, which is a partially pictorial partially sectional illustration of the drug mixing system of FIG. 1D during attachment of spike port adaptor element 60.

As seen in FIG. 20, spike 608 of spike element 606 of spike port adaptor element 60 is preferably inserted into a spike port 61 of receptacle 62. At this stage, receptacle 62 and tube 602 are in fluid flow engagement. However, clamp 604 is closed and prevents fluid from flowing out of the receptacle through bore 612 into tube 602. Additionally, bore 610 is in fluid flow communication with cylindrical portion 620 via bore 616 of neck portion 618.

Reference is now made to FIG. 21, which is a partially pictorial partially sectional illustration of the drug mixing system of FIG. 1D during attachment of needle port adaptor element 70.

As seen in FIG. 21, needle 724 of needle port adaptor element 70 is preferably inserted into needle port 64 of receptacle 62. Preferably, teeth 715 of tabs 714 engage port 64 when needle 724 is inserted. Additionally, after needle 724 is inserted, cover element 740 is preferably moved with respect to main body element 700 along ribbed engagement surface portion 710 (FIG. 13B).

The axial displacement of cover element 740 preferably seals and locks the connection between main body element 700 and port 64, by pressing on tabs 714 and pushing them inward. Displacement of cover element 740 includes a corresponding axial displacement of protrusions 754 with respect to slots 712 of rear portion 702 of main body element 700. The axial displacement terminates when sections 716 of tabs 714 engage inner surface 751 of cover element 740.

At this stage, receptacle 62 is preferably in fluid flow engagement with bore 732 of cylindrical portion 726 via intermediate portion 720 and needle 724. However, fluid does not flow out of cylindrical portion 726, as the cylindrical portion is sealed by septum 728.

Figure 22:
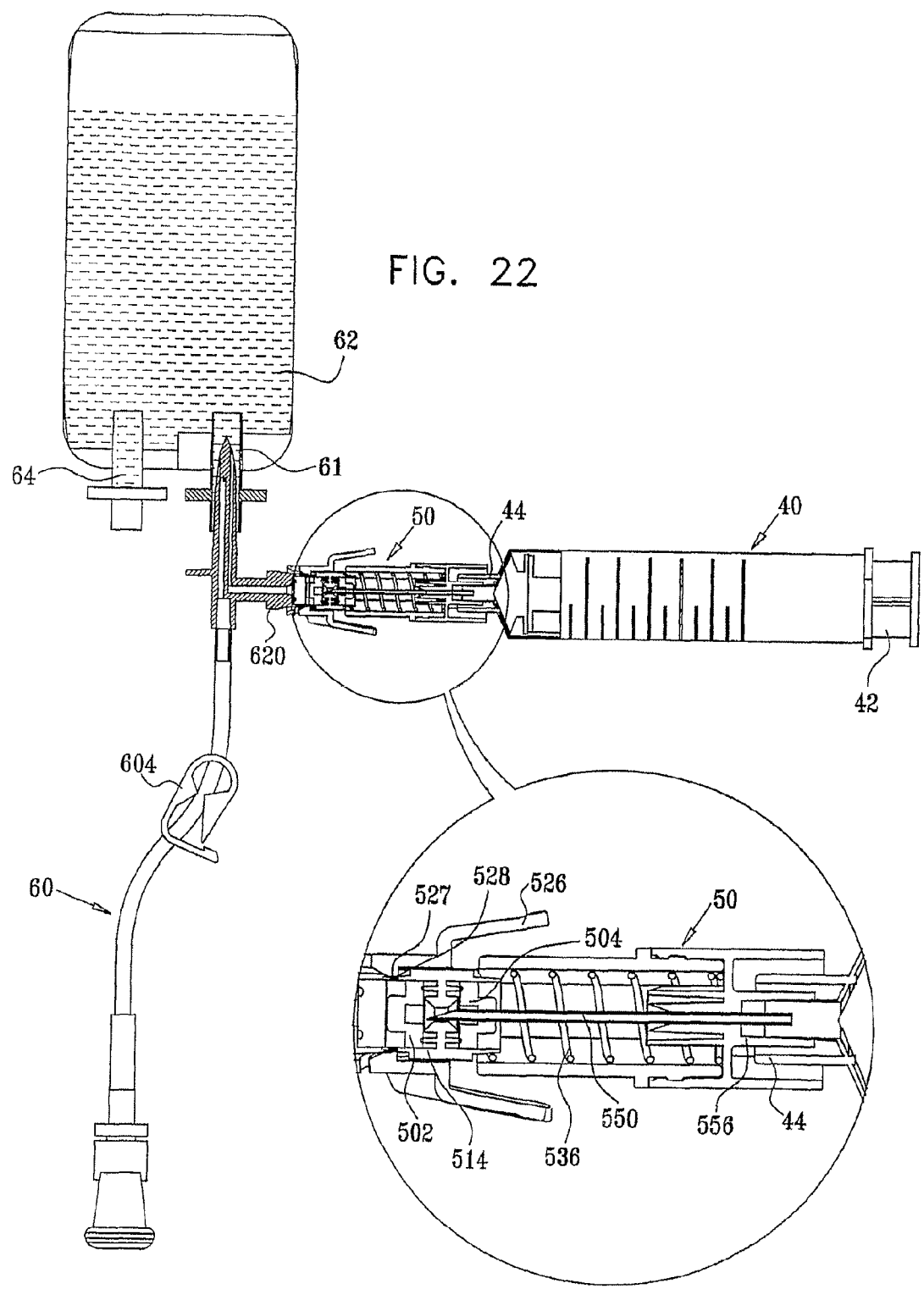
FIG. 22 is a partially pictorial partially sectional illustration of the drug mixing system of FIGS. 1E and 20 prior to syringe attachment.

Reference is now made to FIG. 22, which is a partially pictorial partially sectional illustration of the drug mixing system of FIGS. 1E and 20 prior to the attachment of syringe 40 and syringe adaptor element 50 to spike port adaptor element 60.

As seen in FIG. 22, syringe adaptor element 50 and syringe 40 joined thereto are placed in close proximity to cylindrical portion 620 of spike port adaptor element 60. It is appreciated that at this stage compression spring 536 is relaxed and the sharpened tip of needle 550 is preferably placed between septa 502 and 504. Preferably, surfaces 528 of teeth 527 of arms 526 engage forward facing surfaces on either side of intermediate portion 514 of housing element 500.

Throughout the engagement process, septum 622 of spike port adaptor element 60 and septum 502 of syringe adaptor element 50 are pushed into touching engagement by the biasing force of spring 536, thus preventing exposure of the tip of needle 550 to the environment.

Figure 23:
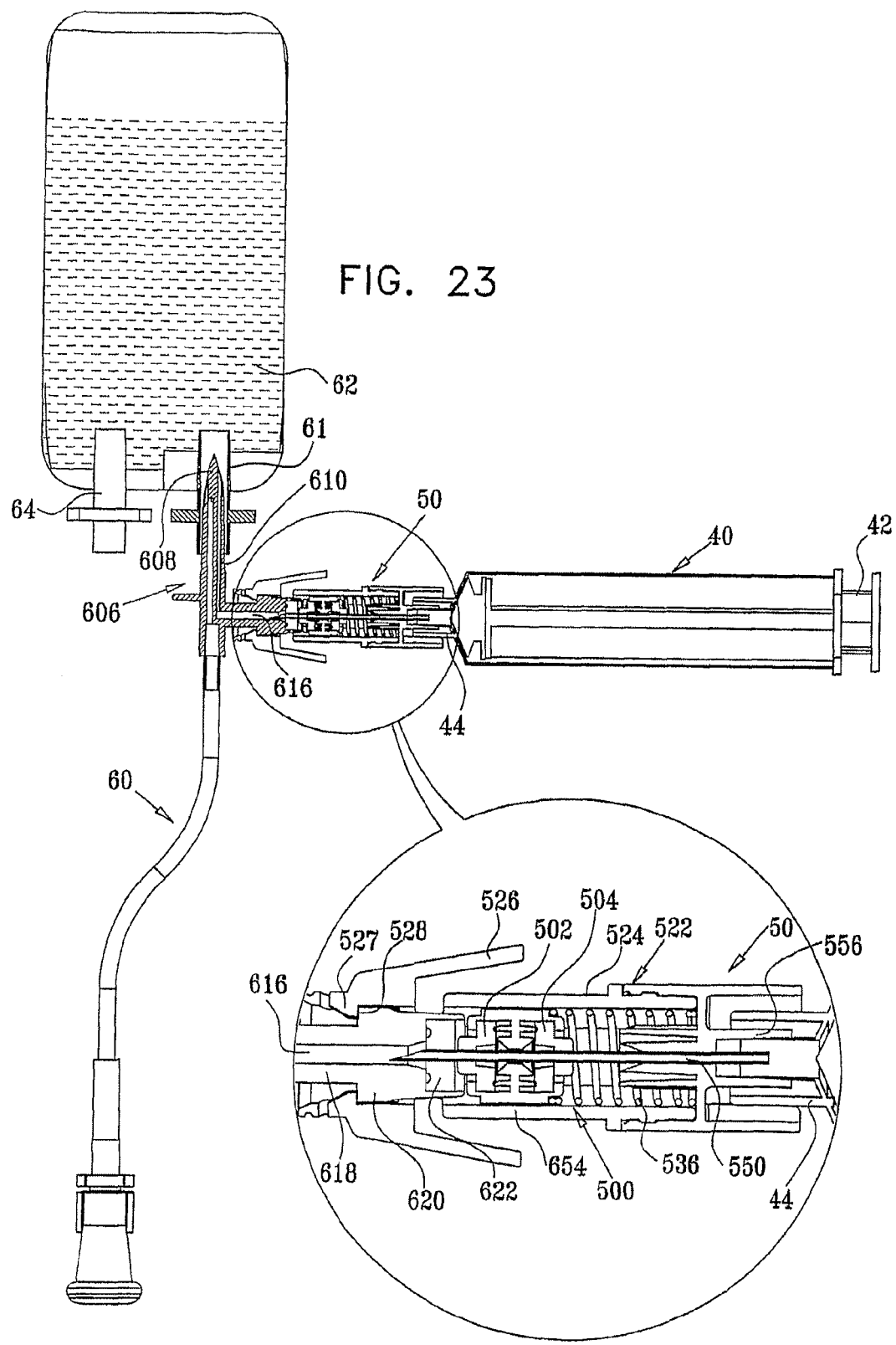
FIG. 23 is a partially pictorial partially sectional illustration of the drug mixing system of FIGS. 1E and 20 following syringe attachment.

Reference is now made to FIG. 23, which is a partially pictorial partially sectional illustration of the drug mixing system of FIGS. 1E and 20 following the attachment of syringe 40 and syringe adaptor element 50 to spike port adaptor element 60.

As seen in FIG. 23 syringe adaptor element 50 and syringe 40 joined thereto are pushed into engagement with cylindrical portion 620 of spike port adaptor element 60. Preferably, surfaces 528 of teeth 527 of arms 526 snap into engagement with wall portion 618, thus ensuring that the engagement between syringe adaptor element 50 and cylindrical portion 620 is secure. At this stage, spring 536 is in a compressed state, and housing element 500 is pushed rearwardly by the pressure from cylindrical portion 620.

The rearward motion of housing element 500 causes the sharpened tip of needle 550 to pierce septa 502 and 622. As a result, needle 550 partially extends through the hollow space in cylindrical portion 620, and is in fluid flow engagement with receptacle 62 via bore 610 of spike 608 of spiked element 606 and via bore 616 of neck portion 618. Due to the fluid flow engagement between luer 44 of syringe 40 and needle 550 of syringe adaptor element 50, the syringe 40 is now in fluid flow engagement with receptacle 62. It is appreciated that when using the syringe adaptor element described in FIG. 9C, needle protector 560 at least partially collapses, thus exposing the needle 550.

In order to draw fluid from receptacle 62 into syringe 40 via spiked element 606, bore 616 of neck portion 618, cylindrical portion 620 and needle 550, a user retracts plunger 42. In order to disengage syringe adaptor element 50 and cylindrical portion 620, a user pushes slightly on arms 526 extending from side surfaces 524 of housing element 522, causing teeth 527 to move outward and release a rearward facing surface of cylindrical portion 620, thus disconnecting the cylindrical portion.

Throughout the disengagement process, septum 622 of spike port adaptor element 60 and septum 502 of syringe adaptor element 50 are pushed into touching engagement by the biasing force of spring 536, thus preventing exposure of the tip of needle 550 to the environment.

Figure 24:
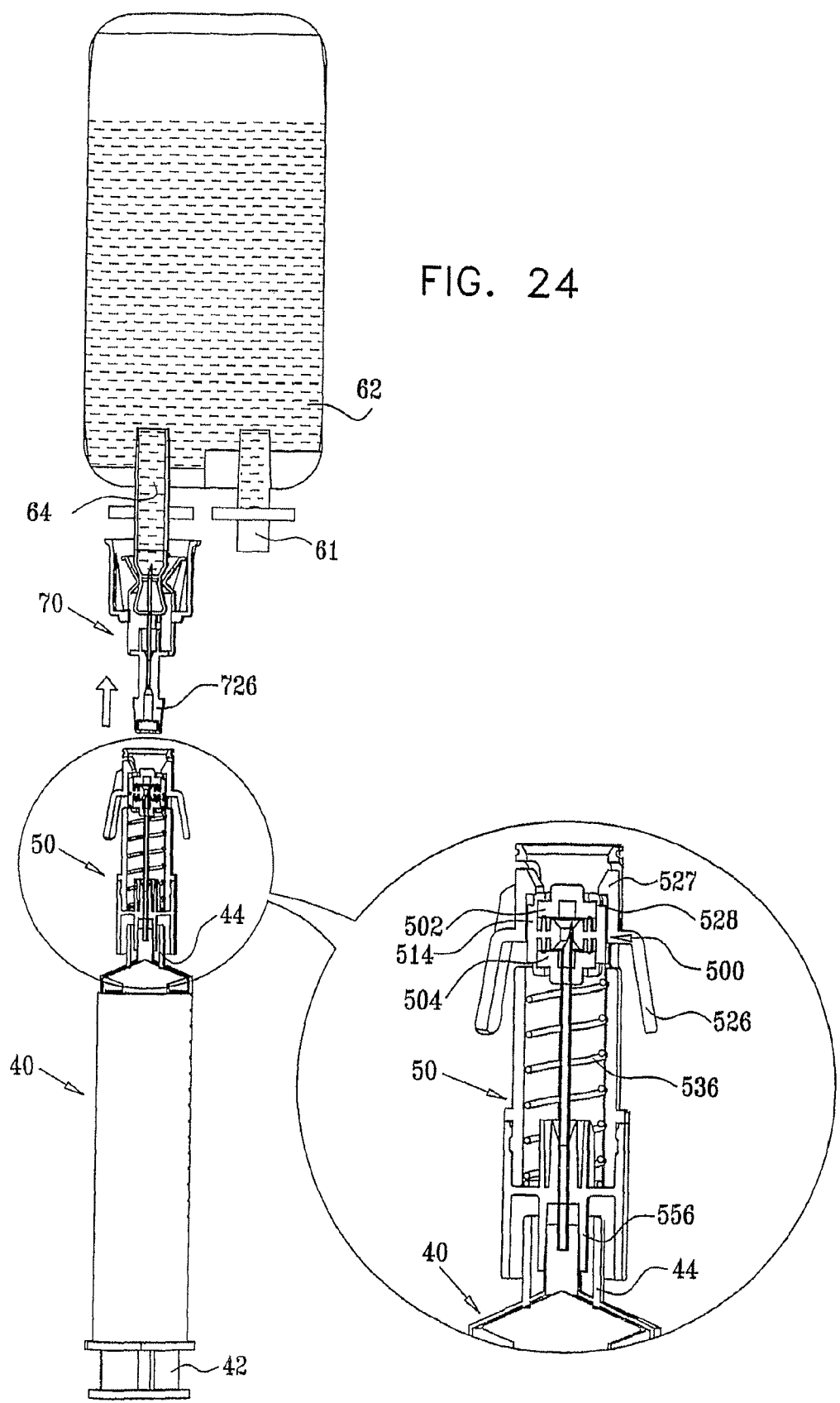
FIG. 24 is a partially pictorial partially sectional illustration of the drug mixing system of FIGS. 1E and 21 prior to syringe attachment.

Reference is now made to FIG. 24, which is a partially pictorial partially sectional illustration of the drug mixing system of FIGS. 1E and 21 prior to the attachment of syringe 40 and syringe adaptor element 50 to needle port adaptor element 70. As seen in FIG. 24, syringe adaptor element 50 and syringe 40 joined thereto are placed in close proximity to cylindrical portion 726 of needle port adaptor element 70. It is appreciated that at this stage compression spring 536 is relaxed and the sharpened tip of needle 550 is preferably located between septa 502 and 504. Preferably, surfaces 528 of teeth 527 of arms 526 engage forward facing surfaces on either side of intermediate portion 514 of housing element 500.

Figure 25:
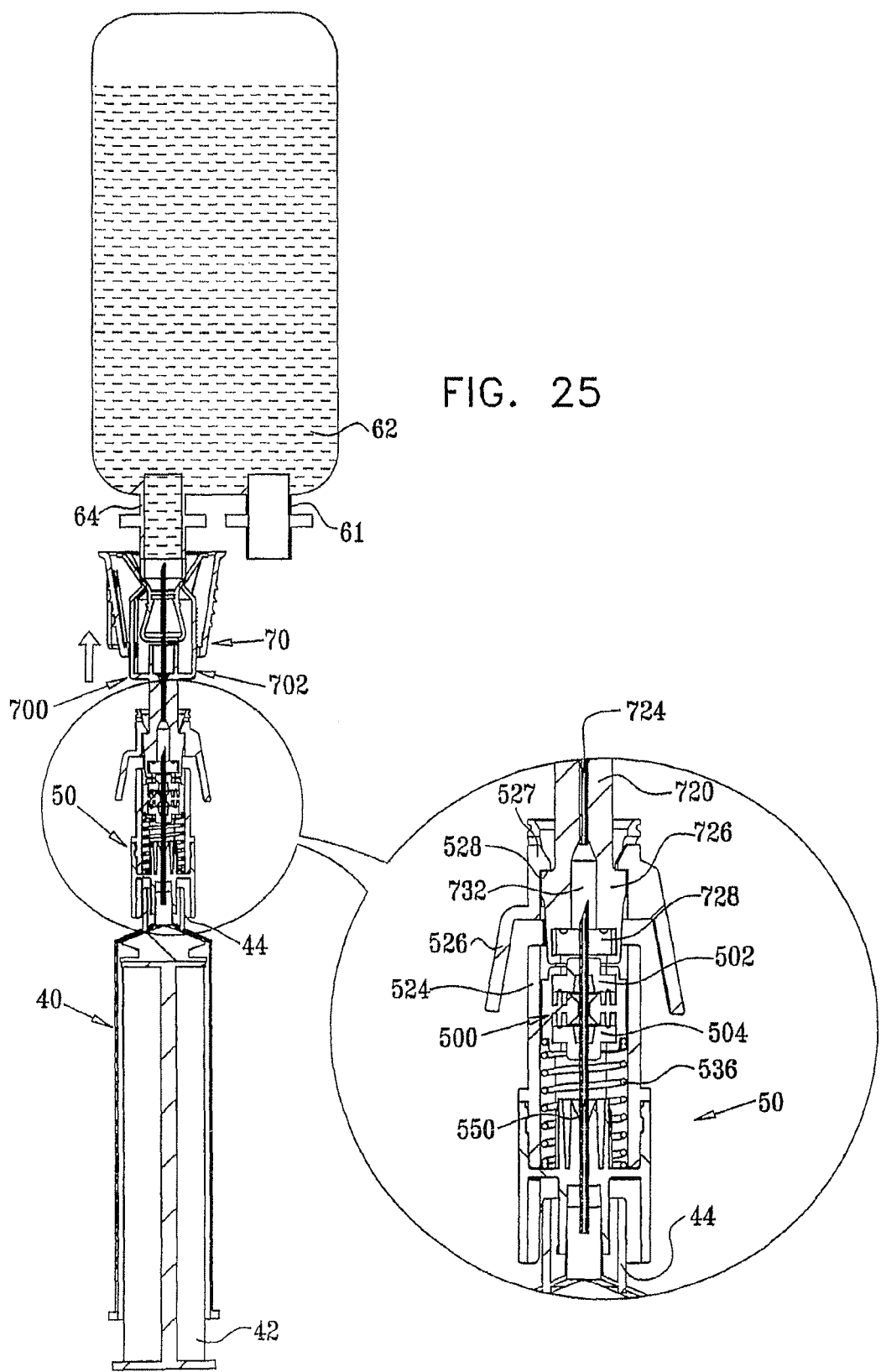
FIG. 25 is a partially pictorial partially sectional illustration of the drug mixing system of FIGS. 1E and 21 following syringe attachment.

Reference is now made to FIG. 25, which is a partially pictorial partially sectional illustration of the drug mixing system of FIGS. 1E and 21 following the attachment of syringe 40 and syringe adaptor element 50 to needle port adaptor element 70. As seen in FIG. 25 syringe adaptor element 50 and syringe 40 joined thereto are pushed into engagement with cylindrical portion 726 of needle port adaptor element 70.

Preferably, surfaces 528 of teeth 527 of arms 526 snap to engage a rearward facing wall portion of cylindrical portion 726, thus ensuring that the engagement between syringe adaptor element 50 and cylindrical portion 726 is secure. At this stage, spring 536 is in a compressed state, and housing element 500 is pushed rearwardly by the pressure from cylindrical portion 726.

The rearward motion of housing element 500 causes the sharpened tip of needle 550 to pierce septa 502 and 728. As a result, needle 550 partially extends through bore 732 of cylindrical portion 726, and is in fluid flow engagement with receptacle 62 via needle 724 of rear portion 702, neck portion 720 of main body element 700 and bore 732 of cylindrical portion 726. Due to the fluid flow engagement between luer 44 of syringe 40 and needle 550 of syringe adaptor element 50, the syringe 40 is now in fluid flow engagement with receptacle 62. It is appreciated that when using the syringe adaptor element described in FIG. 9C, needle protector 560 at least partially collapses, thus exposing the needle 550.

In order to draw fluid from receptacle 62 into syringe 40 via needle 724, bore 732 and needle 550, a user retracts plunger 42. In order to disengage syringe adaptor element 50 and cylindrical portion 726, a user pushes slightly on arms 526 extending from side surfaces 524 of housing element 522, causing teeth 527 to move outward and release a rearward facing wall portion of cylindrical portion 726, thus disconnecting cylindrical portion 726.

Throughout the engagement and disengagement process, septum 728 of needle port adaptor element 70 and septum 502 of syringe adaptor element 50 are pushed into touching engagement by the biasing force of spring 536, thus preventing exposure of the tip of needle 550 to the environment.

Reference is now made to FIG. 26, which is a sectional illustration of the drug mixing system of FIG. 1G prior to drug dilution.

As seen in FIG. 26, syringe adaptor element 50 and syringe 40 joined thereto are placed in close proximity to forward facing portion 348 of vial adaptor element 30. It is appreciated that at this stage compression spring 536 is relaxed and the sharpened tip of needle 550 is preferably located between septa 502 and 504. Preferably, surfaces 528 of teeth 527 of arms 526 engage forward facing surfaces on either side of intermediate portion 514 of housing element 500.

At this stage, syringe 40 is preferably filled with a fluid drawn from receptacle 62 (FIGS. 22-25) and therefore plunger 42 is at least partially retracted.

Reference is now made to FIG. 27, which is a sectional illustration of the drug mixing system of FIG. 1H following drug dilution.

As seen in FIG. 27 syringe adaptor element 50 and syringe 40 joined thereto are pushed into engagement with forward facing portion 348 of vial adaptor element 30.

Preferably, surfaces 528 of teeth 527 of arms 526 snap to engage wall portion 346 of forward facing portion 348, thus ensuring that the engagement between syringe adaptor element 50 and portion 348 is secure. At this stage, spring 536 is in a compressed state, and housing element 500 is pushed rearwardly by the pressure from forward facing portion 348.

The rearward motion of housing element 500 causes the sharpened tip of needle 550 to pierce septa 502 and 350. As a result, needle 550 partially extends through a hollow section of portion 348, and is in fluid flow engagement with vial 10 via bore 350 of neck portion 344 and vial puncturing spike 322 of main body element 302. Due to the fluid flow engagement between luer 44 of syringe 40 and needle 550 of syringe adaptor element 50, the syringe 40 is now in fluid flow engagement with vial 10. It is appreciated that when using the syringe adaptor element described in FIG. 9C, needle protector 560 at least partially collapses, thus exposing the needle 550.

At this stage, a user injects the fluid contained in syringe 40 into vial 10 via bore 350 of neck portion 344 and vial puncturing spike 322 by inwardly pushing plunger 42 of syringe 40. A corresponding volume of air escapes from vial 10 via membrane 336 and optional carbon cloth filter 340. It is appreciated that any drug containing aerosol is blocked by the membrane and any non-aerosolized drug vapor is adsorbed by the charcoal filter, thus protecting users and the environment from contamination.

Preferably, the user ensures that the drug contained in vial 10 is fully dissolved, and then draws at least part of the drug solution contained in vial 10 into syringe 40 by turning the system upside down and retracting plunger 42 (not shown). At this stage, a corresponding volume of sterile air enters vial 10 via membrane 336 and optional carbon cloth filter 340.

In order to disengage syringe adaptor element 50 and forward facing portion 348, a user pushes slightly on arms 526 extending from side surfaces 524 of housing element 522, causing teeth 527 to move outward and release a wall portion 346 of forward facing portion 348, thus disconnecting the forward facing portion.

Throughout the engagement and disengagement process, septum 350 of vial adaptor element 30 and septum 502 of syringe adaptor element 50 are pushed into touching engagement by the biasing force of spring 536, thus preventing exposure of the tip of needle 550 to the environment.

Reference is now made to FIG. 28, which is a sectional illustration of the drug mixing system of FIGS. 1K and 1L in a protected, ready for delivery state, when syringe adaptor element 50 is covered by syringe protection cover 80.

As seen in FIG. 28, syringe adaptor element 50 is preferably covered at a forward end thereof by syringe protection cover 80. At this stage, plunger 42 is preferably at least partially retracted with respect to syringe 40, and the syringe contains a drug solution withdrawn from vial 10 (FIG. 27).

The forwardmost circumference of main body portion 523 is preferably seated in the recess formed by wall portions 806 and 810 of syringe protection cover 80 and surface 804 of syringe cover element 80 preferably engages a forward surface of septum 502.

It is appreciated that at this stage compression spring 536 is relaxed and the sharpened tip of needle 550 is preferably located between septa 502 and 504. Preferably, surfaces 528 of teeth 527 of arms 526 engage forward facing surfaces on either side of intermediate portion 514 of housing element 500.

Reference is now made to FIG. 29, which is a partially pictorial, partially sectional illustration of the drug mixing system of FIGS. 1M and 28 when ready for injection.

As seen in FIG. 29, syringe protection cover 80 has been removed from syringe adaptor element 50, and syringe adaptor element 50 and syringe 40 joined thereto are pushed into engagement with cylindrical portion 902 of infusion set adaptor element 90, while the infusion set adaptor element 90 is connected to a side port of an intravenous cannula located at an injection site.

Preferably, surfaces 528 of teeth 527 of arms 526 snap to engage a rearward facing wall portion of cylindrical portion 902, thus ensuring that the engagement between syringe adaptor element 50 and cylindrical portion 902 is secure. At this stage, spring 536 is in a compressed state, and housing element 500 is pushed rearwardly by the pressure from cylindrical portion 902.

The rearward motion of housing element 500 causes the sharpened tip of needle 550 to pierce septa 502 and 904. As a result, needle 550 partially extends through bore 912 of infusion set adaptor element 90, and is therefore in fluid flow engagement with the injection site. Due to the fluid flow engagement between luer 44 of syringe 40 and needle 550 of syringe adaptor element 50, the syringe 40 is now in fluid flow engagement with the injection site. It is appreciated that when using the syringe adaptor element described in FIG. 9C, needle protector 560 at least partially collapses, thus exposing the needle 550.

In order to disengage syringe adaptor element 50 and cylindrical portion 902, a user pushes slightly on arms 526 extending from side surfaces 524 of housing element 522, causing teeth 527 to move outward and release a the rearward facing wall portion of cylindrical portion 902, thus disconnecting the cylindrical portion.

Reference is now made to FIG. 30, which is a partially pictorial partially sectional illustration of the drug mixing system of FIGS. 1M and 20 when ready for injection.

Preferably, receptacle 62 is connected via spike port adaptor element 60 to an infusion set 92. The infusion set then connects to a standard intravenous cannula 94 such as a Venolit model commercially available from Teva Medical Ltd. of Ashdod, Israel which is located in an infusion site. Typically, prior to connection of spike port adaptor element 60 to infusion set 92, sealing element 630 is removed, and infusion set 92 is connected directly to tube 602.

Alternatively, infusion set 92 may be connected to a new receptacle, not containing a drug, in which case the drug solution is injected directly into the infusion set. If this option is selected, syringe adaptor 50 having syringe 40 (FIG. 28) joined thereto is connected to port 93 after syringe protector cover 80 is removed, and the drug solution contained therein is injected into the infusion line.

Preferably, surfaces 528 of teeth 527 of arms 526 snap to engage a rearward facing wall portion of port 93, thus ensuring that the engagement between syringe adaptor element 50 and port 93 is secure. At this stage, spring 536 is in a compressed state, and housing element 500 is pushed rearwardly by the pressure from port 93.

The rearward motion of housing element 500 causes the sharpened tip of needle 550 to pierce septum 502 and a sealing septum of port 93. As a result, needle 550 partially extends into infusion set 92, and is therefore in fluid flow engagement with the injection site. Due to the fluid flow engagement between luer 44 of syringe 40 and needle 550 of syringe adaptor element 50, the syringe 40 is now in fluid flow engagement with the injection site.

In order to disengage syringe adaptor element 50 and port 93, a user pushes slightly on arms 526 extending from side surfaces 524 of housing element 522, causing teeth 527 to move outward and release a rearward facing wall portion of port 93, thus disconnecting the port.

Reference is now made to FIGS. 31A, 31B, 31C, 31D, 31E, 31F, 31G, 31H, 31I, 31J and 31L which are simplified pictorial illustrations of various stages of assembly and typical use of a drug mixing system constructed and operative in accordance with another preferred embodiment of the present invention.

FIG. 31A shows a spike port adaptor element 1030, as described hereinbelow with reference to FIGS. 34-35, being inserted into a spike port 1031 in a receptacle 1032 containing a fluid. Preferably, a luer connector of spike port adaptor element 1030 is sealed by a luer cover element 1034.

Typically, receptacle 1032 comprises a bag, and the fluid contained therein is sterile salt solution, water, or any other suitable sterile solution or pure fluid.

Figure 31B:
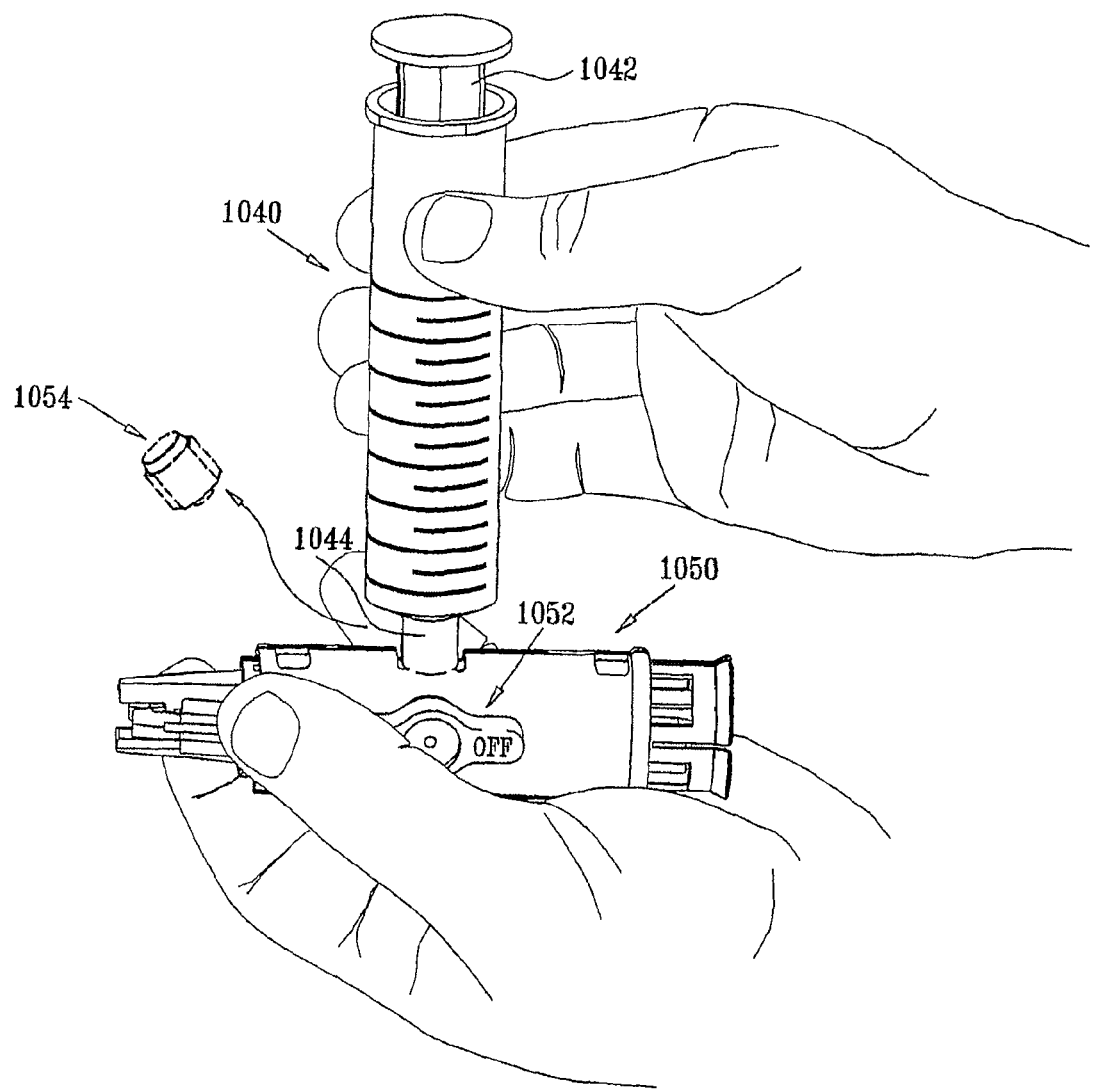

As shown in FIG. 31B, a luer-equipped hypodermic syringe 1040, having a plunger 1042 and a luer tip 1044, is connected to a syringe port of an adaptor assembly 1050, which is described hereinbelow with reference to FIGS. 36 and 44-45B. Preferably, the syringe port is defined by a stopcock 1052 which is described hereinbelow with reference to FIGS. 37-38B and includes a removable protection cap 1054. FIG. 46 shows a sectional view of the drug mixing system at this stage.

Typically, plunger 1042 of syringe 1040 is pushed fully inward before the syringe is connected to the syringe port of stopcock 1052.

Figure 31C:
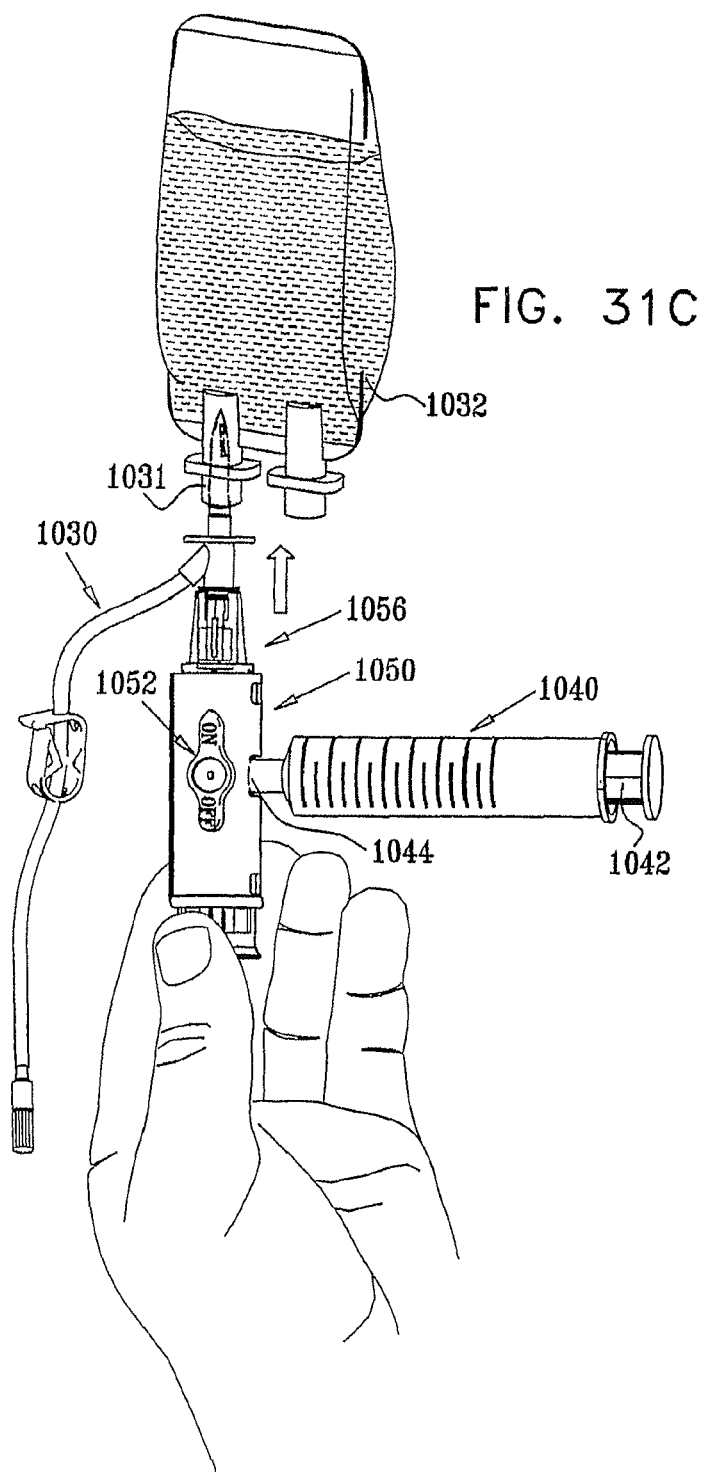
Figure 47:
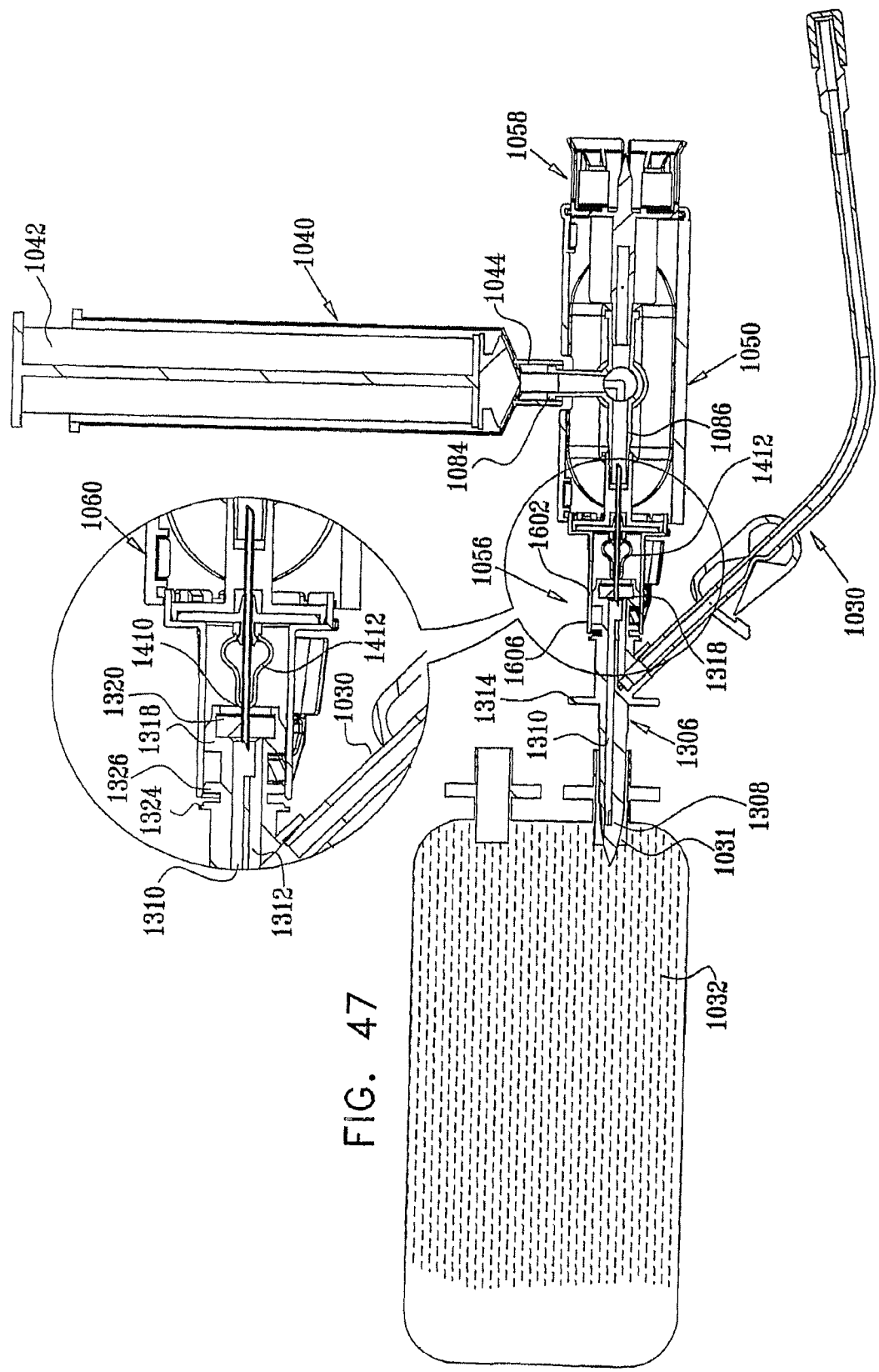
FIG. 47 is a sectional illustration of the drug mixing system of FIG. 31D during attachment of the receptacle adaptor element of FIG. 31B to the adaptor assembly of FIG. 46.

FIG. 31C shows spike port adaptor element 1030 and receptacle 1032 joined thereto being connected to a receptacle adaptor subassembly 1056 of adaptor assembly 1050. Subassembly 1056 is described hereinbelow with reference to FIGS. 39-40B. Preferably, stopcock 1052 is in an operative orientation which enables fluid flow between receptacle adaptor subassembly 1056 and syringe 1040. FIG. 47 shows a sectional view of the drug mixing system at this stage.

Figure 31D:
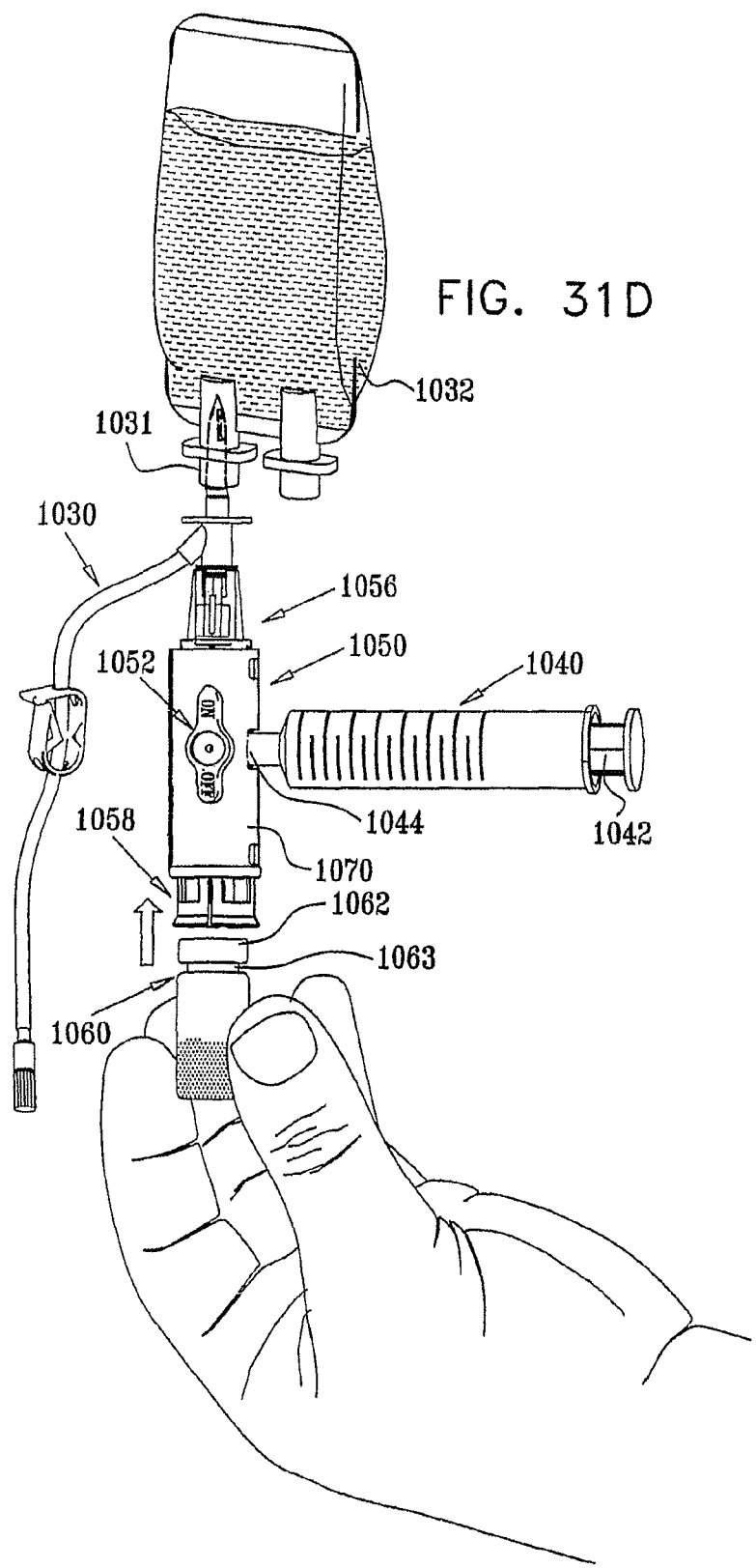

As seen in FIG. 31D, a vial 1060, including a top portion 1062 and a neck portion 1063, is pushed into engagement with a vial adaptor subassembly 1058 of adaptor assembly 1050. Top portion 1062 of vial 1060 preferably has a septum 1064 sealingly seated therein. Subassembly 1058 is described hereinbelow with reference to FIGS. 41-42B.

Figure 31E:
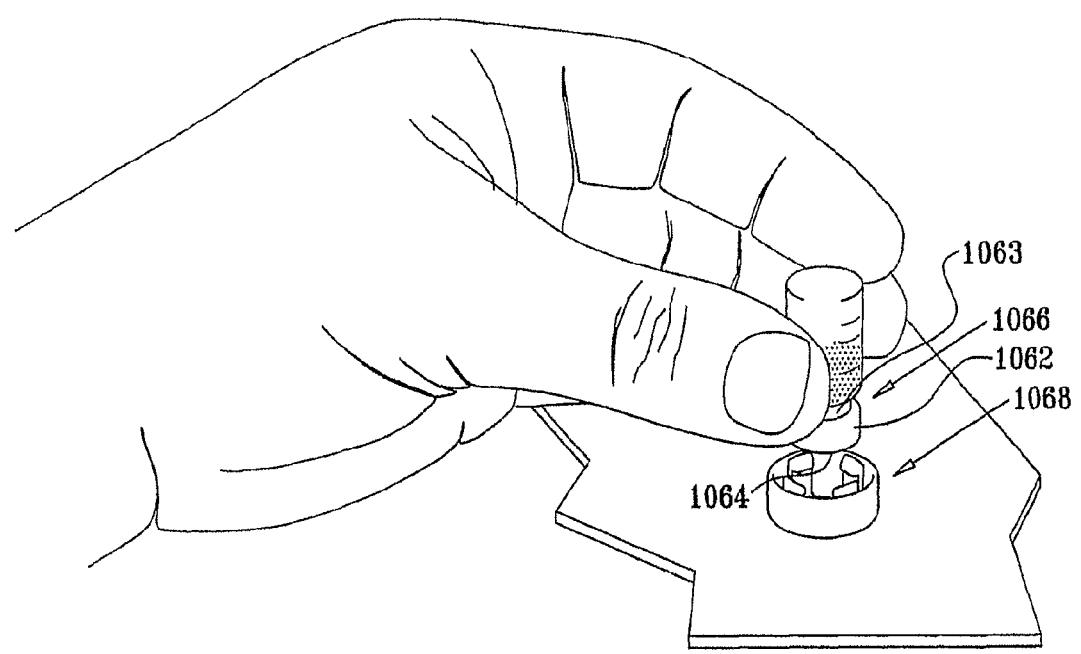
Figure 48:
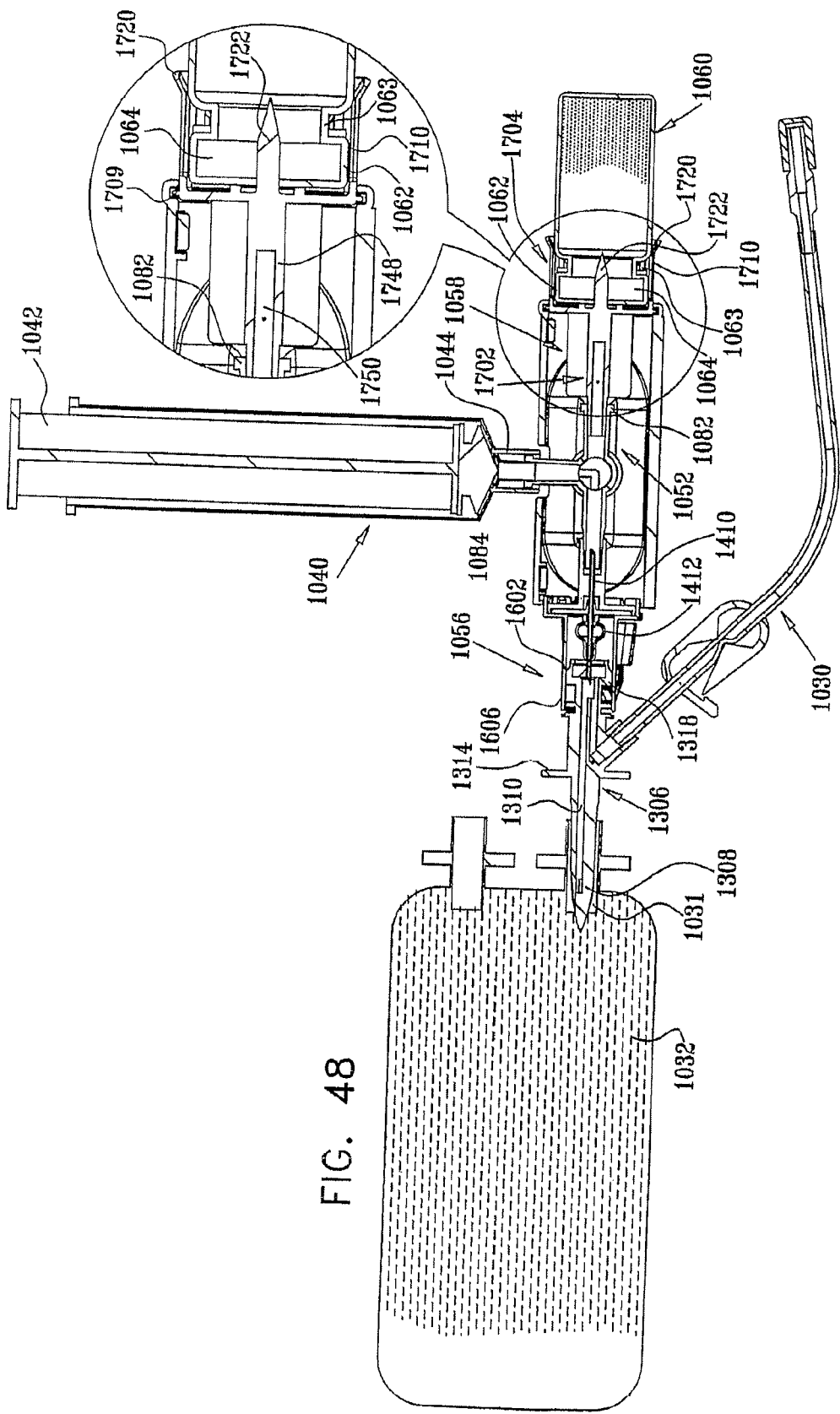
FIG. 48 is a sectional illustration of the drug mixing system of FIG. 31E during attachment of a vial to the adaptor assembly of FIG. 47.

Alternatively, if a small vial 1066 is used, small vial 1066 is pushed into engagement with a vial head adaptor element 1068, which is described hereinbelow with reference to FIGS. 32-33, as shown in FIG. 31E, and is then pushed into engagement with vial adaptor subassembly 1058. Vials 1060 and 1066 typically contain a drug in soluble powder form, in a solution or in other suitable four. FIG. 48 shows a sectional view of the drug mixing system at this stage.

It is appreciated that stopcock 1052, receptacle adaptor subassembly 1056 and vial adaptor subassembly 1058 are preferably enclosed in a housing element 1070 of adaptor assembly 1050, which is described hereinbelow with reference to FIGS. 43A-43B.

It will be appreciated by persons skilled in the art that the assembly steps shown in FIGS. 31C-31E may be performed in any suitable sequence.

Figure 49:
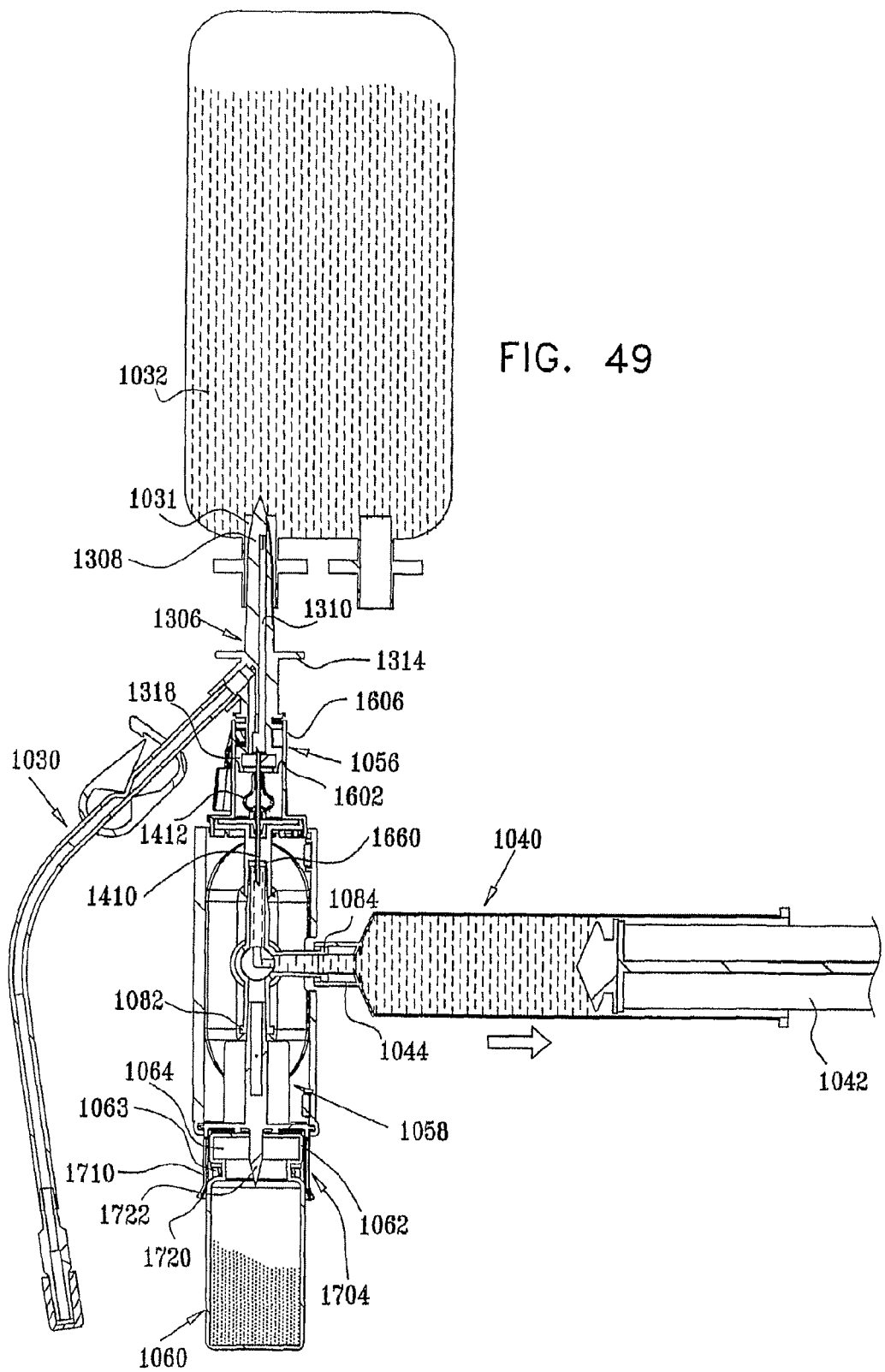
FIG. 49 is a sectional illustration of the drug mixing system of FIGS. 31F and 48 during fluid drawing from a receptacle.

As seen in FIG. 31F, a user retracts plunger 1042 while receptacle 1032 is upright and vial 1060 lies therebelow, thus at least partially filling syringe 1040 with fluid drawn from receptacle 1032. The operative orientation of stopcock 1052 enables this fluid flow from receptacle 1032 to syringe 1040 via spike port adaptor element 1030, receptacle adaptor subassembly 1056 and stopcock 1052 in a manner that ensures that the fluid remains sterile, and that the user is not exposed thereto. FIG. 49 shows a sectional view of the drug mixing system at this stage.

Figure 31G:
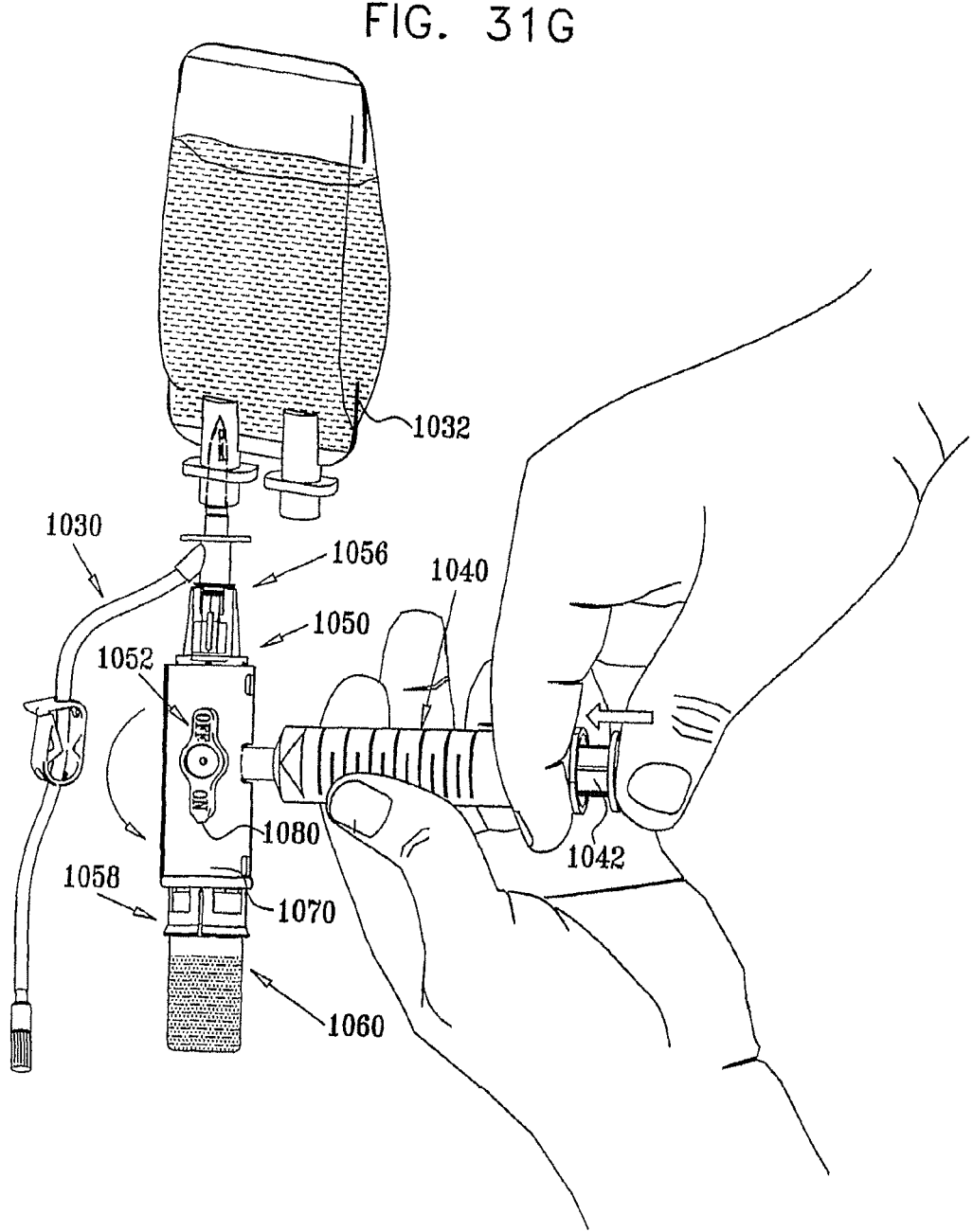
Figure 311:
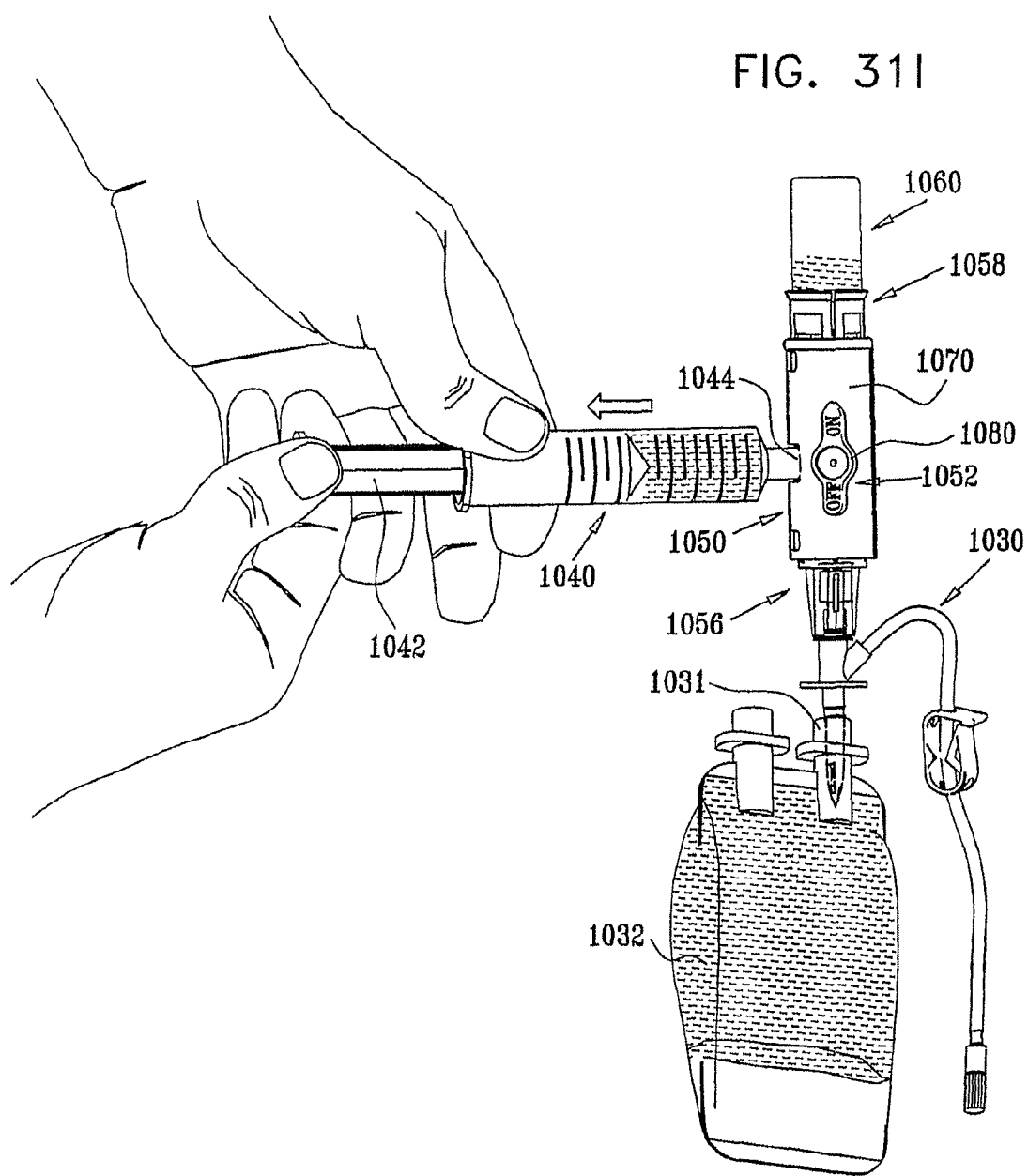

The user then rotates a handle 1080 of stopcock 1052 to enable fluid flow between syringe 1040 and vial adaptor subassembly 1058, having joined thereto vial 1060, as shown in FIG. 31G.

Figure 50:
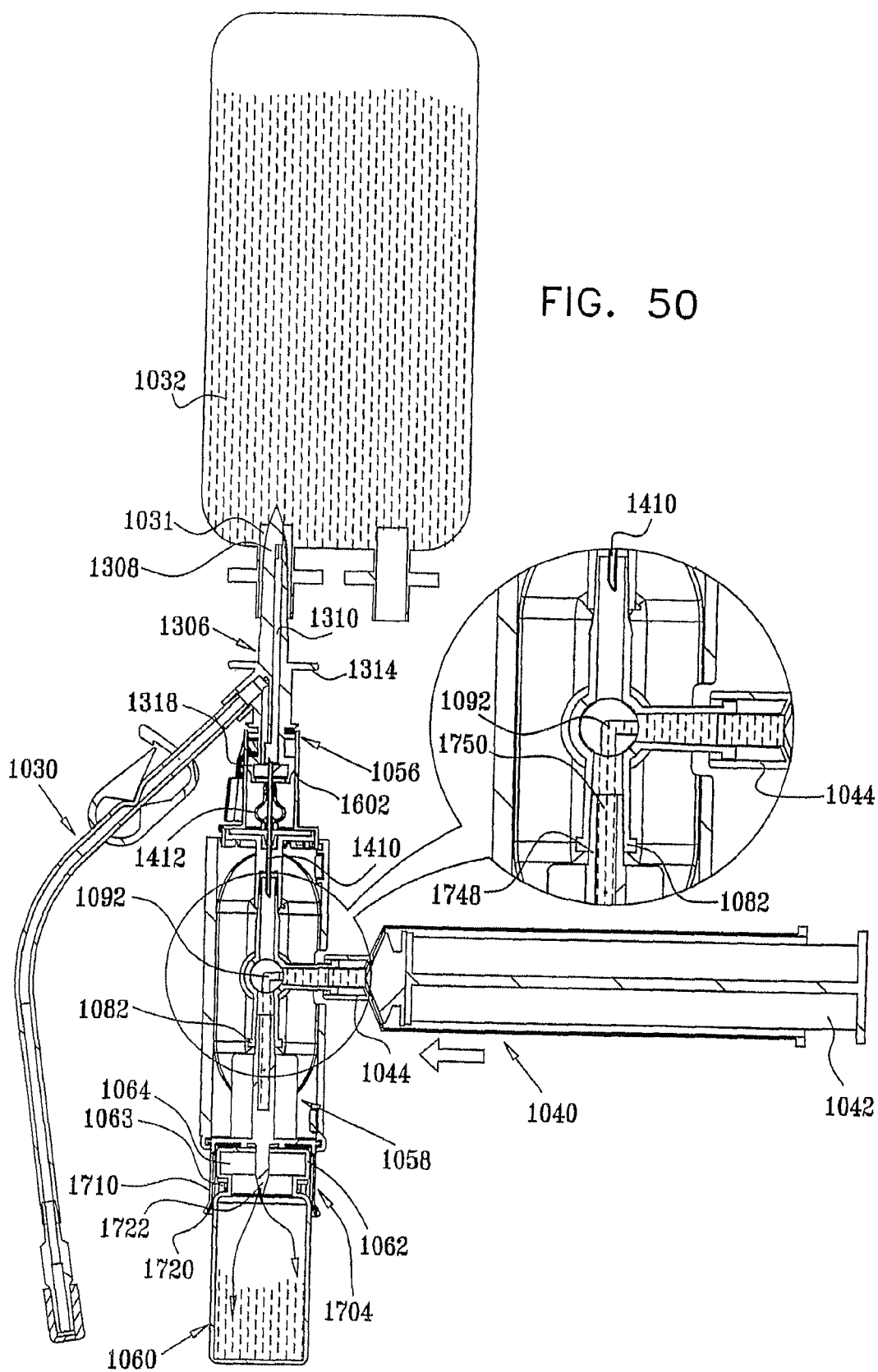
FIG. 50 is a sectional illustration of the drug mixing system of FIGS. 31G and 48 during fluid injection into a vial.

When the syringe 1040 and vial 1060 are in fluid flow engagement, the user pushes plunger 1042 inward, thus injecting the fluid contained in syringe 1040 into vial 1060 and dissolving the drug contained therein. FIG. 50 shows a sectional view of the drug mixing system at this stage.

As seen in FIG. 31H, the user then shakes the drug mixing system of FIG. 31G to ensure that the drug in vial 1060 is fully dissolved and that the resulting solution is homogenous.

Figure 51:
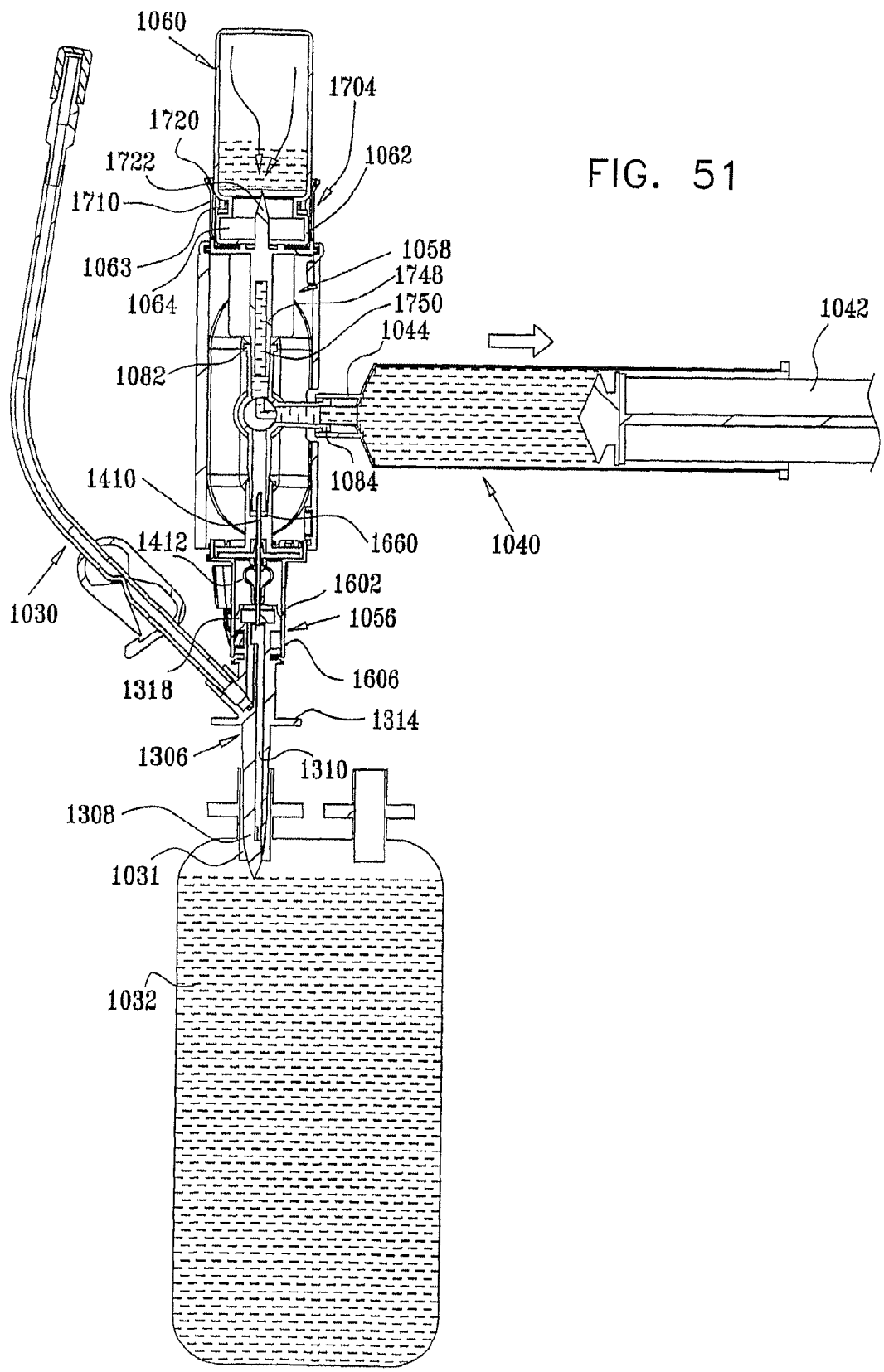
FIG. 51 is a sectional illustration of the drug mixing system of FIGS. 31I and 48 during fluid drawing from a vial.

As seen in FIG. 31I, the user turns the system upside down, so that the vial 1060 faces upward, and then retracts plunger 1042, thus drawing at least part of the solution from vial 1060 into syringe 1040. FIG. 51 shows a sectional view of the drug mixing system at this stage.

It will be appreciated by those skilled in the art that at this stage the drug mixing system of the present invention is preferably held such that vial 1060 lies above syringe 1040, to allow smooth flow of the fluid from vial 1060 to syringe 1040 via vial adaptor subassembly 1058 and stopcock 1052.

Figure 31J:
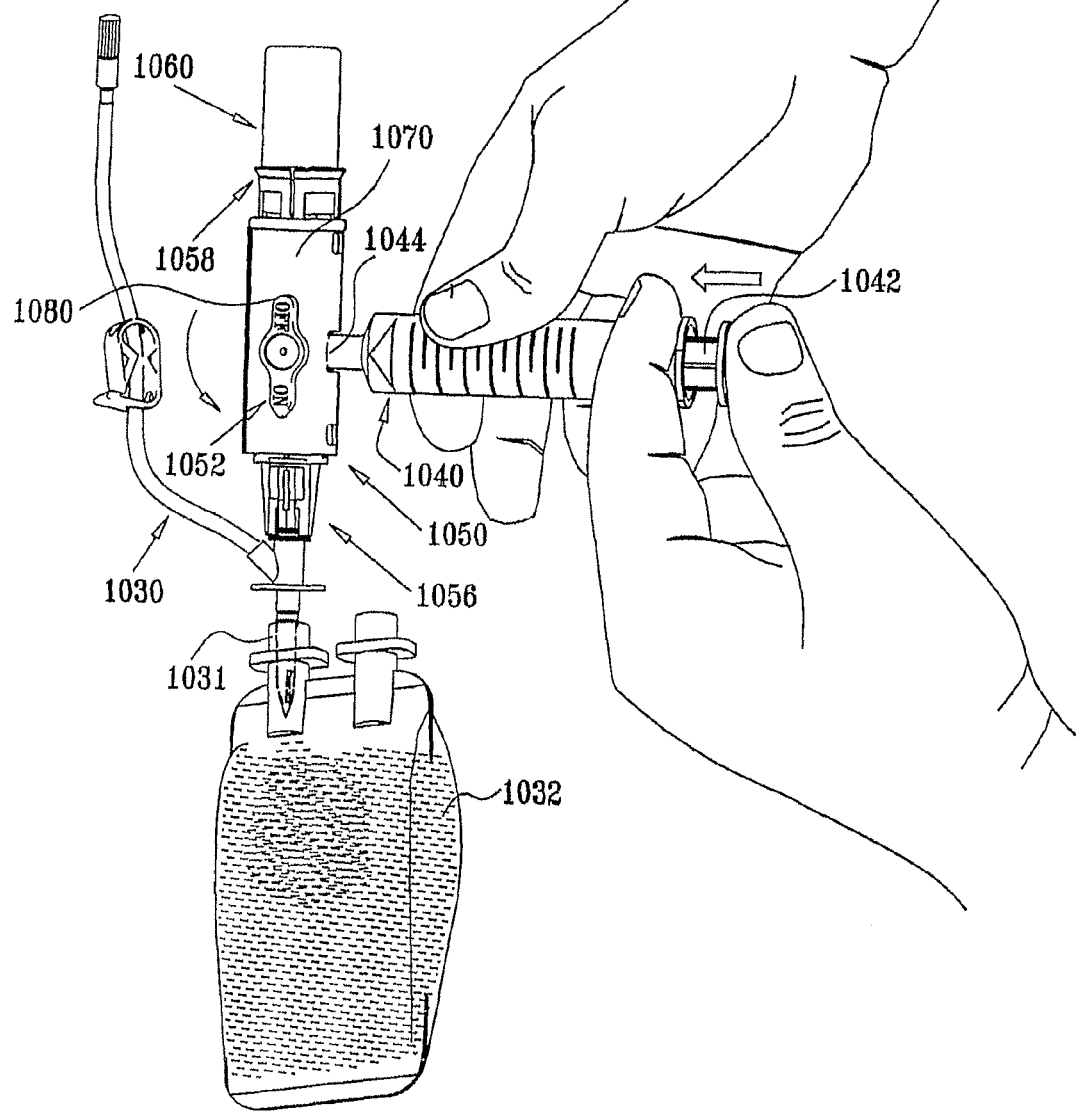
Figure 52:
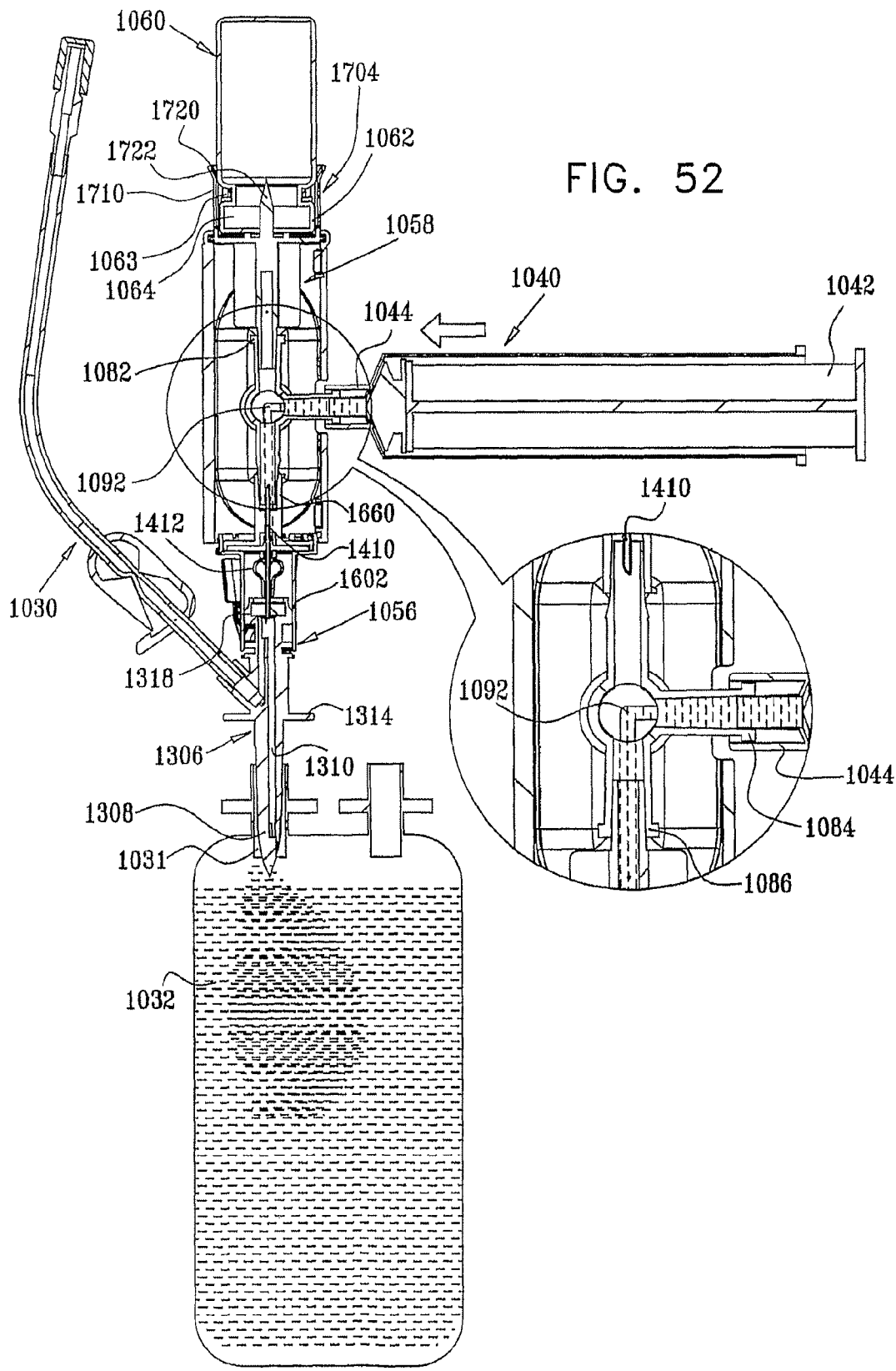
FIG. 52 is a sectional illustration of the drug mixing system of FIGS. 31J and 48 during fluid injection into a receptacle.

As shown in FIG. 31J, handle 1080 of stopcock 1052 is oriented to enable flow of fluid between syringe 1040 and receptacle 1032. The user then pushes plunger 1042 of syringe 1040 inward, thus injecting the drug solution into receptacle 1032 and further diluting it prior to infusion into a patient. FIG. 52 shows a sectional view of the drug mixing system at this stage.

Figure 31K:
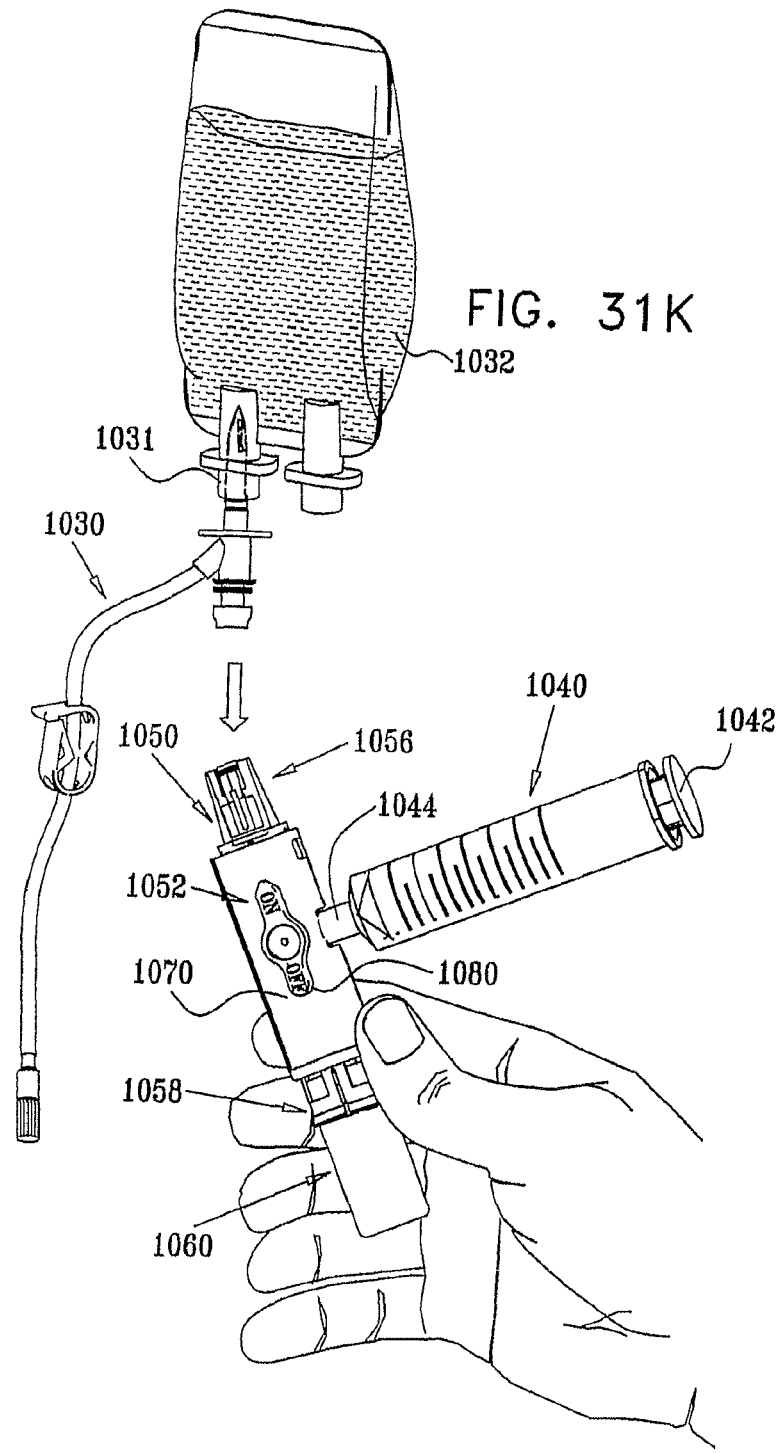

Subsequently, spike port adaptor element 1030, having receptacle 1032 joined thereto, is disconnected from adaptor assembly 1050, which remains connected to vial 1060 as shown in FIG. 31K.

Figure 31L:
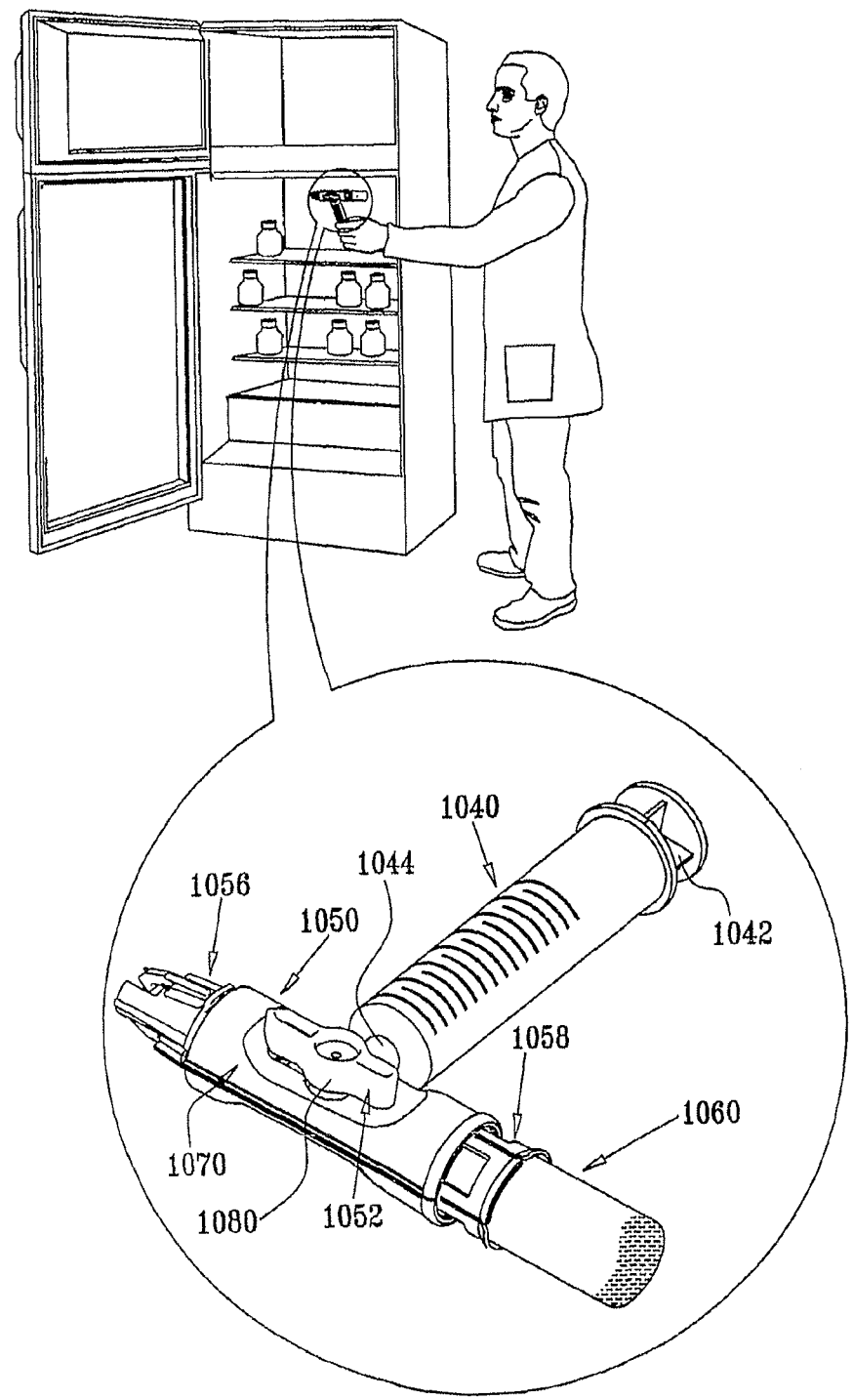

As seen in FIG. 31L, if some of the drug solution is left in vial 1060, vial 1060 and adaptor assembly 1050 joined thereto may be stored in a suitable facility for further use. It is appreciated that at this stage syringe 1040 remains connected to the syringe port of stopcock 1052 of adaptor assembly 1050. FIG. 53 is a sectional view of the drug mixing system at this stage.

The structure of elements of the drug mixing system of FIGS. 31A-31L is described hereinbelow with reference to FIGS. 32-43B.

Figure 32:
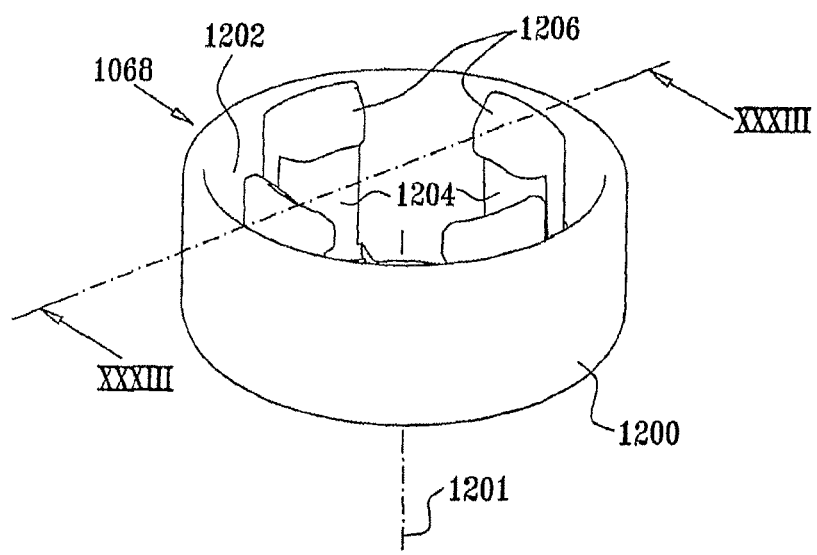
FIG. 32 is a simplified pictorial illustration of a vial head adaptor element which forms part of the drug mixing system of FIGS. 31A-31L.
Figure 33:
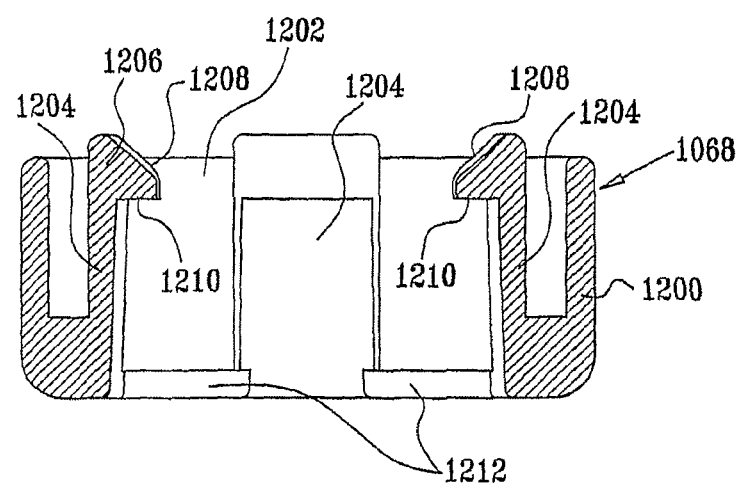
FIG. 33 is a sectional illustration taken along section lines XXXIII-XXXIII in FIG. 32.

Reference is now made to FIG. 32, which is a simplified pictorial illustration of a vial head adaptor element 1068 which forms part of the drug mixing system of FIGS. 31A-31L and to FIG. 33 which is a sectional illustration taken along section lines XXXIII-XXXIII in FIG. 32.

As seen in FIG. 32, vial head adaptor element 1068 is preferably a side-to-side symmetric integrally formed element which is preferably injection molded of plastic.

Vial head adaptor element 1068 preferably includes a main body portion 1200 which is generally cylindrical and has a central axis 1201. An inner cylindrical surface 1202 of main body portion 1200 preferably has four arms 1204 extending therefrom, each arm 1204 being arranged at generally right angles with respect to its neighboring arms.

Each of arms 1204 terminates at an upper end thereof, in the sense of FIG. 31A, in an inwardly facing generally triangular tooth 1206 having a upwardly facing inclined surface 1208 and a bottom-facing engagement surface 1210 extending generally perpendicular to arm 1204.

At the bottom of vial head adaptor element 1068, there are formed four inwardly protruding surfaces 1212, extending generally perpendicular to inner surface 1202 of main body portion 1200. Each of neighboring surfaces 1212 is preferably arranged at a generally right angle with respect to its neighboring surfaces 1212. Surfaces 1212 and arms 1204 are rotationally offset from one another about axis 1201.

Reference is now made to FIG. 34, which is a simplified pictorial illustration of spike port adaptor element 1030 which forms part of the drug mixing system of FIGS. 31A-31L and to FIG. 35 which is a sectional illustration taken along section lines XXXV-XXXV in FIG. 34.

Spike port adaptor element 1030 preferably comprises a hollow flexible plastic tube 1302 having associated therewith a standard clamp 1304, which is commercially available from various manufacturers such as Quosina of Italy.

At a forward end thereof, tube 1302 is connected to a tube port 1305 of a hollow spike element 1306 which is preferably formed of plastic. Spike element 1306 preferably includes a main body portion 1307 which defines at a forward end thereof a spike 1308 which includes an aperture communicating with an axially extending bore 1310 and an additional bore 1312 which extends partially through main body portion 1307 and communicates with a top portion of bore 1310, thus facilitating complete priming before drug injection.

Rearward of spike 1308, main body portion 1307 defines a generally circular planar protrusion 1314 adapted to define the location at which a user grips the spike.

The interior of tube 1302 is in fluid flow communication with bore 1312 via tube port 1305. Bore 1310 preferably terminates in an aperture located in spike 1308 of main body portion 1307, and fully extends through the body portion 1307.

Main body portion 1307 preferably terminates in a connection port 1318 which is adapted to connect spike port adaptor element 1030 to receptacle adaptor subassembly 1056. Connection port 1318 preferably sealingly accommodates a generally circular septum 1320 on a seat 1322. Septum 1320 preferably engages the rear end of bore 1310, thus sealing the rear end of the bore.

Forward of connection port 1318, there is formed on main body portion 1307 a circumferential protrusion 1324, forward of which is formed an additional circumferential protrusion 1326, having an outer circumference which is slightly larger than that of protrusion 1324. Protrusions 1324 and 1326 are adapted to limit the movement of spike port adaptor element 1030 when it is connected to receptacle adaptor subassembly 1056.

A luer connector 1330 is preferably attached to a rear end of tube 1302. Luer connector 1330 preferably includes at a rearwardmost end thereof a narrow hollow port section 1332, forward of which there is formed a connecting tube portion 1334 and a hollow neck portion 1336 which connects port section 1330 to tube 1302. Preferably, luer connector 1330 is sealed by luer cover element 1034.

It is appreciated that spike port adaptor element 1030 may alternatively be identical to spike port adaptor element 630 described hereinabove with reference to FIGS. 10-11B.

Figure 36:
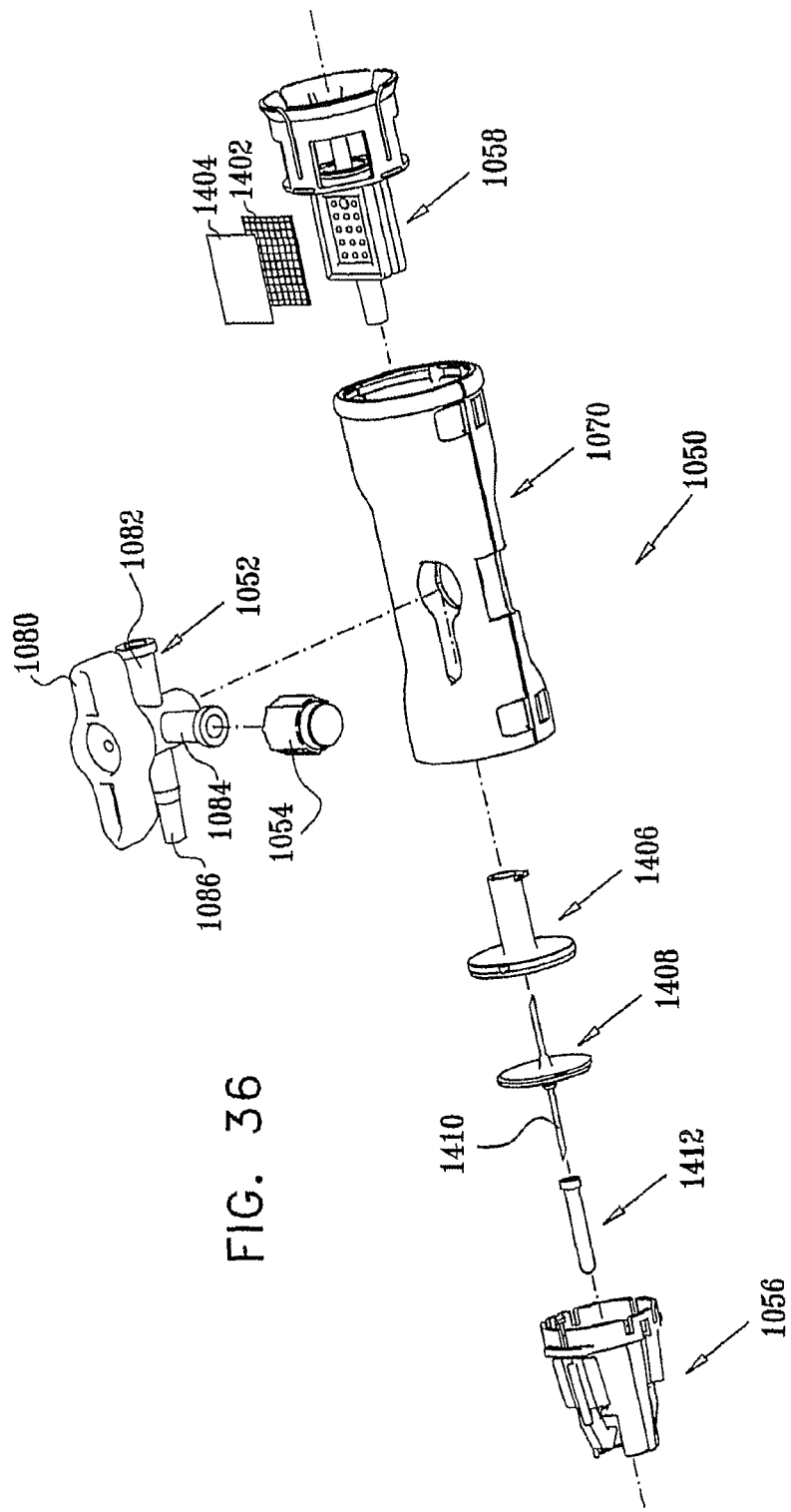
FIG. 36 is a simplified exploded view illustration of an adaptor assembly which forms part of the drug mixing system of FIGS. 31A-31L.

Reference is now made to FIG. 36, which is a simplified exploded view illustration of adaptor assembly 1050 which forms part of the drug mixing system of FIGS. 31A-31L.

As seen with particular clarity in FIG. 36, adaptor assembly 1050 includes vial adaptor subassembly 1058, onto which is placed a hydrophobic membrane 1402, above which is optionally seated a carbon cloth filter 1404. Vial adaptor subassembly 1058 is connected at a forward portion thereof to a vial port 1082 of stopcock 1052, which additionally includes a syringe port 1084 adapted for engagement with luer 1044 of syringe 1040. Stopcock 1052 additionally includes a receptacle port 1086 which is adapted for connection to a rear connection element 1406 of receptacle adaptor subassembly 1056.

Preferably, when syringe 1040 is not connected to the syringe port of stopcock 1052, the syringe port 1084 is sealed by protection cap 1054.

A needle holding element 1408 is preferably seated within rear connection element 1406 and supports a needle 1410. A forward portion of needle 1410 is preferably protected by a flexible latex needle protection element 1412. Receptacle adaptor subassembly 1056 connects at a rearward end thereof to rear connection element 1406, enclosing needle holding element 1408, needle 1410 and needle protection element 1412.

The forward portion of vial adaptor subassembly 1058 as well as stopcock 1052 and the rear portion of receptacle adaptor subassembly 1056 are located within housing element 1070. However, a handle 1080 of stopcock 1052 protrudes from housing element 1070, thus enabling a user to change the operative orientation of the stopcock 1052 and thereby switch the fluid flow pathway.

Figure 37:
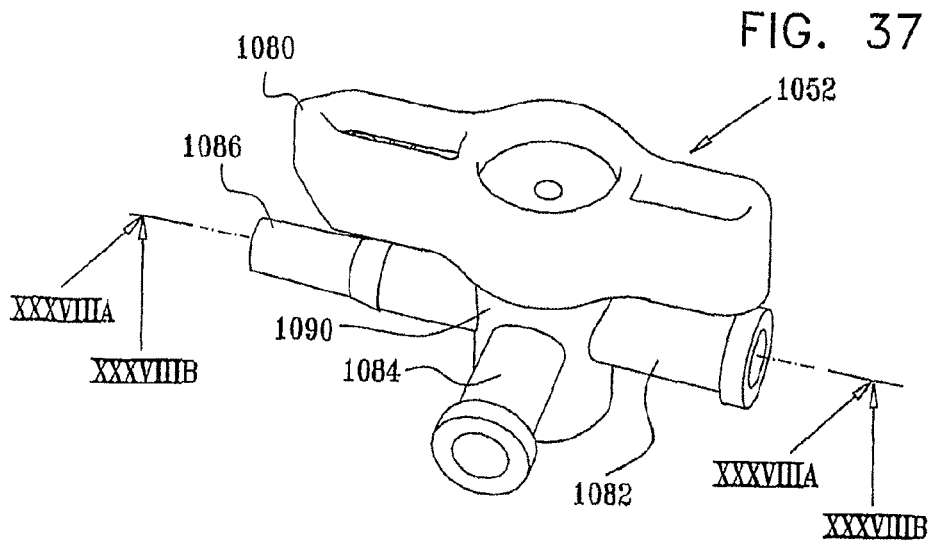
FIG. 37 is a simplified pictorial illustration of a stopcock element which forms part of the adaptor assembly of FIG. 36.
Figure 38A:
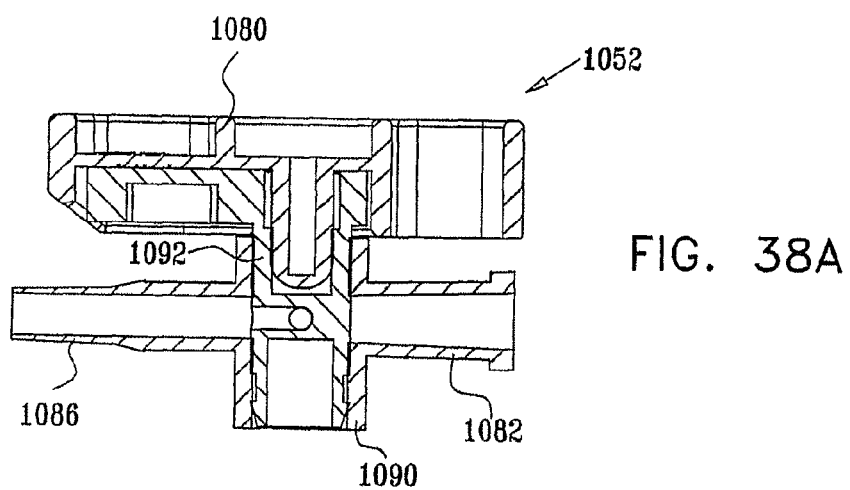
FIGS. 38A and 38B are sectional illustrations taken along respective section lines XXXVIIIA-XXXVIIIA and XXXVIIIB-XXXVIIIB in FIG. 37.
Figure 38B:
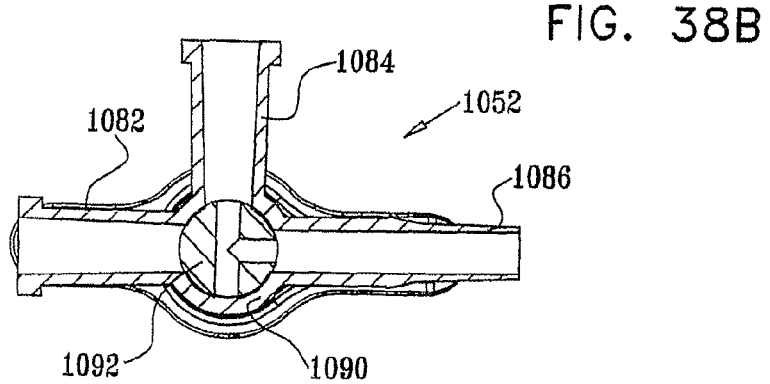

Reference is now made to FIG. 37, which is a simplified pictorial illustration of stopcock 1052 which forms part of the adaptor assembly of FIG. 36 and to FIGS. 38A and 38B, which are sectional illustrations taken along respective section lines XXXVIIIA-XXXVIIIA and XXXVIIIB-XXXVIIIB in FIG. 37.

Stopcock 1052, as noted hereinabove, has a vial port 1082, a syringe port 1084 and a receptacle port 1086, all of which are defined in a housing portion 1090. User operable handle 1080 is fixed to a pathway defining element 1092, which defines a three-way direction pathway, as seen with particularity in FIG. 38B. Selectable rotational orientation of handle 1080 enables any two of ports 1082, 1084 and 1086 to be placed in mutual fluid communication. Stopcock 1052 is commercially available from Elcam Ltd. of Baram, Israel.

Figure 39:
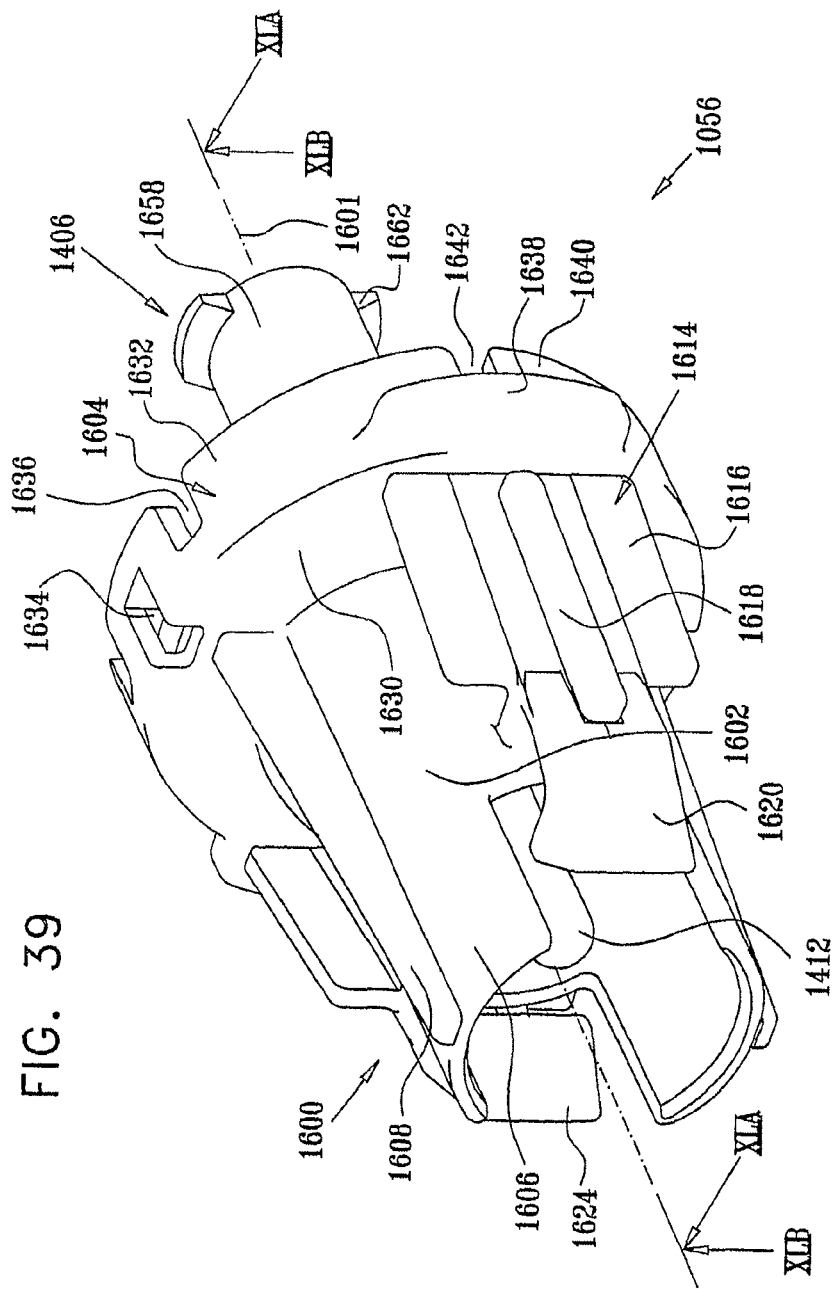
FIG. 39 is a simplified pictorial illustration of a receptacle adaptor subassembly which forms part of the adaptor assembly of FIG. 36.
Figure 40A:
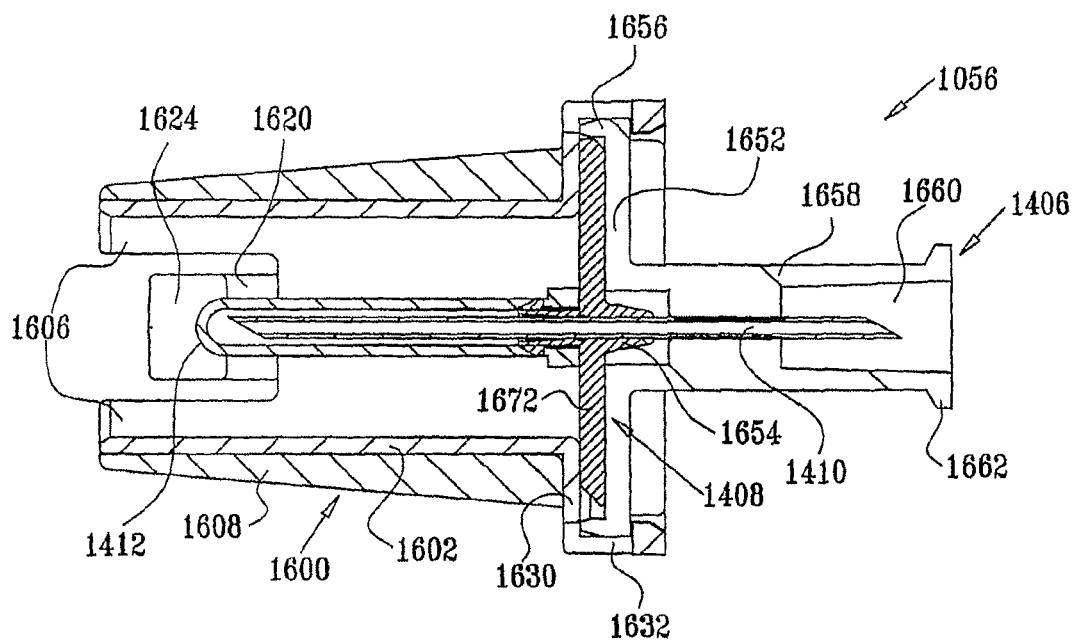
FIGS. 40A and 40B are sectional illustrations taken along respective section lines XLA-XLA and XLB-XLB in FIG. 39.
Figure 40B:
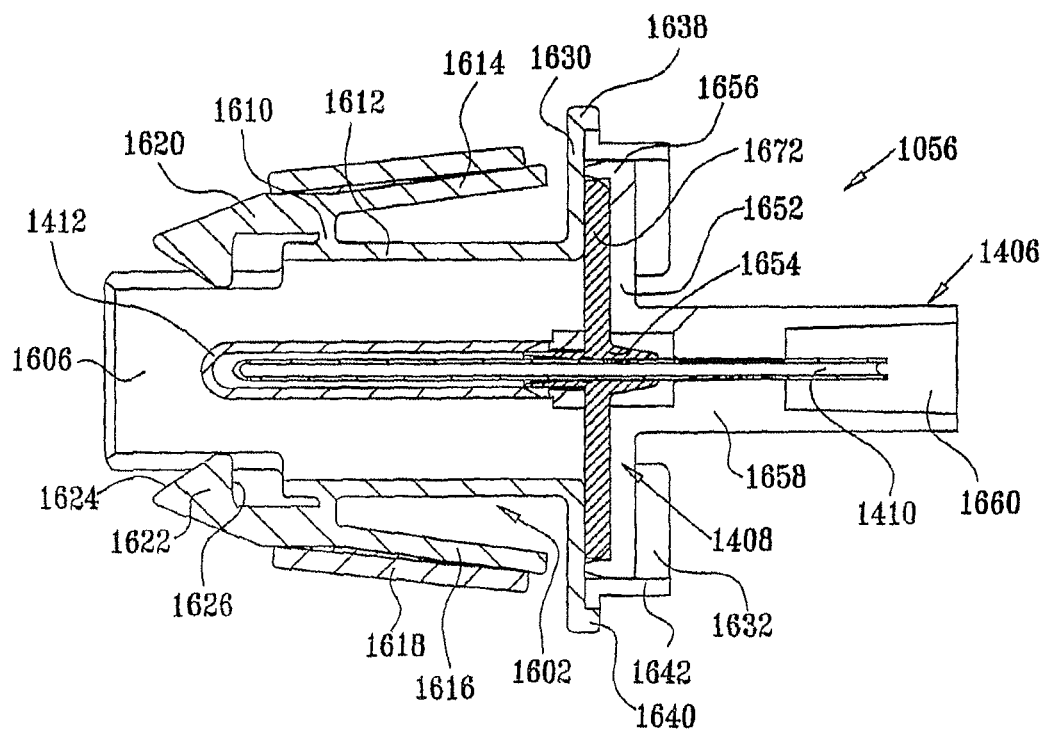

Reference is now made to FIG. 39, which is a simplified pictorial illustration of receptacle adaptor subassembly 1056 which forms part of the adaptor assembly of FIG. 36 and to FIGS. 40A and 40B, which are sectional illustrations taken along respective section lines XLA-XLA and XLB-XLB in FIG. 39.

As seen in FIGS. 39-40B, receptacle adaptor subassembly 1056 includes a main body element 1600 which is arranged generally about an axis 1601. Main body element 1600 is preferably integrally formed of plastic, and is preferably side-to-side symmetric about axis 1601. Main body element 1600 preferably includes a generally cylindrical base portion 1602 terminating in a rear portion 1604.

Top and bottom generally concave wall portions 1606 are formed at a forward end of base portion 1602, each wall portion 1606 defining on an outer surface thereof an outwardly facing axially extending rib 1608, which extends from a forwardmost end of each of wall portions 1606 and along base portion 1602.

A connection surface 1610 extending transversely from side surfaces 1612 of base portion 1602 connects an outwardly extending arm 1614 to each side surface 1612. Each arm 1614 preferably has a generally square rear portion 1616, formed rearwardly of connection surface 1610, and has a radially extending outwardly facing protrusion 1618 formed thereon. Protrusion 1618 preferably extends onto an outer surface of a generally rectangular forward portion 1620 of each of arms 1614, which extends forwardly of connection surface 1610.

An inwardly facing generally triangular tooth 1622 is formed adjacent a top end of each of forward portions 1620. Each tooth 1622 preferably includes a forwardly facing inclined surface 1624 and a rearwardly facing engagement surface 1626.

Rear portion 1604 preferably includes a transversely extending generally circular portion 1630 which forms a base for ribs 1608 and which terminates at a rear end thereof in an axially extending generally cylindrical wall portion 1632.

Wall portion 1632 preferably defines on a top and bottom surface thereof a small generally rectangular window 1634, and two forwardly facing slots 1636 which are formed on either side of window 1634. Two generally symmetric side-facing tabs 1638 are formed on side surfaces 1640 of wall portion 1632, each tab 1638 being formed forwardly of a generally rectangular forwardly facing slot 1642.

Rear connection element 1406 preferably includes a forward disk 1652 defining a central bore 1654. Disk 1652 preferably functions as a terminating wall for a forward facing cylindrical portion 1656. Rearward of disk 1652 there is preferably formed a rear portion 1658, having a narrow bore 1660 extend therethrough. Bore 1660 preferably widens toward the rear end of rear portion 1658, thus enabling rear portion 1658 to connect to an appropriate port. Preferably, two generally symmetric tabs 1662 are formed on top and bottom surfaces of rear portion 1658. Cylindrical portion 1656 preferably has an outer circumference that is slightly smaller than that of wall portion 1632, and is located therein.

Needle holding element 1408 preferably supports needle 1410 on a generally circular disk portion 1672. Needle 1410 extends axially through base portion 1602 of main body element 1600 and through bore 1660 of rear connection element 1650. Disk portion 1672 is preferably seated in cylindrical portion 1656, and is locked into cylindrical portion 1656 by portion 1630.

Figure 41:
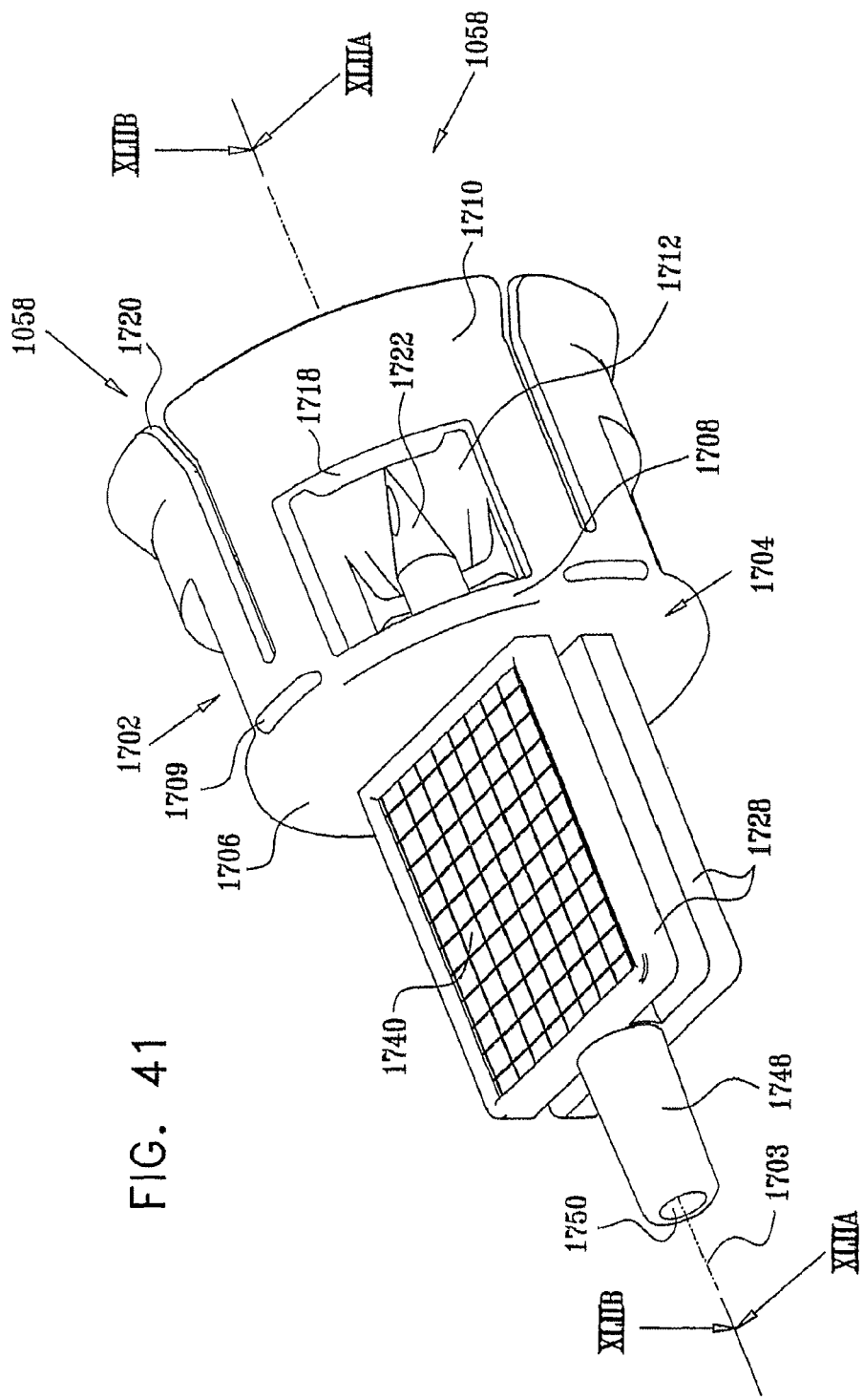
FIG. 41 is a simplified pictorial illustration of a vial adaptor subassembly which forms part of the adaptor assembly of FIG. 36.

Reference is now made to FIG. 41, which is a simplified pictorial illustration of vial adaptor subassembly 1058 which forms part of adaptor assembly 1050 of FIG. 36 and to FIGS. 42A and 42B, which are sectional illustrations taken along respective section lines XLIIA-XLIIA and XLIIB-XLIIB in FIG. 41.

As seen in FIGS. 41-42B, vial adaptor subassembly 1058 comprises a main body element 1702 arranged generally about an axis 1703. Main body element 1702 is preferably integrally formed and preferably injection molded of plastic.

Main body element 1702 is preferably side-to-side symmetric about axis 1703, and preferably includes a rear portion 1704, which is generally cylindrical and terminates in a forward wall 1706. Rear portion 1704 comprises a forward base section 1708, preferably having four transversely extending outwardly facing protrusions 1709 extend therefrom, each protrusion being arranged at generally right angles with respect to its neighboring protrusions.

Rearward of base section 1708 there are formed four tabs 1710 each having a rectangular window 1712. Rearward of rectangular windows 1712 and on an inner surface 1714 of each of tabs 1710 there are preferably formed two radially extending inwardly facing protrusions 1716 each having an inclined surface. Protrusions 1716 preferably terminate at a forward end thereof in an inwardly facing transversely extending protrusion 1718. Rearward of protrusions 1716, each of tabs 1710 preferably includes an outwardly tapered portion 1720.

A hollow vial puncturing spike 1722 extends rearwardly from a rearward surface 1724 of forward wall 1706, and is surrounded by base section 1708 and by tabs 1710. Rearward surface 1724 additionally includes a circular cylindrical protrusion 1725, surrounding puncturing spike 1722. Two axially extending bores 1726 and 1727 extend through vial puncturing spike 1722.

Forward of forward wall 1706 of rear portion 1704 there is formed an intermediate portion which is formed of two generally rectangular surfaces 1728, and which includes an axial tubular portion 1730 having a bore 1731 extend therethrough, bore 1731 being in fluid flow engagement with bore 1726 of hollow vial puncturing spike 1722.

On the top rectangular surface 1728 and slightly recessed with respect thereto there is formed a plastic membrane support surface 1732, having formed thereon a plurality of generally evenly distributed spherical protrusions 1734, which are adapted to support hydrophobic membrane 1402 and prevent it from excessive inflation and from cracking. Membrane 1402 is adapted to allow free passage of air to and from main body element 1702, but to prevent passage of liquid and air borne particles, microorganisms and aerosol. A preferred membrane 1402 is Model Versapor R 0.2 Micron which is commercially available from Pall Corporation of New York, U.S.A. Membrane 1402 is in fluid flow engagement with vial puncturing spike via bore 1727 and via a recess 1737 formed in top rectangular surface 1728.

A rim 1738 surrounding support surface 1732 is adapted to support a carbon cloth filter 1404 and maintain it in a raised position above and spaced from membrane 1402. Carbon filter 1404 is adapted to prevent toxic vapors from escaping from main body element 1702, thus protecting users. A preferred carbon cloth filter 1404 is Model No. Zorflex EMI which is commercially available from Charcoal Cloth International Ltd. of Houghton-le-Spring, England.

Rectangular surfaces 1728 of the intermediate portion terminate at a forward end thereof in a forward facing cylindrical portion 1748, having a bore 1750 extend therethrough. Preferably, bore 1750 is a continuation of tubular portion 1730 of the intermediate portion.

It is appreciated that the functionalities of membrane 1402 and carbon cloth filter 1404, to allow free passage of air into the drug mixing system while preventing passage thereinto of liquid and air-borne particles, microorganisms and aerosol and preventing toxic vapors from escaping from the drug mixing system, may be incorporated, using similar elements, into spike port adaptor element 1030 or receptacle adaptor subassembly 1056.

Reference is now made to FIGS. 43A and 43B, which are simplified pictorial illustrations of the housing element 1070 which forms part of the adaptor assembly 1050 of FIG. 36 in closed and open orientations, respectively.

As seen in FIGS. 43A and 43B, housing element 1070 is preferably integrally formed about an axis 1800 and includes a top housing portion 1801 and a bottom housing portion 1802. Preferably, housing portions 1801 and 1802 are side-to-side symmetric about axis 1800. Preferably, each of housing portions 1801 and 1802 includes a semi-cylindrical forward portion 1804 and a semi-cylindrical rearward portion 1806.

Top housing portion 1801 includes an inwardly recessed portion 1808 including a generally round aperture 1810 which extends forwardly into an elongate aperture 1812. Rearward of aperture 1810 there is preferably formed an elongate protrusion 1814. Preferably, apertures 1810 and 1812 lie below handle 1080 of stopcock 1052 when adaptor assembly 1050 is assembled.

Bottom housing portion 1802 includes an inwardly recessed portion 1816 which is generally symmetrical to recessed portion 1808 of top housing portion 1801, and which includes a central generally round aperture 1818. Two elongate protrusions 1820 are formed on either side of aperture 1818, such that rearward protrusion 1820 is generally symmetrical to protrusion 1814 of top housing portion 1801. Preferably, a bottom portion of pathway defining element 1090 of stopcock 1052 extends through aperture 1818 when adaptor assembly 1050 is assembled.

Top housing portion 1801 includes at forward and rearward ends thereof outwardly extending fingers 1822 terminating in a generally triangular teeth 1824 which include inclined outwardly facing surfaces 1826 and engagement surfaces 1828. Bottom housing portion 1802 preferably includes at forward and rearward ends thereof two generally rectangular windows 1830 which are placed generally below fingers 1822 and are adapted to engage engagement surfaces 1828 of fingers 1822 when housing element 1070 is assembled.

An inner surface 1834 of housing element 1070 preferably includes at a rearward end thereof a circumferential recess 1836 which is adapted to engage protrusions 1709 of rear portion 1704 of vial adaptor subassembly 1058. An outer surface of housing element 1070 which lies above recess 1836 preferably includes an outwardly facing protrusion 1840 which protrudes out of cylindrical forward portion 1804.

Preferably, side surfaces of top housing portion 1801 and bottom housing portion 1802 include generally parallel generally rectangular slots 1842, through which syringe port 1084 of stopcock 1052 extends when adaptor assembly 1050 is assembled.

Figure 44:
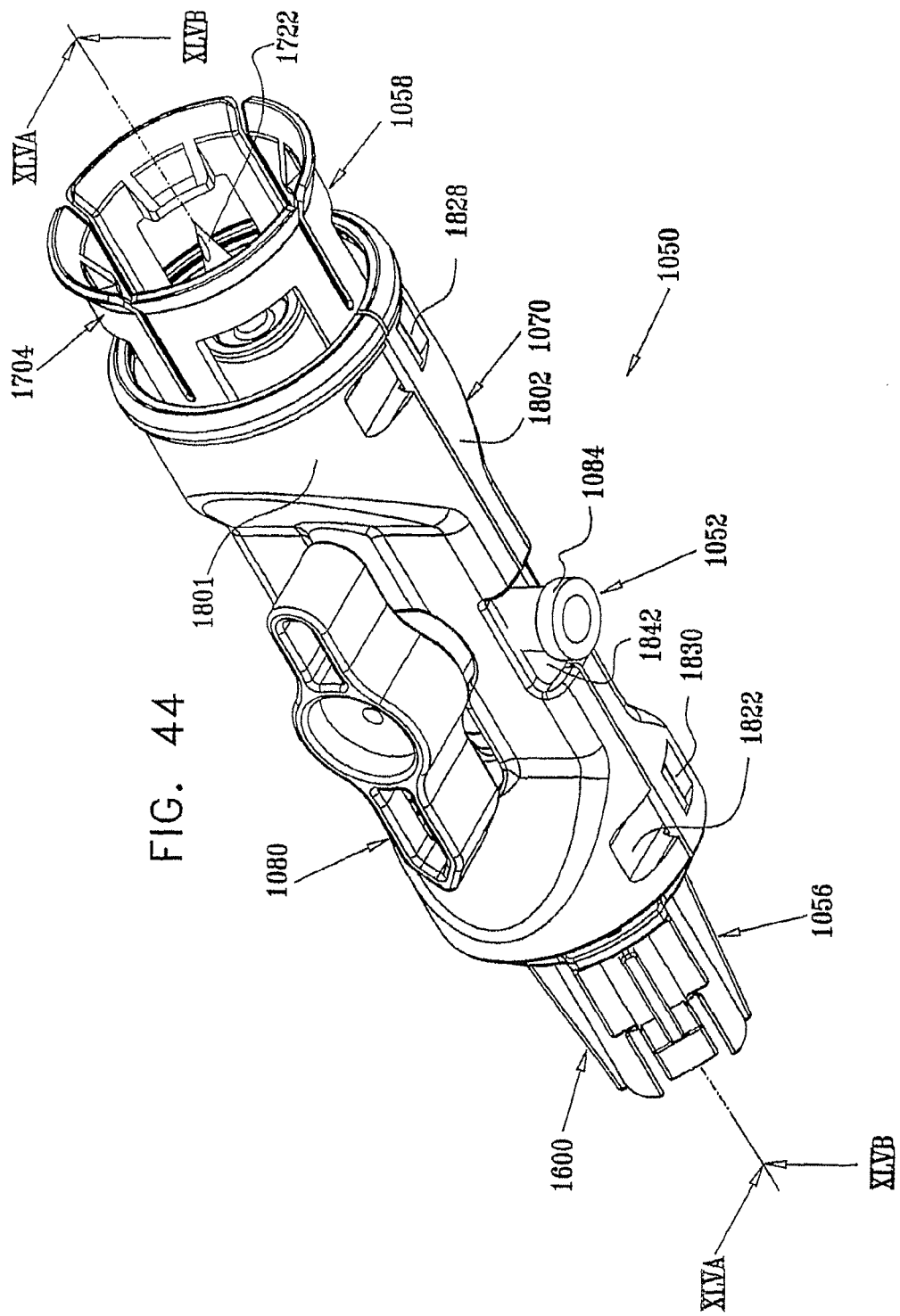
FIG. 44 is a simplified assembled pictorial illustration of the adaptor assembly of FIG. 36.
Figure 45A:
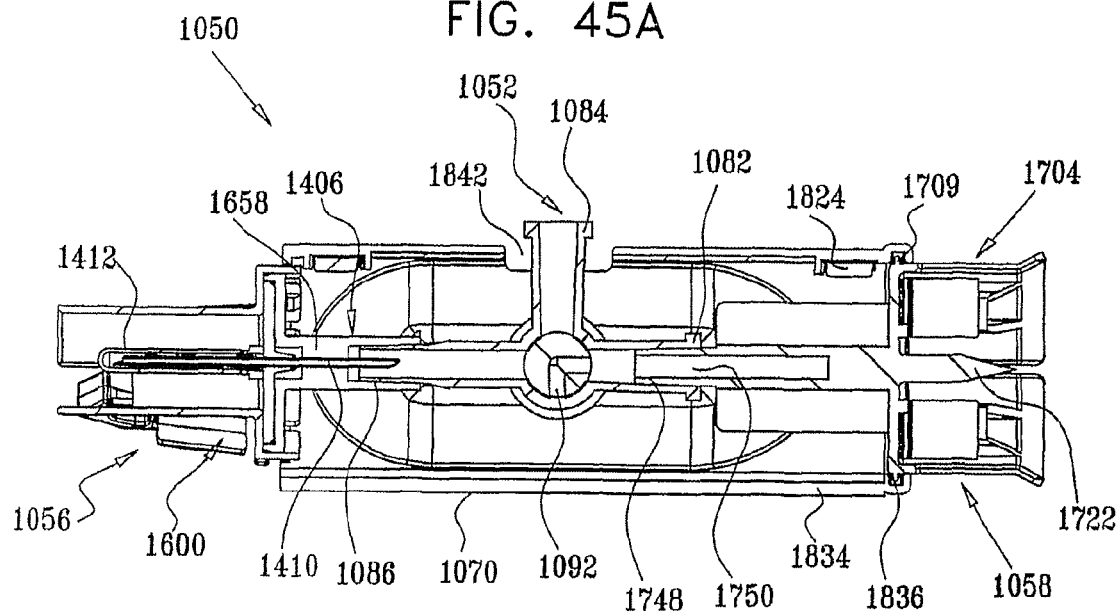
FIGS. 45A and 45B are sectional illustrations taken along respective section lines XVA-XVA and XVB-XVB in FIG. 44.
Figure 45B:
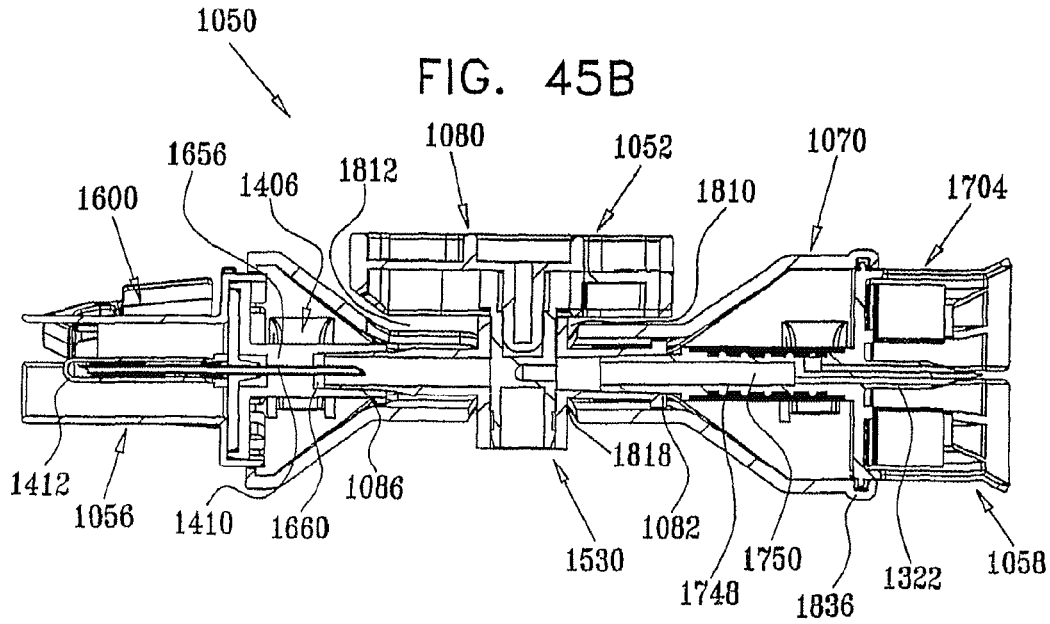

Reference is now made to FIG. 44, which is a simplified assembled pictorial illustration of the adaptor assembly of FIG. 36 and to FIGS. 45A and 45B, which are sectional illustrations taken along respective section lines XLVA-XLVA and XLVB-XLVB in FIG. 44.

As seen in FIGS. 44-45B, rear portion 1704 of vial adaptor subassembly 1058 extends from a rear portion of housing element 1070. Vial puncturing spike 1722 preferably extends out of housing element 1070, and is accessible for connection of vial 1060 or of vial 1066 (FIG. 31E) thereto.

Preferably, circumferential recess 1836 of inner surface 1834 of housing element 1070 engages protrusions 1709 of rear portion 1704 of vial adaptor subassembly 1058. Preferably, forward facing cylindrical portion 1748 engages vial port 1082 of stopcock 1052.

A forward portion of main body element 1600 of receptacle adaptor subassembly 1056 preferably extends from a forward portion of housing element 1070 of adaptor assembly 1050, and surrounds needle 1410 enclosed in needle protection element 1412. Main body element including needle 1410 and needle protection cover 1412 is preferably accessible for connection of spike port adaptor element 1030 (FIGS. 34-35) thereto.

Preferably, rear portion 1658 of rear connection element 1406 engages receptacle port 1086 of stopcock 1052. A rear end of needle 1410 at least partially extends through bore 1660 such that needle 1410 is in fluid flow communication with receptacle port 1086.

Syringe port 1084 of stopcock 1052 preferably extends from housing element 1070 through slots 1842 formed in side surfaces thereof. Preferably, pathway defining element 1092 extends from apertures 1810 and 1812 of top housing portion 1801, and a bottom portion of stopcock 1052 extends through aperture 1818 of bottom housing element.

Housing element 1070 is preferably assembled such that top housing portion 1801 and bottom housing portion 1802 are connected by engagement of engagement surfaces 1828 of teeth 1824 of top housing portion 1801 and windows 1830 of bottom housing portion 1802.

Reference is now made to FIG. 46, which is a sectional illustration of the drug mixing system of FIG. 31B during attachment of syringe 1040 to the adaptor assembly 1050 of FIGS. 44-45B.

As seen in FIG. 46, luer tip 1044 of syringe 1040 is attached to syringe port 1084 of stopcock 1052. At this stage, handle 1080 of stopcock 1052 is positioned such that fluid can flow from receptacle port 1086 to syringe 1040 thereof. It is appreciated that at this stage plunger 1042 of syringe 1040 is preferably pushed fully inward in the syringe.

Reference is now made to FIG. 47, which is a sectional illustration of the drug mixing system of FIG. 31C during attachment of spike port adaptor element 1030 and receptacle 1032 of FIG. 31A to the receptacle adaptor subassembly 1056 of the adaptor assembly 1050 of FIG. 46.

As seen in FIG. 47, spike port adaptor element 1030, having receptacle 1032 joined thereto, is connected to receptacle adaptor subassembly 1056 of adaptor assembly 1050.

Spike 1308 is preferably previously inserted into spike port 1031 of receptacle 1032, such that bore 1310 of spike element 1306 engages fluid content of receptacle 1032. Connection port 1318 of spike port adaptor element 1030 engages wall portions 1606 and base portion 1602 of main body element 1600 of receptacle adaptor subassembly 1056.

Connection port 1318 is preferably locked into connection with receptacle adaptor subassembly 1056 by engagement of engagement surfaces 1626 of forward portions 1620 of arms 1614 (FIG. 40B) and a rearward facing wall portion of connection port 1318.

Preferably, needle 1410 punctures needle protection cover 1412 and septum 1320, resulting in a change to the structure of the needle protection cover. At this stage, receptacle 1032 is in fluid flow communication with syringe 1040 via bore 1310 of spike 1308 of spike port adaptor element 1030, needle 1410, bore 1660 and receptacle port and syringe port 1084 of stopcock 1052.

Reference is now made to FIG. 48, which is a sectional illustration of the drug mixing system of FIG. 31D during attachment of vial 1060 to vial adaptor subassembly 1058 of the adaptor assembly 1050 of FIG. 47.

Vial 1066 and vial head adaptor element 1068 joined thereto (FIG. 31E) or vial 1060 is preferably pushed into engagement with vial puncturing spike 1722 of vial adaptor subassembly 1058.

Typically, vial puncturing spike 1722 of vial adaptor subassembly 1058 punctures septum 1064 located inside top portion 1062 of vial 1060, thus enabling fluid flow between the main body of vial 1060 and cylindrical portion 1748 of main body element 1702 of vial adaptor subassembly 1058. Preferably, puncturing of septum 1064 releases any vacuum in vial 1060 by entrance of air into vial 1060 through carbon filter 1404 (FIG. 42B) and membrane 1402 (FIG. 42B).

Engagement between vial adaptor subassembly 1058 and vial 1060 is preferably maintained by snap engagement of protrusions 1716 and 1718 (FIGS. 42A and 42B) of rear portion 1704 of main body element 1702 with a neck portion 1063 of vial 1060. The engagement of protrusions 1716 and 1718 with neck portion 1063 ensures that vial adaptor subassembly 1058 is latched onto vial 1060 and cannot be removed therefrom. Tabs 1710 and outwardly tapered portions 1720 generally surround top portion 1062 and neck portion 1063 of vial 1060.

At this stage, the main body of vial 1060 is in fluid flow communication with syringe port 1084 via vial puncturing spike 1722, bore 1750 of cylindrical portion 1748 and vial port 1082 of stopcock 1052.

Reference is now made to FIG. 49, which is a sectional illustration of the drug mixing system of FIGS. 31F and 48 during fluid drawing from receptacle 1032 into syringe 1040.

At this stage, plunger 1042 of syringe 1040 is preferably retracted, thus drawing fluid from receptacle 1032 into syringe 1040. Fluid drawn from receptacle 1032 reaches syringe 1040 via bore 1310 of spike 1308 of spike port adaptor element 1030, needle 1410, bore 1660 of receptacle adaptor subassembly 1056, receptacle port 1086, pathway defining element 1092, syringe port 1084 and luer tip 1044.

Reference is now made to FIG. 50, which is a sectional illustration of the drug mixing system of FIGS. 31G and 48 during injection of fluid from syringe 1040 into vial 1060.

Initially, the user rotates handle 1080 of stopcock 1052, thus bringing syringe port 1084 into fluid flow engagement with vial port 1082.

Preferably, the user pushes plunger 1042 of syringe 1040 inwardly with respect to syringe 1040, resulting in injection of fluid from syringe 1040 to vial 1060, thus dissolving the drug contained in the vial. The fluid injected from syringe 1040 flows to vial 1060 via luer tip 1044 of syringe 1040, syringe port 1084, pathway defining element 1092, vial port 1082, bore 1750 of cylindrical portion 1748 and vial puncturing spike 1722.

The user preferably shakes the drug mixing system of FIG. 50 as shown in FIG. 31H, in order to ensure that the drug contained in vial 1060 is fully dissolved, and that the drug solution is homogenous.

Reference is now made to FIG. 51, which is a sectional illustration of the drug mixing system of FIGS. 31I and 48 during drawing of fluid from vial 1060 into syringe 1040.

At this stage, the user positions the system such that vial 1060 is on top, and preferably draws at least part of the drug solution contained in vial 1060, by at least partially retracting plunger 1042 of syringe 1040. The fluid drawn from vial 1060 flows into syringe 1040 via vial puncturing spike 1722, bore 1750 of cylindrical portion 1748, vial port 1082, pathway defining element 1092 and syringe port 1084 of stopcock 1052 and luer tip 1044 of syringe 1040.

Reference is now made to FIG. 52, which is a sectional illustration of the drug mixing system of FIGS. 31J and 48 during injection of fluid from syringe 1040 into receptacle 1032.

At a first stage, the user rotates handle 1080 of stopcock 1052, resulting in syringe port 1084 being in fluid flow engagement with vial port 1082.

Subsequently, plunger 1042 of syringe 1040 is preferably pushed inward with respect to the main body portion of the syringe. The inward displacement of plunger 1042 causes injection of fluid from syringe 1040 into receptacle 1032. Fluid drawn from syringe 1040 reaches receptacle 1032 via luer tip 1044, syringe port 1084, pathway defining element 1092, receptacle port 1086 of stopcock 1052, bore 1660 of receptacle adaptor subassembly 1056, needle 1410 and bore 1310 of spike 1308 of spike port adaptor element 1030.

Reference is now made to FIG. 53, which is a sectional illustration of the drug mixing system of FIG. 31L when ready for storage.

As shown in FIG. 53, spike port adaptor element 1030 (FIGS. 34-35) and receptacle 1032 joined thereto are disconnected from receptacle adaptor subassembly 1056 of adaptor assembly 1050. Typically, spike port adaptor element 1030 is disconnected from receptacle adaptor subassembly 1056 by slightly pushing arms 1614 extending from side surfaces 1612 (FIGS. 39-40B) of base portion 1602, causing teeth 1620 to move outward and release the rearward facing wall portion of connection port 1318 (FIGS. 34-35), thus disconnecting the connection port. Typically, needle 1410 is released from connection port 1318, and needle protection cover 1412 is deployed and once again fully encloses needle 1410, thus preventing liquid spill and aerosol spray.

Adaptor assembly 1050, including vial adaptor subassembly 1058, stopcock 1052, receptacle adaptor subassembly 1056 and housing element 1070, is preferably stored in a suitable cooling facility. During cooling thereof, adaptor assembly is preferably connected to syringe 1040, having plunger 1042 fully pushed inward, and to vial 1060 containing a drug solution therein. Typically, pathway defining element 1092 of stopcock 1052 connects receptacle port 1086 to syringe port 1084 at this stage.

Reference is now made to FIGS. 54A, 54B, 54C, 54D, 54E, 54F, 54G and 54H which are simplified pictorial illustrations of various stages of assembly and typical use of a drug mixing system constructed and operative in accordance with yet another preferred embodiment of the present invention.

Figure 54A:
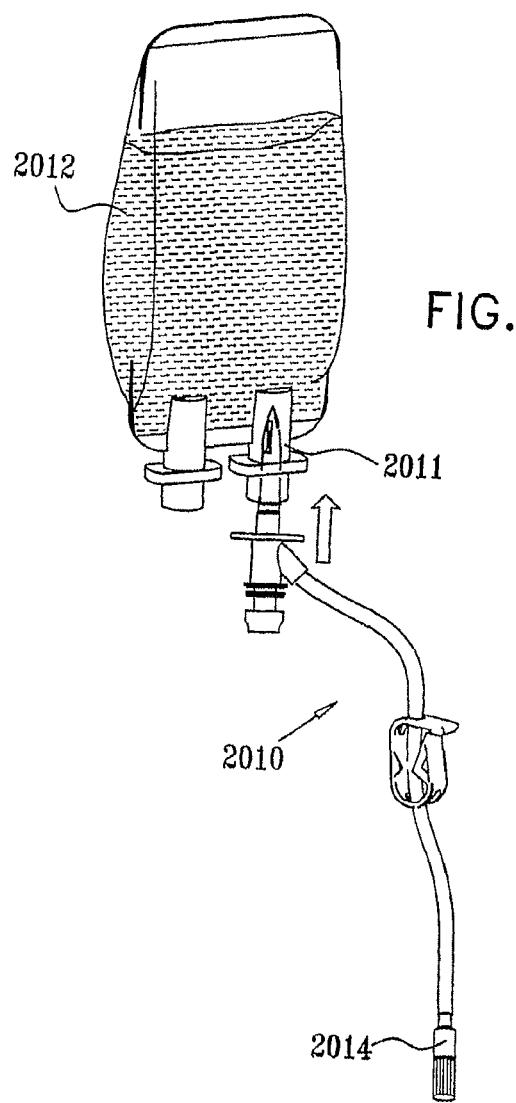

FIG. 54A shows a spike port adaptor element 2010, as described hereinbelow with reference to FIGS. 57-58, being inserted into a spike port 2011 in a receptacle 2012 containing a fluid. Preferably, a luer connector of spike port adaptor element 2010 is sealed by a luer cover element 2014.

Typically, receptacle 2012 comprises a bag, and the fluid contained therein is sterile salt solution, water, or any other suitable sterile solution or pure fluid.

Figure 54B:
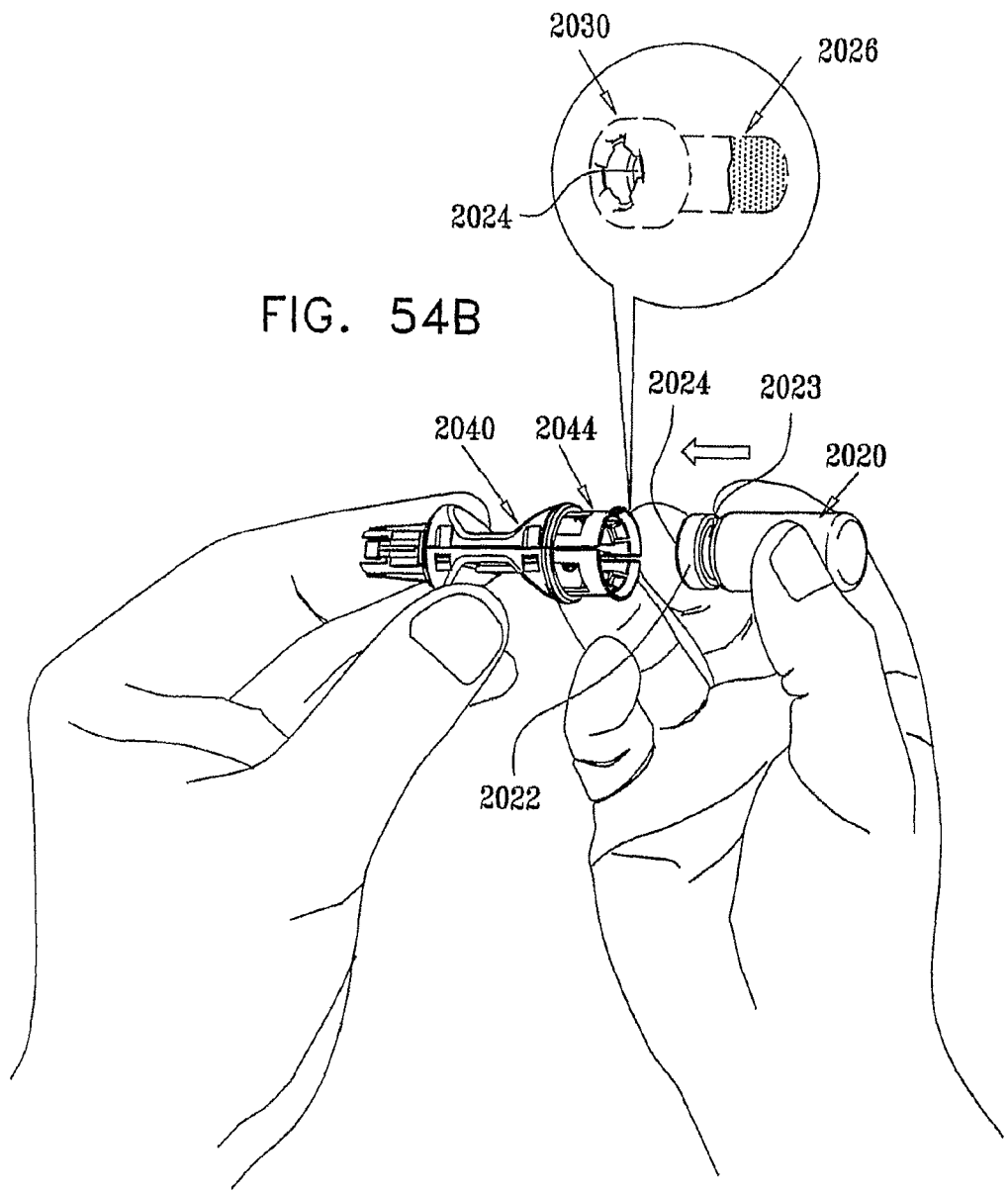

As seen in FIG. 54B, a vial 2020, including a top portion 2022 and a neck portion 2023, is pushed into engagement with a vial adaptor subassembly 2044 of adaptor assembly 2040. Top portion 2022 of vial 2020 preferably has a septum 2024 sealingly seated therein. Subassembly 2044 is described hereinbelow with reference to FIGS. 60-61B.

Figure 54C:
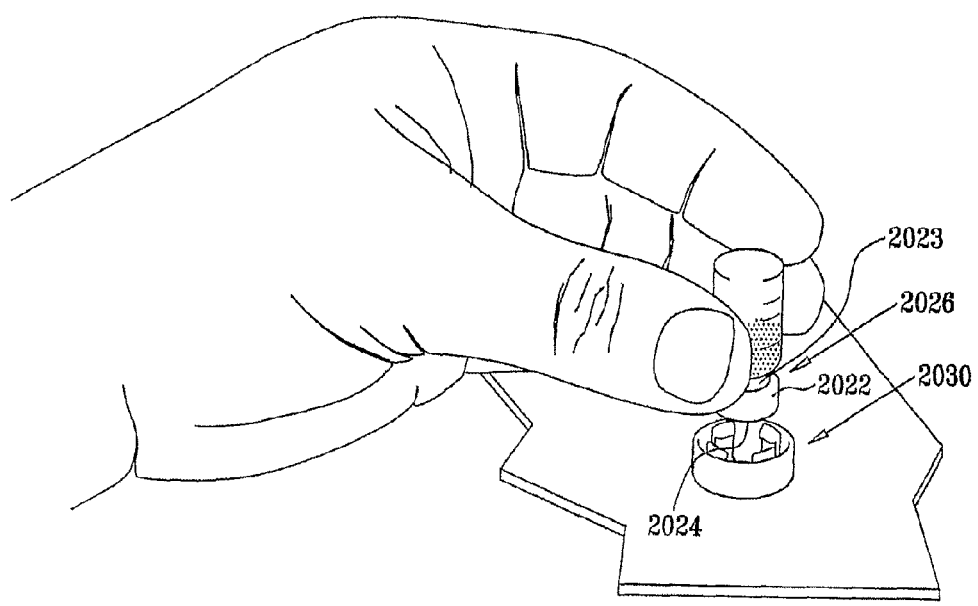
Figure 67A:
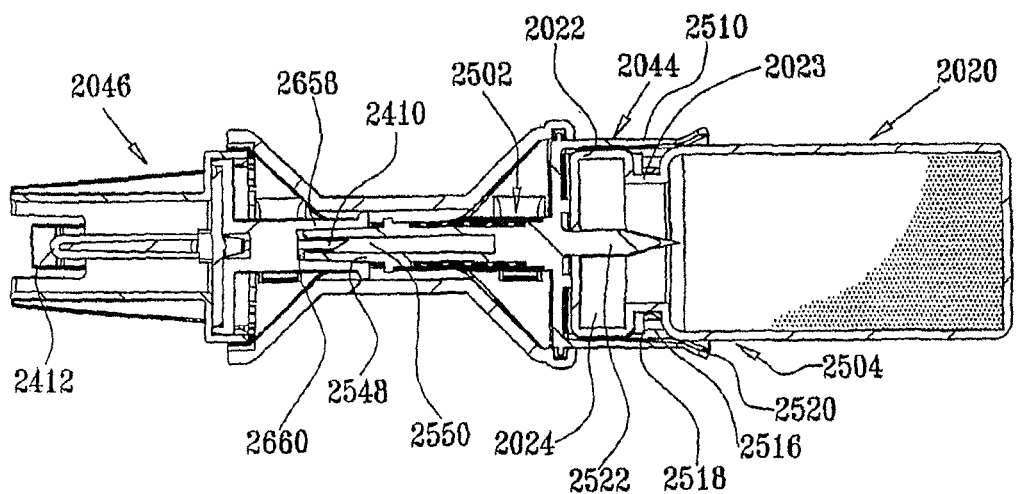
FIGS. 67A and 67B are sectional illustrations of the drug mixing system of FIG. 54C during attachment of a vial to the adaptor assembly of FIG. 65.
Figure 67B:
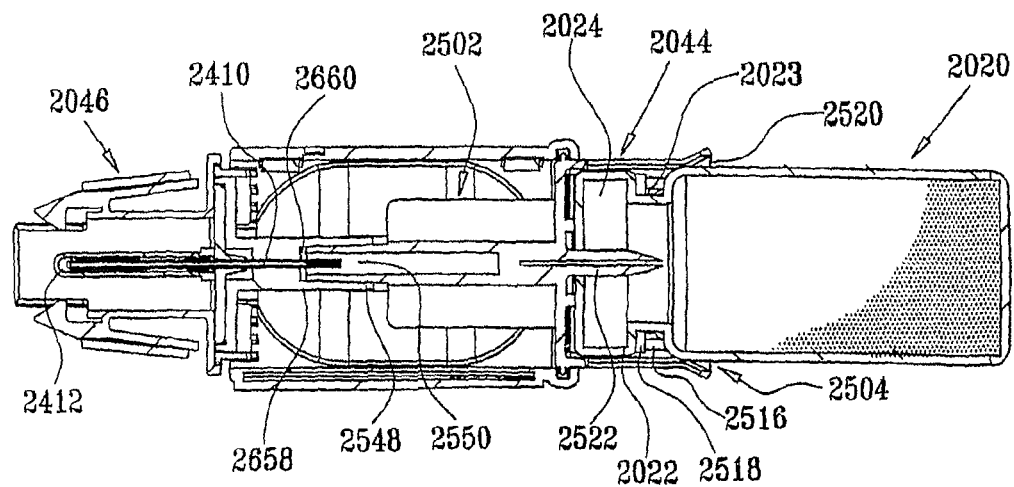

Alternatively, if a small vial 2026 is used, small vial 2026 is pushed into engagement with a vial head adaptor element 2030 which is described hereinbelow with reference to FIGS. 55-56 as shown in FIG. 54C, and is then pushed into engagement with vial adaptor subassembly 2044. Vials 2020 and 2026 typically contain a drug in soluble powder form, in a solution or in other suitable form. FIGS. 67A and 67B show a sectional view of the drug mixing system at this stage.

Figure 54D:
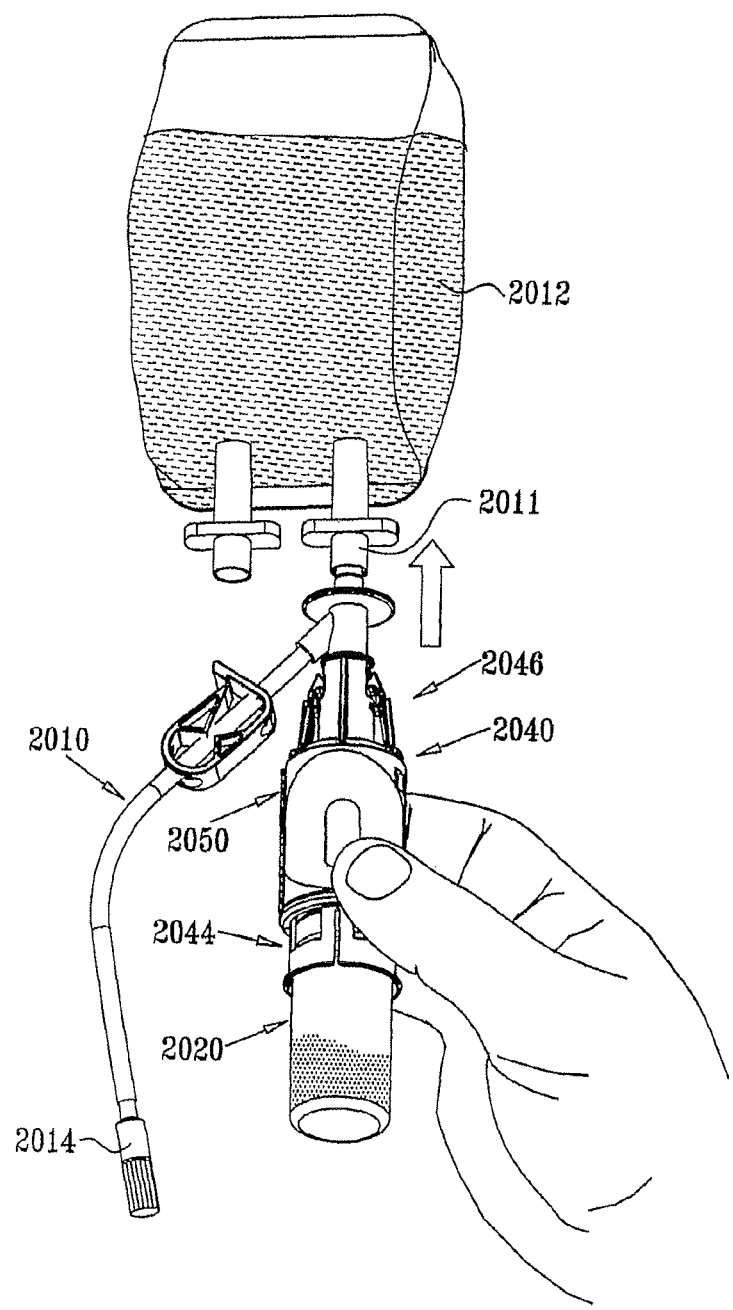

FIG. 54D shows spike port adaptor element 2010 and receptacle 2012 joined thereto, being connected to a receptacle adaptor subassembly 2046 of adaptor assembly 2040, which is described hereinbelow with reference to FIGS. 62-63B.

It is appreciated that receptacle adaptor subassembly 2046 and vial adaptor subassembly 2044 are preferably enclosed in a housing element 2050 of adaptor assembly 2040, which is described hereinbelow with reference to FIGS. 64A-64B.

It is appreciated by persons skilled in the art that the assembly steps shown in FIGS. 54A-54D may be performed in any suitable sequence.

Figure 54E:
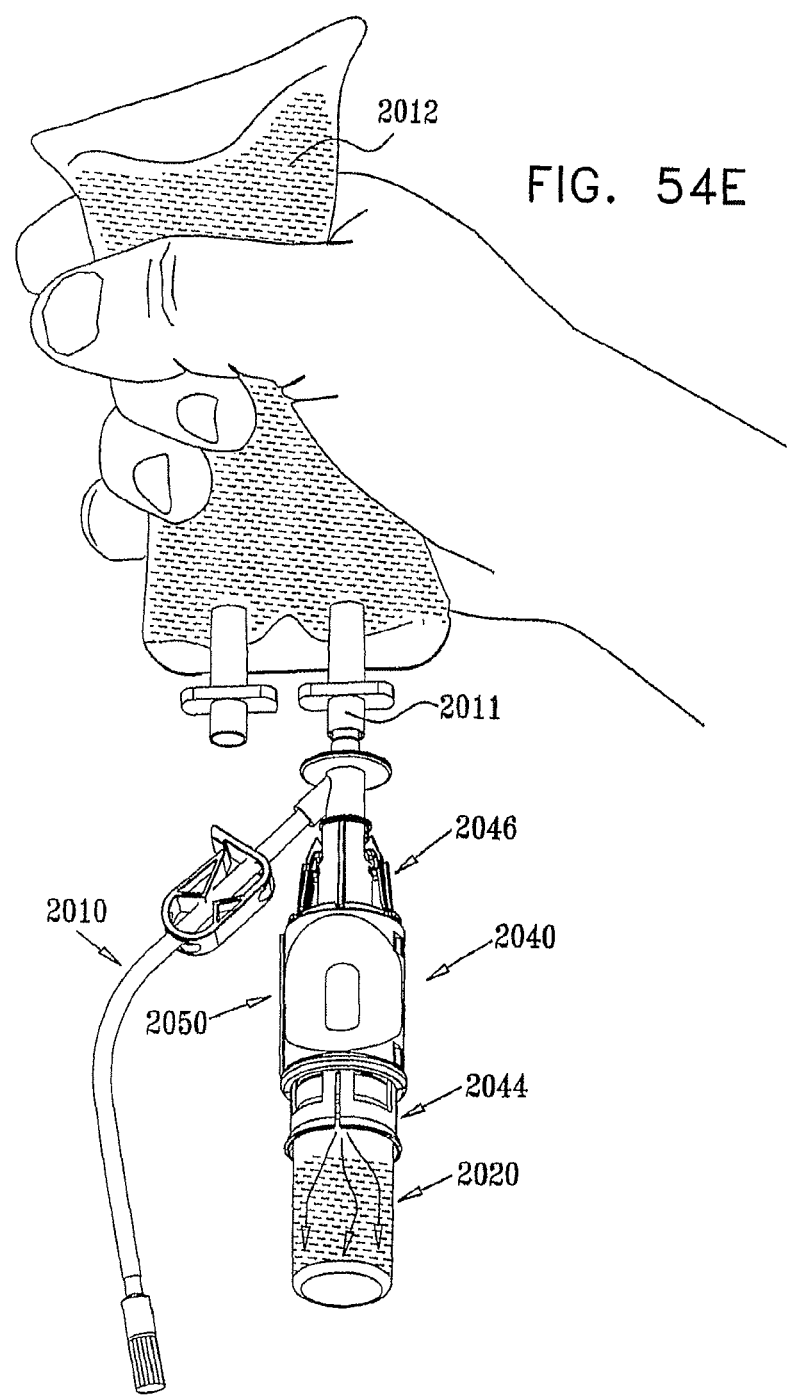

As seen in FIG. 54E, a user holds receptacle 2012 upright and squeezes the receptacle, thus at least partially filling vial 2020 with fluid squeezed out of receptacle 2012. This flow of fluid ensures that the fluid remains sterile, and that the user is not exposed thereto.

As seen in FIG. 54F, the user then shakes the drug mixing system of FIG. 54E to ensure that the drug in vial 2020 is fully dissolved and that the resulting solution is homogenous.

Figure 54G:
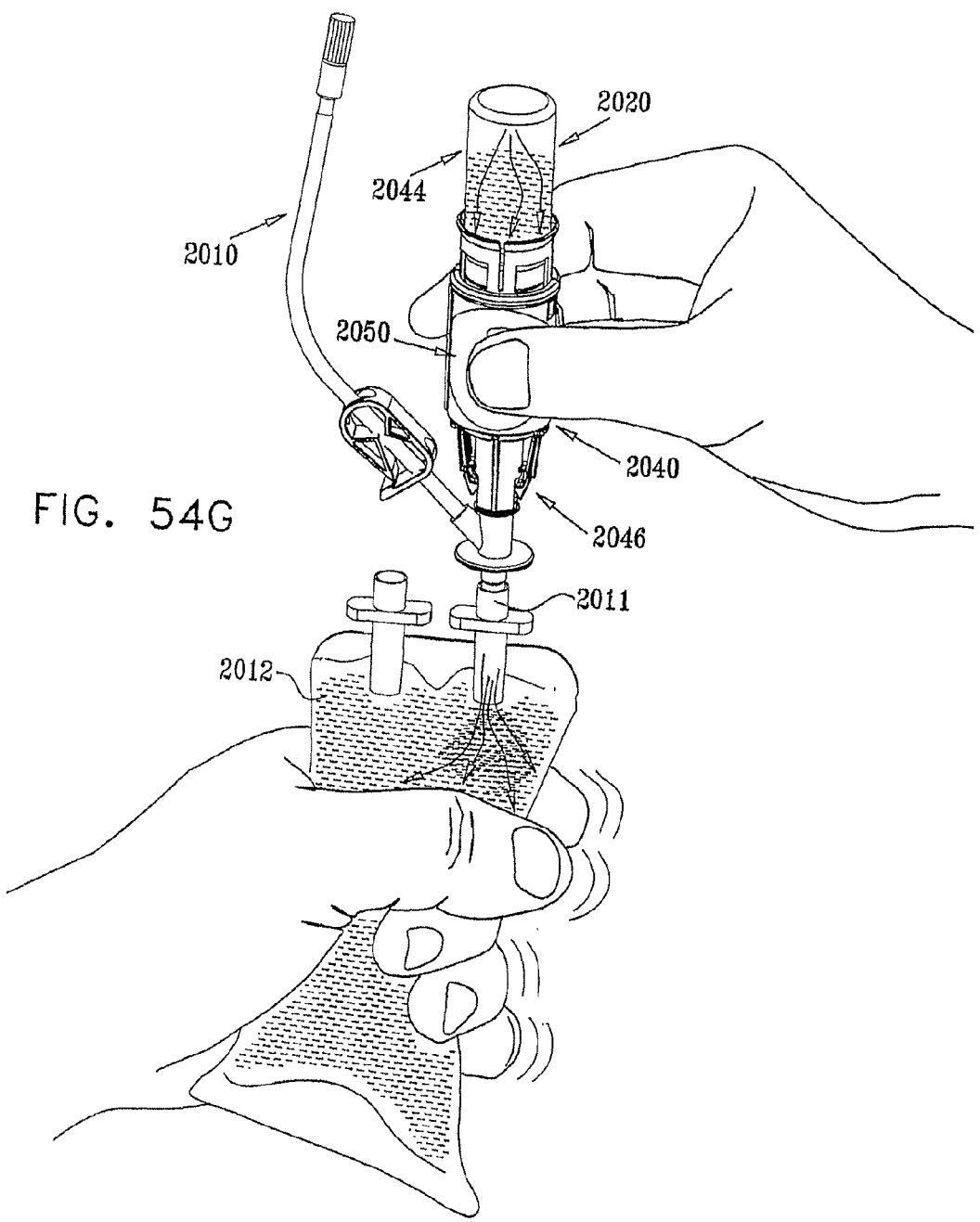

As seen in FIG. 54G, the user reverses the direction of the receptacle 2012, such that it is now facing downward, and then squeezes the receptacle. Squeezing of the receptacle 2012 causes the drug solution contained in vial 2020 to be drawn into the receptacle, thus further diluting the solution. The user preferably repeats this action until vial 2020 is empty, thus diluting the entire content of the vial in a single receptacle.

Figure 54H:
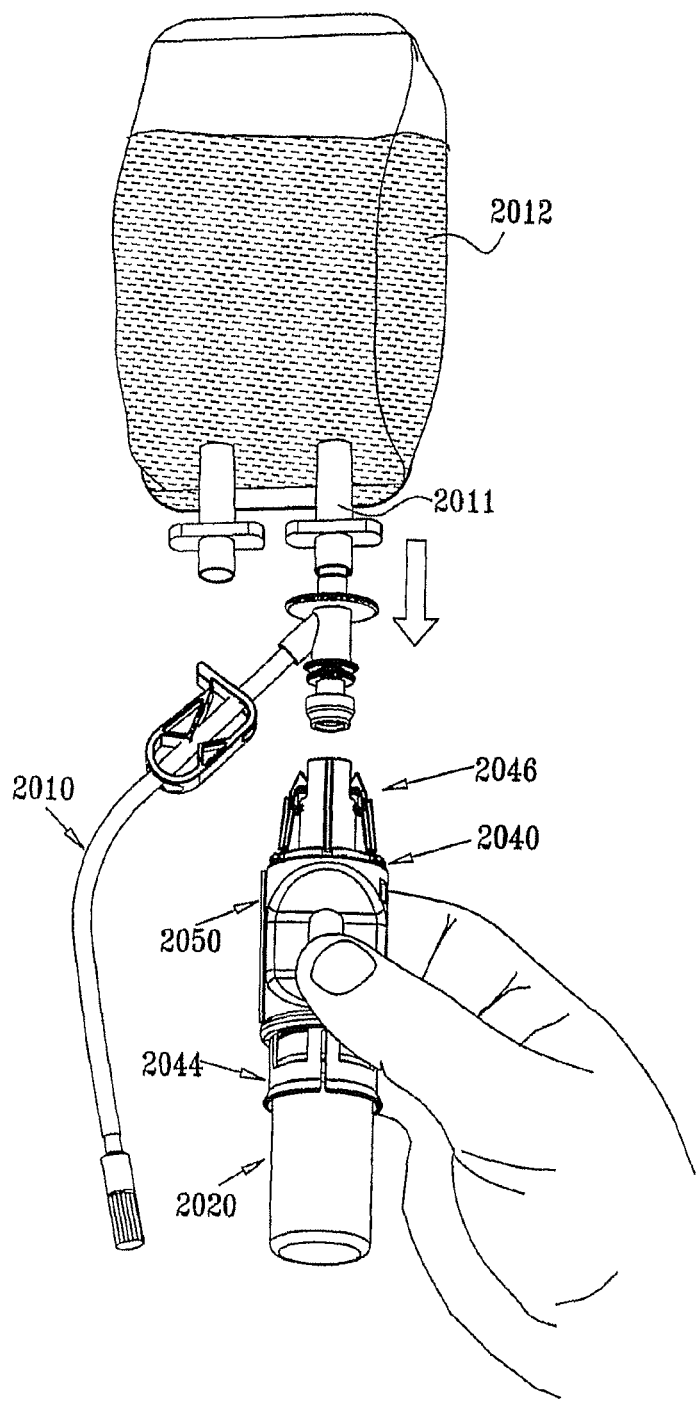

As shown in FIG. 54H, spiked receptacle adaptor element 2010 having receptacle 2012 joined thereto is disconnected from adaptor assembly 2040, which remains connected to vial 2020. It is appreciated that at this stage adaptor assembly 2040 and vial 2020 may be disposed of.

The structure of elements of the drug mixing system of FIGS. 54A-54H is described hereinbelow with reference to FIGS. 55-64B.

Figure 55:
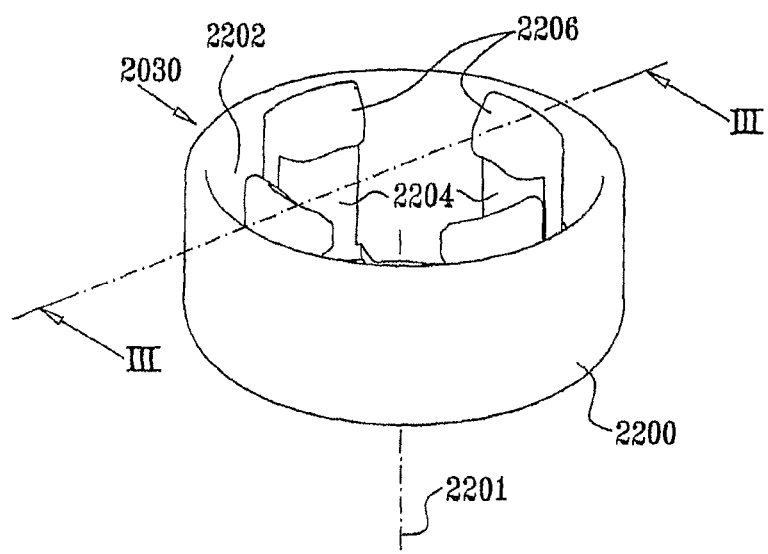
FIG. 55 is a simplified pictorial illustration of a vial head adaptor element which forms part of the drug mixing system of FIGS. 54A-54H.
Figure 56:
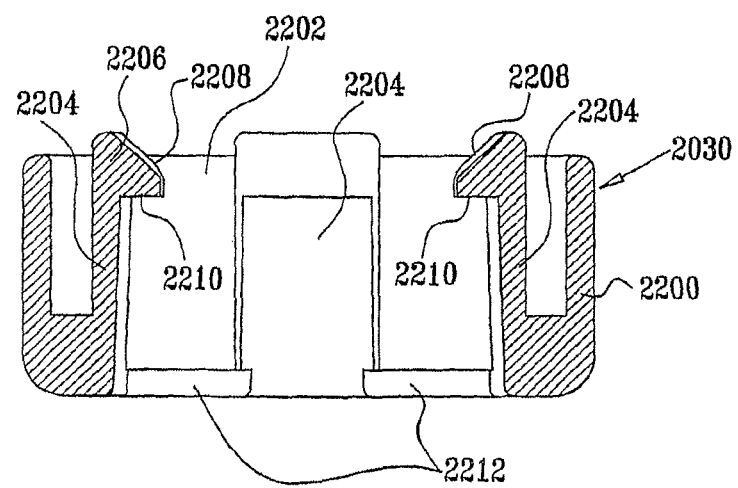
FIG. 56 is a sectional illustration taken along section lines LVI-LVI in FIG. 55.

Reference is now made to FIG. 55, which is a simplified pictorial illustration of a vial head adaptor element 2030 which forms part of the drug mixing system of FIGS. 54A-54H and to FIG. 56 which is a sectional illustration taken along section lines LVI-LVI in FIG. 55.

As seen in FIG. 55, vial head adaptor element 2030 is preferably a side-to-side symmetric integrally formed element which is preferably injection molded of plastic.

Vial head adaptor element 2030 preferably includes a main body portion 2200 which is generally cylindrical and has a central axis 2201. An inner cylindrical surface 2202 of main body portion 2200 preferably has four arms 2204 extending therefrom, each arm 2204 being arranged at generally right angles with respect to its neighboring arms.

Each of arms 2204 terminates at an upper end thereof, in the sense of FIG. 54C, in an inwardly facing generally triangular tooth 2206 having a forwardly facing inclined surface 2208 and a bottom-facing engagement surface 2210 extending generally perpendicular to arm 2204.

At bottom surface of vial head adaptor element 2030, there are formed four inwardly protruding surfaces 2212, extending generally perpendicular to inner surface 2202 of main body portion 2200. Each of neighboring surfaces 2212 is preferably arranged at a generally right angle with respect to its neighboring surfaces 2212. Surfaces 2212 and arms 2204 are rotationally offset from one another about axis 2201.

Reference is now made to FIG. 57, which is a simplified pictorial illustration of spike port adaptor element 2030 which forms part of the drug mixing system of FIGS. 54A-54H and to FIG. 58 which is a sectional illustration taken along section lines LVIII-LVIII in FIG. 57.

Spike port adaptor element 2010 preferably comprises a hollow flexible plastic tube 2302 having associated therewith a standard clamp 2304, which is commercially available from various manufacturers, such as Qosina of Italy.

At a forward end thereof, tube 2302 is connected to a tube port 2305 of a hollow spike element 2306 which is preferably formed of plastic. Spike element 2306 is preferably formed of a main body portion 2307 which preferably defines at a forward end thereof a spike 2308, having formed therein an aperture communicating with an axially extending bore 2310 and an additional bore 2312 which extends partially through main body portion 2307 and communicates with a top portion of bore 2310.

Rearward of spike 2308, main body portion 2307 defines a generally circular planar protrusion 2314 adapted to define the location at which a user grips the spike.

The interior of tube 2302 is in fluid flow communication with bore 2312 via tube port 2305. Bore 2310 preferably terminates in an aperture located in spike 2308 of main body portion 2307 and fully extends through the main body portion.

Main body portion 2307 preferably terminates in a connection port 2318 which is adapted to connect spike port adaptor element 2010 to receptacle adaptor subassembly

2046. Connection port 2318 preferably sealingly accommodates a generally circular septum 2320 on a seat 2322. Septum 2320 preferably engages the rear end of bore 2310, thus sealing the rear end of the bore.

Forward of connection port 2318, there is formed on main body portion 2307 a circumferential protrusion 2324, forward of which is formed an additional circumferential protrusion 2326, having an outer circumference which is slightly larger than that of protrusion 2324. Protrusions 2324 and 2326 are adapted to limit the movement of spike port adaptor element 2010 when it is connected to receptacle adaptor subassembly 2044.

A luer connector 2330 is preferably attached to a rear end of tube 2302. Luer connector 2330 preferably includes at a rearwardmost end thereof a narrow hollow port section 2332, forward of which there is formed a connecting tube portion 2334 and a hollow neck portion 2336 which is adapted to connect luer connector 2330 to tube 2302. Preferably, luer connector 2330 is sealed by luer cover element 2014.

It is appreciated that spike port adaptor element 2010 may alternatively be identical to spike port adaptor element 630 described hereinabove with reference to FIGS. 10-11B.

Figure 59:
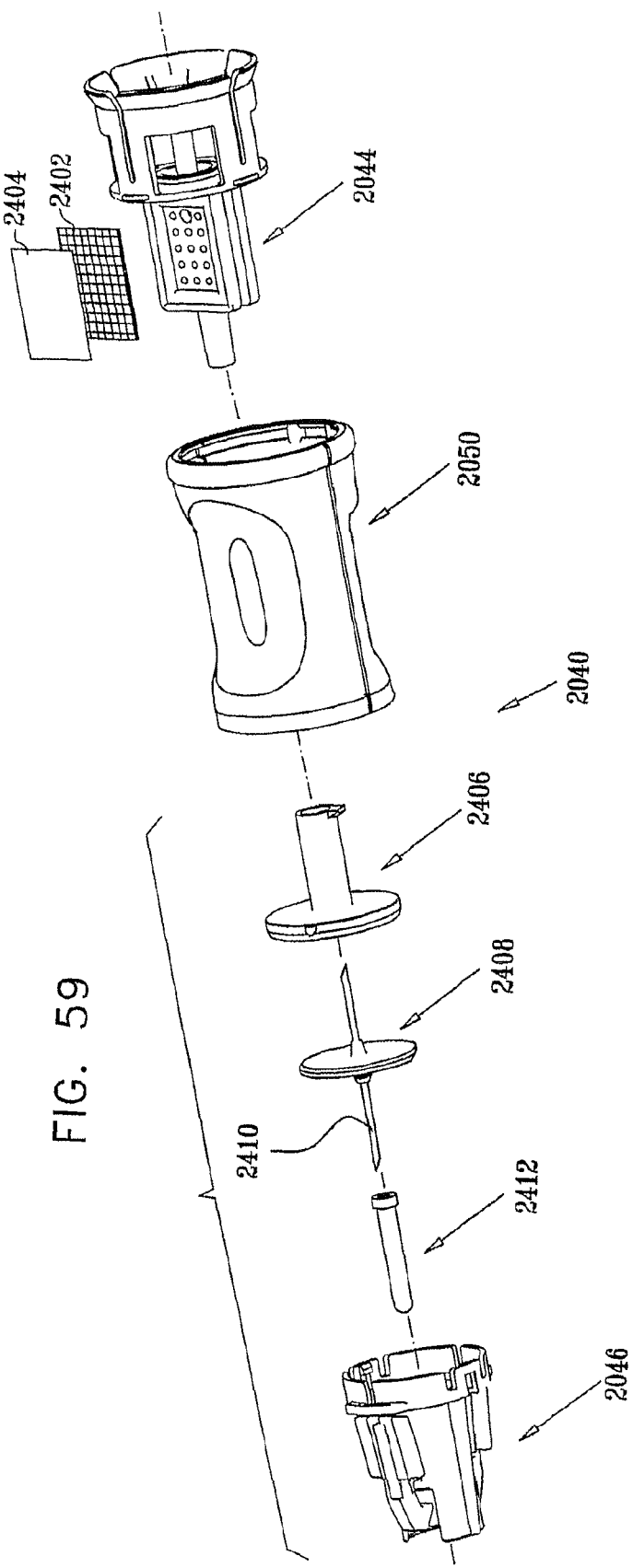
FIG. 59 is a simplified exploded view illustration of an adaptor assembly which forms part of the drug mixing system of FIGS. 54A-54H.

Reference is now made to FIG. 59, which is a simplified exploded view illustration of adaptor assembly 2040 which forms part of the drug mixing system of FIGS. 54A-54H.

As seen with particular clarity in FIG. 59, adaptor assembly 2040 comprises vial adaptor subassembly 2044, onto which are placed a hydrophobic membrane 2402, above which is optionally seated a carbon cloth filter 2404. Vial adaptor subassembly 2044 is connected at a forward portion thereof to a rear connection element 2406 of receptacle adaptor subassembly 2046.

A needle holding element 2408 is preferably seated within rear connection element 2406 and supports a needle 2410. A forward portion of needle 2410 is preferably protected by a flexible latex needle protection element 2412. Receptacle adaptor subassembly 2046 connects at a rearward end thereof to rear connection element 2406, enclosing needle holding element 2408 and needle protection element 2412.

The forward portion of vial adaptor subassembly 2044 as well as the rear portion of receptacle adaptor subassembly 2046 are located within housing element 2050.

Figure 60:
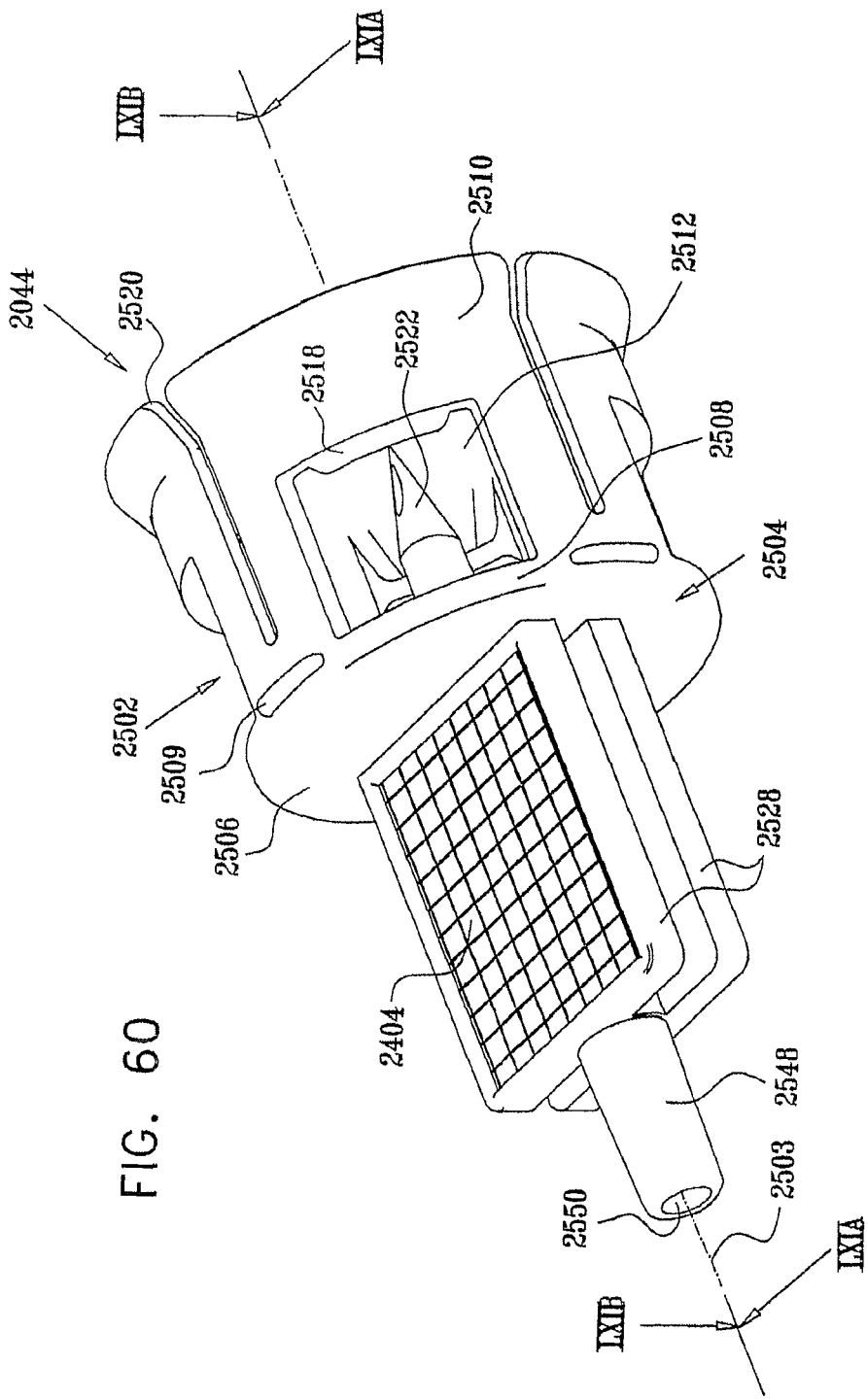
FIG. 60 is a simplified pictorial illustration of ad vial adaptor subassembly which forms part of the adaptor assembly of FIG. 59.

Reference is now made to FIG. 60, which is a simplified pictorial illustration of vial adaptor subassembly 2044 which forms part of adaptor assembly 2040 of FIG. 59 and to FIGS. 61A and 61B, which are sectional illustrations taken along respective section lines LXIA-LXIA and LXIB-LXIB in FIG. 60.

As seen in FIGS. 60-61B, vial adaptor subassembly 2044 comprises a main body element 2502 arranged generally about an axis 2503. Main body element 2502 is preferably integrally formed and preferably injection molded of plastic.

Main body element 2502 is preferably side-to-side symmetric about axis 2503, and preferably includes a rear portion 2504, which is generally cylindrical and terminates in a forward wall 2506. Rear portion 2504 comprises a forward base section 2508, preferably having four transversely extending outwardly facing protrusions 2509 extend therefrom, each protrusion being arranged at generally right angles with respect to its neighboring protrusions.

Rearward of base section 2508 there are formed a plurality of tabs 2510 each having a rectangular window 2512. Rearward of rectangular windows 2512 and on an inner surface 2514 of each of tabs 2510 there are preferably formed two radially extending inwardly facing protrusions 2516 each having an inclined surface. Protrusions 2516 preferably terminate at a forward end thereof in an inwardly facing transversely extending protrusion 2518. Rearward of protrusions 2516, each of tabs 2510 preferably includes an outwardly tapered portion 2520.

A hollow vial puncturing spike 2522 extends rearwardly from a rearward surface 2524 of forward wall 2506, and is surrounded by base section 2508 and by tabs 2510. Rearward surface 2524 additionally includes a circular cylindrical protrusion 2525, surrounding puncturing spike 2522. Two axially extending bores 2526 and 2527 extend through vial puncturing spike 2522.

Forward of forward wall 2506 of rear portion 2504 there is formed an intermediate portion which formed of two generally rectangular surfaces 2528, and includes an axial tubular portion 2530 having a bore 2531 extend therethrough, bore 2531 being in fluid flow engagement with bore 2526 of hollow vial puncturing spike 2522.

On the top rectangular surface 2528 and slightly recessed with respect thereto there is formed a plastic membrane support surface 2532, having formed thereon a plurality of generally evenly distributed spherical protrusions 2534, which are adapted to support hydrophobic membrane 2402 and prevent it from excessive inflation and from cracking. Membrane 2402 is adapted to allow free passage of air to and from main body element 2502, but to prevent passage of liquid and air borne particles, microorganisms and aerosol. A preferred membrane 2402 is Model Versapor R 0.2 Micron which is commercially available from Pall Corporation of New York, U.S.A.

A narrow bore 2537 connects membrane 2402 to bore 2531, thus allowing pressure equalization in an evacuated drug vial 2020 upon connection of vial 2020 to the vial adaptor subassembly 2044. When fluid first passes through the system during drug dilution, bore 2537 irreversibly fills with liquid, thus preventing air from escaping the system.

Prevention of the escape of air from the system is necessary for the reversible transfer of liquid from the receptacle 2012 to the vial 2020 and vice versa. Air movement between vial 2020 and receptacle 2012 causes changes in pressure in the vial, thereby pushing liquid from the vial into the receptacle.

A rim 2538 surrounding support surface 2532 is adapted to support an optional carbon cloth filter 2404 and maintain it in a raised position above and spaced from membrane 2402. Carbon filter 2404 is adapted to prevent toxic vapors from escaping from main body element 2502, thus protecting users. A preferred carbon cloth filter 2404 is Model No. Zorflex EMI which is commercially available from Charcoal Cloth International Ltd. of Houghton-le-Spring, England.

Rectangular surfaces 2528 of the intermediate portion terminate at a forward end thereof in a forward facing cylindrical portion 2548, having a bore 2550 extend therethrough. Preferably, bore 2550 is a continuation of tubular portion 2530 of the intermediate portion.

It is appreciated that the functionalities of membrane 2402 and carbon cloth filter 2404, to allow free passage of air into the drug mixing system while preventing passage thereinto of liquid and air-borne particles, microorganisms and aerosol and preventing toxic vapors from escaping from the drug mixing system, may be incorporated, using similar elements, into any receptacle adaptor subassembly 2046.

Figure 62:
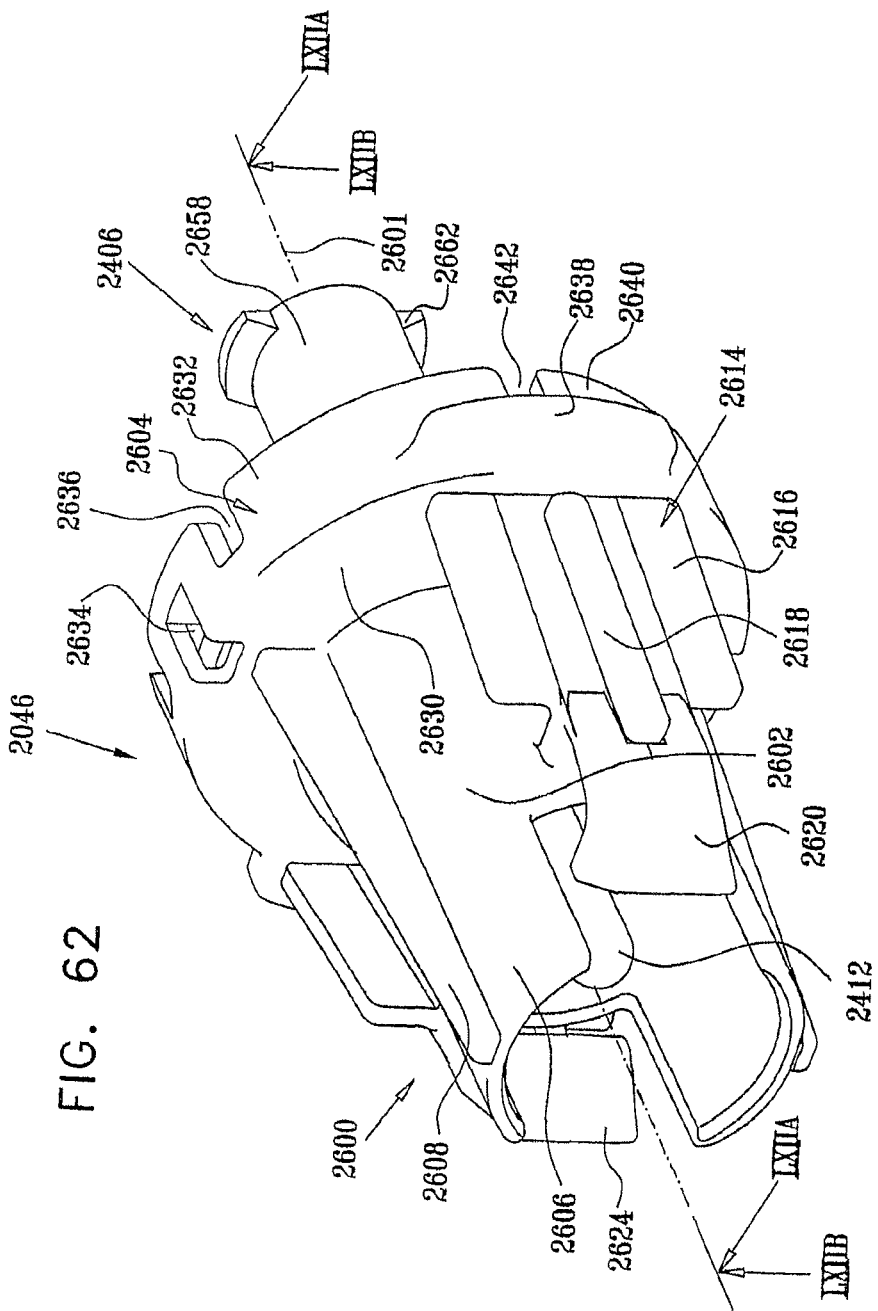
FIG. 62 is a simplified pictorial illustration of a receptacle adaptor subassembly which forms part of the adaptor assembly of FIG. 59.

Reference is now made to FIG. 62, which is a simplified pictorial illustration of receptacle adaptor subassembly 2046 which forms part of the adaptor assembly 2040 of FIG. 59 and to FIGS. 63A and 63B, which are sectional illustrations taken along respective section lines LXIIIA-LXIIIA and LXIIIB-LXIIIB in FIG. 62.

As seen in FIGS. 62-63B, receptacle adaptor subassembly 2046 includes a main body element 2600 which is arranged generally about an axis 2601. Main body element 2600 is preferably integrally formed of plastic, and is preferably side-to-side symmetric about axis 2601. Main body element 2600 preferably includes a generally cylindrical base portion 2602 terminating in a rear portion 2604.

Top and bottom generally concave wall portions 2606 are formed at a forward end of base portion 2602, each wall portion 2606 defining on an outer surface thereof an outwardly facing axially extending rib 2608, which extends from a forwardmost end of each of wall portions 2606 and along base portion 2602.

A connection surface 2610 extending transversely from side surfaces 2612 of base portion 2602 connects an outwardly extending arm 2614 to each side surface 2612. Each arm 2614 preferably has a generally square rear portion 2616, formed rearwardly of connection surface 2610, and has a radially extending outwardly facing protrusion 2618 formed thereon. Protrusion 2618 preferably extends onto an outer surface of a generally rectangular forward portion 2620 of each of arms 2614, which extends forwardly of connection surface 2610.

An inwardly facing generally triangular tooth 2622 is formed adjacent a top end of each of forward portions 2620. Each tooth 2622 preferably includes a forwardly facing inclined surface 2624 and a rearwardly facing engagement surface 2626.

Rear portion 2604 preferably includes a transversely extending generally circular portion 2630 which forms a base for ribs 2608 and which terminates at a rear end thereof in an axially extending generally cylindrical wall portion 2632.

Wall portion 2632 preferably defines on a top and bottom surface thereof a small generally rectangular window 2634, and two forwardly facing slots 2636 which are formed on either side of window 2634. Two generally symmetric side-facing tabs 2638 are formed on side surfaces 2640 of wall portion 2632, each tab 2638 being formed forwardly of a generally rectangular forwardly facing slot 2642.

Rear connection element 2406 preferably includes a forward disk 2652 defining a central bore 2654. Disk 2652 preferably functions as a terminating wall for a forward facing cylindrical portion 2656. Rearward of disk 2652 there is preferably formed a rear portion 2658, having a narrow bore 2660 extend therethrough. Bore 2660 preferably widens toward the rear end of rear portion 2658, thus enabling rear portion 2658 to connect to an appropriate port. Preferably, two generally symmetric tabs 2662 are formed on top and bottom surfaces of rear portion 2658. Cylindrical portion 2656 preferably has an outer circumference that is slightly smaller than that of wall portion 2632, and is located therein.

Needle holding element 2408 preferably supports needle 2410 on a generally circular disk portion 2672. Needle 2410 extends axially through base portion 2602 of main body element 2600 and through bore 2660 of rear connection element 2650. Disk portion 2672 is preferably seated in cylindrical portion 2656, and is locked into cylindrical portion 2656 by portion 2630.

Figure 64A:
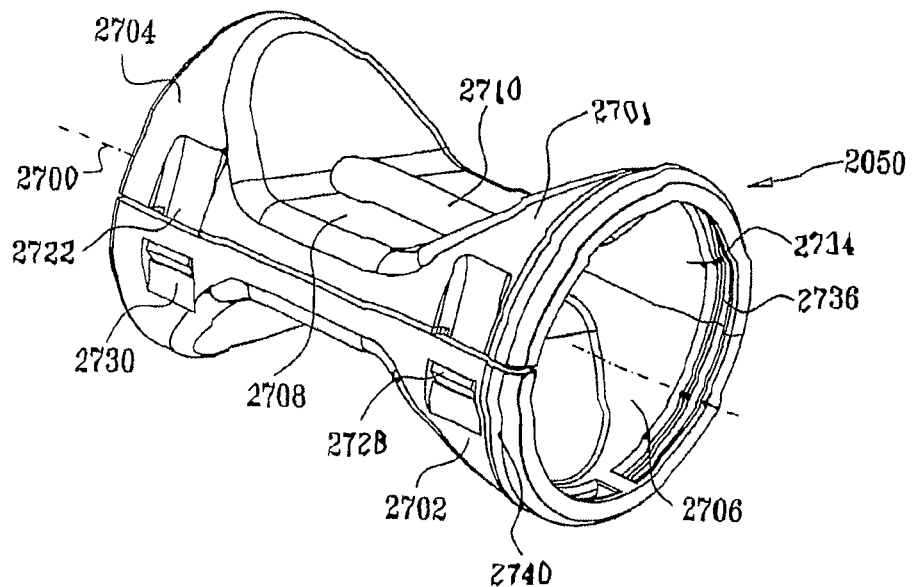
FIGS. 64A and 64B are simplified pictorial illustrations of a housing element which forms part of the adaptor assembly of FIG. 59 in closed and open orientations, respectively.
Figure 64B:
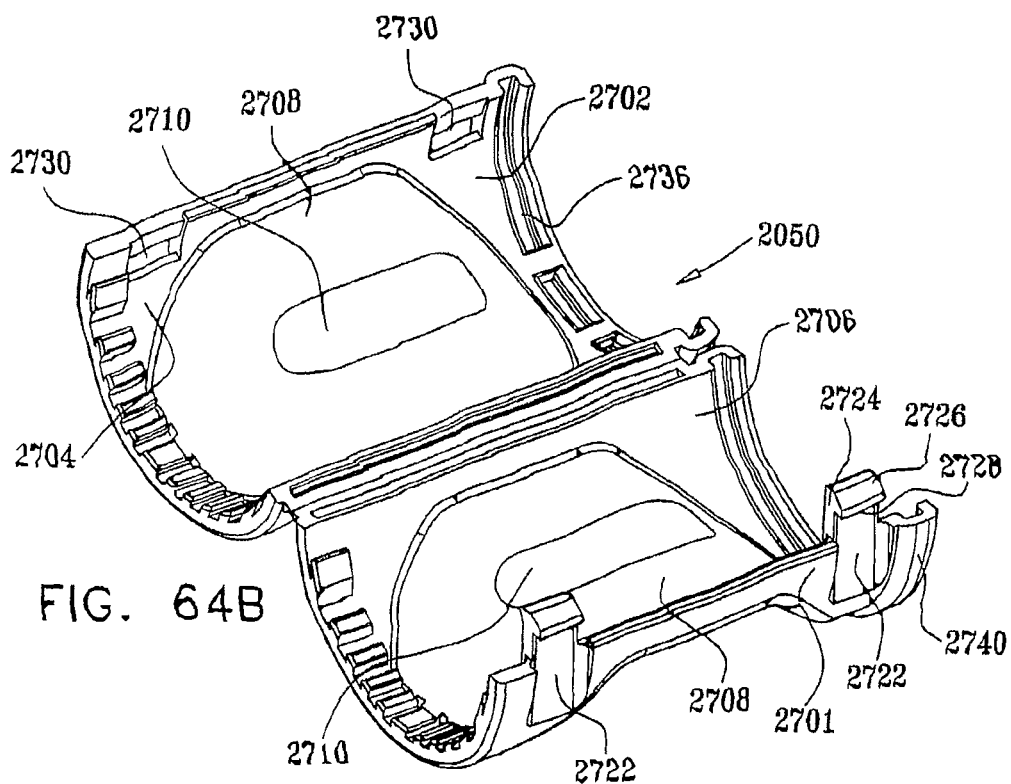

Reference is now made to FIGS. 64A and 64B, which are simplified pictorial illustrations of the housing element 2050 which forms part of the adaptor assembly 2040 of FIG. 59 in closed and open orientations, respectively.

As seen in FIGS. 64A and 64B, housing element 2050 is preferably integrally formed about an axis 2700 and includes a top housing portion 2701 and a bottom housing portion 2702. Preferably, housing portions 2701 and 2702 are side-to-side symmetric about axis 2700. Preferably, each of housing portions 2701 and 2702 includes a semi-cylindrical forward portion 2704 and a semi-cylindrical rearward portion 2706.

Top and bottom housing portions 2701 and 2702 each include an inwardly recessed portion 2708 including a generally central elongate protrusion 2710.

Top housing portion 2701 includes at forward and rearward ends thereof outwardly extending fingers 2722 terminating in a generally triangular teeth 2724 which include inclined outwardly facing surfaces 2726 and engagement surfaces 2728. Bottom housing portion 2702 preferably includes at forward and rearward ends thereof two generally rectangular windows 2730 which are placed generally below fingers 2722 and are adapted to engage engagement surfaces 2728 of fingers 2722 when housing element 2050 is assembled.

An inner surface 2734 of housing element 2050 preferably includes at a rearward end thereof a circumferential recess 2736 which is adapted to engage protrusions 2509 of rear portion 2504 of vial adaptor subassembly 2044. An outer surface of housing element 2050 which lies above recess 2736 preferably includes an outwardly facing protrusion 2740 which protrudes out of cylindrical rearward portion 2706.

Figure 65:
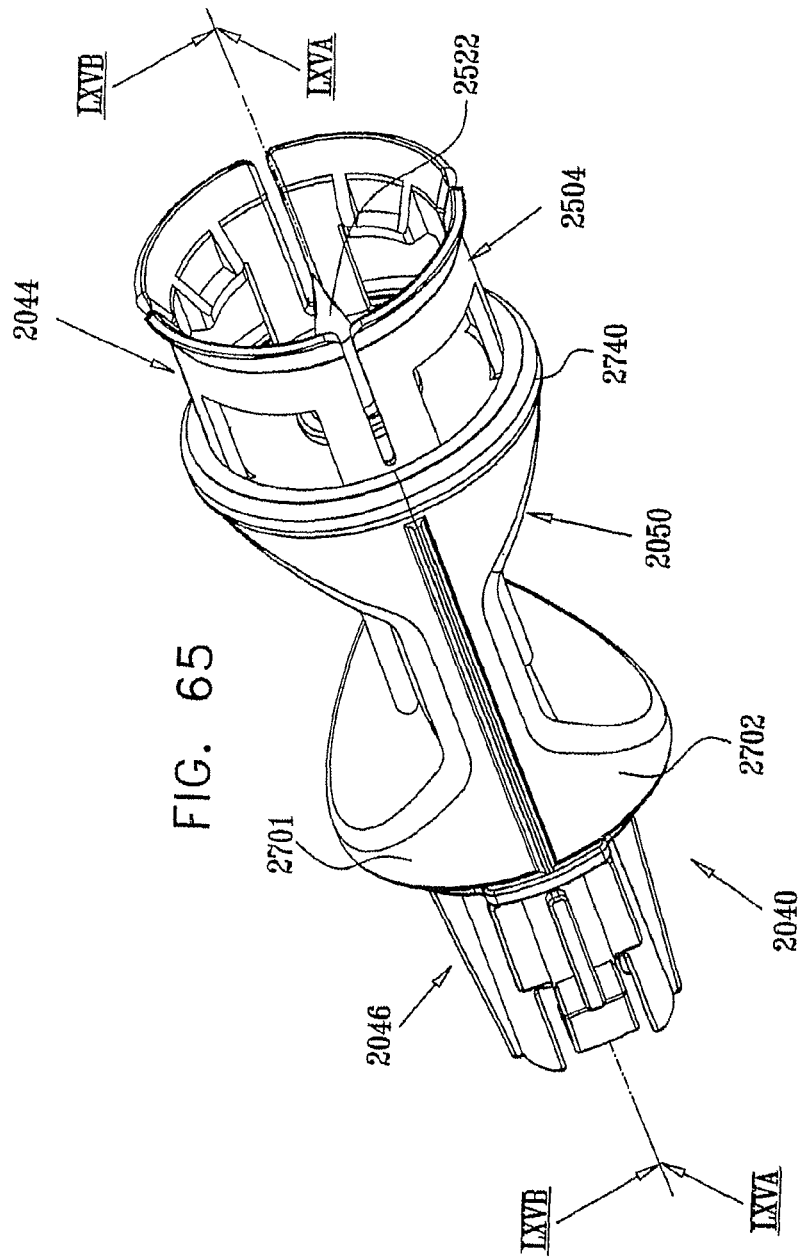
FIG. 65 is a simplified assembled pictorial illustration of the adaptor assembly of FIG. 59.
Figure 66A:
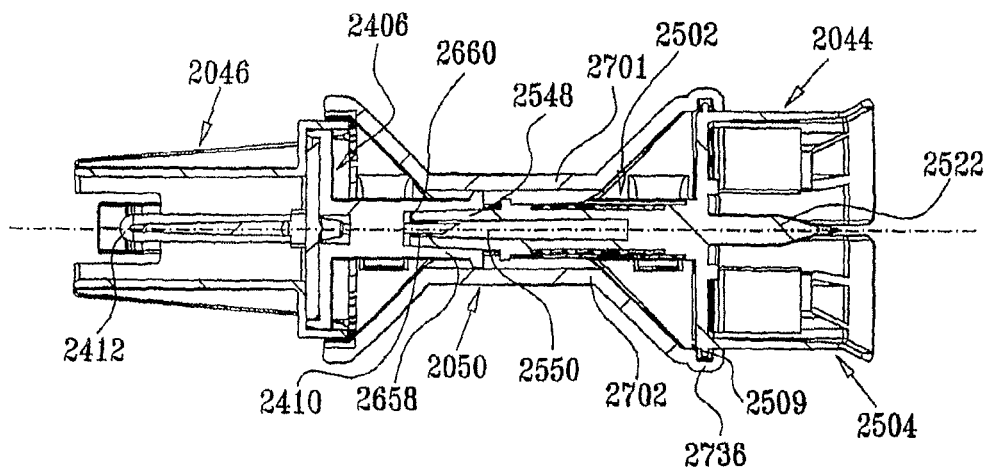
FIGS. 66A and 66B are sectional illustrations taken along respective section lines LXVIA-LXVIA and LXVIB-LXVIB in FIG. 65.
Figure 66B:
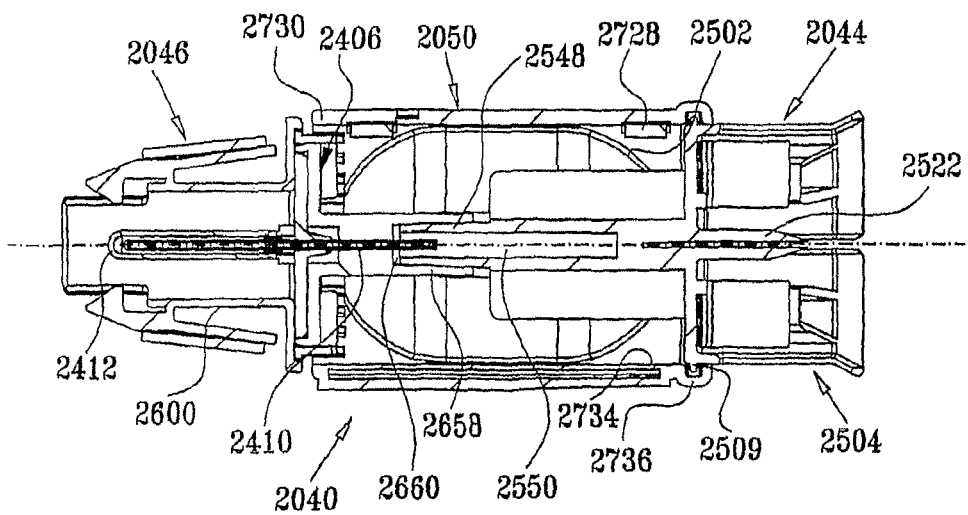

Reference is now made to FIG. 65, which is a simplified assembled pictorial illustration of the adaptor assembly 2040 of FIG. 59 and to FIGS. 66A and 66B, which are sectional illustrations taken along respective section lines LXVIA-LXVIA and LXVIB-LXVIB in FIG. 65.

As seen in FIGS. 65-66B, rear portion 2504 of vial adaptor subassembly 2044 extends from a rear portion of housing element 2050. Vial puncturing spike 2522 preferably extends out of housing element 2050, and is accessible for connection of vial 2020 or of vial 2026 (FIG. 54B) thereto.

Preferably, circumferential recess 2736 of inner surface 2734 of housing element 2050 engages protrusions 2509 of rear portion 2504 of vial adaptor subassembly 2044. Preferably, forward facing cylindrical portion 2548 engages rear portion 2658 of rear connection element 2406. A rear end of needle 2410 at least partially extends through bore 2660 and through bore 2550 such that bore 2550 is in fluid flow communication with needle 2410 of receptacle adaptor subassembly 2046.

A forward portion of main body element 2600 of receptacle adaptor subassembly 2046 preferably extends from a forward portion of housing element 2050 of adaptor assembly 2040, and surrounds needle 2410 enclosed in needle protection element 2412. Main body element 2600 including needle 2410 and needle protection cover 2412 is preferably accessible for connection of spike port adaptor element 2010 (FIGS. 57-58) thereto.

Housing element 2050 is preferably assembled, such that top housing portion 2701 and bottom housing portion 2702 are connected by engagement of engagement surfaces 2728 of teeth 2724 of top housing portion 2701 and windows 2730 of bottom housing portion 2702.

Reference is now made to FIGS. 67A and 67B, which are sectional illustrations of the drug mixing system of FIG. 54B during attachment of vial 2020 to the vial adaptor subassembly 2044 of adaptor assembly 2040 of FIG. 65.

Vial 2026 and vial head adaptor element 2030 joined thereto (FIG. 54C) or vial 2020 is preferably pushed into engagement with vial puncturing spike 2522 of vial adaptor subassembly 2044.

Typically, vial puncturing spike 2522 of vial adaptor subassembly 2044 punctures septum 2024 located inside top portion 2022 of vial 2020, thus enabling fluid flow between the main body of vial 2020 and bore 2550 of cylindrical portion 2548 of main body element 2502 of vial adaptor subassembly 2044. Preferably, puncturing of septum 2024 releases any vacuum in vial 2020 by entrance of air into vial 2020 through optional carbon cloth filter 2404 (FIG. 61A) and membrane 2402 (FIG. 61A).

Engagement between vial adaptor subassembly 2044 and vial 2010 is preferably maintained by snap engagement of protrusions 2516 and 2518 of rear portion 2504 of main body element 2600 with neck portion 2023 of vial 2020. The engagement of protrusions 2516 and 2518 with neck portion 2023 ensures that vial adaptor subassembly 2044 is latched onto vial 2020 and cannot be removed therefrom. Tabs 2510 and outwardly tapered portions 2520 generally surround top portion 2022 and neck portion 2023 of vial 2020.

At this stage, the main body of vial 2020 is in fluid flow communication with needle 2410 via vial puncturing spike 2522, bore 2550 of cylindrical portion 2548 and bore 2660 of cylindrical portion 2658.

Figure 68:
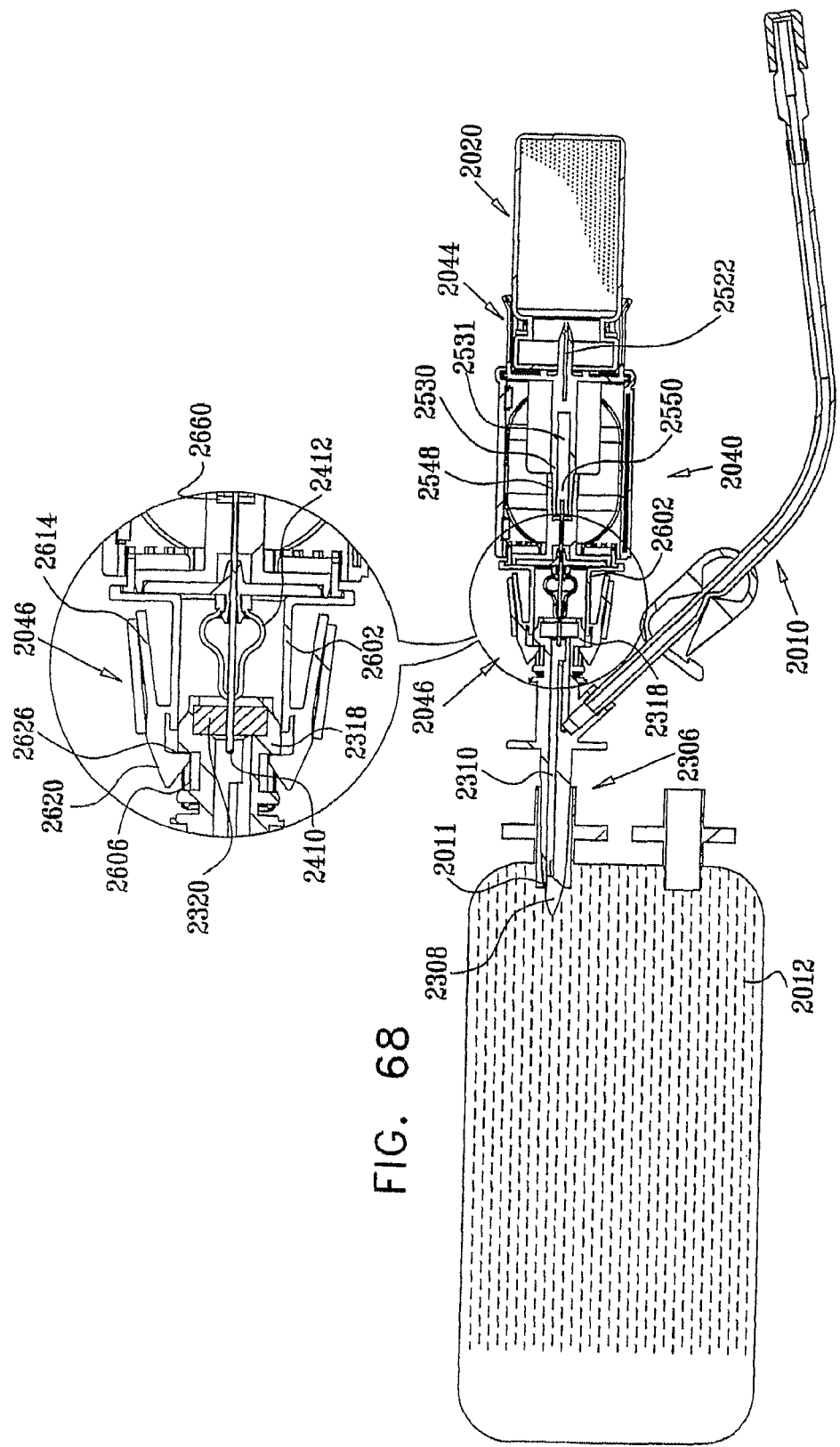
FIG. 68 is a sectional illustration of the drug mixing system of FIG. 54D-54G during attachment of the receptacle port adaptor element of FIG. 54B to the adaptor assembly of FIG. 67.

Reference is now made to FIG. 68, which is a sectional illustration of the drug mixing system of FIG. 54D-54G during attachment of the receptacle port adaptor element 2010 and receptacle 2012 of FIG. 54A to the receptacle adaptor subassembly 2046 of adaptor assembly 2040 of FIG. 67, having vial 2020 attached thereto.

As seen in FIG. 68, spike port adaptor element 2010, having receptacle 2012 joined thereto, is connected to receptacle adaptor subassembly 2046 of adaptor assembly 2040.

Spike 2308 is preferably previously inserted into spike port 2011 of receptacle 2012, such that bore 2310 of spike element 2306 engages fluid content of receptacle 2012. Connection port 2318 of spike port adaptor element 2010 engages wall portions 2606 and base portion 2602 of main body element 2600 of receptacle adaptor subassembly 2046.

Connection port 2318 is preferably locked into connection with receptacle adaptor subassembly 2046 by engagement of engagement surfaces 2626 of forward portions 2620 of awls 2614 and a rearward facing wall portion of connection port 2318.

Preferably, needle 2410 punctures needle protection cover 2412 and septum 2320, resulting in partial collapse of the needle protection cover. At this stage, receptacle 2012 is in fluid flow communication with the main body of vial 2020 via bore 2310 of spike 2308 of spike port adaptor element 2010, needle 2410, bore 2660, bore 2550 of cylindrical portion 2548, bore 2531 of tubular portion 2530 and vial puncturing spike 2522.

Figure 69:
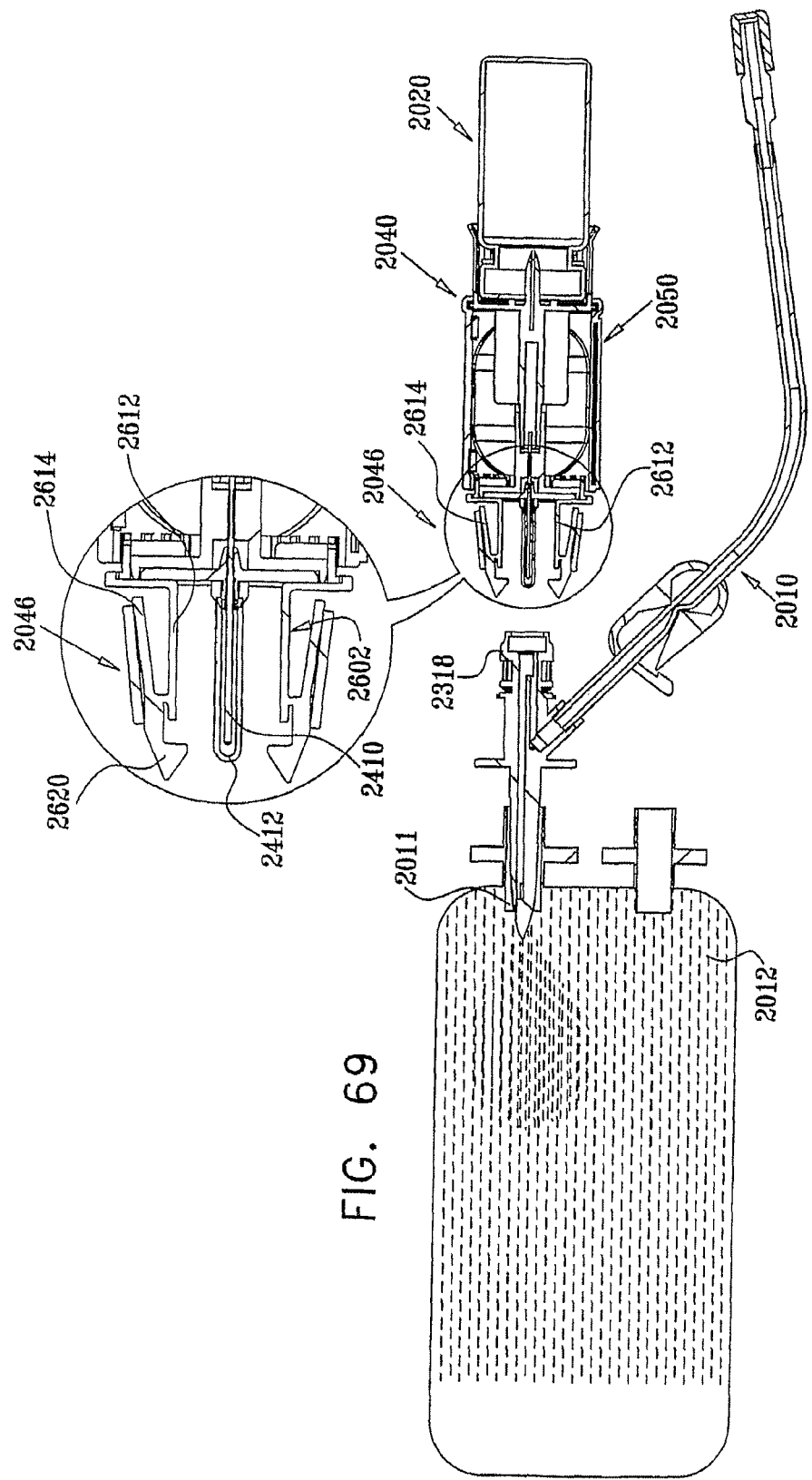
FIG. 69 is a sectional illustration of the drug mixing system of FIGS. 54H and 68 during disconnection of the receptacle port adaptor element of FIG. 54B from the adaptor assembly of FIG. 67.

Reference is now made to FIG. 69, which is a sectional illustration of the drug mixing system of FIGS. 54H and 68 during disconnection of the spike port adaptor element 2010 and receptacle 2012 from the receptacle adaptor subassembly 2046 of adaptor assembly 2040 of FIG. 67.

As shown in FIG. 69, spike port adaptor element 2010 and receptacle 2012 joined thereto are disconnected from receptacle adaptor subassembly 2046 of adaptor assembly 2040. Typically, spike port adaptor element 2010 is disconnected from receptacle adaptor subassembly 2046 by slightly pushing arms 2614 extending from side surfaces 2612 of base portion 2602, causing teeth 2620 to move outward and release the rearward facing wall portion of connection port 2318, thus disconnecting the connection port. Typically, needle 2410 is released from connection port 2318, and needle protection cover 2412 is deployed and once again fully encloses needle 2410, thus sealing it to prevent leakage.

Figure 70:
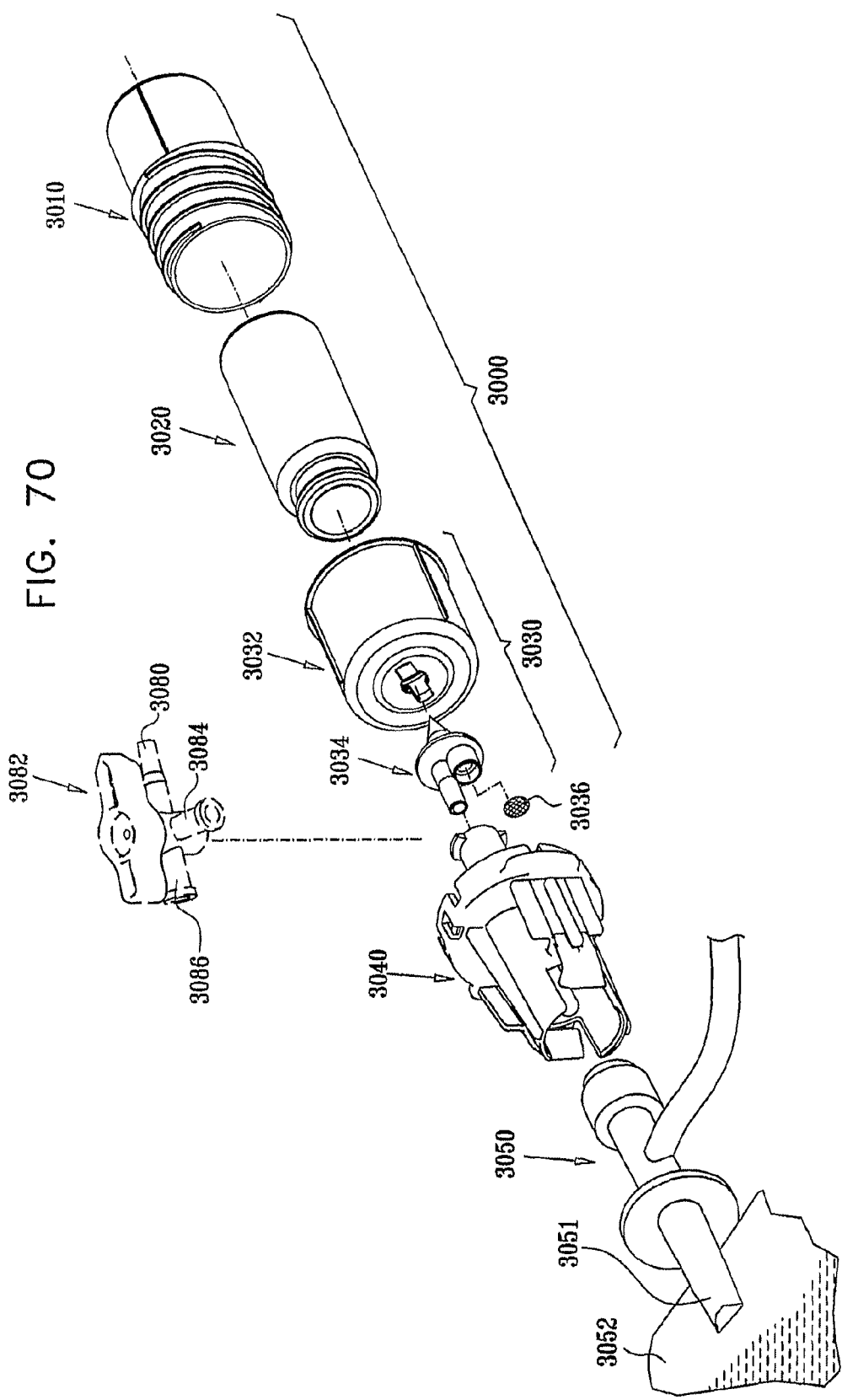
FIG. 70 is an exploded view illustration of a drug mixing system which is constructed and operative in accordance with a further preferred embodiment of the present invention.

Reference is now made to FIG. 70 which is a simplified exploded view illustration of a drug mixing system constructed and operative in accordance with a further preferred embodiment of the present invention. The embodiment of FIG. 70 is a modification of the embodiments of FIGS. 31A-53 and 54A-69. Accordingly, for the sake of conciseness, it is described hereinbelow in somewhat abbreviated form with reference to FIGS. 71-78.

In this embodiment the drug vial is enclosed in a protective housing used during storage and dilution, thereby preventing spills in case of breakage.

As seen with particular clarity in FIG. 70, the drug mixing system comprises a vial adaptor subassembly 3000, which preferably comprises an externally threaded vial support element 3010, into which is placed a vial 3020.

A vial puncturing cover assembly 3030 comprises an internally threaded covering element 3032, which connects at a forward end thereof to the externally threaded portion of vial support element 3010. At a top end thereof, covering element 3032 engages a vial puncturing spike element 3034, which supports a hydrophobic membrane 3036.

Vial puncturing cover assembly 3030 connects at a forward end thereof to a connection port of a receptacle adaptor subassembly 3040, which is adapted to engage a spike port receptacle adaptor element 3050. Spike port receptacle adaptor element 3050 is preferably inserted into a receptacle port 3051 of a receptacle 3052.

Alternatively, vial puncturing cover assembly 3030 may connect at a forward end thereof to a vial port 3080 of a stopcock 3082, and the connection port of receptacle port adaptor assembly 3040 connects to a receptacle port 3084 of stopcock 3082. When this option is used, a syringe port 3086 of stopcock 3082 preferably engages a luer fitted syringe.

It is appreciated that vial 3020 may be identical to either of vials 2020 and 2026, and that receptacle 3052 may be identical to receptacle 2012, described hereinabove with reference to FIGS. 54A-54C.

Receptacle adaptor subassembly 3040 may be identical to receptacle adaptor subassembly 2046, described hereinabove with reference to FIGS. 62-63B.

Spike port adaptor element 3050 may be identical to spike port adaptor element 2010, described hereinabove with reference to FIGS. 57-58.

Figure 71:
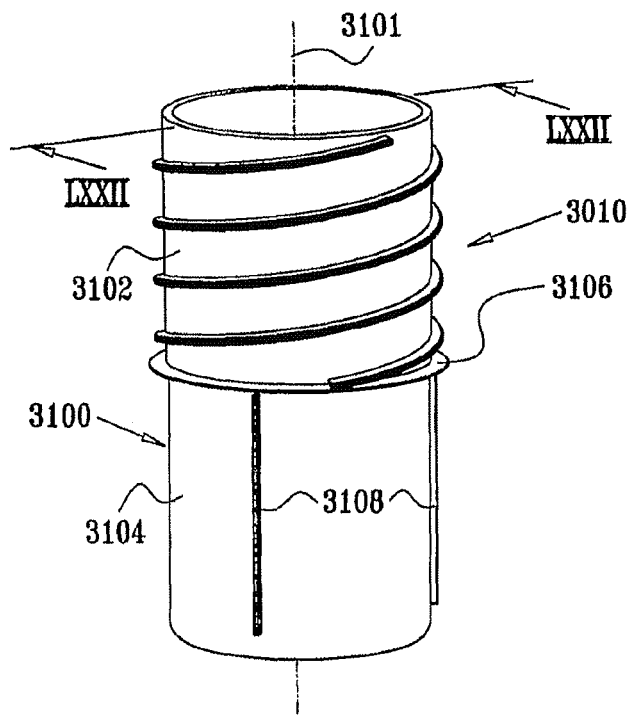
FIG. 71 is a simplified pictorial illustration of a vial support element which forms part of the drug mixing system of FIG. 70.
Figure 72A:
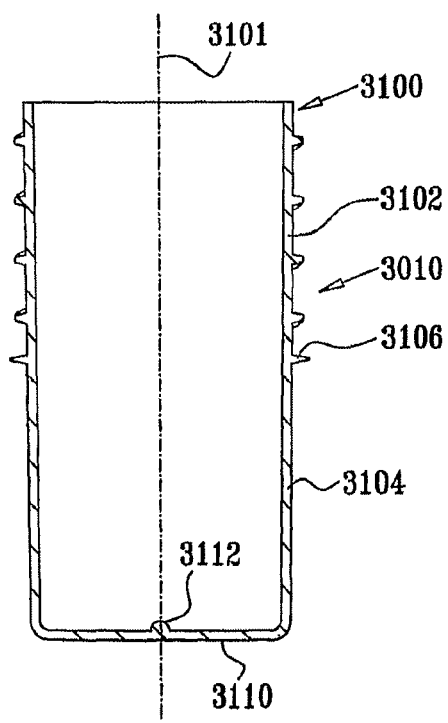
FIGS. 72A and 72B are, respectively, a sectional illustration and a pictorial sectional illustration taken along section lines LXXII-LXXII in FIG. 71.
Figure 72B:
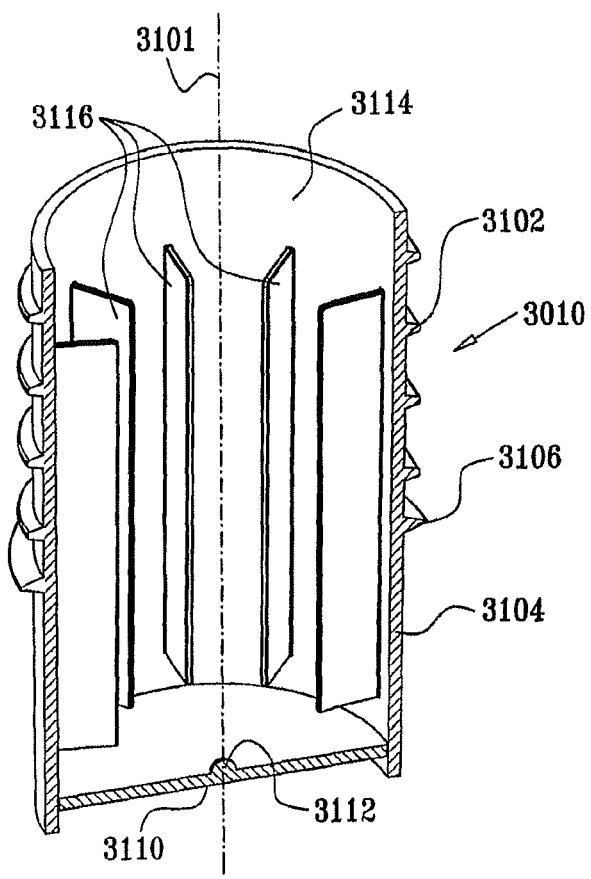

Reference is now made to FIG. 71 which is a simplified pictorial illustration of a vial support element 3010 which forms part of vial adaptor subassembly 3000 of the drug mixing system of FIG. 70 and to FIGS. 72A and 72B which are, respectively, a sectional illustration and a pictorial sectional illustration taken along section lines LXXII-LXXII in FIG. 71.

Vial support element 3010 comprises a generally cylindrical body element 3100 arranged generally about an axis 3101. Body element 3100 is preferably integrally formed and preferably is generally side-to-side symmetric about axis 3101.

Body element 3100 preferably includes a top portion 3102, which is externally threaded and which is separated from a bottom portion 3104 by an outwardly facing circumferential protrusion 3106. Four axially extending outwardly facing protrusions 3108 are preferably formed on bottom portion 3104, each protrusion 3108 being arranged at generally right angles with respect to its neighboring protrusions.

Body element 3100 preferably terminates in a transversely extending base wall portion 3110, which includes a central spherical protrusion 3112 which is adapted to center vial 3020 in vial support element 3010.

As seen with particular clarity in FIG. 72B, an inner surface 3114 of body element 3100 may optionally include a plurality of axially extending inwardly facing generally rectangular protrusions 3116, which are operative to adapt vial support element 3010 to support a smaller vial. Different body elements 3100, molded with protrusions 3116 of different sizes, may be used for different vial sizes. Similarly, base wall portion 3110 may optionally be molded at various heights with respect to bottom portion 3104, thus enabling different vial support elements 3010 to support vials of different heights.

Figure 73:
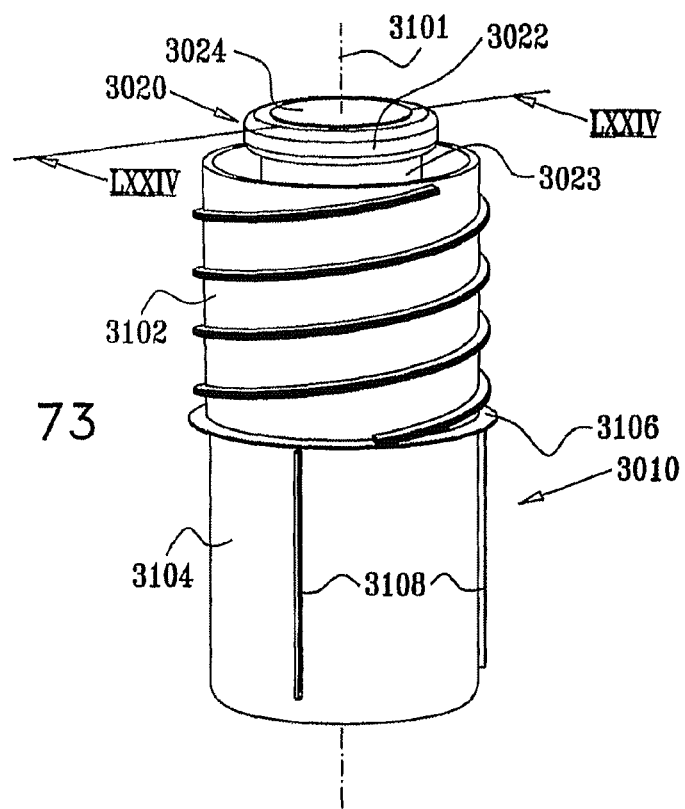
FIG. 73 is a simplified pictorial illustration of the vial support element of FIG. 71, when containing a vial.
Figure 74:
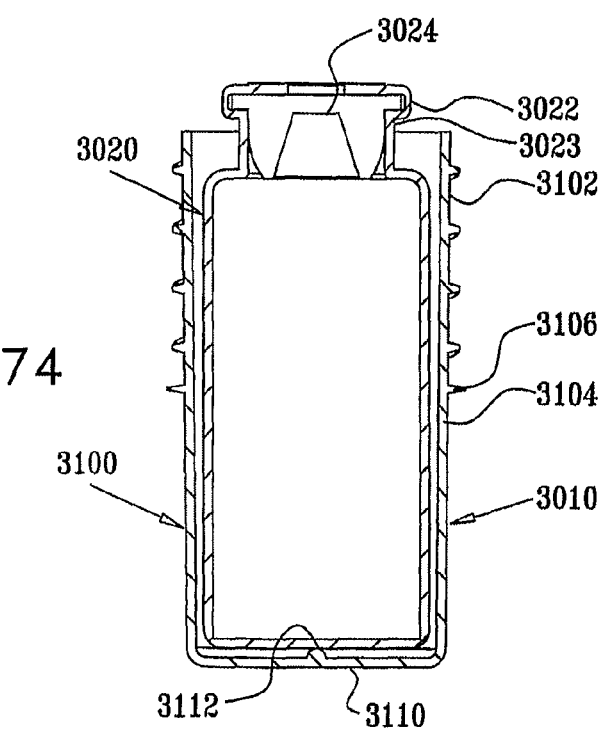
FIG. 74 is a sectional illustration taken along section lines LXXIV-LXIV in FIG. 73.

Reference is now made to FIG. 73, which is a simplified pictorial illustration of vial support element 3010 of FIGS. 71-72B containing a vial 3020 and to FIG. 74, which is a sectional illustration taken along section lines LXXIV-LXXIV in FIG. 73.

As seen in FIGS. 73 and 74, vial 3020 is placed within vial support element 3010, such that top portion 3022, septum 3024 and at least part of neck portion 3023 extend above the vial support element and are accessible to a user.

A base of vial 3020 is preferably seated on base wall portion 3110 and engages spherical protrusion 3112.

Figure 75A:
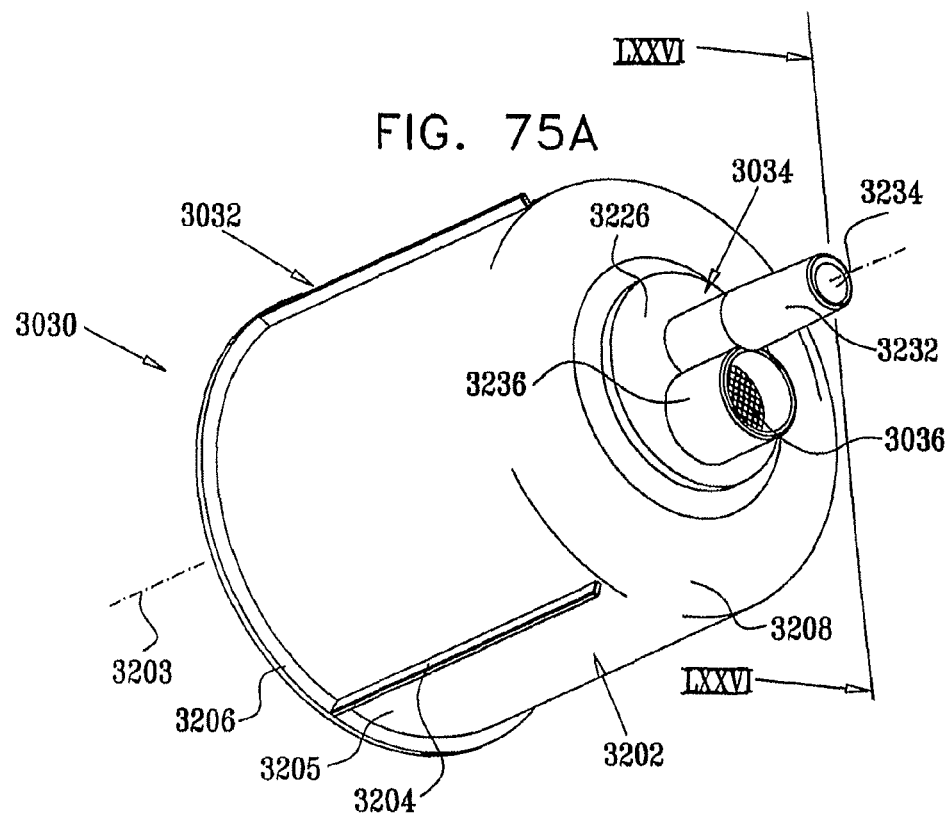
FIGS. 75A and 75B are simplified pictorial illustrations of a vial puncturing cover element which forms part of the vial adaptor subassembly of FIG. 70.
Figure 75B:
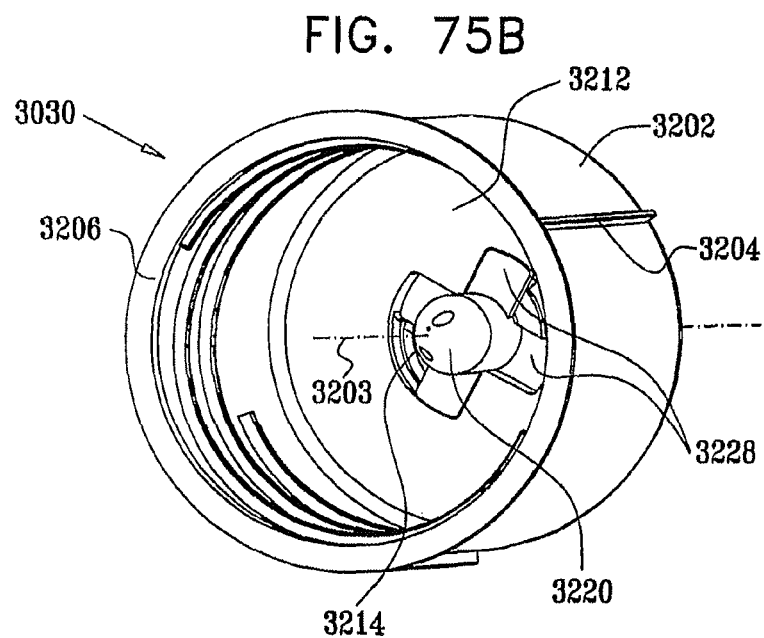
Figure 76:
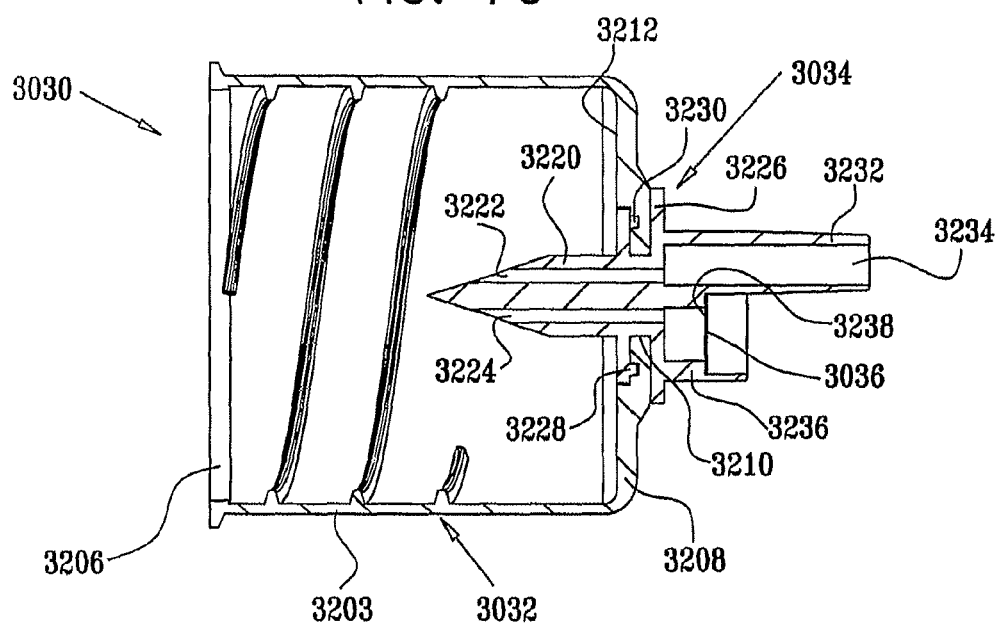
FIG. 76 is a sectional illustration taken along section lines LXXVI-LXXVI in FIG. 75A.

Reference is now made to FIGS. 75A and 75B, which are simplified pictorial illustrations of vial puncturing cover assembly 3030 which forms part of the vial adaptor subassembly 3000 of FIG. 70 and to FIG. 76 which is a sectional illustration taken along section lines LXXVI-LXXVI in FIG. 75A.

Vial puncturing cover assembly 3030 includes covering element 3032, which comprises a generally cylindrical main body portion 3202 arranged generally about an axis 3203.

Main body portion 3202 is preferably internally threaded and is adapted to engage the externally threaded top portion 3102 of vial support element 3010. Four axially extending outwardly facing protrusions 3204 are preferably formed on an outer surface 3205 of main body portion 3202, each protrusion 3204 being arranged at generally right angles with respect to its neighboring protrusions. An outwardly facing radially extending wall portion 3206 extends from a bottom end of main body portion 3202.

Main body portion 3202 terminates in a wall portion 3208, which preferably extends transversely with respect to axis 3203 and includes a generally round aperture 3210. An inner surface 3212 of wall portion 3208 preferably includes two semi-circular tracks 3214.

Vial puncturing spike element 3034 preferably includes a vial puncturing spike 3220 extending through aperture 3210 of wall portion 3208. Vial puncturing spike 3220 preferably has two axial bores 3222 and 3224 extending therethrough.

Preferably membrane 3036 is in fluid flow engagement with cover element 3032 via bore 3224 of vial puncturing spike 3220.

Spike 3220 preferably extends forwardly from a generally circular wall portion 3226, which engages a top surface of wall portion 3208. Four generally rectangular wall portions 3228 extend radially from spike 3220, each wall portion 3228 being arranged at generally right angles with respect to its neighboring wall portions.

Wall portions 3228 preferably define at top surfaces thereof four spherical protrusions 3230, which engage tracks 3214 and are adapted to lock vial puncturing spike element 3034 with respect to covering element 3032.

A generally cylindrical portion 3232, including an axial bore 3234, preferably extends rearwardly from wall portion 3226. Cylindrical portion 3232 is preferably adapted to engage rear portion 3658 of receptacle adaptor subassembly 3040.

A second generally cylindrical portion 3236 preferably extends rearwardly of wall portion 3226 and adjacent cylindrical portion 3232. Portion 3236 preferably defines a seat 3238 which is adapted to support unidirectional breathing membrane 3036 and prevent it from excessive inflation and from cracking. Membrane 3036 is adapted to allow free passage of air into the main body element 3032, but prevent passage therethrough of liquid and air-borne particles, microorganisms and aerosol. A preferred membrane 3036 is Model Versapor R 0.2 Micron which is commercially available from Pall Corporation of New York, U.S.A.

Figure 77:
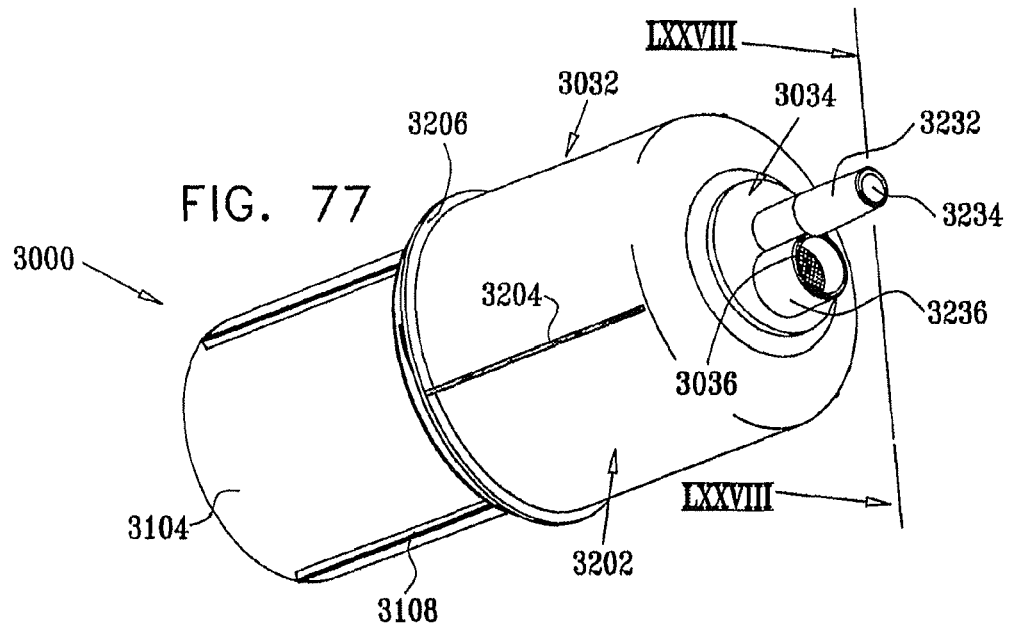
FIG. 77 is a simplified assembled pictorial illustration of the vial adaptor subassembly of FIG. 70.
Figure 78:
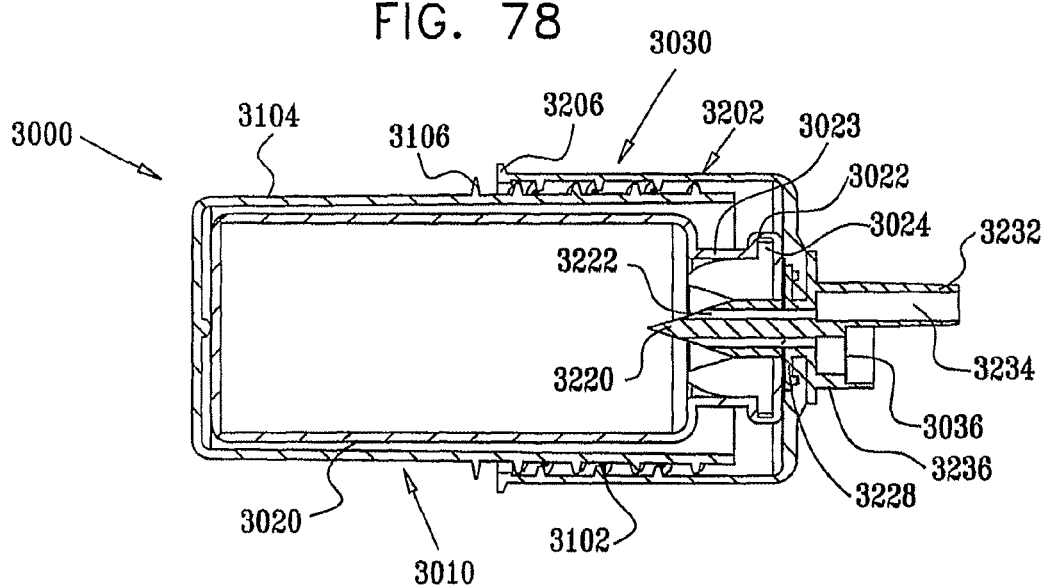
FIG. 78 is a sectional illustration taken along section lines LXXVIII-LXXVIII in FIG. 77.

Reference is now made to FIG. 77, which is a simplified assembled pictorial illustration of the vial adaptor subassembly 3000 of FIG. 70 and to FIG. 78, which is a sectional illustration taken along section lines LXXVIII-LXXVIII in FIG. 77.

As seen in FIGS. 77 and 78, vial puncturing cover assembly 3030 threadably engages vial support element 3010, thus enclosing therein vial 3020.

The threaded engagement between vial support element 3010 and vial puncturing cover element 3032 causes puncturing spike 3220 to be pushed into engagement with vial 3020.

Typically, vial puncturing spike 3220 of vial puncturing cover element 3030 punctures septum 3024 located inside top portion 3022 of vial 3020, thus enabling fluid flow between the main body of vial 3020 and bore 3234 of cylindrical portion 3232 via bore 3222 of puncturing spike 3220. Preferably, puncturing of septum 3024 releases any vacuum in vial 3020.

Figure 79:
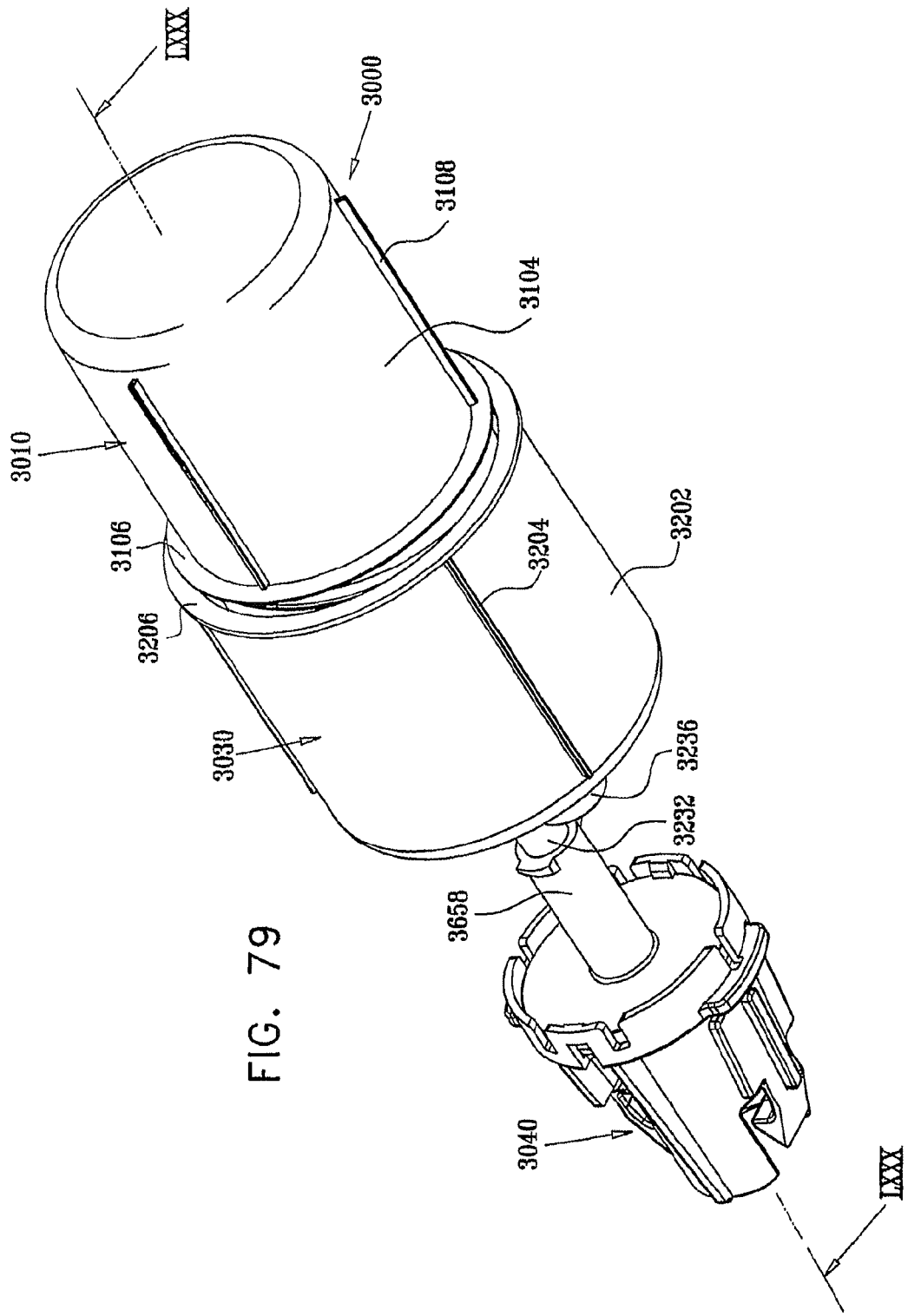
FIG. 79 is a pictorial illustration of the vial adaptor assembly of FIG. 77 when assembled to an adaptor assembly in accordance with a preferred embodiment of the present invention.
Figure 80:
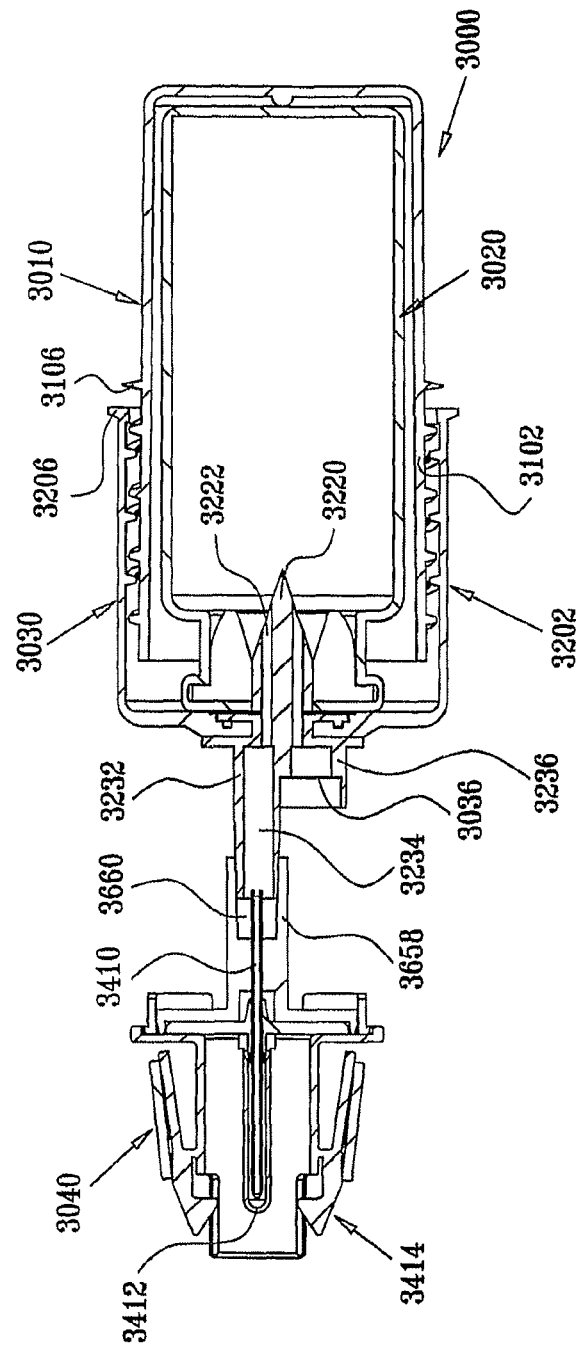
FIG. 80 is a sectional illustration taken along section lines LXXX-LXXX in FIG. 79.

Reference is now made to FIG. 79, which is a pictorial illustration of the vial adaptor subassembly 3000 of FIG. 77 when assembled to receptacle adaptor subassembly 3040 thus forming an adaptor assembly in accordance with a preferred embodiment of the present invention, and to FIG. 80, which is a sectional illustration taken along section lines LXXX-LXXX in FIG. 79.

As seen in FIGS. 79 and 80, cylindrical portion 3232 of vial cover element 3030 engages rear portion 3658 of receptacle adaptor subassembly 3040. A rear end of needle 3410 at least partially extends through bore 3660 and through bore 3234 such that bore 3234 is in fluid flow communication with needle 3410 of receptacle adaptor subassembly 3040. Due to fluid flow communication between bore 3234 and the main body of vial 3020, needle 3410 is in fluid flow communication with vial 3020.

A forward portion of main body element 3414 of receptacle adaptor subassembly 3040 preferably surrounds needle 3410 enclosed in needle protection element 3412. Main body element 3600 including needle 3410 and needle protection cover 3412 is preferably accessible for connection of spike port adaptor element 3050 thereto.

It is appreciated that cylindrical portion 3232 of vial cover element 3030 may alternatively engage a stopcock 3052, which additionally engages receptacle adaptor subassembly 3040 and a syringe as described hereinabove with reference to FIGS. 31A-53. In such a case, the method of use of the system would be similar to that described in FIGS. 31A-31L.

Figure 81:
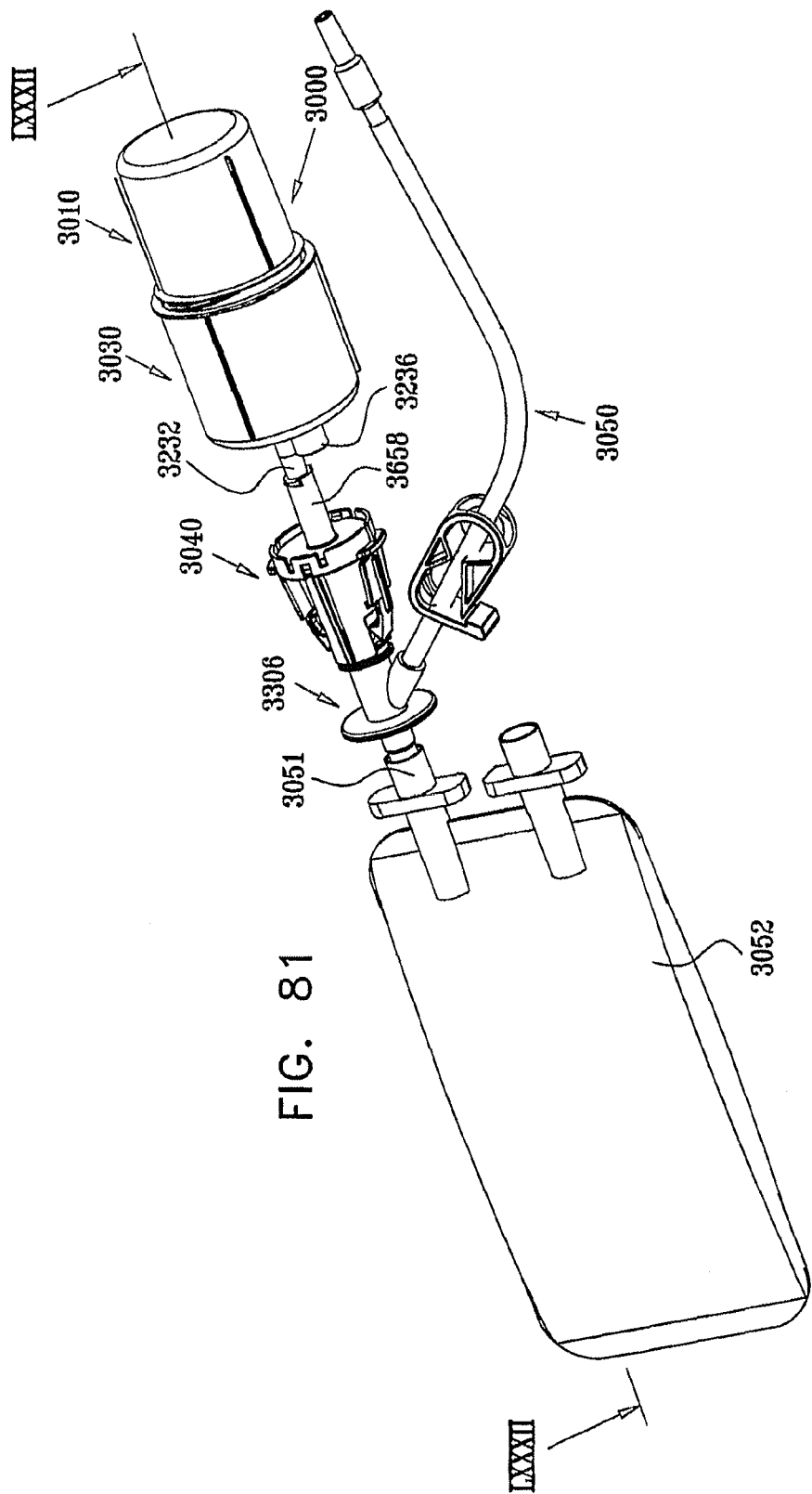
FIG. 81 is a pictorial illustration taken of the vial adaptor assembly and adaptor assembly of FIG. 79 when connected to a receptacle port adaptor element and a receptacle in accordance with a preferred embodiment of the present invention.
Figure 82:
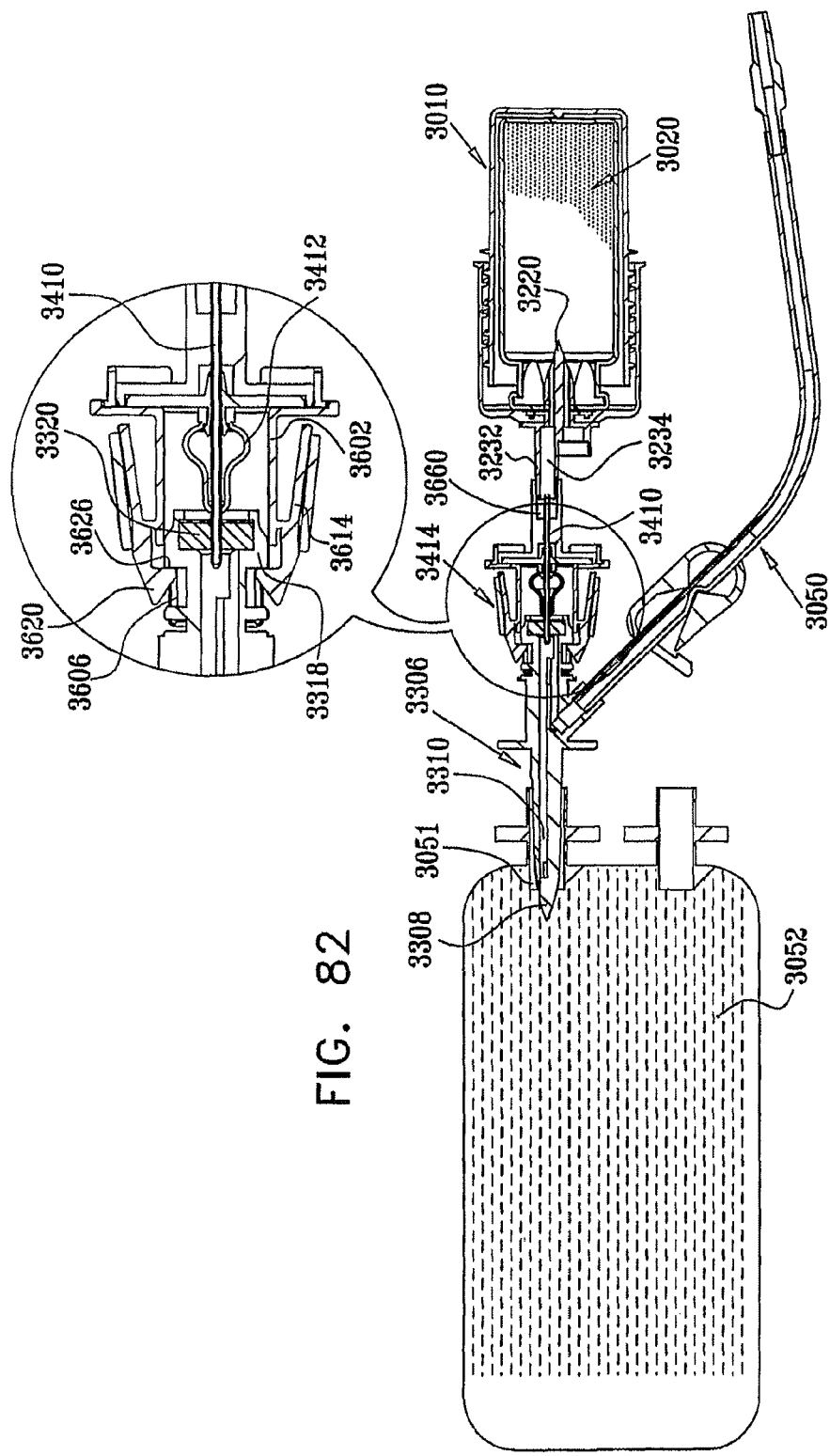
FIG. 82 is a sectional illustration taken along section lines LXXXII-LXXXII in FIG. 81.

Reference is now made to FIG. 81, which is a pictorial illustration of vial adaptor subassembly 3000 connected to receptacle adaptor subassembly 3040 of FIG. 79 when connected to a spike port adaptor element 3050 and receptacle 3052 and to FIG. 82, which is a sectional illustration taken along section lines LXXXII-LXXXII in FIG. 81.

As seen in FIGS. 81 and 82, spike port adaptor element 3050, having receptacle 3052 joined thereto, is connected to receptacle adaptor subassembly 3040.

A spike 3308 is preferably previously inserted into spike port 3051 of receptacle 3052, such that a bore 3310 of a spike element 3306 engages fluid content of receptacle 3052. A connection port 3318 of spike port adaptor element 3050 engages wall portions 3606 and base portion 3602 of main body element 3414 of receptacle adaptor subassembly 3040.

Connection port 3318 is preferably locked into connection with receptacle adaptor subassembly 3040 by engagement of engagement surfaces 3626 of forward portions 3620 of arms 3614 and a rearward facing wall portion of connection port 3318.

Preferably, needle 3410 punctures needle protection cover 3412 and septum 3320, resulting in partial collapse of the needle protection cover. At this stage, receptacle 3052 is in fluid flow communication with the main body of vial 3020 via bore 3310 of spike 3308 of spike port adaptor element 3050, needle 3410, bore 3660, bore 3234 of cylindrical portion 3232 and vial puncturing spike 3220.

Figure 83:
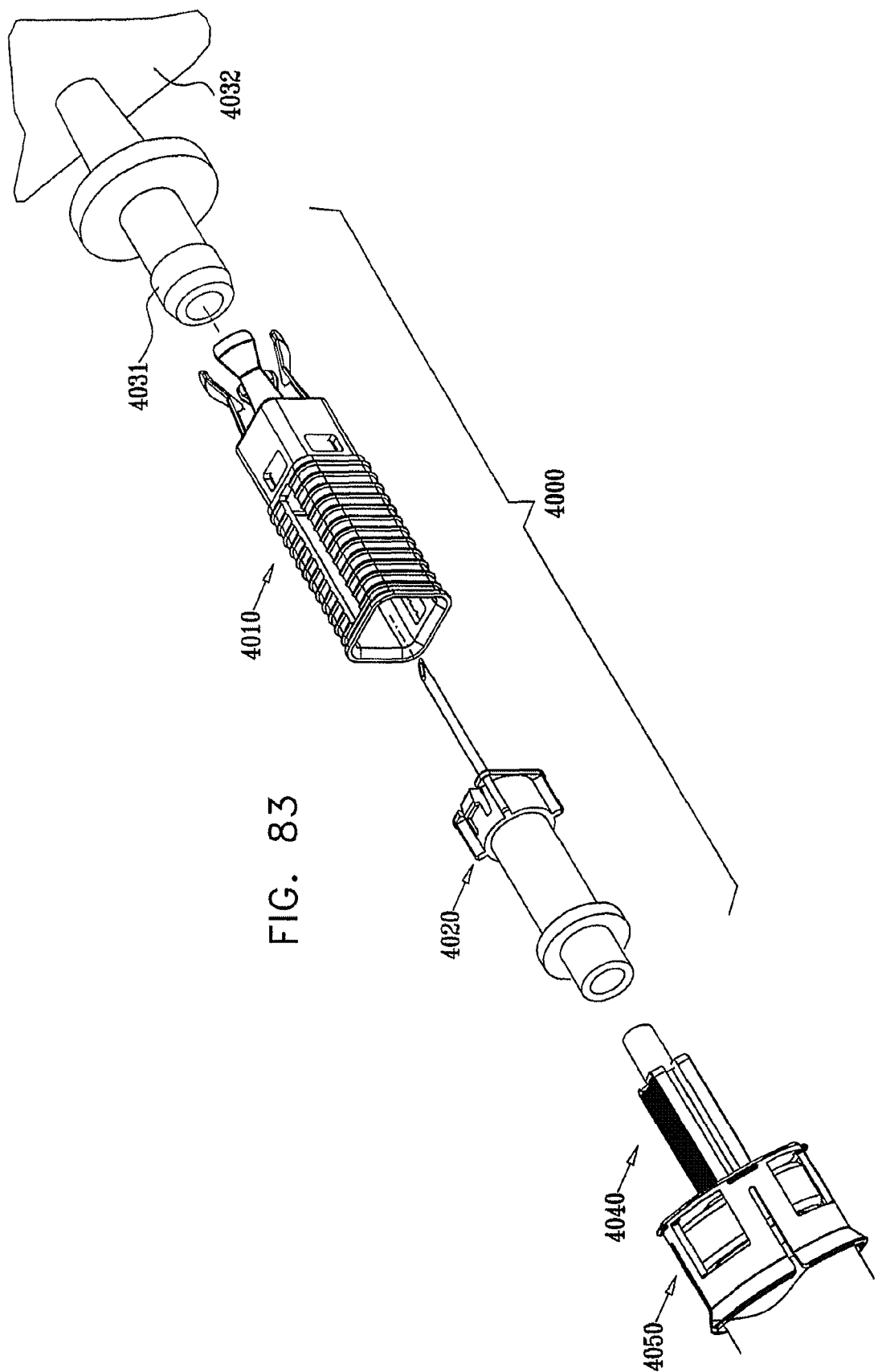
FIG. 83 is an exploded view illustration of a drug mixing system which is constructed and operative in accordance with a still further preferred embodiment of the present invention.

Reference is now made to FIG. 83, which is a simplified exploded view illustration of a drug mixing system constructed and operative in accordance with a still further preferred embodiment of the present invention. The embodiment of FIG. 83 is a modification of the embodiment of FIGS. 54A-69. Accordingly, for the sake of conciseness, it is described hereinbelow in somewhat abbreviated form with reference to FIGS. 84-92.

As seen with particular clarity in FIG. 83, the drug mixing system comprises a receptacle adaptor subassembly 4000 which preferably comprises a receptacle adaptor housing element 4010. Receptacle adaptor housing element 4010 preferably engages a receptacle adaptor needle assembly 4020. Receptacle adaptor subassembly 4000 preferably engages a port such as a receptacle port 4031 of a receptacle 4032.

Receptacle adaptor needle assembly 4020 connects at a rearward end thereof to a connection port of a vial adaptor subassembly 4040, which is adapted to engage a vial 4050.

It is appreciated that vial 4050 may be identical to either of vials 2020 and 2026, and receptacle 4032 may be identical to receptacle 2032, described hereinabove with reference to FIGS. 54A-54C.

Vial adaptor subassembly 4040 may be identical to vial adaptor subassembly 2046, described hereinabove with reference to FIGS. 60-61B.

Receptacle port 4031 may be identical receptacle port 2031, described hereinabove. It is appreciated that receptacle adaptor subassembly 4000 may engage a spike port adaptor element such as spike port adaptor element 2030 described hereinabove with reference to FIGS. 57-58.

Figure 84:
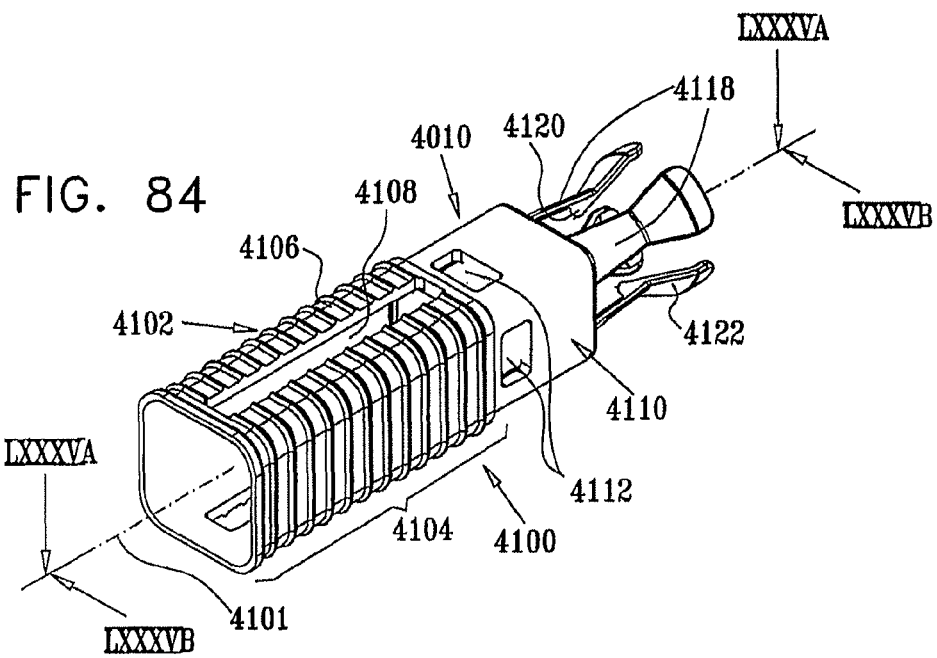
FIG. 84 is a simplified pictorial illustration of a receptacle adaptor housing assembly which forms part of the drug mixing system of FIG. 83.
Figure 85A:
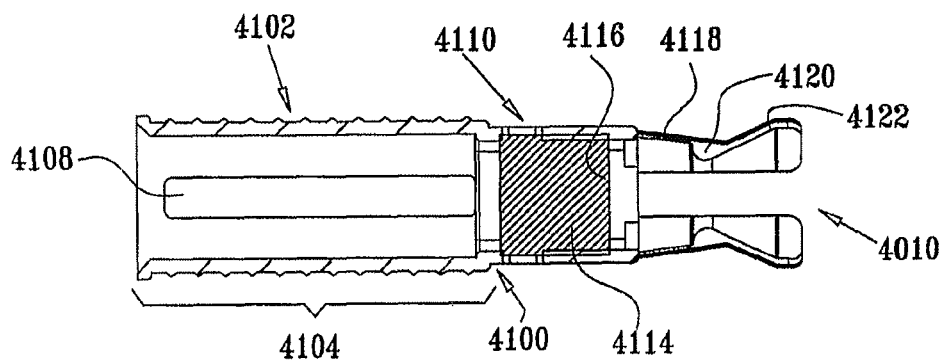
FIGS. 85A and 85B are sectional illustrations taken along section lines LXXXVA-LXXXVA and LXXXVB-LXXXVB in FIG. 84.
Figure 85B:
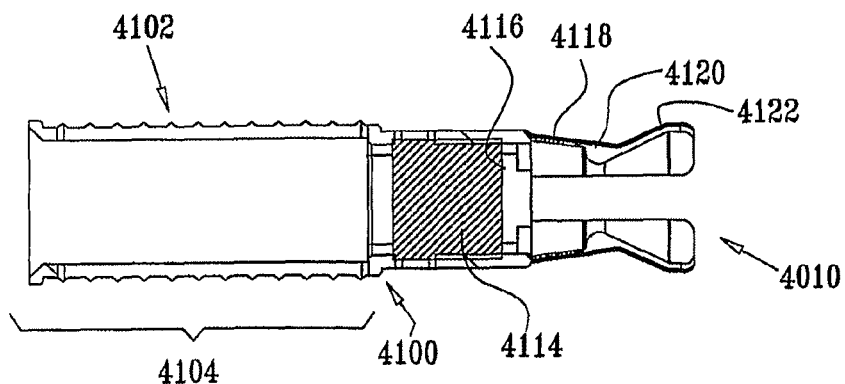

Reference is now made to FIG. 84, which is a simplified pictorial illustration of receptacle adaptor housing element 4010 which forms part of the drug mixing system of FIG. 83 and to FIGS. 85A and 85B, which are sectional illustrations taken along section lines LXXXVA-LXXXVA and LXXXVB-LXXXVB in FIG. 84.

Receptacle adaptor housing element 4010 comprises a body element 4100, arranged generally about an axis 4101. Body element 4100 comprises a tube of generally rectangular cross-section, is preferably integrally formed and preferably is generally side-to-side symmetric about axis 4101.

Body element 4100 preferably includes a rear portion 4102 which is formed with ribbed grip regions 4104 on an outer surface 4106. Two elongate windows 4108 are preferably formed on top and bottom surfaces of rear portion 4102.

A forward portion 4110 of body element 4100 has a slightly smaller outer circumference than that of rear portion 4102, and includes a generally rectangular window 4112 on each of the surfaces thereof. Forward portion 4110 preferably sealingly accommodates a septum 4114 in a seat 4116.

Four axially extending tabs 4118 extend forwardly of forward portion 4110, each tab 4118 being arranged at generally right angles with respect to its neighboring tabs. Each tab 4118 preferably includes and an inwardly facing tooth 4120 and preferably terminates in an outwardly tapered portion 4122.

Figure 86:
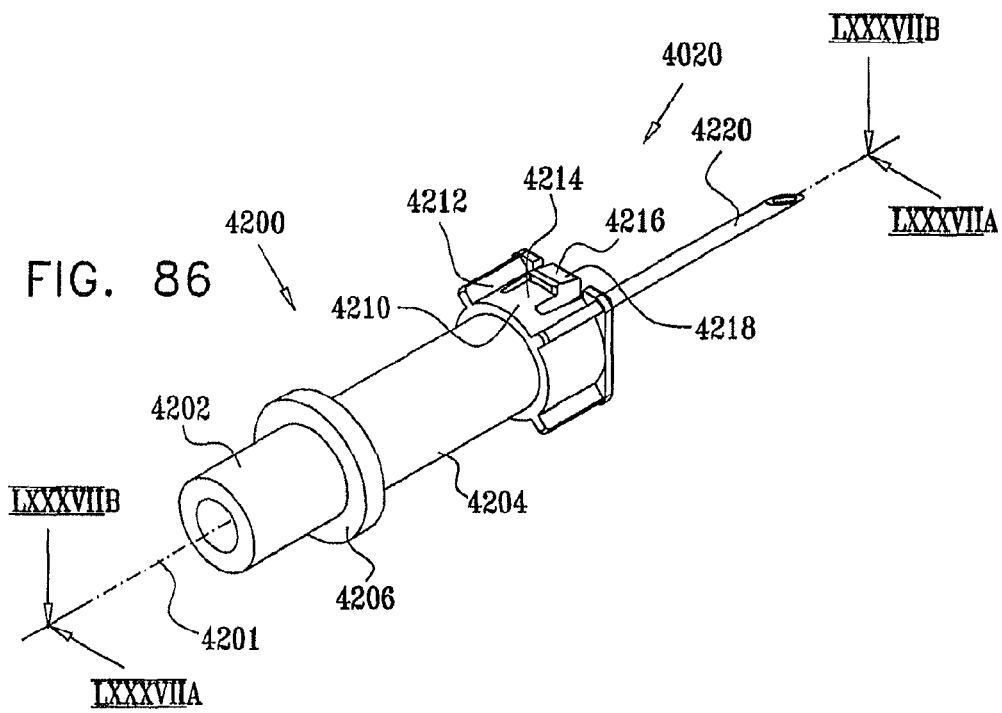
FIG. 86 is a simplified pictorial illustration of a receptacle adaptor needle element which forms part of the drug mixing system of FIG. 83.
Figure 87A:
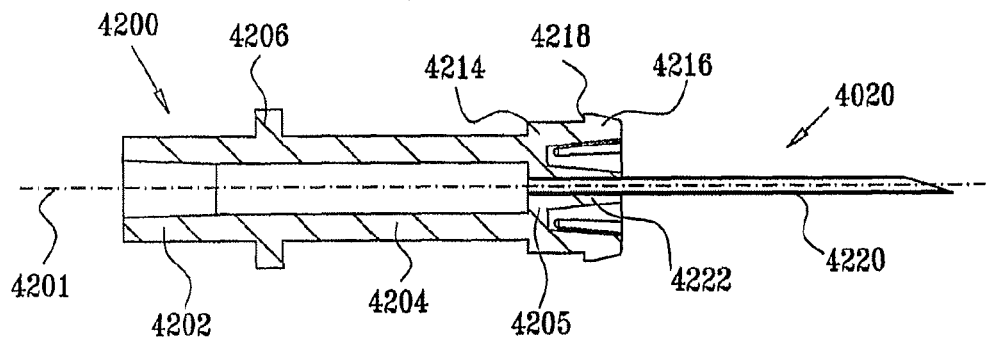
FIGS. 87A and 87B are sectional illustrations taken along section lines LXXXVIIA-LXXXVIIA and LXXXVIIB-LXXXVIIB in FIG. 86.
Figure 87B:
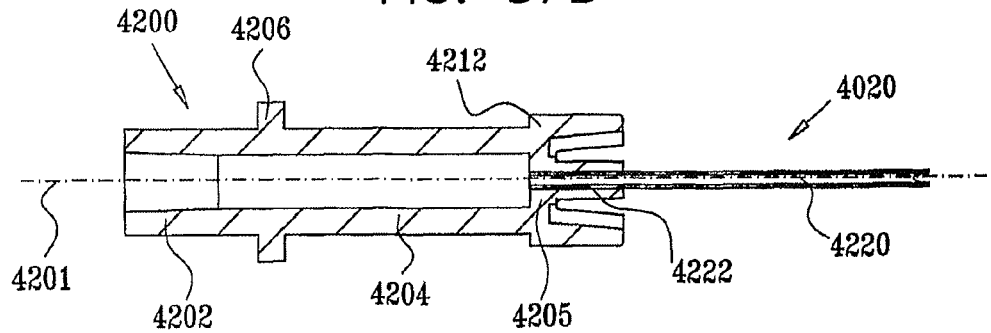

Reference is now made to FIG. 86, which is a simplified pictorial illustration of receptacle adaptor needle assembly 4020 which forms part of the drug mixing system of FIG. 83 and to FIGS. 87A and 87B, which are sectional illustrations taken along section lines LXXXVIIA-LXXXVIIA and LXXXVIIB-LXXXVIIB in FIG. 86.

Receptacle adaptor needle assembly 4020 comprises a generally cylindrical body element 4200, arranged generally about an axis 4201. Body element 4200 is preferably integrally formed and preferably is generally side-to-side symmetric about axis 4201.

Body element 4200 preferably includes a rear connection port 4202 which is separated from a forward portion 4204 by a circumferential outwardly extending protrusion 4206. Protrusion 4206 is adapted to limit the extent to which receptacle adaptor needle assembly 4020 is inserted into receptacle adaptor housing element 4010.

Forward portion 4204 preferably terminates in a forward wall portion 4205 from which extends a cylindrical portion 4210 having an outer circumference which is slightly larger than that of forward portion 4204. Cylindrical portion 4210 preferably has formed thereon four axially extending protrusions 4212, each protrusion 4212 being arranged at generally right angles with respect to its neighboring protrusions.

Two outwardly extending arms 4214 are formed at a forward end of cylindrical portion 4210, each arm 4214 being generally across from the other arm. Protrusions 4212 and arms 4214 are preferably rotationally offset from one another about axis 4201. Each arm 4214 preferably defines at a forward most end thereof a generally triangular tooth 4216 including an engagement surface 4218.

A hollow needle 4220 is preferably sealingly mounted in a cylindrical portion 4222 which is formed within cylindrical portion 4210 of receptacle adaptor needle assembly 4020.

Figure 88:
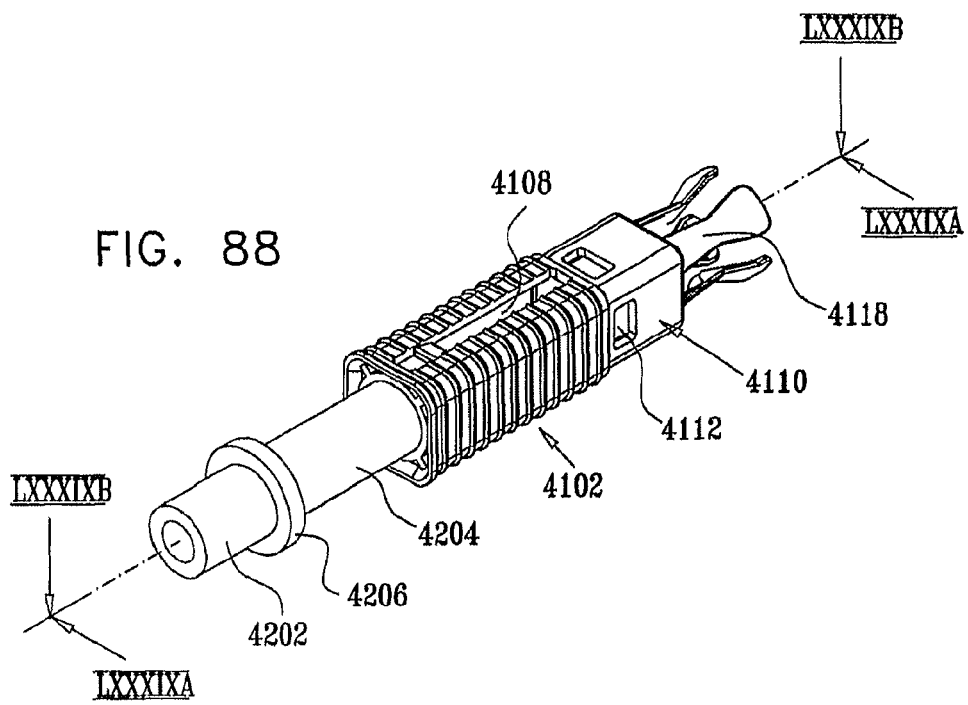
FIG. 88 is a simplified assembled pictorial illustration of the receptacle adaptor subassembly of FIG. 83.
Figure 89A:
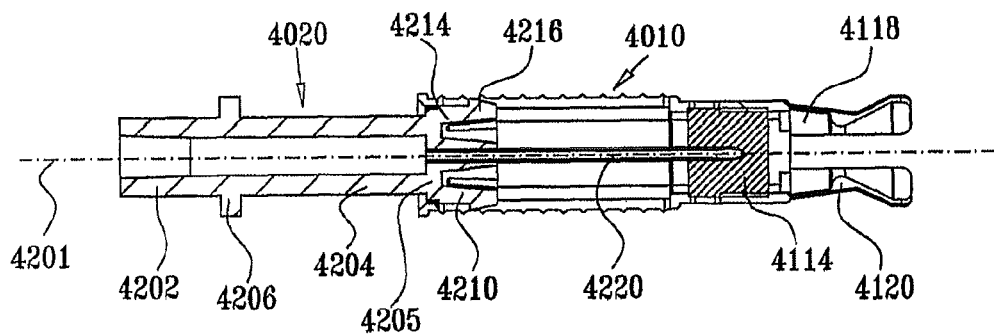
FIGS. 89A and 89B are sectional illustrations taken along section lines LXXXIXA-LXXXIXA and LXXXIXB-LXXXIXB in FIG. 88.
Figure 89B:
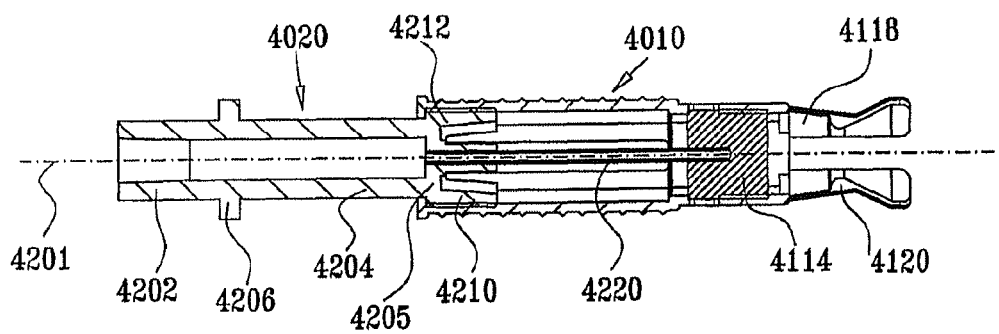

Reference is now made to FIG. 88, which is a simplified assembled pictorial illustration of the receptacle adaptor subassembly 4000 of FIG. 83 and to FIGS. 89A and 89B, which are sectional illustrations taken along section lines LXXXIXA-LXXXIXA and LXXXIXB-LXXIXB in FIG. 88.

As seen in FIG. 88-89B, cylindrical portion 4210 of receptacle adaptor needle assembly 4020 preferably engages a rearwardmost portion of rear portion 4102 of receptacle adaptor housing element 4010. Teeth 4216 of arms 4214 of cylindrical portion 4210 preferably extend through windows 4108 and maintain receptacle adaptor needle assembly 4020 locked in receptacle adaptor housing element 4010.

It is appreciated that a user may push receptacle adaptor needle assembly 4020 inward with respect to receptacle adaptor housing element 4010. Such inward motion of receptacle adaptor needle assembly 4020 is limited by protrusion 4206.

Figure 91:
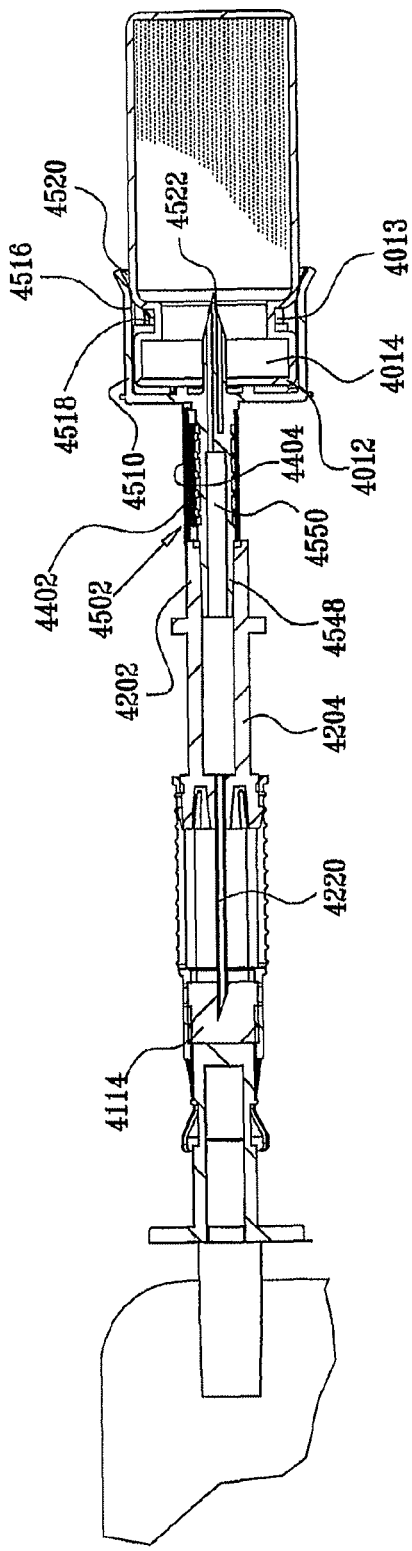
FIG. 91 is a sectional illustration taken along section lines XCI-XCI in FIG. 90.

Reference is now made to FIG. 90, which is a pictorial illustration of the receptacle adaptor subassembly 4000 of FIG. 88 when assembled to a vial adaptor subassembly 4040 and to port 4031 of receptacle 4032, prior to insertion of needle 4220 into the receptacle port 4031 and to FIG. 91, which is a sectional illustration taken along section lines XCI-XCI in FIG. 90.

Vial 4050 is preferably pushed into engagement with a vial puncturing spike 4522 of vial adaptor subassembly 4040.

Typically, vial puncturing spike 4522 of vial adaptor subassembly 4050 punctures a septum 4014 located inside a top portion 4012 of vial 4050, thus enabling fluid flow between the main body of vial 4050 and a bore 4550 of a cylindrical portion 4548 of main body element 4502 of vial adaptor subassembly 4050. Preferably, puncturing of septum 4014 releases any vacuum in vial 4050 by entrance of air into vial 4050 through a carbon filter 4404 and a membrane 4402.

Engagement between vial adaptor subassembly 4040 and vial 4050 is preferably maintained by snap engagement of protrusions 4516 and 4518 of rear portion 4504 of main body element 4502 with neck portion 4013 of vial 4050. The engagement of protrusions 4516 and 4518 with neck portion 4013 ensures that vial adaptor subassembly 4040 is latched onto vial 4050 and cannot be removed therefrom. Tabs 4510 and outwardly tapered portions 4520 generally surround top portion 4012 and neck portion 4013 of vial 4050.

Cylindrical portion 4548 preferably engages connection port 4202 of receptacle adaptor needle assembly 4020, such that needle 4220 is in fluid flow communication with vial 4050 via forward portion 4204, bore 4550 of cylindrical portion 4548 and vial puncturing spike 4522. The sharpened tip of needle 4220 preferably partially extends through septum 4114.

Teeth 4120 of arms 4118 preferably engage receptacle port 4031 of receptacle 4032, or may alternatively engage any other suitable port such as a spike port adaptor element 4030 as described hereinabove.

Figure 92:
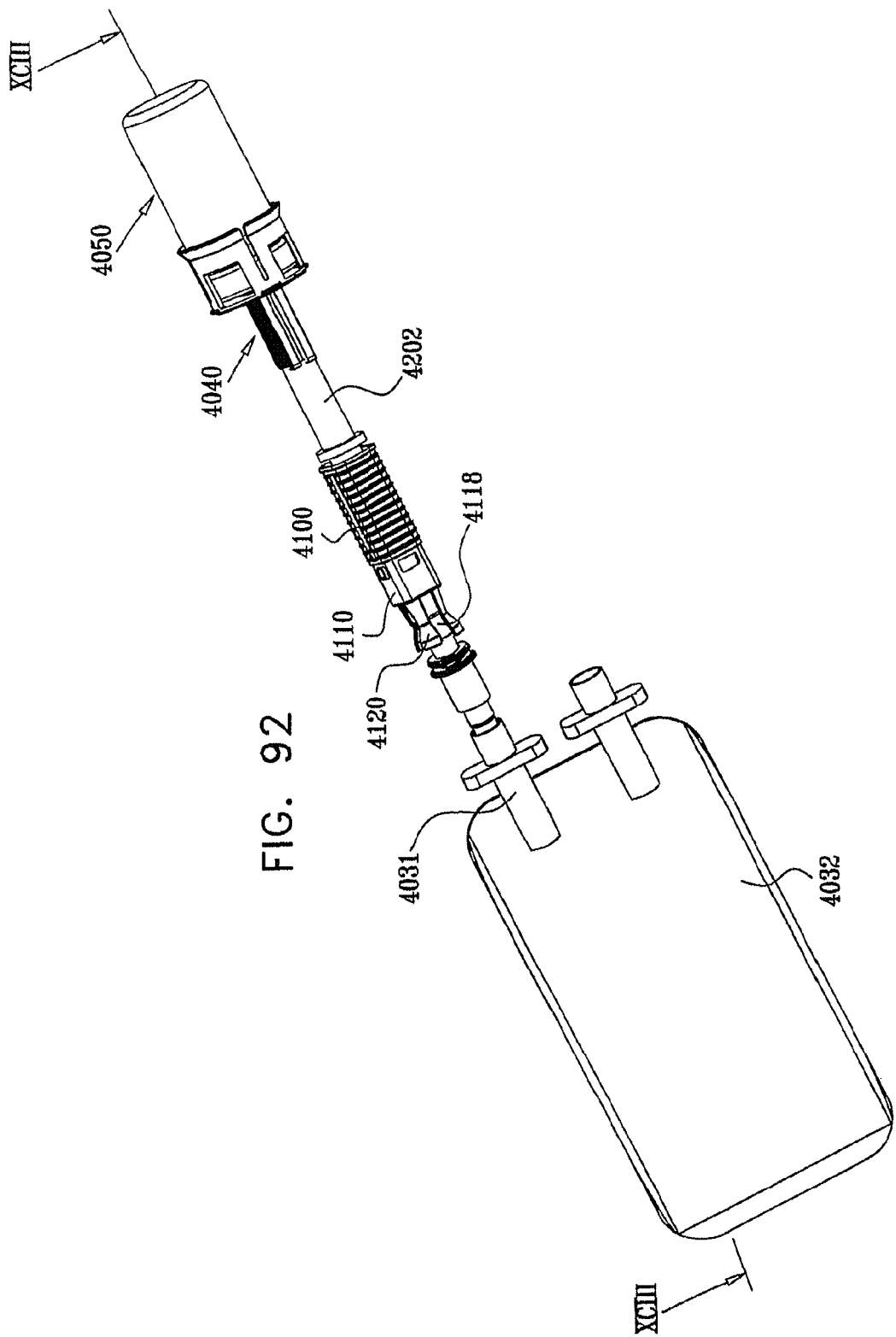
FIG. 92 is a pictorial illustration of the receptacle adaptor subassembly of FIG. 88 when assembled to a vial adaptor subassembly, following connection of a needle to a receptacle port element.
Figure 93:
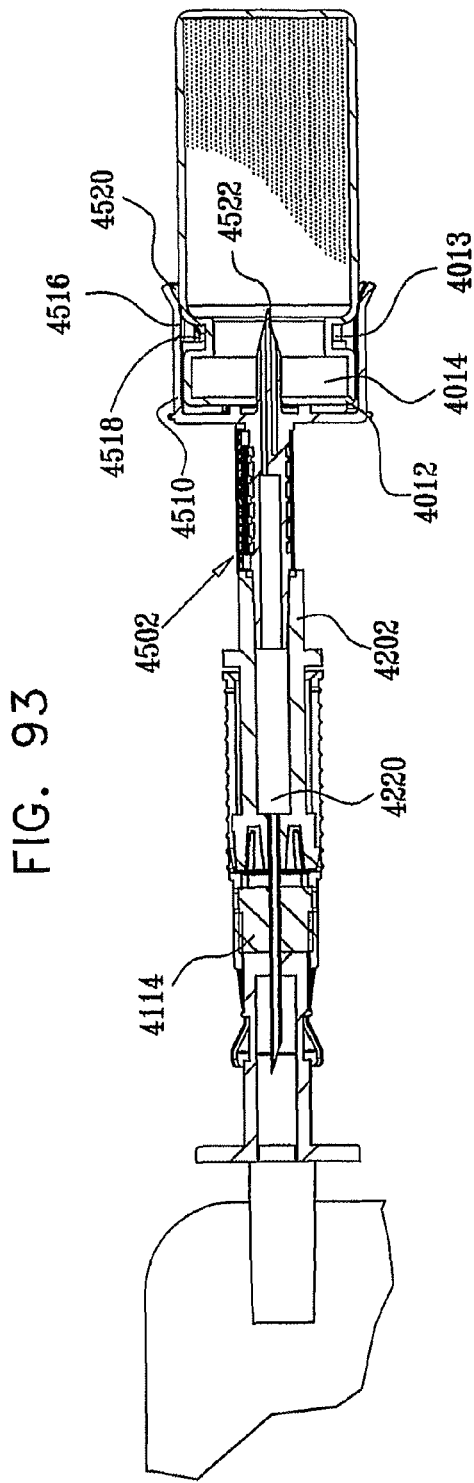
FIG. 93 is a sectional illustration taken along section lines XCIII-XCIII in FIG. 92.

Reference is now made to FIG. 92, which is a pictorial illustration of the receptacle adaptor subassembly 4000 of FIG. 88 when assembled to a vial adaptor subassembly 4040 and to port 4031 of receptacle 4032, following insertion of needle 4220 into receptacle port 4031 and to FIG. 93, which is a sectional illustration taken along section lines XCIII-XCIII in FIG. 92.

As seen in FIGS. 92 and 93, a user preferably pushes receptacle adaptor needle assembly 4020 inward, such that needle 4220 pierces septum 4114, resulting in fluid flow communication between receptacle 4032 and vial 4050.

It will be appreciated by persons skilled in the art that the present invention is not limited to what has been particularly shown and described hereinabove. Rather the scope of the present invention includes both combinations and subcombinations of various features described hereinabove as well as modifications thereof which would occur to persons skilled in the art upon reading the foregoing specification and which are not in the prior art.

The invention claimed is:

1. A syringe adaptor adapted for connection to a syringe and adapted for connection to at least one other element of a drug handling system, said syringe adaptor comprising:
    a septa housing;
    at least one septum enclosed in said septa housing;
    a generally cylindrical main body portion having side surfaces;
    an outwardly protruding arm extending from a forward portion of each of said side surfaces and defining at an inner facing forward end thereof a tooth; and
    a hollow needle, including a tip located in said septa housing when said syringe adaptor is not connected to said at least one other element of said drug handling system,
    said septa housing being rearwardly movable relative to said main body portion, and thereby relative to said hollow needle, to expose said tip.

2. A syringe adaptor according to claim 1 wherein said tooth has a transversely extending rearward facing surface.

3. A syringe adaptor according to claim 2 wherein said at least one other element of a drug handling system comprises at least one of a spike port adaptor, a needle port adaptor, a vial adaptor, an infusion set adaptor and an infusion set port not being part of said syringe adaptor.

4. A syringe adaptor according to claim 2 and wherein said arm and said tooth are adapted for snap engagement with said at least one other element of a drug handling system.

5. A syringe adaptor according to claim 4 wherein said transversely extending rearward facing surfaces are configured to engage a portion of said at least one other element of a drug handling system, thereby providing said snap engagement.

6. A syringe adaptor according to claim 4 and also comprising a housing element, wherein:
    said main body portion surrounds said housing element; and
    said snap engagement pushes said housing element rearwardly relative to said main body portion.

7. A syringe adaptor according to claim 1 wherein said at least one other element of a drug handling system comprises at least one of a spike port adaptor, a needle port adaptor, a vial adaptor, an infusion set adaptor and an infusion set port not being part of said syringe adaptor.

8. A syringe adaptor according to claim 1 and wherein said arm and said tooth are adapted for snap engagement with said at least one other element of a drug handling system.

9. A syringe adaptor according to claim 8 and wherein said arm is adapted to release said at least one other element of a drug handling system when pushed by a user, thereby causing said tooth to move outwardly.

10. A syringe adaptor according to claim 1 and wherein said arm and said tooth are adapted for snap engagement with said at least one other element of a drug handling system.

11. A syringe adaptor according to claim 10 and wherein said arm is adapted to release said at least one other element of a drug handling system when pushed by a user, thereby causing said tooth to move outwardly.

12. A syringe adaptor according to claim 2 and wherein said arm and said tooth are adapted for snap engagement with said at least one other element of a drug handling system.

13. A syringe adaptor according to claim 12 and wherein said arm is adapted to release said at least one other element of a drug handling system when pushed by a user, thereby causing said tooth to move outwardly.

14. A syringe adaptor according to claim 4 and wherein said arm is adapted to release said at least one other element of a drug handling system when pushed by a user, thereby causing said tooth to move outwardly.

15. A syringe adaptor adapted for connection to a syringe and adapted for connection to at least one other element of a drug handling system, said syringe adaptor comprising:
   a generally cylindrical main body portion having side surfaces;
   an outwardly protruding arm extending from a forward portion of each of said side surfaces and defining at an inner facing forward end thereof a tooth, said tooth having a transversely extending rearward facing surface, said arm and said tooth being adapted for snap engagement with said at least one other element of a drug handling system;
   a housing element; and
   a needle,
   said main body portion surrounding said housing element;
   said snap engagement pushing said housing element rearwardly relative to said main body portion,
   a tip of said needle being located within said housing element prior to said snap engagement; and
   said snap engagement causing said tip of said needle to protrude from said housing element.

16. A syringe adaptor according to claim 15 and also comprising a spring located within said housing element.

17. A syringe adaptor according to claim 16 wherein said tip of said needle is located within said housing element when said spring is relaxed.

18. A syringe adaptor according to claim 16 wherein said snap engagement compresses said spring.

19. A syringe adaptor according to claim 16 wherein said tip of said needle protrudes from said housing element when said spring is compressed.

* * * * *